(12) United States Patent
Bradley et al.

(10) Patent No.: US 9,175,273 B2
(45) Date of Patent: Nov. 3, 2015

(54) COMPOSITIONS AND METHODS FOR PATHOGEN CONTROL IN PLANTS

(75) Inventors: John Bradley, St. Louis, MO (US); Michael J. Crawford, St. Louis, MO (US); William P. Haakenson, Jr., St. Louis, MO (US); Michelle Coutu Hresko, Chesterfield, MO (US); Deryck J. Williams, University City, MO (US); Amy L. Caruano-Yzermans, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 532 days.

(21) Appl. No.: 13/578,095

(22) PCT Filed: Feb. 14, 2011

(86) PCT No.: PCT/US2011/024693
§ 371 (c)(1),
(2), (4) Date: Nov. 27, 2012

(87) PCT Pub. No.: WO2011/100650
PCT Pub. Date: Aug. 18, 2011

(65) Prior Publication Data
US 2013/0067620 A1 Mar. 14, 2013

Related U.S. Application Data

(60) Provisional application No. 61/304,391, filed on Feb. 12, 2010, provisional application No. 61/364,350, filed on Jul. 14, 2010.

(51) Int. Cl.
C12N 9/16 (2006.01)
C12N 15/82 (2006.01)

(52) U.S. Cl.
CPC .............. *C12N 9/16* (2013.01); *C12N 15/8279* (2013.01)

(58) Field of Classification Search
None
See application file for complete search history.

(56) References Cited

U.S. PATENT DOCUMENTS

2008/0254013 A1* 10/2008 Angst et al. ................. 424/93.46

FOREIGN PATENT DOCUMENTS

WO 2009/000433 A1 12/2008

OTHER PUBLICATIONS

Gu et al., 2007. Soil Biology and Biochemistry, 39(10), 2567-2575.*
Kennedy, G. G., & Farrar, R. R. 1987. Entomologia experimentalis et applicata, 45(2):187-192.*
Chan and Vogel, 2010. Biochem. J. 430: 1-19.*
Ben-Israel et al., 2009, Plant Physiol. 151(4):1952-64.*

(Continued)

*Primary Examiner* — Russell Kallis
*Assistant Examiner* — Weihua Fan
(74) *Attorney, Agent, or Firm* — Thompson Coburn LLP; J. Wendy Davis

(57) ABSTRACT

Methods and compositions for use in reducing biotic stress in plants by providing recombinant DNA molecules encoding methkyletone thioesterase into the cells of a plant in order to achieve a reduction in infestation by nematodes, insects and other pests are described. The plant cells in some cases produce one or more of 2-nonanone, 2-undecanone, 2-tridecanone and 2-pentadecanone. Also described are methods for making transgenic plants that express the recombinant DNA molecule for use in protecting plants from pest infestations.

20 Claims, 7 Drawing Sheets

(56) References Cited

OTHER PUBLICATIONS

Antonious, "Production and Quantification of Methyl Ketones in Wild Tomato Accessions", Journal of Environmental Science and Health, Part B: Pesticides, Food Contaminants, and Agricultural Wastes, 2001, pp. 835-848, vol. 36, No. 6.

Fridman et al., "Metabolic, Genomic, and Biochemical Analyses of Glandular Trichromes from the Wild Tomato Species *Lycopersicon hirsutum* Identify a Key Enzyme in the Biosynthesis of Methylketones", Plant Cell, 2005, pp. 1252-1267, vol. 17, No. 4.

Kennedy, "Tomato, Pests, Parasitoids, and Predators: Tritophic Interactions Involving the Genus *Lycopersicon*", Annual Review of Entomology, 2003, pp. 51-72, vol. 48.

* cited by examiner

COMPOSITIONS AND METHODS FOR PATHOGEN CONTROL IN PLANTS

CROSS-REFERENCE TO RELATED APPLICATIONS

This application is a 35 U.S.C. §371 application of International Patent Application No. PCT/US2011/024693, filed Feb. 14, 2011 and incorporated herein by reference in its entirety, which claims the benefit under 35 U.S.C. §119 of U.S. Provisional Patent Application No. 61/304,391 filed Feb. 12, 2010 and U.S. Provisional Patent Application No. 61/364,350 filed Jul. 14, 2010, each of which are incorporated herein by reference in their entirety.

INCORPORATION OF SEQUENCE LISTING

A Sequence Listing is contained in the file named "58527_C.txt" which is 314,659 bytes (measured in MS-Windows) and was created on Aug. 9, 2012. This Sequence Listing is electronically filed herewith and is incorporated herein by reference.

FIELD

The present disclosure relates to methods and compositions for pathogen control in plants. More particularly, it discloses compositions and methods, isolated nucleic acid sequences, expression vectors, recombinant bacterial cells, transgenic plant cells, plants and seeds, comprising a recombinant DNA, and methods of making and using such plant cells, plants, and seeds that are associated with pest resistance.

BACKGROUND

Effective, environmentally safe control of plant parasitic nematode infection is one of the largest unmet needs in crop protection. For example, it is estimated that nematodes annually cause soybean losses of approximately $3.2 billion worldwide (Barker et al., 1994) and that parasitic nematodes cost the horticulture and agriculture industries in excess of $78 billion worldwide a year, based on an estimated average 12% annual loss spread across all major crops. Therefore, improved methods for protecting plants from nematode infection are highly desirable since they would increase the amount and stability of food production.

Nematodes are active, flexible, elongate organisms that live on moist surfaces or in liquid environments, including films of water within soil and moist tissues within other organisms. Nematodes grow through a series of lifecycle stages and molts. Typically, there are five stages and four molts: egg stage; J1 (i.e. first juvenile stage); M1 (i.e. first molt); J2 (second juvenile stage; sometimes hatch from egg); M2; J3; M3; J4; M4; A (adult). Juvenile ("J") stages are also sometimes referred to as larval ("L") stages. Nematode parasites of plants can inhabit all parts of plants, including roots, developing flower buds, leaves, and stems.

There are numerous plant-parasitic nematode species, including various lesion nematodes (i.e. *Pratylenchus* spp.), root knot nematodes (i.e. *Meloidogyne* spp.), cyst nematodes (i.e. *Heterodera* spp.), dagger nematodes (i.e. *Xiphinema* spp.) and stem and bulb nematodes (i.e. *Ditylenchus* spp.), among others. However, the largest and most economically important groups of plant-parasitic nematodes are the families Pratylenchidae (lesion nematodes), Meloidogynidae (root knot nematodes) and Heteroderidae (cyst nematodes) with lesion and root knot nematodes being particularly noteworthy for their very broad host rages. Plant parasitic nematodes are classified on the basis of their feeding habits into the broad categories of migratory ectoparasites, migratory endoparasites, and sedentary endoparasites. Sedentary endoparasites, which include the root knot nematodes (*Meloidogyne* spp.) and cyst nematodes (*Globodera* and *Heterodera* spp.) induce feeding sites ("giant cells" in the case of root knot nematodes and "syncytia" for cyst nematodes) and establish long-term infections within roots. In contrast, while spending most of their lifecycles within host tissues, migratory endoparasitic nematodes like lesion neamtodes (*Pratylenchus* spp.) do not induce permanent feeding sites but feed while migrating between or through plant cells.

Traditional approaches to control plant diseases have relied on crop rotation, the construction of interspecific hybrids between resistant crops and their wild-type relatives as sources of resistant germplasm, and chemical treatment. However these traditional approaches all suffer from significant limitations in providing broad spectrum nematode control. Crop rotation or fallowing without weeding is not an effective strategy for controlling root lesion nematodes because of their broad host ranges which includes most crops, native grasses and weeds. Rotation is also less effective with the very broad host range *Meloidogyne incognita*, *Meloidogyne javanica* and *Meloidogyne arenaria* root knot nematodes. Genetic resistance is usually narrow spectrum (e.g., race specific in the case of cyst nematodes and species specific for lesion nematodes). Deployment of narrow resistance quickly results in race or species shifts in fields with nematode problems leading to loss of effectiveness of the resistant germplasm. Other challenges with genetic resistance include loss of potency at higher temperatures (e.g., Mi resistance to root knot nematodes) or reduction in the yields of elite germplasm when introgressing resistance traits from wild relatives.

In contrast, most chemical nematode control agents though broad spectrum, are not effective in eradicating nematode infestations. Nematodes deeper in the soil or inside roots are largely protected and can cause significant crop damage later in the growing season. The few agents like the fumigant methyl bromide that can effectively get to nematode reservoirs are biocides effectively sterilizing a field for a period of time. Furthermore, methyl bromide, which was once the most widely used fumigant nematicide, is scheduled to be soon retired from use, and at present there are very few, if any, promising candidate to replace this treatment. The non-fumigant organophosphate and carbamate nematicides like ethoprop, terbufos, carbofuran and aldicarb though not as broad spectrum also show poor selectivity. In particular these chemical nematode control agents are highly toxic to mammals, birds, fish, and to non-target beneficial insects. These agents can in some cases accumulate in the water table, the food chain, and in higher trophic level species. These agents may also act as mutagens and/or carcinogens to cause irreversible and deleterious genetic modifications. As a result, government restrictions have been imposed on the use of these chemicals. Additionally, few chemical nematicides (fumigant or non-fumigant) are cost effective for use in large acreage row crops such as soybeans and corn. There has been renewed interest recently in chemical seed treatments which can be economically applied in large acreage row crops but these only provide early season protection under moderate levels of nematode infestation.

In addition to nematode pests, plants are typically subject to multiple disease causing agents such as fungi and insects which often potentiate the effect of the nematode. Examples of these disease complexes include the *Fusarium solani* gal/ soybean cyst nematode pairing in soybean sudden death syndrome and the rootknot nematode/*fursarium* wilt complex in cotton. Therefore methods of controlling nematodes having broader pesticidal effects are particularly desirable.

The methods of plant biotechnology have been shown to provide an effective means to control insect infestations by having the plant express an insect control agent. However, there are few examples of effectively applied biotechnology methods to simultaneously control nematode and other plant pathogens such as insects and fungi.

SUMMARY

The present disclosure provides agents effective plant nematode control which also, in some embodiments, express other desirable pesticidal properties such as insecticidal activity. The effective compounds are, in one embodiment, combinations of methylketones and related compounds that are produced in plants or bacteria used to treat plants, whose composite action results in effective nematode and insect control. Also disclosed are compositions and methods to produce improved mixtures of methylketones, e.g., mixtures comprising two or more methylketones selected from 2-nonanone, 2-undecanone, 2-tridecanone, 2-tridecenone, 2-pentadecanone and related compounds such as 2-undecanol or 2-tridecanol, in plants that nematodes infect. Also disclosed are compositions and methods to produce improved mixtures of methylketones, e.g., mixtures comprising two or more methylketones selected from 2-nonanone, 2-undecanone, 2-tridecanone, 2-tridecenone, 2-pentadecanone and related compounds such as 2-undecanol or 2-tridecanol, in bacteria that are then applied to plants that nematodes infect. These compounds can reduce or inhibit nematode growth, development, or the plant disease caused by nematode infection. Plant parasitic nematodes are obligate parasites of plants. Thus the reduction in infestation can be achieved by killing the nematodes directly and/or reducing the viability of the plant cells on which the nematodes feed and/or repelling the nematodes or otherwise disrupting their ability to locate appropriate host plants and host tissues. In some embodiments the method comprises production of transgenic plants containing (and capable of expressing) one or more transgenes that provide for the production of mixtures of two or more methylketones selected from 2-undecanone, 2-tridecanone, 2-tridecenone, 2-pentadecanone and/or related compounds such as 2-undecanol or 2-tridecanol, in plant tissues susceptible to nematode infection and/or insect predation.

In other embodiments the method comprises production of recombinant or recombinant bacteria containing (and capable of expressing) one or more transgenes that provide for the production of mixtures of two or more methylketones selected from 2-undecanone, 2-tridecanone, 2-tridecenone, 2-pentadecanone and/or related compounds such as 2-undecanol or 2-tridecanol, and using these bacteria to treat plant seeds, bulbs, cuttings, corms or other plant propagation material, and plant roots, stems or leaves in plant tissues susceptible to nematode infection and/or insect predation.

In another aspect, this disclosure provides methods for construction and use of a transgene expression cassette comprising a modified or unmodified (i.e., wild-type) methylketone thioesterase coding region and expression of the thioesterase in a plant cell, particularly in the root cells of a plant, or in a bacterial cell which bacterial cell is then applied to plant propagation material, e.g., seeds or plant roots. The invention provides for a transgenic plant comprising the transgene wherein the roots of the transgenic plant produce at least one methylketone and/or a related alcohol. The modified or unmodified methylketone thioesterase transgene, in certain embodiments, additionally comprises a sequence encoding a region comprising a heterologous plastid transit peptide molecule in operable linkage to the modified methylketone thioesterase coding region. In certain embodiments, the methylketone thioesterase encoded by the transgene is unmodified and the transgene comprises a sequence encoding a heterologous plastid transit peptide. In certain embodiments, the methylketone thioesterase encoded by the transgene is modified and the transgene comprises a sequence encoding a heterologous plastid transit peptide. In certain embodiments, the methylketone thioesterase encoded by the transgene is modified and the transgene does not comprise a sequence encoding a heterologous plastid transit peptide. In certain embodiments, the methylketone thioesterase encoded by the transgene is modified and the transgene comprises a sequence encoding a heterologous plastid transit peptide. By "heterologous" it is meant that a given sequence is not in its native context with respect to any other referenced sequence. Thus, one sequence may be heterologous with respect to second, operably linked, sequence where both sequences can be isolated from the same species, but will be not be in their native orientation. In other cases, the two sequences can be from different species (i.e., from a first species and a second species) or from the same species, but from different genes (i.e., from a first gene and a second gene). A heterologous transit peptide operably linked to a selected modified or unmodified methylketone thioesterase coding region is therefore a transit peptide not normally found in nature in an unmodified state in operable linkage to the particular selected methylketone thioesterase coding region. A "modified" polypeptide or peptide has one or more amino acid modifications (e.g, changes, insertions, deletions or combinations thereof) compared to a reference sequence. A modified polypeptide or peptide can have 1, 2, 3, 4, 5, 6, 7, 8, 9, 10, 15 or more amino acid modifications compared to a reference sequence. In many cases, a modified polypeptide or peptide has unaltered or only slightly altered activity compared to a reference polypeptide.

A polypeptide having "methylketone thioesterase activity" exhibits thioesterase activity towards a beta keto acyl carrier protein (ACP) fatty acid ester or towards a beta keto acyl CoA fatty acid ester. In some cases, the polypeptide exhibits thioesterase activity towards a beta keto acyl carrier protein (ACP) fatty acid ester and towards a beta keto acyl CoA fatty acid ester. In certain cases, a polypeptide having methylketone thioesterase activity may also have decarboxylase activity.

In yet another aspect of the disclosure, modified DNA coding sequences SEQ ID NO: 5-8, SEQ ID NO: 11-56 and SEQ ID NO: 131-168 and their amino acid sequences comprising SEQ ID NO: 61-64 and SEQ ID NO: 67-112 and SEQ ID NO: 188-225 are provided that encode a modified methylketone thioesterase. In certain embodiments, the DNA coding sequence encoding a polypeptide with methylketone thioesterase activity shares at least about 80%, 85%, 90%, 95%, 98%, or 99% percent sequence identity to any one or more of said SEQ ID NO: 5-8, SEQ ID NO: 11-56 and SEQ ID NO: 131-168. In some cases the polypeptide with methylketone thioesterase activity has 10 (e.g., 9, 8, 7, 6, 5, 4, 3, 2, 1) or fewer amino acid changes compared to any one of SEQ ID NO: 5-8, SEQ ID NO: 11-56 and SEQ ID NO: 131-168. In some cases the amino acid changes will be conservative changes. In some cases a sequence encoding one of the forgoing methylketone thioesterase is operably liked to a heterologous promoter, e.g., root specific promoter.

In still yet another aspect of the disclosure, a heterologous fusion protein is provided that comprises a plastid transit peptide polypeptide (such as SEQ ID NO: 230 or 232) and a modified methylketone thioesterase polypeptide (such as SEQ ID NO: 57-60 and SEQ ID NO: 170-187) or methylketone thioesterase polypeptide variant (such as SEQ ID NO: 61-64, SEQ ID NO: 67-112 and SEQ ID NO: 188-225) with methylketone thioesterase activity. In some cases the polypeptide with methylketone thioesterase activity has 10 (e.g., 9, 8, 7, 6, 5, 4, 3, 2, 1) or fewer amino acid changes compared to any one of SEQ ID NO: 57-60, SEQ ID NO: 170-187, SEQ ID NO: 61-64, SEQ ID NO: 67-112 and SEQ ID NO: 188-225. In some cases the amino acid changes will be conservative changes. Also provided is a heterologous fusion protein that comprises a plastid transit peptide (such as SEQ ID NO: 230 or 232) and a methylketone thioesterase molecule having at least about 80%, 85%, 90%, 95%, 98%, or 99% percent sequence identity to any one or more of said SEQ ID NO: 65, SEQ ID NO: 66 or SEQ ID NO: 226. In some cases the polypeptide with methylketone thioesterase activity has 10 (e.g., 9, 8, 7, 6, 5, 4, 3, 2, 1) or fewer amino acid changes compared to any one of SEQ ID NO: 5-8, SEQ ID NO: 65, SEQ ID NO: 66 or SEQ ID NO:226. In some cases the amino acid changes will be conservative changes. In some cases a sequence encoding one of the foregoing fusion proteins is operably linked to a heterologous promoter, e.g., a root specific promoter.

In still yet another aspect of the invention, a transgene expression cassette is provided comprising a heterologous methylketone synthase protein coding region that encodes a methylketone synthase such as those disclosed in WO 2009/00433 (hereby incorporated by reference) that is expressed in plant tissues with the transgene comprising the modified methylketone thioesterase coding region.

In still yet another aspect of the invention, a transgenic seed is provided comprising a heterologous plastid transit peptide molecule in operable linkage to the methylketone thioesterase coding region. The transgenic seed may additionally comprise a transgene expression cassette comprising a heterologous acyl carrier protein coding region.

Other aspects of the invention are specifically directed to transgenic plant cells, and transgenic plants comprising a plurality of the plant cells, nuclei and organelles, and progeny transgenic seed, embryo, ovule and transgenic pollen from such plants. A plant cell including parts thereof is selected from a population of transgenic plant cells transformed with a heterologous methylketone thioesterase coding region and may additionally comprise a heterologous acyl carrier protein coding region by selecting the transgenic plant cell from any population comprising the heterologous coding region as compared to a cell that does not have the heterologous coding region.

This invention also provides methods for manufacturing non-natural, transgenic seed that can be used to produce a crop of transgenic plants with pest resistance resulting from expression of a heterologous methylketone thioesterase coding region and in certain embodiments the co-expression of a heterologous acyl carrier protein coding region in the nucleus or organelle or cytoplasm of the plant cells making up the transgenic plants. The various aspects of this invention are especially useful for transgenic plants having nematode resistance activity that include, without limitation, cereals including corn, wheat, barley, rye, and rice; vegetables; tomatoes; potatoes; clovers; legumes including beans, soybeans, peas and alfalfa; sugar cane; sugar beets; tobacco; cotton; rapeseed (canola); sunflower; safflower; and sorghum.

The present invention provides for a transgenic plant such as a soybean, corn, cotton, sugar cane or wheat plant comprising within its genome a heterologous methylketone thioesterase coding region and may additionally comprise a heterologous acyl carrier protein coding region, wherein the plant has increased resistance to infection by one or more species of nematode (ie., compared to an otherwise genetically identical plant that does not a harbor a heterologous methylketone thioesterase coding region or a heterologous methylketone thioesterase coding region and a heterologous acyl carrier protein coding region) or displays reduced disease symptoms caused by infection by one or more species of nematode (ie., compared to an otherwise genetically identical plant that does not a harbor a heterologous methylketone thioesterase coding region or a heterologous methylketone thioesterase coding region and a heterologous acyl carrier protein coding region).

The present invention further provides a method of increasing the yield of a nematode tolerant crop plant. The method comprises growing a crop plant comprising a heterologous methylketone thioesterase coding region which may additionally comprise a heterologous methylketone synthase coding region in the presence of nematodes.

Another aspect of the invention provides a method of producing a hybrid seed comprising acquiring hybrid seed from a nematode tolerant plant which also has a stably-integrated heterologous nucleotide sequence encoding a methylketone thioesterase and may also have integrated a heterologous nucleotide sequence encoding methylketone synthase. The method further comprises producing a crop from plants grown from the hybrid seed, wherein a fraction of the plants produced from said hybrid seed are homozygous for the heterologous methylketone thioesterase coding sequence and if present, the heterologous methylketone synthase coding sequence, a fraction of the plants produced from said hybrid seed are hemizygous for the heterologous methylketone thioesterase coding sequence and if present, the heterologous methylketone synthase coding sequence, and a fraction of the plants produced from the hybrid have no heterologous methylketone thioesterase coding sequence or heterologous methylketone synthase coding sequence; selecting plants which are homozygous and hemizygous; collecting seed from the selected plants, and planting the seed to produce further progeny plants; repeating the selecting and collecting steps at least once from these progeny plants to produce an inbred line; and crossing the inbred line with a second line to produce hybrid seed. The plants of the invention are selected, without limitation, from the group of corn (maize), soybean, cotton, canola (rape), wheat, sunflower, sorghum, alfalfa, barley, millet, rice, tobacco, tomato, potato, fruit and vegetable crops, turfgrass, sugar cane, sugar beets, and safflower.

In a further aspect of the invention, control of agronomically important insects is contemplated, which include, but are not limited to Beet armyworm (*Spodoptera exigua*), Boll weevil (*Anthonomus grandis grandis*), Cabbage looper (*Trich oplusiani*), Clouded plant bug (*Neurocolpus nubilus*), Corn Rootworm (*Diabrotica* spp), Cotton aphid (*Aphis gossypii*), Cotton bollworm (*Heliocoverpa zea*), Cutworms (*Feltia subterranea, Peridroma saucia, Agrotis ipsilon*), European corn borer (*Ostrinia nubilalis*), Fall armyworm (*Spodoptera frugiperda*), Seedling thrips (*Frankliniella* spp.), Soybean looper (*Pseudoplusia includens*), Stink bugs (*Nezara viridula, Acrosternum hilare, Euschistus servus*), Tarnished plant bug (*Lygus lineolaris*), Tobacco budworm (*Heliothis virescens*) and Whiteflies (*Trialeurodes abutilonea, Bemisia tabaci*) among others. Broader acaricidal, insecticidal, and pest repellent properties are also contemplated.

Described herein are isolated nucleic acid molecules comprising a nucleotide sequence encoding a polypeptide comprising an amino acid sequence that is at least 85% identical to any of SEQ ID NOs:61-64, 67-112 and 188-225. In various embodiments: the polypeptide does not comprise the amino acid sequence of any of SEQ ID NOs:57-60 and 170-187.

Also described is an isolated nucleic acid molecule comprising (or consisting of) a nucleotide sequence encoding a polypeptide comprising an amino acid sequence selected from the group consisting of:

$X_0X_1X_2X_6X_7X_8VELX_9VRDYELDQX_{10}GVVNNAX_{11}YASYCQHX_{12}RH$
$X_{13}X_{14}LEX_{15}IGX_{16}X_{17}X_{18}DX_{19}VX_{20}RX_{21}GX_{22}ALAX_{23}X_{24}E$
$X_{25}X_{26}LKX_{27}LAPLRSGDRFX_{28}VX_{29}X_{30}RX_{31}SX_{32}X_{33}X_{34}X_{35}A$
$RLX_{36}FEHFIFKLPX_{37}X_{38}EPILEAX_{39}X_{40}X_{41}AVX_{42}LX_{43}X_{44}X_{45}$
$YRPX_{46}RIPX_{47}EX_{48}X_{49}SKX_{50}VX_{51}FLX_{52}X_{53}EX_{54}X_{55};$ $X_0X_1X_2X_3X_4X_5X_6X_7X_8VELX_9VRDYELDQX_{10}GVVNNAX_{11}YASYCQH$
$X_{12}RHX_{13}X_{14}LEX_{15}IGX_{16}X_{17}X_{18}DX_{19}VX_{20}RX_{21}GX_{22}ALAX_{23}$
$X_{24}EX_{25}X_{26}LKX_{27}LAPLRSGDRFX_{28}VX_{29}X_{30}RX_{31}SX_{32}X_{33}$
$X_{34}X_{35}ARLX_{36}FEHFIFKLPX_{37}X_{38}EPILEAX_{39}X_{40}X_{41}AVX_{42}L$
$X_{43}X_{44}X_{45}YRPX_{46}RIPX_{47}EX_{48}X_{49}SKX_{50}VX_{51}FLX_{52}X_{53}KSC$
$GX_{56}QHX_{57}L;$
and $X_0X_1X_2X_3X_4X_5X_6X_7X_8VEMX_9VRDYELDQX_{10}GVVNNAX_{11}YASYCQH$
$X_{12}RHX_{13}X_{14}LEX_{15}VGX_{16}X_{17}X_{18}DX_{19}VX_{20}RX_{21}GX_{22}SLAX_{23}$
$X_{24}EX_{25}X_{26}LKX_{27}FAPLRSGDRFX_{28}VX_{29}X_{30}RX_{31}AX_{32}X_{33}X_{34}$
$X_{35}ARLX_{36}FEHFIFKLPX_{37}X_{38}EPILEAX_{39}X_{40}X_{41}AVX_{42}LX_{43}$
$X_{44}X_{45}YRPX_{46}RIPX_{47}EX_{48}X_{49}SKX_{50}QX_{51}FX_{58}SX_{59}X_{60}SX_{61}$
$X_{62};$ wherein $X_0$=L, M, MA, X where X=1 to 15 amino acids; $X_1$=$\underline{S}$, $\underline{N}$, $\underline{R}$, $\underline{A}$, T, G; $X_2$=$\underline{D}$, $\underline{E}$, $\underline{G}$, $\underline{R}$, S, L, deletion; $X_3$=$\underline{Q}$, L, $\underline{E}$, $\underline{V}$; $X_4$=$\underline{V}$, $\underline{L}$, $\underline{D}$, $\underline{E}$; $X_5$=$\underline{Y}$, $\underline{K}$, Q; $X_6$=$\underline{F}$, $\underline{H}$, Q, $\underline{P}$, L, V; $X_7$=$\underline{H}$, $\underline{Y}$, $\underline{F}$, L, V; $X_8$=$\underline{D}$, $\underline{E}$, G; $X_9$=$\underline{K}$, $\underline{T}$, Q; $X_{10}$=$\underline{F}$, $\underline{Y}$; $X_{11}$=$\underline{T}$, $\underline{I}$, $\underline{V}$; $X_{12}$=$\underline{C}$, $\underline{G}$; $X_{13}$=$\underline{E}$, $\underline{A}$; $X_{14}$=$\underline{L}$, $\underline{F}$, V; $X_{15}$=$\underline{K}$, $\underline{R}$, $\underline{A}$, $\underline{S}$, N, T, C; $X_{16}$=$\underline{V}$, $\underline{I}$, $\underline{F}$, L; $X_{17}$=$\underline{S}$, $\underline{N}$; $X_{18}$=$\underline{A}$, $\underline{V}$, $\underline{C}$, $\underline{P}$; $X_{19}$=$\underline{E}$, $\underline{A}$, $\underline{V}$; $X_{20}$=$\underline{A}$, $\underline{T}$, C, S; $X_{21}$=$\underline{S}$, $\underline{N}$, T, I; $X_{22}$=$\underline{D}$, $\underline{E}$, $\underline{N}$; $X_{23}$=$\underline{L}$, $\underline{V}$, $\underline{I}$, T; $X_{24}$=$\underline{T}$, $\underline{S}$; $X_{25}$=$\underline{L}$, M; $X_{26}$=$\underline{S}$, $\underline{T}$, $\underline{H}$, $\underline{N}$; $X_{27}$=$\underline{F}$, $\underline{Y}$; $X_{28}$=$\underline{V}$, $\underline{I}$; $X_{29}$=$\underline{T}$, $\underline{K}$, $\underline{R}$; $X_{30}$=$\underline{V}$, $\underline{A}$, $\underline{T}$; $X_{31}$=$\underline{L}$, $\underline{I}$, $\underline{V}$; $X_{32}$=$\underline{H}$, $\underline{R}$, $\underline{D}$, $\underline{G}$, $\underline{S}$, N; $X_{33}$=$\underline{S}$, $\underline{T}$, $\underline{I}$, $\underline{F}$, A; $X_{34}$=$\underline{S}$, $\underline{T}$, $\underline{K}$; $X_{35}$=$\underline{A}$, $\underline{G}$, V, M; $X_{36}$=$\underline{F}$, $\underline{Y}$, $\underline{I}$; $X_{37}$=$\underline{D}$, $\underline{N}$; $X_{38}$=$\underline{R}$, $\underline{Q}$, $\underline{E}$, $\underline{H}$; $X_{39}$=$\underline{R}$, $\underline{K}$; $X_{40}$=$\underline{G}$, $\underline{A}$; $X_{41}$=$\underline{I}$, $\underline{T}$, M; V; $X_{42}$=$\underline{Y}$, $\underline{W}$, $\underline{C}$, R; $X_{43}$=$\underline{N}$, $\underline{D}$; $X_{44}$=$\underline{R}$, $\underline{K}$, $\underline{N}$; $X_{45}$=$\underline{I}$, $\underline{S}$, $\underline{N}$, $\underline{K}$, $\underline{D}$, R; $X_{46}$=$\underline{I}$, $\underline{V}$, $\underline{T}$, A; $X_{47}$=$\underline{S}$, $\underline{T}$, $\underline{A}$, $\underline{P}$, $\underline{R}$; $X_{48}$=$\underline{F}$, $\underline{I}$, $\underline{M}$, $\underline{L}$; $X_{49}$=$\underline{K}$, $\underline{R}$, $\underline{N}$, $\underline{S}$, $\underline{L}$; $X_{50}$=$\underline{F}$, $\underline{L}$, $\underline{I}$, $\underline{M}$; $X_{51}$=$\underline{L}$, $\underline{Q}$, $\underline{K}$, $\underline{H}$, $\underline{F}$; $X_{52}$=$\underline{H}$, $\underline{R}$, $\underline{K}$; $X_{53}$=$\underline{Q}$, $\underline{N}$, $\underline{H}$, C, I; $X_{54}$=$\underline{A}$, $\underline{E}$, D; $X_{55}$=nothing, S, SH, SN, LN, PS; $X_{56}$=$\underline{V}$, $\underline{T}$, I; $X_{57}$=$\underline{H}$, $\underline{R}$, K; $X_{58}$=$\underline{T}$, $\underline{S}$, L; $X_{59}$=$\underline{E}$, K, R, V; $X_{60}$=$\underline{G}$, $\underline{D}$; $X_{61}$=$\underline{S}$, $\underline{R}$, K; $X_{62}$=$\underline{S}$, $\underline{G}$, GX where X=1 to 15 amino acids. In this notation, "MA" refers to the amino acid sequence MA. In preferred embodiments, each of the variable positions is selected from a preferred (underlined) amino acid.

In some cases: the polypeptide comprises an amino acid sequence that is identical to amino acids 1-25 of any of SEQ ID NOs:61-64, 67-112 and 188-225; the polypeptide comprises an amino acid sequence that is identical to amino acids 1-50 of any of SEQ ID NOs:61-64, 67-112 and 188-225; the polypeptide comprises an amino acid sequence that is identical to amino acids 1-75 of any of SEQ ID NOs:61-64, 67-112 and 188-225; the polypeptide comprises an amino acid sequence that is identical to amino acids 1-100 of any of SEQ ID NOs:61-64, 67-112 and 188-225; the polypeptide comprises an amino acid sequence that is identical to amino acids 100-140 of any of SEQ ID NOs:61-64, 67-112 and 188-225; the polypeptide comprises an amino acid sequence that is identical to amino acids 75-100 of any of SEQ ID NOs:61-64, 67-112 and 188-225; the polypeptide comprises an amino acid sequence that is identical to amino acids 50-75 of any of SEQ ID NOs:61-64, 67-112 and 188-225; the polypeptide comprises an amino acid sequence that is identical to amino acids 25-50 of any of SEQ ID NOs:61-64, 67-112 and 188-225; the polypeptide comprises an amino acid sequence that is identical to amino acids 10-25 of any of SEQ ID NOs:61-64, 67-112 and 188-225; the polypeptide comprises an amino acid sequence that is identical to amino acids 35-65 of any of SEQ ID NOs:61-64, 67-112 and 188-225; the polypeptide comprises an amino acid sequence that is identical to amino acids 80-88 of any of SEQ ID NOs:61-64, 67-112 and 188-225; and the polypeptide comprises an amino acid sequence that is identical to amino acids 120-135 of any of SEQ ID NOs:61-64, 67-112 and 188-225.

In certain embodiments of the nucleic acid molecules: the polypeptide does not comprise the amino acid sequence of any of SEQ ID NOs:57-60 and 170-187; the polypeptide consists of an amino acid sequence that is at least 85% identical to any of SEQ ID NO:61-64, 67-112 and 188-225; the polypeptide has methylketone thioesterase activity; the polypeptide catalyzes the synthesis of one or more of 2-nonanone, 2-undecanone, 2-tridecanone, and 2-pentadecanone; the polypeptide catalyzes the synthesis of two or more of 2-nonanone, 2-undecanone, 2-tridecanone, and 2-pentadecanone; the polypeptide catalyzes the synthesis of 2-nonanone, 2-undecanone and 2-tridecanone; the polypeptide further comprises the amino acid sequence of a plastid transit peptide (e.g., a plastid transit peptide that mediates transit of the polypeptide); the nucleic acid molecule further comprises a nucleotide sequence encoding a polypeptide comprising a methylketone synthase; the methylketone synthase is a plant methylketone synthase; the methylketone synthase is operably linked to a plastid transit peptide.

Also described are vectors comprising any of the nucleic acid molecules described herein. In some cases, the nucleic acid molecule is operably linked to a promoter functional in plants. In some cases, the vector is a plant expression vector.

Also described is a plant cell comprising any of the nucleic acids molecules described herein. In certain cases: the plant cell is from plant propagation material (e.g., a seed), root, leaf, shoot, flower, pollen, or ovule; the plant cells comprises two or more or three or more of the nucleic acid molecules described herein wherein the two or three nucleic acid molecules encode different polypeptides.

In some cases: the plant cell produces one or more of or more of 2-nonanone, 2-undecanone, 2-tridecanone and 2-pentadecanone; the plant cell produces two or more of 2-nonanone, 2-undecanone, 2-tridecanone, and 2-pentadecanone; the plant cell is a crop plant cell; the plant cell is from a plant selected from the group selected from cotton, soybean, canola, corn, wheat, rice, sunflower, sorghum, sugarcane, potato, tomato, and a tree.

Also described is a plant or a part thereof comprising a nucleic acid molecule described herein. In some cases, the part thereof is selected from the group consisting of a seed, pollen, a root, a leaf, a shoot, a flower and an ovule. In some cases the plant or part thereof comprises a nucleic acid molecule encoding an acyl carrier protein.

Also described is a processed product comprising plant tissue and a processed product produced comprising a nucleic acid molecule described herein. In some cases, the processed product is selected from the group consisting of meal, flour, oil, hay, starch, juice, protein extract, and fiber.

Described herein is a method for controlling a pathogen or pest in a plant comprising expressing in the plant the polypeptide encoded by a nucleic acid molecule described herein. In some cases: the pest is a nematode (e.g., *Heterodera* species, *Globodera* species, *Meloidogyne* species, *Rotylenchulus* species, *Hoplolaimus* species, *Belonolaimus* species, *Pratylenchus* species, *Longidorus* species, *Paratrichodorus* species, *Ditylenchus* species, *Xiphinema* species, *Dolichodorus* species, *Helicotylenchus* species, *Radopholus* species, *Hirschmanniella* species, *Tylenchorhynchus* species, and *Trichodorus* species); the pest is an insect (e.g., *Coleoptera, Diptera, Hemiptera* (including *Homoptera* and *Heteroptera*), *Hymenoptera* and *Lepidoptera*).

In various embodiments: the method comprises expressing in the plant two or more (or three or more) of the polypeptides encoded by the nucleic acid molecules described herein or the vectors described herein wherein the nucleic acids or vectors encode different two polypeptides.

Described herein is an isolated nucleic acid molecule described herein further comprising a bacterial expression sequences operably linked to the nucleotide sequence encoding the polypeptide. Also described is a bacterial vector comprising the nucleic acid molecule described herein (e.g., an expression vector).

Also described is a recombinant bacterial cell comprising a nucleic acid molecule or vector described herein. In some cases: the bacterial cell expresses a polypeptide encoded by the nucleic acid; the bacterial cell produces one or more of or more of 2-nonanone, 2-undecanone, 2-tridecanone and 2-pentadecanone; the bacterial cell of claim 56 wherein the bacterial cell produces two or more of 2-nonanone, 2-undecanone, 2-tridecanone, and 2-pentadecanone; the bacterial cell is selected from the group consisting of *Pasteuria* spp., *Pseudomonas* spp., *Bacillus* spp., *Corynebacterium*, *Agrobacterium* spp., and *Paenibacillus* spp.; the bacterial cell comprises two or more or three or more of the nucleic acid molecules or vectors described herein wherein the nucleic acid molecules or vectors encode different polypeptides.

Described herein is plant material admixed or coated with a composition comprising a recombinant bacterial cell described herein. In some cases: The plant material is selected from the group consisting of: plant propagation material (e.g., a seed), shoot, seedling, tuber and sprout; the plant material is from a plant selected from the group selected from cotton, soybean, canola, corn, wheat, rice, sunflower, sorghum, sugarcane, potato, tomato, and a tree.

Described herein is a method for treating plant material comprising applying a composition a recombinant bacterial cell described herein to the plant material. In some cases: the composition further comprises an insecticide or a nematicide; the plant material is selected from the group consisting of: plant propagation material (e.g., a seed), shoot, seedling, tuber and sprout; the plant material is from a plant selected from the group selected from cotton, soybean, canola, corn, wheat, rice, sunflower, sorghum, sugarcane, potato, tomato, and a tree.

Also described is a method for controlling a pathogen or pest in a plant comprising providing the roots of the plant with a composition comprising the bacteria of any of claims 55-61 to plant material. In certain cases: the pest or pathogen is a nematode (e.g., *Heterodera* species, *Globodera* species, *Meloidogyne* species, *Rotylenchulus* species, *Hoplolaimus* species, *Belonolaimus* species, *Pratylenchus* species, *Longidorus* species, *Paratrichodorus* species, *Ditylenchus* species, *Xiphinema* species, *Dolichodorus* species, *Helicotylenchus* species, *Radopholus* species, *Hirschmanniella* species, *Tylenchorhynchus* species, and *Trichodorus* species); the pest is an insect (e.g., the insect is selected from the orders consisting of *Coleoptera, Diptera, Hemiptera* (including *Homoptera* and *Heteroptera*), *Hymenoptera* and *Lepidoptera*).

DETAILED DESCRIPTION

Figure 1A:
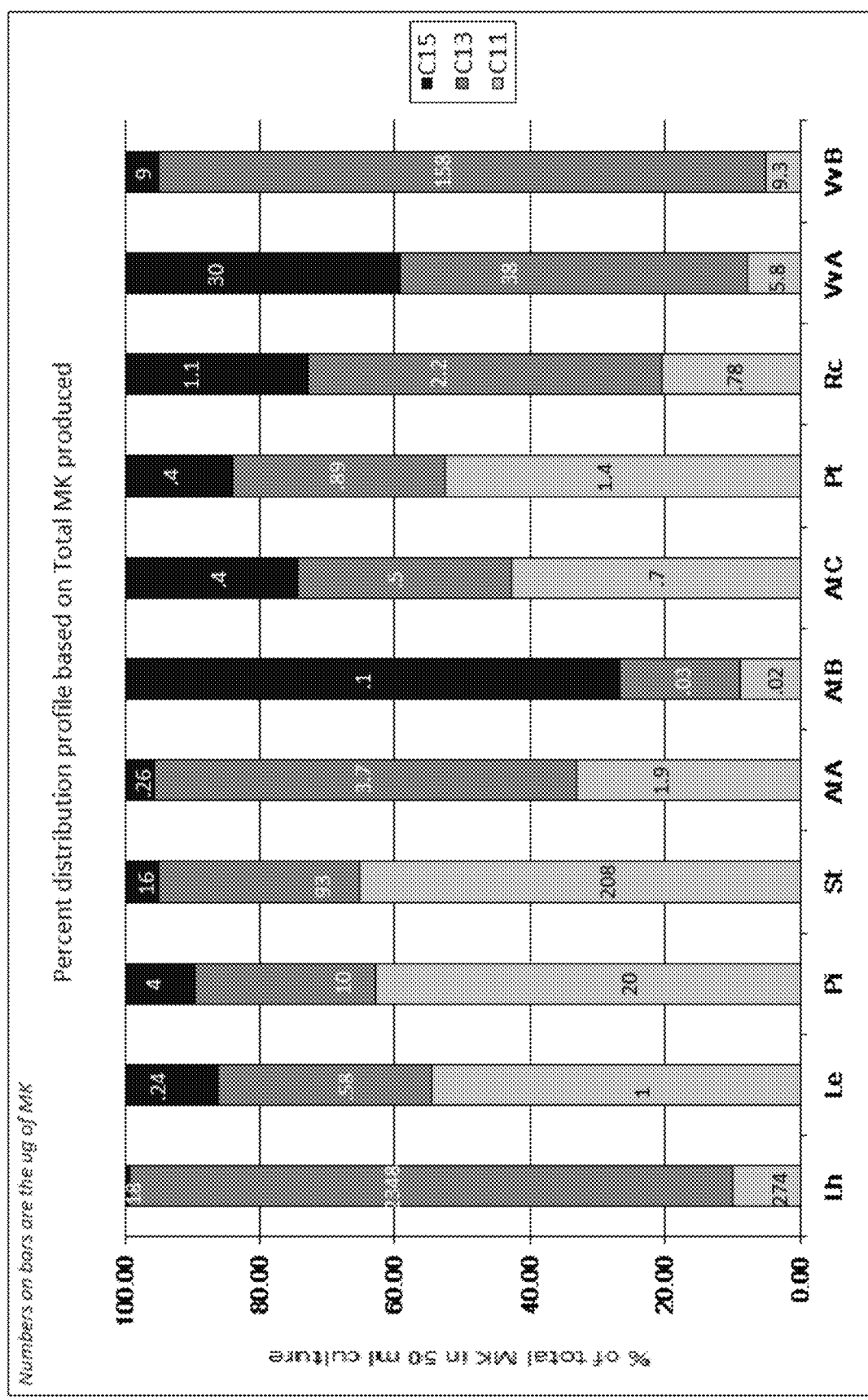
FIG. 1A: Comparisons of ratios and amounts of C11, C13 and C15 methylketone metabolites produced in *E. coli* by methylketone thioesterases from *L. esculentum, P. integrifolia, L. hirsutum, R. communis, P. trichocarpa, V. vinifera, A. thaliana* and *S. tuberosum*. Bottom portion of each bar is C11, middle portion of each bar is C13, and top portion of each bar is C15. Lh: *L. hirsutum*, Le: *L. esculentum*, Pi: *P. integrifolia*, St: *S. tuberosum*, AtA: *A. thaliana*, At B: *A. thaliana*, At C: *A. thaliana*, Pt: *Populus trichocarpa* Rc: *Ricinus communis*, Vv A: *Vitis vinifera*, Vv B: *Vitis vinifera*.

The present disclosure relates to methods and compositions for pest control in plants, in particular nematode and insect control. In one aspect, the disclosure relates to controlling, preventing or treating nematode and/or insect infection in transgenic plants or in plants treated with transgenic bacteria. The method comprises, in one embodiment, generation of transgenic plants containing a recombinant construct and expression of such construct to impart increased nematode and/or insect resistance to plants. In another embodiment, transgenic bacteria are generated containing a recombinant construct. The expression of such a construct causes the bacteria to produce agents that impart nematode and/or insect resistance to plants when treated with the bacteria. In some cases, the construct allows the bacteria to produce an agent that they do not produce in the absence of the contrsuct. In other cases, the bacetia produce more of an agent that they produce in the absence of the construct. The recombinant construct may comprise a nucleotide sequence encoding one or more proteins, wherein the sequence is operably linked to a heterologous promoter functional in a plant cell or a bacterial cell. Cells comprising (meaning including but not limited to) the recombinant construct may be prokaryotic or eukaryotic. In particular, they may be plant cells or bacterial cells. Plants and seeds derived from such transformed plant cells are also contemplated. The transgenic plants or parts thereof of the present invention, in one embodiment produce two or more plant metabolites from among 2-nonanone, 2-undecanone and 2-tridecanone.

2-undecanone is the major methylketone in the *Lycopersicon hirsutum* LA 407 accession whereas in other *L. hirsutum* accessions (e.g., PI 251304, PI 126449, PI 134418) 2-tridecanone is the major methylketone (Antonious. J Environ Sci Health B. 2001 36(6):835-48). A methylketone synthase of the alpha/beta hydrolase fold has been cloned from the wild tomato *L. hirsutum* PI126449, expressed in *Escherichia coli* and shown in vitro to be capable of inefficiently catalyzing the conversion of beta ketolauroyl-ACP, beta ketomyristoyl-ACP and beta ketopalmitoyl-ACP to 2-undecanone, 2-tridecanone and 2-pentadecanone, respectively (Fridman et al. Plant Cell. 2005 17(4):1252-67). Bradley et al. (WO 2009100433) have shown that 2-tridecanone and 2-undecanone are nematicidal and that the expression of tomato methylketone synthase genes similar to those cloned by Fridman et al., optimized for plant expression and operably linked to a heterologous transit peptide, produce transgenic plants that are nematode resistant. In addition the 2-nonanone (a C9 methylketone) has been shown to be a repellant to *C. elegans* (Bargmann et al. Cell. 1993 74(3):515-27). More recently two novel methylketone thioesterases of the hotdog fold type from *L. hirsutum* and *L. esculentum* have been shown by Ben-Israel et al. to produce various methylketones and related metabolites (e.g., alcohols) when expressed in *E. coli* (Ben-Israel et al. Plant Physiol. 2009 151(4):1952-64). The methylketone thioesterase from *L. hirsutum* produced significant amounts of 2-tridecanone and small amounts of 2-unedecanone whereas the methylketone thioesterase from *L. esculentum* produces moderate amounts of 2-undecanone and trace quantities of 2-tridecanone.

Methylketones differ in their intrinsic potency against various pests. As discussed by Kennedy (Annu Rev. Entomol. 2003 48:51-72), 2-undecanone is less toxic to *Helicoverp zea* (tomato fruit worm) and *Manduca sexta* (tobacco hornworm) than 2-tridecanone, whereas the two metabolites have equivalent potency against *Keiferia lycopersicella* (tomato pinworm) and *Spodoptera exigua* (beet armyworm). Surprisingly mixtures of 2-undecanone and 2-tridecanone have synergistic toxicity effects on *H. zea, K. lycopersicella* and *S. exigua* (Kennedy Annual Rev. Entomol. 2003 48:51-72). Methylketones also differ in their level of cytotoxicity. Modulating the ratio and levels is therefore critical to maximizing pesticidal activity while minimizing phytotoxic effects.

The present disclosure provides heterologous molecules that are modified methylketone thioesterases which are expressed in plants to provide optimal ratios and levels of methylketones, especially mixtures of at least 2-tridecanone, 2-undecanone and 2-noneanone to provide insecticidal and nematicidal activity while minimizing phytotoxicity. These methylketone thioesterases include, but not limited to, nucleotides that encode polypeptides having methylketone thioesterase activity such as SEQ ID NO: 61-64, SEQ ID NO: 67-112 and SEQ ID NO: 188-225. In certain embodiments, the polypeptide having methylketone thioesterase activity may share at least 80%, at least 85%, at least 90%, at least 95%, at least 98%, at least 99%, or 100% sequence identity, to any one or more amino acid sequence(s) set forth in SEQ ID NO: 61-64 and SEQ ID NO: 67-112 and SEQ ID NO: 188-225, where the sequences comprise (or consist of) the following motif.

(SEQ ID NO: 242)
$X_0X_1X_2X_6X_7X_8$VELX$_9$VRDYELDQX$_{10}$GVVNNAX$_{11}$YASYCQHX$_{12}$RH $X_{13}X_{14}$LEX$_{15}$IGX$_{16}X_{17}X_{18}$DX$_{19}$VX$_{20}$RX$_{21}$GX$_{22}$ALAX$_{23}X_{24}$ EX$_{25}X_{26}$LKX$_{27}$LAPLRSGDRFX$_{28}$VX$_{29}X_{30}$RX$_{31}$SX$_{32}X_{33}X_{34}X_{35}$ ARLX$_{36}$FEHFIFKLPX$_{37}X_{38}$EPILEAX$_{39}X_{40}X_{41}$AVX$_{42}$LX$_{43}X_{44}$ $X_{45}$YRPX$_{46}$RIPX$_{47}$EX$_{48}X_{49}$SKX$_{50}$VX$_{51}$FLX$_{52}X_{53}$EX$_{54}X_{55}$ or (SEQ ID NO: 243)
$X_0X_1X_2X_3X_4X_5X_6X_7X_8$VELX$_9$VRDYELDQX$_{10}$GVVNNAX$_{11}$YASYCQH $X_{12}$RHX$_{13}X_{14}$LEX$_{15}$IGX$_{16}X_{17}X_{18}$DX$_{19}$VX$_{20}$RX$_{21}$GX$_{22}$ALAX$_{23}$ $X_{24}$EX$_{25}X_{26}$LKX$_{27}$LAPLRSGDRFX$_{28}$VX$_{29}X_{30}$RX$_{31}$SX$_{32}X_{33}X_{34}$ $X_{35}$ARLX$_{36}$FEHFIFKLPX$_{37}X_{38}$EPILEAX$_{39}X_{40}X_{41}$AVX$_{42}$LX$_{43}$ $X_{44}X_{45}$YRPX$_{46}$RIPX$_{47}$EX$_{48}X_{49}$SKX$_{50}$VX$_{51}$FLX$_{52}X_{53}$KSCGX$_{56}$Q HX$_{57}$L or (SEQ ID NO: 244)
$X_0X_1X_2X_3X_4X_5X_6X_7X_8$VEMX$_9$VRDYELDQX$_{10}$GVVNNAX$_{11}$YASYCQH $X_{12}$RHX$_{13}X_{14}$LEX$_{15}$VGX$_{16}X_{17}X_{18}$DX$_{19}$VX$_{20}$RX$_{21}$GX$_{22}$SLAX$_{23}$ $X_{24}$EX$_{25}X_{26}$LKX$_{27}$FAPLRSGDRFX$_{28}$VX$_{29}X_{30}$RX$_{31}$AX$_{32}X_{33}X_{34}$ $X_{35}$ARLX$_{36}$FEHFIFKLPX$_{37}X_{38}$EPILEAX$_{39}X_{40}X_{41}$AVX$_{42}$LX$_{43}$ $X_{44}X_{45}$YRPX$_{46}$RIPX$_{47}$EX$_{48}X_{49}$SKX$_{50}$QX$_{51}$FX$_{58}$SX$_{59}X_{60}$S $X_{61}X_{62}$

With preferred residues (underlined) and other residue (or sequences of residues) examples as follows:
$X_0$=L, M, MA, X (where X=1 to 15 amino acids); $X_1$=S, N, R, A, T, G; $X_2$=D, E, G, R, S, L, deletion; $X_3$=Q, L, E, V; $X_4$=V, L, D, E; $X_5$=Y, K, Q; $X_6$=F, H, Q, P, L, V; $X_7$=H, Y, F, L, V; $X_8$=D, E, G; $X_9$=K, T, Q; $X_{10}$=F, Y; $X_{11}$=T, I, V; $X_{12}$=C, G; $X_{13}$=E, A; $X_{14}$=L, F, V; $X_{15}$=K, R, A, S, N, T, C; $X_{16}$=V, I, F, L; $X_{17}$=S, N; $X_{18}$=A, V, C, P; $X_{19}$=E, A, V; $X_{20}$=A, T, C, S; $X_{21}$=S, N, T, I; $X_{22}$=D, E, N; $X_{23}$=L, V, I, T; $X_{24}$=T, S; $X_{25}$=L, M; $X_{26}$=S, T, H, N; $X_{27}$=F, Y; $X_{28}$=V, I; $X_{29}$=T, K, R; $X_{30}$=V, A, T; $X_{31}$=L, I, V; $X_{32}$=H, R, D, G, S, N; $X_{33}$=S, T, I, F, A; $X_{34}$=S, T, K; $X_{35}$=A, G, V, M; $X_{36}$=F, Y, I; $X_{37}$=D, N; $X_{38}$=R, Q, E, H; $X_{39}$=R, K; $X_{40}$=G, A; $X_{41}$=I, T, M; V; $X_{42}$=Y, W, C, R; $X_{43}$=N, D; $X_{44}$=R, K, N; $X_{45}$=I, S, N, K, D, R; $X_{46}$=I, V, T, A; $X_{47}$=S, T, A, P, R; $X_{48}$=F, I, M, L; $X_{49}$=K, R, N, S, L; $X_{50}$=F, L, I, M; $X_{51}$=L, Q, K, H, F; $X_{52}$=H, R, K; $X_{53}$=Q, N, H, C, I; $X_{54}$=A, E, D; $X_{55}$=nothing, S, SH, SN, LN, PS; $X_{56}$=V, T, I; $X_{57}$=H, R, K; $X_{58}$=T, S, L; $X_{59}$=E, K, R, V; $X_{60}$=G, D; $X_{61}$=S, R, K; $X_{62}$=S, G, GX (where X=1 to 15 amino acids).

Also contemplated are examples where 1 to 10 of the conserved residues (i.e., the residues shown in bold) are substituted with another amino acid. Particularly preferred are cases where the conserved residue substitutions are conservative (e.g., D to E, A to G, L to V, K to R, etc). In some embodiments each X independently represents 1, 2, 3, 5, 6, 7, 8, 9, or 10 amino acids.

The function of the encoded polypeptide may also be determined by measuring the efficacy of the presence of the transgene that encodes it in reducing nematode infection, growth, reproduction, or symptomatology. For instance, a reduction in root galls, cysts, or worm number of 20% or more, 25% or more, 50% or more, 80% or more, or 95% or more, in a transgenic plant comprising a heterologous nucleotide construct encoding methylketone thioesterase activity, relative to a control plant, for instance an otherwise isogenic plant not comprising the heterologous molecule, under similar conditions, indicates the presence of a functional molecule.

In certain embodiments, a heterologous polypeptide provided by the present disclosure that is directed into the plastid of a plant to provide production of a methylketone may share at least 80%, at least 85%, at least 90%, at least 95%, at least 98%, at least 99%, or 100% sequence identity at the nucleotide level with one or more sequence(s) as set forth in SEQ ID NO: 5-8, SEQ ID NO: 11-56 and SEQ ID NO: 131-168. In particular embodiments, the heterologous molecule may also comprise a sequence encoding a heterologous chloroplast transit peptide, for instance, without limitation, as shown in SEQ ID NO: 229 or SEQ ID NO: 231.

Likewise, in certain embodiments, a nucleotide of the present invention may further comprise a sequence that encodes a methylketone synthase as set forth WO 2009100433 (methylketone synthase *L. hirsutum* amino acid sequence: GenBank® AAV87156.1, methylketone synthase *L. hirsutum* nucleotide GenBank® gb|AY701574.1, MKS *L. esculentum* nucleotide GenBank® gb|BT012867.1).

Yet another aspect of the invention provides methods for production and for use of one or more methylketone(s), such as 2-undecanone and 2-tridecanone, to control insect and nematode infestations.

Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, *Genes V*, Oxford University Press: New York, 1994. The nomenclature for DNA bases as set forth at 37 CFR §1.822 is used.

As used herein, a "transgenic plant" is any plant in which one or more, or all, of the cells of the plant include a transgene. A transgene may be integrated within a nuclear genome or organelle genome, or it may be extrachromosomally replicating DNA. The term "transgene" means a nucleic acid that is partly or entirely heterologous, foreign, to a transgenic microbe, plant, animal, or cell into which it is introduced. A plant is comprised of cells that make up various cell and tissue types, these include but are not limited to seed, root, leaf, shoot, flower, pollen and ovule.

"Recombinant DNA" is a polynucleotide having a genetically engineered modification introduced through combination of endogenous and/or exogenous molecules in a transcription unit, manipulation via mutagenesis, restriction enzymes, and the like or simply by inserting multiple copies of a native transcription unit. Recombinant DNA may comprise DNA segments obtained from different sources, or DNA segments obtained from the same source, but which have been manipulated to join DNA segments which do not naturally exist in the joined form. An isolated recombinant polynucleotide may exist, for example as a purified molecule, or integrated into a genome, such as a plant cell, or organelle genome or a microbe plasmid or genome. The polynucleotide comprises linked regulatory molecules that cause transcription of an RNA in a plant cell.

As used herein, "percent identity" means the extent to which two optimally aligned DNA or protein segments are invariant throughout a window of alignment of components, for example nucleotide sequence or amino acid sequence. An "identity fraction" for aligned segments of a test sequence and a reference sequence is the number of identical components that are shared by sequences of the two aligned segments divided by the total number of sequence components in the reference segment over a window of alignment which is the smaller of the full test sequence or the full reference sequence. "Percent identity" ("% identity") is the identity fraction times 100.

"Expression" includes transcription of DNA to produce RNA. The resulting RNA may be without limitation mRNA encoding a protein, antisense RNA, or a double-stranded RNA for use in RNAi technology. Expression also refers to production of encoded protein from an mRNA.

As used herein, "promoter" means regulatory DNA molecules for initializing transcription. A "plant promoter" is a promoter capable of initiating transcription in plant cells whether or not its origin is a plant cell, for example it is well known that certain *Agrobacterium* promoters are functional in plant cells. Thus, plant promoters include promoter DNA obtained from plants, plant viruses (in particular, double stranded DNA viruses) and bacteria such as *Agrobacterium* and *Bradyrhizobium* bacteria. Constitutive promoters generally provide transcription in most or all of the cells of a plant, in particular, promoters such as the FMV promoter (FMV, U.S. Pat. No. 6,051,753), the enhanced 35S promoter (E35S, U.S. Pat. No. 5,359,142), rice actin promoter (U.S. Pat. No. 5,641,876), and various chimeric promoters (U.S. Pat. No. 6,660,911) are herein incorporated by reference and are useful in the present invention. Examples of promoters under developmental control include promoters that preferentially initiate transcription in certain tissues, such as leaves, roots, or seeds. Such promoters are referred to as "tissue preferred". Promoters that initiate transcription only in certain tissues are referred to as "tissue specific".

The term "resistance," or "tolerance" when used in the context of comparing the effectiveness of a transgene in a transgenic plant and another plant, refers to the ability of the invention transgenic plant to maintain, to some degree, a desirable phenotype in the face of nematode infection relative to a non-transgenic plant of sensitive genome. The level of resistance can be determined by comparing the physical characteristics of the invention plant to non-transgenic plants that either have or have not been exposed to nematode infection. Exemplary physical characteristics to observe in the presence and absence of parasitic nematode pressure include: plant height, weight, coloration, germination rate, fruit or grain yield, overall growth rate and root growth rate. Exemplary characteristics in the presence of nematode pressure may additionally include: nematode infection rates, nematode reproduction rates, feeding site choice and establishment, nematode growth and maturation rates. Desirable outcomes of the invention transgenic plants include an increase in the population of plants that exhibit positive changes in the above characteristics when compared to control plants. Transgenic invention plants that come in contact with parasitic nematodes may exhibit enhanced root growth, enhanced fruit or grain yield, reduction of nematode infection or decreases in nematode population growth compared to the control plants. The product of expression of the recombinant DNA may be directly toxic to the nematode (nematicidal) or may affect the mobility, host affinity, feeding site establishment or fecundity of the parasitic nematodes, or may have other measurable nematistatic effects.

"Transformed seed" is the seed which has been generated from the transformed plant. A transformed plant contains transformed cells. A transformed cell is a cell that has been altered by the introduction of an exogenous DNA molecule or in the present invention comprises a chimeric promoter comprising viral enhancer elements and promoters having activity in cells from which plant parasitic nematodes such as *Heterodera glycines* (soybean cyst nematode), *Meloidogyne incognita* (root knot nematode), or *Pratylenchus scribneri* (root lesion nematode) feed.

Nematodes include, but are not limited to plant parasitic species, for example, *Pratylenchus* species, *Heterodera* species, *Globodera* species, *Meloidogyne* species, *Rotylenchulus* species, *Hoplolaimus* species, *Belonolaimus* species, *Longidorus* species, *Paratrichodorus* species, *Ditylenchus* species, *Xiphinema* species, *Dolichodorus* species, *Helicotylenchus* species, *Radopholus* species, *Hirschmanniella* species, *Tylenchorhynchus* species, and *Trichodorus* species.

The term "insect" refers to any embryonic, larval, nymph or adult form of the arthropod classes Arachnida or Insecta. Insecta includes *Coleoptera* (e.g. *Leptinotarsa decemlineata, Diabrotica* spp.), *Diptera* (e.g. *Hylemya platura*), *Hemiptera* (e.g. *Lygus* spp., *Aphis gossypii*, Homoptera such as *Trialeurodes abutilonea, Bemisia tabaci*; Heteroptera such as *Nezara viridula*), Hymenoptera, and Lepidoptera (e.g. *Helicoverpa armigera, Ostrinia nubilalis*).

Bacteria suitable for production of methylketones and treating of plant propagation material, roots or other tissue include but are not limited to, a rhizobacterial species. In particular embodiments, the species can be selected from *Pasteuria* spp., *Pseudomonas* spp., *Bacillus* spp., *Corynebacterium, Agrobacterium* spp., and *Paenibacillus* spp. As non-limiting examples, the bacterial species can be *Bacillus firmus, Bacillus cereus, Pseudomonas cepacia, Corynebacterium pauronietabolum* or species of the genus *Pasteuria*, e.g. *Pasteuria penetrans, P. thornei, P. nishizawae, Candidatus Pasteuria usgae* sp. nov., or *Candidatus Pasteuria* sp. strain HG and others.

Bacterial Transformation

As is known to a person skilled in the art, many bacterial strains are suitable as host cells for the over-expression of methylketone thioesterase proteins according to the present technology, including *E. coli* strains and many other species and genera of prokaryotes including bacilli such as *Bacillus subtilis*, other enterobacteriaceae such as *Salmonella typhimurium* or *Serratia marcesans*, and various *Pseudomonas* species. Prokaryotic host cells or other host cells with rigid cell walls can be transformed using a calcium chloride method as described in section 1.82 of Sambrook et al., Molecular Cloning—A Laboratory Manual (3rd Ed.), Vol. 1-3, Cold Spring Harbor Laboratory, Cold Spring Harbor, N.Y., 2000. Alternatively, electroporation may be used for transformation of such cells. Various prokaryote transformation techniques are known in the art; e.g. Dower, W. J., in Genetic Engineering, Principles and Methods, 12:275-296, Plenum Publishing Corp., 1990; Hanahan et al., Meth. Enzymol., 204:63 1991.

Plant Expression Cassette

The present invention provides recombinant DNA constructs comprising a polynucleotide disclosed herein that when incorporated into a plant cell imparts increased resistance to nematode infection or plant disease caused by the nematode infection. Such constructs also typically comprise a promoter operatively linked to said polynucleotide to provide for expression in the plant cells. Other construct components may include additional regulatory molecules, such as 5' leader regions or 3' untranslated regions (such as polyadenylation sites), intron regions, and transit or signal peptides fused to the transgene. Such recombinant DNA constructs can be assembled using methods known to those of ordinary skill in the art.

Recombinant constructs prepared in accordance with the present invention also generally include a 3' untranslated DNA region (UTR) that typically contains a polyadenylation sequence following the polynucleotide coding region. Examples of useful 3' UTRs include but are not limited to those from the nopaline synthase gene of *Agrobacterium tumefaciens* (nos), a gene encoding the small subunit of a ribulose-1,5-bisphosphate carboxylase-oxygenase (rbcS), and the T7 transcript of *Agrobacterium tumefaciens*.

Constructs and vectors may also include a transit peptide for targeting of a protein product, particularly to a chloroplast, leucoplast or other plastid organelle, or mitochondria, or peroxisome, or vacuole or an extracellular location. For descriptions of the use of plastid transit peptides, see U.S. Pat. No. 5,188,642 and U.S. Pat. No. 5,728,925, herein incorporated by reference in their entirety. Many chloroplast-localized proteins are expressed from nuclear genes as precursors and are targeted to the chloroplast by a chloroplast transit peptide (CTP). Examples of other such isolated chloroplast proteins include, but are not limited to those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS) and transit peptides described in U.S. Pat. No. 7,193,133, herein incorporated by reference. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide, such as, the *Lycopersicon esculentum* DCL1 CTP (Gnanasambandam et al. Plant Biotechnol J. 2007 5(2):290-6.), the *Arabidopsis thaliana* EPSPS CTP (CTP2, Klee et al., Mol. Gen. Genet. 210:437-442), and the *Petunia hybrida* EPSPS CTP (CTP4, della-Cioppa et al., Proc. Natl. Acad. Sci. USA 83:6873-6877) has been show to target heterologous EPSPS protein sequences to chloroplasts in transgenic plants. The production of glyphosate tolerant plants by expression of a fusion protein comprising an amino-terminal CTP with a glyphosate resistant EPSPS enzyme is well known by those skilled in the art, (U.S. Pat. No. 5,627,061, U.S. Pat. No. 5,633,435, U.S. Pat. No. 5,312,910, EP 0218571, EP 189707, EP 508909, and EP 924299). Those skilled in the art will recognize that various chimeric constructs can be made that utilize the functionality of a CTP to import various methylketone thioesterases into the plant cell plastid.

Plant Transformation

Stable methods for plant transformation include virtually any method by which DNA can be introduced into a cell, such as by direct delivery of DNA (for example, by PEG-mediated transformation of protoplasts, by electroporation, by agitation with silicon carbide fibers, and by acceleration of DNA coated particles), by *Agrobacterium*-mediated transformation, by viral or other vectors. One preferred method of plant transformation is microprojectile bombardment, for example, as illustrated in U.S. Pat. No. 5,015,580 (soy), U.S. Pat. No. 5,550,318 (maize), U.S. Pat. No. 5,538,880 (maize), U.S. Pat. No. 6,153,812 (wheat), U.S. Pat. No. 6,160,208 (maize), U.S. Pat. No. 6,288,312 (rice) and U.S. Pat. No. 6,399,861 (maize), and 6,403,865 (maize), herein incorporated by reference in their entirety.

Detailed procedures for *Agrobacterium*-mediated transformation of plants, especially crop plants, include, for example, procedures disclosed in U.S. Pat. Nos. 5,004,863, 5,159,135, 5,518,908, 5,846,797, and 6,624,344 (cotton); U.S. Pat. Nos. 5,416,011, 5,569,834, 5,824,877, 5,914,451 6,384,301, and 7,002,058 (soy); U.S. Pat. Nos. 5,591,616 5,981,840, and 7,060,876 (maize); U.S. Pat. Nos. 5,463,174 and 5,750,871 (*Brassica* species, including rapeseed and canola), and in U.S. Patent Application Publications 2004/0244075 (maize), 2004/0087030 (cotton) and 2005/0005321 (soybean). Additional procedures for *Agrobacterium*-mediated transformation are disclosed in WO9506722 (maize). Similar methods have been reported for many plant species, both dicots and monocots, including, among others, peanut (Cheng et al. (1996) *Plant Cell Rep.*, 15:653); asparagus (Bytebier et al. (1987) *Proc. Natl. Acad. Sci. U.S.A.*, 84:5345); barley (Wan and Lemaux (1994) *Plant Physiol.*, 104:37); rice (Toriyama et al. (1988) *Bio/Technology*, 6:10; Zhang et al. (1988) *Plant Cell Rep.*, 7:379; wheat (Vasil et al. (1992) *Bio/Technology*, 10:667; Becker et al. (1994) *Plant J.*, 5:299), alfalfa (Masoud et al. (1996) *Transgen. Res.*, 5:313); *Brassica* species (Radke et al. (1992) *Plant Cell Rep.*, 11:499-505); and tomato (Sun et al. (2006) *Plant Cell Physiol.*, 47:426-431). Transgenic plant cells and transgenic plants can also be obtained by transformation with other vectors, such as, but not limited to, viral vectors (for example, tobacco etch virus (TEV), barley stripe mosaic virus (BSMV), and the viruses referenced in Edwardson and Christie, "The Potyvirus Group: Monograph No. 16, 1991, Agric. Exp. Station, Univ. of Florida), plasmids, cosmids, YACs (yeast artificial chromosomes), BACs (bacterial artificial chromosomes) or any other suitable cloning vector, when used with an appropriate transformation protocol, for example, bacterial infection (for example, with *Agrobacterium* as described above), binary bacterial artificial chromosome constructs, direct delivery of DNA (for example, via PEG-mediated transformation, desiccation/inhibition-mediated DNA uptake, electroporation, agitation with silicon carbide fibers, and microprojectile bombardment). It would be clear to one of ordinary skill in the art that various transformation methodologies can be used and modified for production of stable transgenic plants from any number of plant species of interest. For example the construction of stably inherited recombinant DNA constructs and minichromosomes can be used as vectors for the construction of transgenic plants (U.S. Pat. No. 7,235,716, herein incorporated by reference).

Transformation methods to provide transgenic plant cells and transgenic plants containing stably integrated recombinant DNA are preferably practiced in tissue culture on media and in a controlled environment. Recipient cell targets include, but are not limited to, meristem cells, callus, immature embryos or parts of embryos, and gametic cells such as microspores, pollen, sperm, and egg cells. Any cell from which a fertile plant can be regenerated is contemplated as a useful recipient cell for practice of the invention. Callus can be initiated from various tissue sources, including, but not limited to, immature embryos or parts of embryos, seedling apical meristems, microspores, and the like. Those cells which are capable of proliferating as callus can serve as recipient cells for genetic transformation. Practical transformation methods and materials for making transgenic plants of this invention (for example, various media and recipient target cells, transformation of immature embryos, and subsequent regeneration of fertile transgenic plants) are disclosed, for example, in U.S. Pat. Nos. 6,194,636 and 6,232,526 and U.S. Patent Application Publication 2004/0216189, which are incorporated herein by reference.

In general transformation practice, DNA is introduced into only a small percentage of target cells in any one transformation experiment. Marker genes are generally used to provide an efficient system for identification of those cells that are transformed by a transgenic DNA construct. Preferred marker genes provide selective markers which confer resistance to a selective agent, such as an antibiotic or herbicide. Any of the antibiotics or herbicides to which a plant cell may be resistant can be a useful agent for selection. Potentially transformed cells are exposed to the selective agent. In the population of surviving cells will be those cells where, generally, the resistance-conferring gene is expressed at sufficient levels to permit cell survival. Cells can be tested further to confirm integration of the recombinant DNA. Commonly used selective marker genes include those conferring resistance to antibiotics such as kanamycin or paromomycin (nptII), hygromycin B (aph IV), gentamycin (aac3 and aacC4) and glufosinate (bar or pat), glyphosate (EPSPS), and dicamba (dicamba monooxygenase). Examples of useful selective marker genes and selection agents are illustrated in U.S. Pat. Nos. 5,550,318, 5,633,435, 5,780,708, and 6,118,047, all of which are incorporated by reference. Screenable markers or reporters, such as markers that provide an ability to visually identify transformants can also be employed. Non-limiting examples of useful screenable markers include, for example, a gene expressing a protein that produces a detectable color by acting on a chromogenic substrate (for example, betaglucuronidase, GUS, uidA, or luciferase, luc) or that itself is detectable, such as green fluorescent protein (GFP, gfp) or an immunogenic molecule. Those of skill in the art will recognize that many other useful markers or reporters are available for use.

Trait Stacking and Breeding

The recombinant DNA constructs of the invention can be stacked with other recombinant DNA for imparting additional agronomic traits (such as in the case of transformed plants, traits including but not limited to herbicide resistance, insect resistance, cold germination tolerance, water deficit tolerance, enhanced yield, enhanced quality, fungal, viral, and bacterial disease resistance) for example, by expressing other transgenes. The recombinant DNA constructs of the present invention can also be transformed into plant varieties that carry natural pest resistance genes to enhance the efficacy of the pest resistance phenotype. Constructs for coordinated decrease and/or increase of gene expression are disclosed in U.S. Patent Application Publication 2004/0126845 A1. Seeds of transgenic, fertile plants can be harvested and used to grow progeny generations, including hybrid generations, of transgenic plants of this invention that include the recombinant DNA construct in their genome. Thus, in addition to direct transformation of a plant with a recombinant DNA construct of this invention, transgenic plants of the invention can be prepared by crossing a first plant having the recombinant DNA with a second plant lacking the construct. For example, the recombinant DNA can be introduced into a plant line that is amenable to transformation to produce a transgenic plant, which can be crossed with a second plant line to introduce the recombinant DNA into the resulting progeny. A transgenic plant of the invention can be crossed with a plant line having other recombinant DNA or naturally occurring genetic regions that confers one or more additional trait(s) (such as, but not limited to, herbicide resistance, pest or disease resistance, environmental stress resistance, modified nutrient content, and yield improvement) to produce progeny plants having recombinant DNA that confers both the desired target sequence expression behavior and the additional trait(s). Typically, in such breeding for combining traits the transgenic plant donating the additional trait is a male line and the transgenic plant carrying the base traits is the female line. The progeny of this cross segregate such that some of the plant will carry the DNA for both parental traits and some will carry DNA for one parental trait; such plants can be identified by markers associated with parental recombinant DNA Progeny plants carrying DNA for both parental traits can be crossed back into the female parent line multiple times, for example, usually 6 to 8 generations, to produce a progeny plant with substantially the same genotype as one original transgenic parental line but for the recombinant DNA of the other transgenic parental line.

The transgenic plant, plant part, seed or progeny plants of the present invention can be processed into products useful in commerce. These products include but are not limited to meal, flour, oil, hay, starch, juice, protein extract, and fiber.

EXAMPLES

The following examples are included to illustrate embodiments of the invention. It should be appreciated by those of skill in the art that the techniques disclosed in the examples that follow represent techniques discovered by the inventor to function well in the practice of the invention. However, those of skill in the art should, in light of the present disclosure, appreciate that many changes can be made in the specific embodiments which are disclosed and still obtain a similar result without departing from the concept, spirit and scope of the invention. More specifically, it will be apparent that certain agents which are both chemically and physiologically related may be substituted for the agents described herein while achieving the same or similar results. All such similar substitutes and modifications apparent to those skilled in the art are deemed to be within the spirit, scope and concept of the invention.

Example 1

*Escherichia Coli* Expression and Methylketone Analysis

Expression of MKT Constructs in *E. coli*:

Theoretical sequences were used to design oligonucleotide sets for artificial gene assembly. Sequence used was either wild-type sequence, wild-type sequence with silent mutations to avoid certain restriction enzymes, or sequence filtered through a plant-expression optimization scheme. In some cases N- and/or C-terminal extensions were added to the theoretical sequences to be assembled. Oligonucleotides of lengths between 40 and 60 nucleotides were designed that alternated between matching portions of the desired sequence or were antiparallel to the desired sequence. In general, odd numbered oligos matched the sequence of the coding (parallel) strand, and even numbered oligos matched the non-coding (anti-parallel) strand of desired DNA. The 5'-most and 3'-most 18 to 30 nucleotides of each oligonucleotide are antiparallel to the 5'-most and 3'-most 18 to 30 nucleotides of the adjoining oligonucleotides, such that assembly of the oligonucleotides by at least four cycles of PCR will result in a template that matches the desired sequence. Oligonucleotides that add restriction sites are used to further amplify the construct in secondary PCR reactions. Forward oligonucleotides for secondary amplification usually have the sequence ATA-CATCCATGG+(n15+) (SEQ ID NO:245) where CCATGG is an NcoI site overlapping the initiation codon (ATG) and n 15+ equals the 15 or greater nucleotides following the initiation codon in the assembled gene. Reverse amplification oligonucleotides usually have the sequence ATACATAAGCTT (ap-n15+) (SEQ ID NO:246) where AAGCTT is a HindIII restriction site, and ap-n15+ references sequence antiparallel to the 3' end of the assembled gene, including a stop codon. Following secondary PCR reactions, correct length amplicons were identified by agarose gel electrophoresis, purified using QIAQuick Gel Extraction Kits, and NcoI/HindIII subcloned to the bacterial expression plasmid pET28-a (Novagen). Sequence-confirmed constructs were transformed into BL21 Codon Plus (Stratagene) cells which harbor a plasmid encoding tRNAs to facilitate recombinant expression of codons rarely used by *E. coli*. Bacterial cultures were grown to an optical density at 600 nm of 0.8 to 1.0, induced with 1 mM IPTG and grown overnight at 30° C.

Methylketone Extraction and Detection:

After overnight induction of protein at 30° C., the 50 ml bacterial culture was centrifuged at 3,273×g for 20 min at room temperature. The pelleted bacteria was resuspended in 2 ml of chloroform and lysed using a FastPrep 24 Instrument with Lysing Matrix D tubes (MP Biomedicals, Inc.) at a setting of 6.0 m/s for 30 seconds. The resulting extract was centrifuged at 16,000×g for 10 min to pellet any debris prior to derivatization. Methylketones from the bacterial extract were detected by UV-HPLC post derivatization with 2,4 dinitrophenylhydrazine (DNPH). Extract (200 ul) was derivatized in the presence of 1 umol of DNPH and 1.5 umol of HCl for 1 hour at room temperature. Different dilutions of extract were evaluated to ensure an excess of DNPH which was monitored by the presence of a DNPH peak by UV-HPLC. UV-HPLC analysis was performed on an Eclipse XDB C18 column (5 um particle size, 4.6×250 mm) or a C8 column (5 um particle size, 4.6×250 mm) with a gradient mobile phase consisting of water and acetonitrile. DNPH derivatives were monitored by UV absorption at 362 nm. Peaks were identified by comparison of retention times of commercial standards of 2-undecanone, 2-tridecanone, and 2-pentadecanone (C18 column) or 2-nonanone, 2-undecanone, 2-tridecanone, and 2-pentadecanone (C8 column) post DNPH derivatization.

Figure 1B:
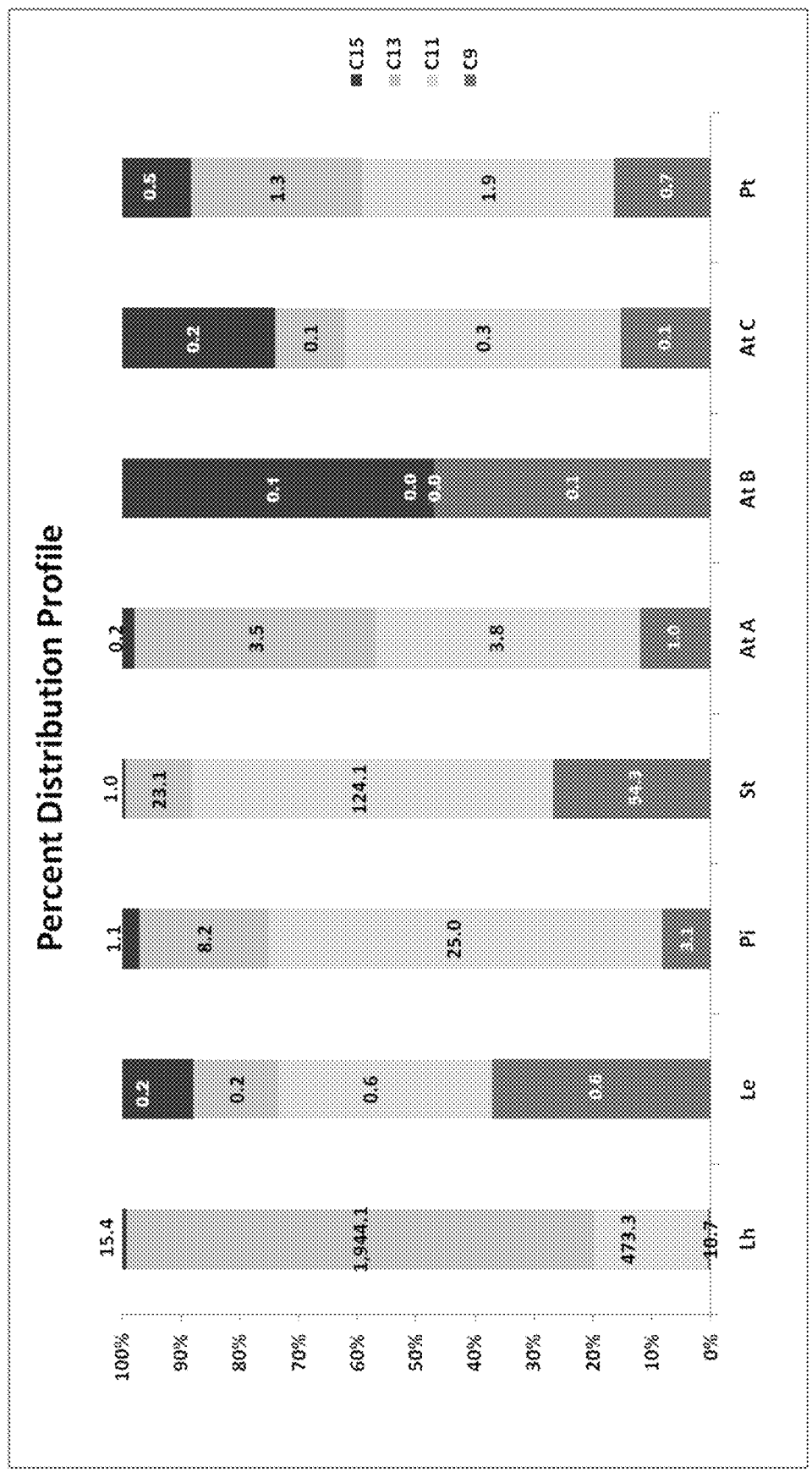
FIG. 1B: Comparisons of ratios and amounts of C9, C11, C13 and C15 methylketone metabolites produced in *E. coli* by methylketone thioesterases from *L. hirsutum, L. esculentum, P. integrifolia, S. tuberosum, A. thaliana*, and *Populus trichocarpa*. Each bar shows the fraction of C9, C11, C13 and C15 methylketone (numbers on bars are the ug of MK). Lh: *L. hirsutum*, Le: *L. esculentum*, Pi: *P. integrifolia*, St: *S. tuberosum*, AtA: *A. thaliana*, At B: *A. thaliana*, At C: *A. thaliana*, Pt: *Populus trichocarpa*.
Figure 1C:
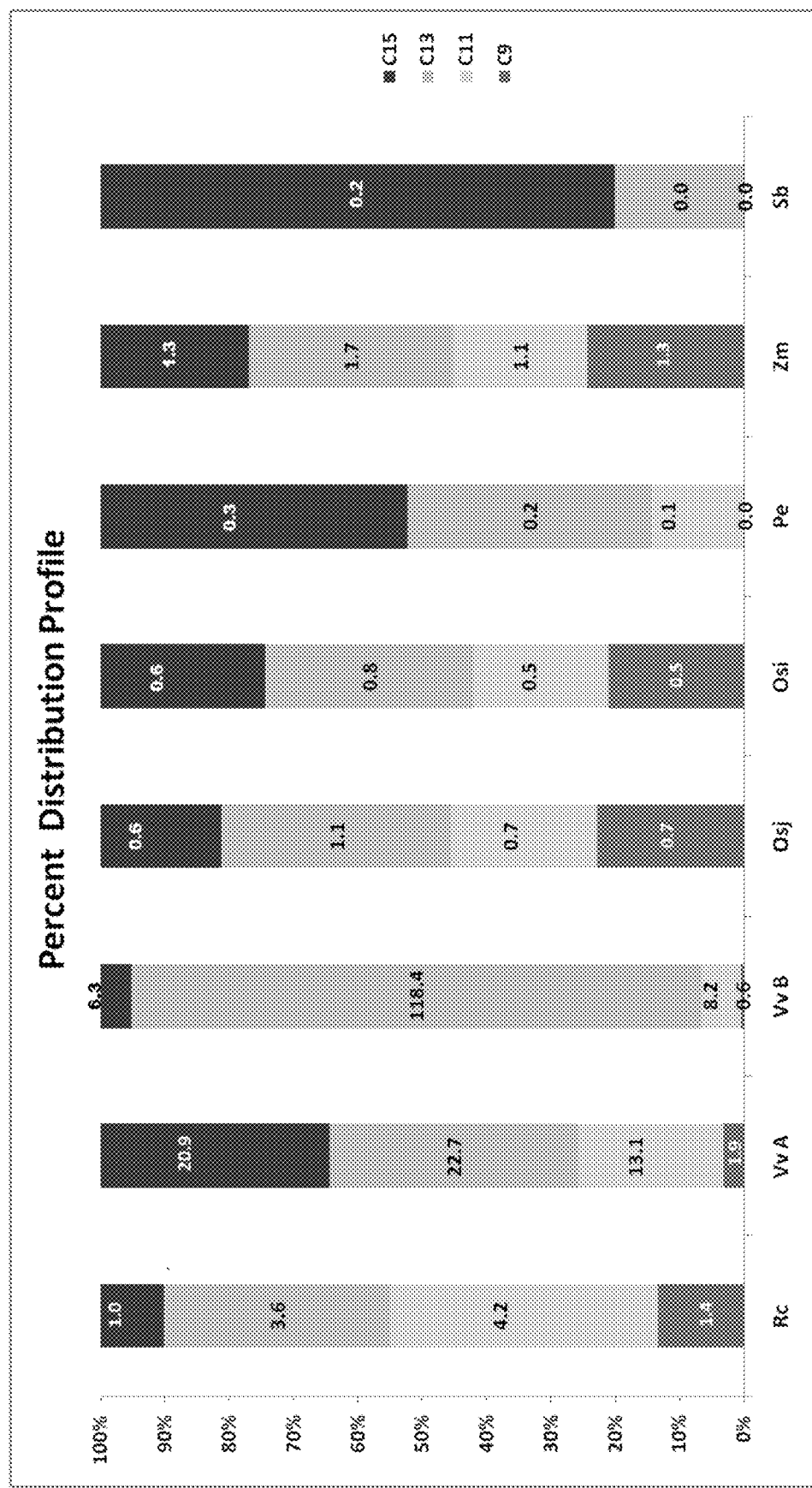
FIG. 1C: Comparisons of ratios and amounts of C9, C11, C13 and C15 methylketone metabolites produced in *E. coli* by methylketone thioesterases from *Ricinus communis, Vitis vinifera, Oryza sativa japonica, Oryza sativa indica, Phyllostachys edulis, Zea mays* and *Sorghum bicolor*. Each bar shows the fraction of C9, C11, C13 and C15 methylketone (numbers on bars are the ug of MK). Rc: *Ricinus communis*, Vv A: *Vitis vinifera*, Vv B *Vitis vinifera*, Osj: *Oryza sativa japonica*, Osi: *Oryza sativa indica*, Pe: *Phyllostachys edulis*, Zm: *Zea mays*, Sb: *Sorghum bicolor*.
Figure 2A:
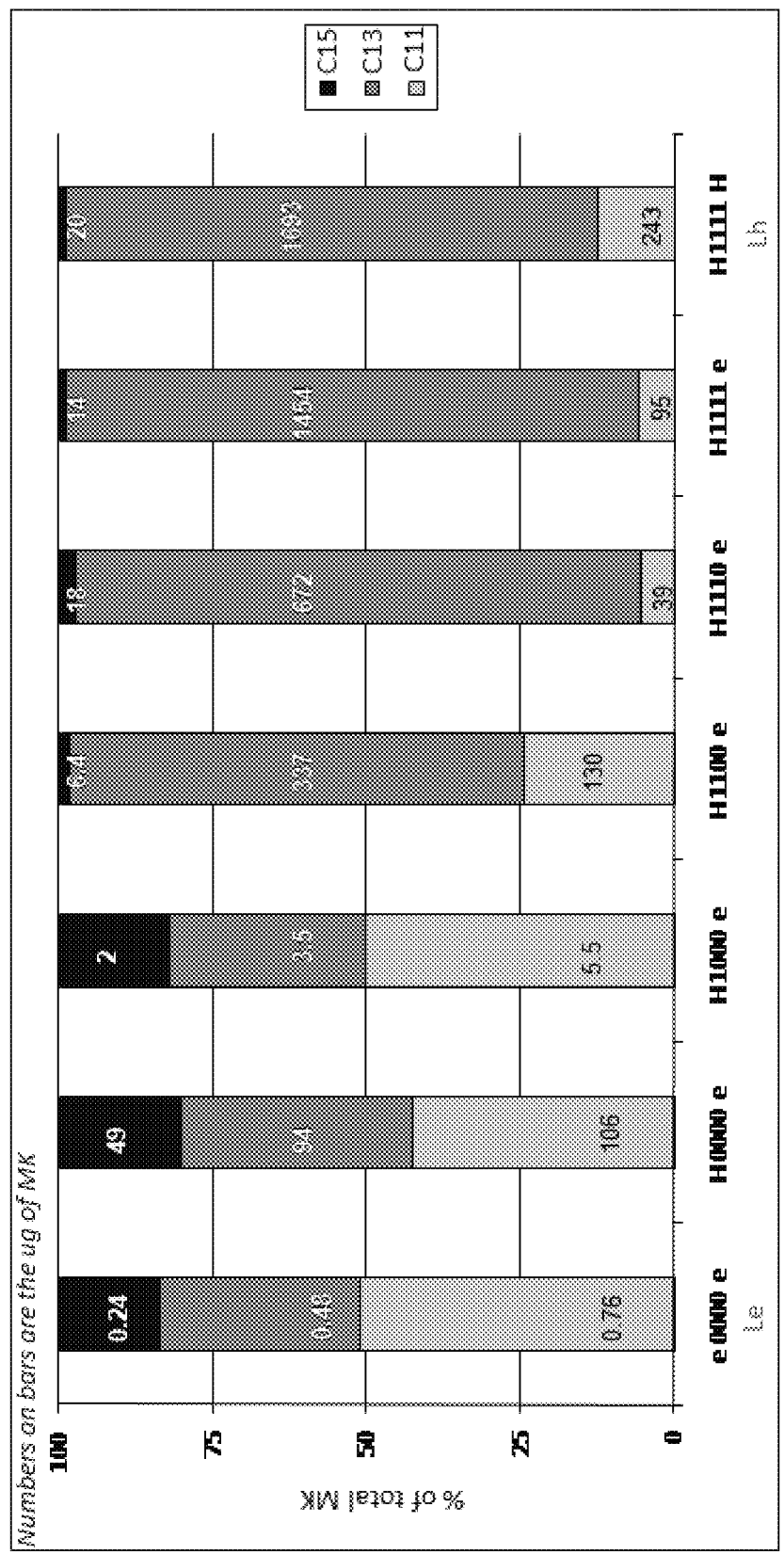
FIG. 2A: Comparisons of ratios and amounts of C11, C13 and C15 methylketone metabolites produced in *E. coli* by *L. esculentum/L. hirsutum* chimeric methylketone thioesterases Bottom portion of each bar is C11, middle portion of each bar is C13, and top portion of each bar is C15.
Figure 2B:
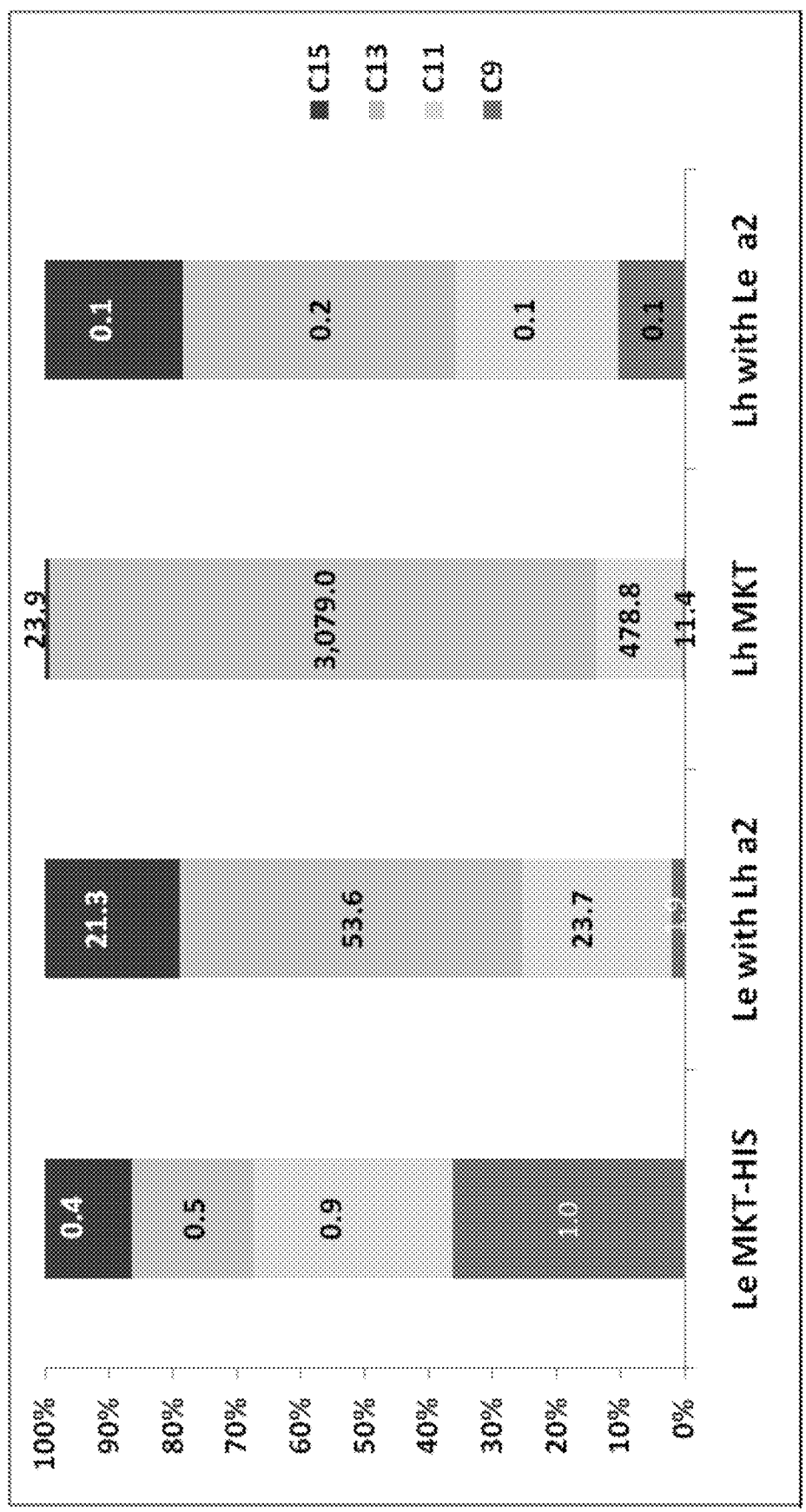
FIG. 2B: Comparisons of ratios and amounts of C9, C11, C13 and C15 methylketone metabolites produced in *E. coli* by *L. esculentum/L. hirsutum* chimeric methylketone thioesterases. Each bar shows the fraction of C9, C11, C13 and C15 methylketone (numbers on bars are the ug of MK). *L. esculentum* parent sequence with an C-terminal 6-HIS tag (SEQ ID NO:279), *L. esculentum/L. hirsutum* chimera with the second alpha helix of Le (residues of 25 to 42 of Le) replaced with the second alpha helix of Lh (residues of 28 to 45 of Lh), *L. hirsutum* parent sequence, *L. hirsutum/L. esculentum* chimera with the second alpha helix of Lh (residues of 28 to 45 of Lh) replaced with the second alpha helix of Le (residues of 25 to 42 of Le).
Figure 3:
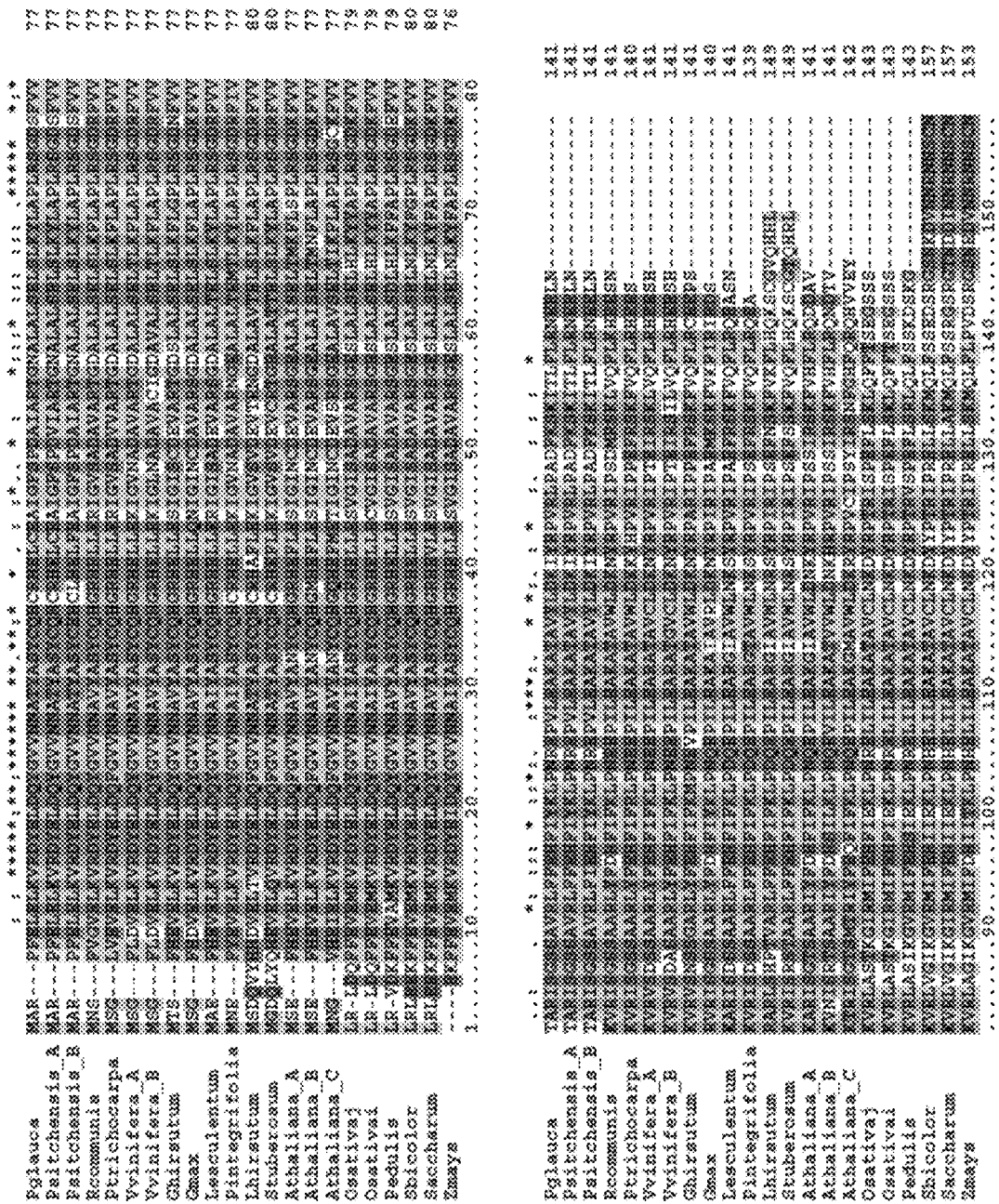
FIG. 3: Multiple alignment of various methylketone thioesterases from dicot and monocot plants. Depicted is a multiple sequence alignment (SEQ ID NOs:253-274, respectively, in order of appearance) generated with ClustalX for several methylketone thioesterases from a variety of dicot plants including spruce, castor, grape, poplar, cotton, soybeans, tomato, petunia, potato and *Arabidopsis*) and several moncot plants including rice, bamboo, sorghum, sugarcane and corn.
Figure 4:
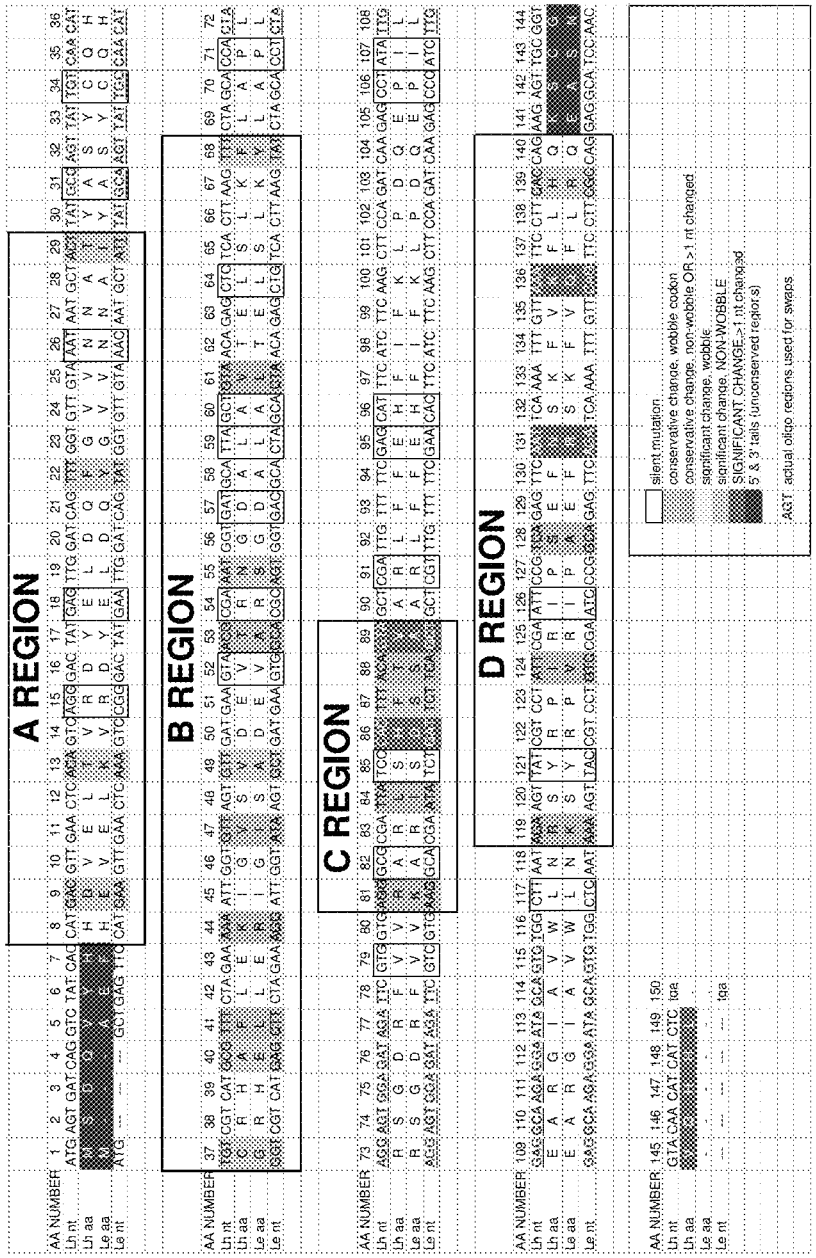
FIG. 4: Sequence aligned depicting various region. The *L. hirsutum* (SEQ ID NOs:275-276, respectively, in order of appearance) and *L. esculentum* (SEQ ID NOs:278 and 277, respectively, in order of appearance) sequences were aligned as shown in the graphic and then two tail regions and four internal regions defined (N-terminal tail, A region, B region, C region, D region, C-terminal terminal tail). For the external tails if the sequence is from *L. esculentum* it is e; if it is from *L. hirsutum* it is H. For the internal regions if the sequence is from *L. esculentum* it is 0; if it is from *L. hirsutum* it is 1. Example: e0000e is the *L. esculentum* parent; H1111H is the *L. hirsutum* parent.

As can be seen in FIGS. 1a-c and 2a and 2b the ratios and amounts of C9, C11, C13 and C15 metabolites can differ significantly between various methylketone thioesterases and for chimeric versions of the enzyme made by swapping regions between MKTs.

Example 2

Hairy Root Generation Protocols

For soybean Williams 82 hairy roots, *A. rhizogenes* strain K599 (NCPPB 2659; NCPPB, Sand Hutton, York, UK) was grown and maintained on LB (Luria Bertani), or yeast extract and peptone (YEP) media. Yeast extract is the water-soluble portion of autolyzed yeast. The autolysis is carefully controlled to preserve naturally occurring B-complex vitamins. Yeast extract is typically prepared by growing baker's yeast, *Saccharomyces* spp., in a carbohydrate-rich plant medium. The yeast is harvested, washed, and resuspended in water, where it undergoes autolysis, i.e., self-digestion using the yeast's enzymes. Yeast extract is the total soluble portion of this autolytic action. The autolytic activity is stopped by a heating step. The resulting yeast extract is filtered clear and dried into a powder by spray drying. Methods for generation of transgenic tomato Mountain Spring (susceptible) or Fresh Mountain Plus (resistant) hairy root cultures using *A. rhizogenes* strain D1 are similar, except that MgL media containing yeast extract, NaCl, tryptone, L-glutamic acid, potassium phosphate, magnesium sulfate and biotin is used. Soybean seeds were surface-sterilized by contacting with chlorine gas under controlled conditions for 12-16 hours, followed by aeration in a clean air hood for at least 30 minutes. Seeds were germinated in Petri dishes containing ¼ MS (Murashige & Skoog, 1962). The hypocotyl or cotyledons of 6-day-old seedlings were wounded using a scalpel, and wounded cotyledons were then immersed in a culture of freshly grown *A. rhizogenes* containing a DNA construct of interest, and vacuum infiltrated. Cotyledons were cultured under similar conditions used for seed germination with the exception that the antibiotic cefotaxime is added to the ¼ MS agar plates to prevent subsequent overgrowth by *A. rhizogenes*. Adventitious roots were excised from hypocotyls or cotyledons inoculated with *A. rhizogenes*. The putative transformed roots were cultured on Gamborg's B-5 agar (Gamborg et al., 1976) containing 3% sucrose plus 3 g/l Gelrite®, BASTA, and cefotaxime). Roots surviving selection were transferred to fresh media and maintained on Gamborg's B-5 agar in an incubator, without light, at about 24-30° C. A piece of root tip was typically excised and transferred to fresh medium every 2-4 weeks.

Example 3

Nematode Bioassays on Hairy Root Material

Hairy Root Efficacy Testing Setup:

Following hairy root line selection, roots for the plant nematode bioassay are transferred to fresh plates containing Gamborg's B-5 medium and allowed to grow for approximately two weeks to provide sufficient tissue for nematode infection before inoculation with a mixed population of root lesion nematodes or second-stage juveniles of soybean cyst nematode (SCN) or root knot nematode (RKN). Individual hairy root tips are placed on infection plates. 20 plates are used for testing transformed roots for reaction to lesion, SCN or RKN. Each plate contains a transformed root from a separate integration. An additional 20 plates containing a transformed lesion susceptible, SCN-susceptible or RKN-susceptible control and an additional 20 plates containing a transformed SCN-resistant or RKN-resistant control are also tested. Transformed controls are empty vectors. Plates are then inoculated with approximately 400 sterile lesion worms or 1000 sterile *H. glycines* J2s or 450 sterile *M. incognita* J2s and incubated at 26-28° C. (SCN or RKN) or 25° C. or 30° C. (lesion nematode). Approximately six weeks for *M. incognita* or five weeks for *H. glycines* after inoculation with nematodes, infected tomato or soybean hairy roots are removed from the agar plates and the number of galls or cysts counted. For SCN hairy root plates exact cyst counts are done whereas for RKN gall numbers are estimated. For RKN, galls are noted and marked off on each plate. Gall scores are weighted estimates based on size. A scale is created at the beginning of scoring process. The smallest galls are given a score of 1 and as the galled areas become larger the gall score increases. The scale is then used to rate each gall on each plate in the experiment. Egg numbers are also scored at 42 days for RKN infections in tomato hairy roots. At 42 days post infection plates are microwaved and sieved to collect the roots. The roots are then blended in a 10% bleach solution and poured over a series of sieves to remove the root debris and collect the eggs. Eggs removed from each plate are counted and the roots are weighed. For lesion nematodes plates are harvested after approximately 56 days by placing roots in glass bowls filled with sterilized water containing 50 mg/L carbenicillin and 50 mg/L kanamycin. After 9-10 days to allow the worms to exit the roots, the solution is poured off and the worms counted under a microscope. To determine weights, root masses are removed from the bowls and micro-waved to melt the agar and the roots are collected with a sieve. The extra water is absorbed with a paper towel and the root weights recorded.

Sterile Lesion, SCN and RKN Larvae Preparation for Use with the Hairy Root Culture System:

Sterile SCN J2s are produced as follows. Clean soybean cyst nematode eggs (i.e., eggs with soil and other debris removed) are collected and placed in a 50 ml centrifuge vial containing 30 ml of a 10% bleach solution. The bleach solution is mildly agitated and then left to settle for 2-3 minutes. The vial is mildly agitated again to re-suspend the eggs and then centrifuged for 1 minute at 1000 rpm. Under a sterile hood, the bleach solution is removed into a receptacle and 25 ml of sterile water is added into the vial of eggs. The vial is recapped under the sterile hood, mildly agitated to re-suspend the eggs and centrifuged for 1 minute at 1000 rpm. Under the sterile hood, this liquid is poured off and 25 ml of sterile water is again placed in the vial. The vial is recapped under the sterile hood and the process of agitation and centrifugation repeated. This process of washing the eggs with sterile water is repeated approximately 4 times to thoroughly rinse the bleach from the eggs. Following the last rinse under the sterile hood the liquid is removed leaving about 1-2 ml of egg concentrate. Sterilized eggs are hatched by incubating them on the surface of moist filter paper resting in a solution of 5 mM zinc sulfate just deep enough to cover the surface of the filter paper. After 2-3 days J2 larvae are collected in the solution underneath the filter paper. J2s are centrifuged and further sterilized using chlorhexidine (Atkinson et al. (1996) J. Nematol. 28:209-215).

Sterile RKN larvae are prepared by collecting eggs by placing chopped RKN infected roots into a blender with a sufficient quantity of 10% bleach solution. The blender is pulsed on/off for 5 second intervals. This process is repeated 5-6 times. The root slurry is then passed through a series of sieves where the eggs and small debris are collected in a 500 micron sieve. Any remaining bleach solution is thoroughly rinsed from this egg/debris. Twenty milliliters of the egg/debris is added to a 50 ml conical tube and 20 ml of a 40% sucrose solution is added into the bottom of the tube, bringing the total volume to 40 milliliters. This solution is then centrifuged at 3750 rpm for 5 minutes to separate the eggs from the debris. After centrifugation, the eggs are removed and thoroughly rinsed to remove any remaining sucrose solution. Eggs are then placed into a hatch bowl containing filter paper moistened with just enough aerated tap water to cover the eggs. After 1-2 days J2 larvae are collected in the solution underneath the filter paper. J2 larvae are centrifuged and further sterilized using chlorhexidine (Atkinson et al. (1996) J. Nematol. 28:209-215).

Sterile lesion larvae are prepared from lesion nematodes grown on corn explant plates. The nematodes are harvested by putting the roots with medium onto filter paper supported by a wire sieve in a sterilized glass bowl, which has been filled with sterilized water containing 50 mg/L carbenicillin and 50 mg/L kanamycin. The amount of the water is enough to just submerge the agar. The bowls are stored at room temperature (25° C.) for two days. The sieve is removed and the solution poured into a 50 ml conical tube, which is then centrifuged for 5 minutes at 3500 g at room temperature. The tube is then let to sit for 15 minutes to allow the worms to set to the bottom of the tube and the supernatant sucked out with a sterilized one ml tip connected to a vacuum. Sterilized water is then added to the worms containing 12 mg/L of the antifungal compound Imazilil and 50 mg/L kanamycin.

TABLE 1

*Heterodera glycines* (soybean cyst nematode) infection assay in soybean hairy roots

|  | avg cysts | percent reduction |
|---|---|---|
| Wild type control construct | 21.7 | — |
| Ubi3 DC44 LeMKT | 15.0 | 30.9 |
| Ubi3 DC44 LeMKT opt | 15.0 | 30.7 |
| Ubi3 DC44 LhMKT opt | 18.5 | 14.7 |

TABLE 2

*Meloidogyne incognita* (root knot nematode) infection assay in tomato hairy roots

|  | avg egg # | % Red avg egg # | avg egg/gm | % Red egg/gm | avg root wt |
|---|---|---|---|---|---|
| Wild type control construct | 1528.3 | — | 1573.5 | — | 1.2 |
| Ubi3 DC44 LhMKT opt | 720.9 | 52.8 | 672.6 | 57.3 | 1.2 |
| Ubi3 DC44 Le MKT | 826.7 | 45.9 | 850.9 | 45.9 | 1.1 |
| Ubi3 DC44 Le MKT HA | 1200.1 | 21.5 | 1233.8 | 21.6 | 1.1 |

TABLE 3

*Heterodera glycines* (soybean cyst nematode) infection assay in soybean hairy roots

|  | avg cysts | percent reduction |
|---|---|---|
| Wild type control construct | 29 | — |
| Ubi3 DC44 opt At C MKT opt | 18.3 | 36.9 |
| Ubi3 DC44 opt PtMKT opt | 4.0 | 86.2 |
| Ubi3 DC44 opt RcMKT opt | 16.3 | 43.8 |
| Ubi3 DC44 opt Vv A MKT opt | 24.5 | 15.4 |
| Ubi3 DC44 opt OsjMKT opt | 14.1 | 51.4 |
| Ubi3 DC44 opt OsiMKT opt | 18.1 | 37.5 |
| Ubi3 DC44 opt PeMKT opt | 19.6 | 32.6 |
| Ubi3 DC44 opt ZmMKT opt | 15.6 | 46.1 |
| Ubi3 DC44 opt SbMKT opt | 24.2 | 16.4 |

TABLE 4

*Meloidogyne incognita* (root knot nematode) infection assay in tomato hairy roots

|  | avg egg # | % Red avg egg # | avg egg/gm | % Red egg/gm | avg root wt |
|---|---|---|---|---|---|
| Wild type control construct | 3501.8 | — | 4048.2 | — | 1.1 |
| Ubi3 DC44 opt LeMKT HA | 708.7 | 79.8 | 682.6 | 83.1 | 1.1 |
| Ubi3 DC44 opt LeMKT opt | 700.4 | 80.0 | 603.6 | 85.1 | 1.1 |
| Ubi3 DC44 opt LhMKT opt HA | 580.7 | 83.4 | 604.4 | 85.1 | 1.4 |
| Ubi3 DC44 opt LhMKT opt | 1450.7 | 58.6 | 1322.0 | 67.3 | 1.2 |
| Ubi3 DC44 opt PiMKT opt HA | 575.3 | 83.6 | 807.2 | 80.1 | 1.1 |
| Ubi3 DC44 opt PiMKT opt | 1293.0 | 63.1 | 1031.7 | 74.5 | 1.4 |
| Ubi3 DC44 opt StMKT opt | 1067.2 | 69.5 | 1218.2 | 69.9 | 1.2 |

TABLE 5

*Pratylenchus scribneri* (root lesion nematode) infection assay in tomato hairy roots

|  | avg worm # | % Red avg worm # | avg worms/gm | % Red worms/gm | avg root wt | % Red Root wt |
|---|---|---|---|---|---|---|
| Wild type control construct | 14221.0 | — | 19690.2 | — | 0.86 | — |
| Ubi3 DC44 opt LeMKT opt HA | 8,076.3 | 43.2 | 13,062.0 | 33.7 | 0.92 | −7.1 |
| Ubi3 DC44 opt LeMKT opt | 9476.5 | 33.4 | 9134.7 | 53.6 | 1.05 | −23.0 |
| Ubi3 DC44 opt LhMKT opt HA | 11,382.8 | 20.0 | 13,607.9 | 30.9 | 1.15 | −34.4 |
| Ubi3 DC44 opt LhMKT opt | 11602.1 | 18.4 | 15689.4 | 20.3 | 1.06 | −24.4 |
| Ubi3 DC44 opt PiMKT opt HA | 6,089.7 | 57.2 | 6,594.1 | 66.5 | 1.23 | −43.5 |
| Ubi3 DC44 opt PiMKT opt | 9594.4 | 32.5 | 9888.9 | 49.8 | 1.19 | −38.8 |
| Ubi3 DC44 opt StMKT opt | 11,395.2 | 19.9 | 11,043.4 | 43.9 | 1.03 | −20.0 |

TABLE 6

*Pratylenchus scribneri* (root lesion nematode) infection assay in tomato hairy roots

|  | avg worm # | % Red avg worm # | avg worms/gm | % Red worms/gm | avg root wt | % Red Root wt |
|---|---|---|---|---|---|---|
| Wild type control construct | 10381.1 | — | 33784.5 | — | 0.48 | — |
| Ubi3 DC50 opt StMKT opt | 6942.2 | 33.1 | 22136.2 | 34.5 | 0.49 | −2.2 |
| RB7 DC50 opt LhMKT opt HA | 7129.9 | 31.3 | 17377.8 | 48.6 | 0.54 | −11.1 |
| RB7 DC50 opt StMKT opt | 4505.0 | 56.6 | 7101.5 | 79.0 | 0.62 | −27.6 |
| 35S/Ubi3 DC50 opt StMKT opt | 6482.7 | 37.6 | 11733.2 | 65.3 | 0.55 | −14.6 |
| RB7 LhMKT opt HA | 7537.1 | 27.4 | 13357.0 | 60.5 | 0.60 | −24.1 |
| RB7 DC50 opt PiMKT opt HA | 7777.2 | 25.1 | 17666.8 | 47.7 | 0.61 | −25.5 |

As can be seen in the Tables 1 through 6 above, the expression of certain monocot or dicot methylketone thioesterases under the control of heterologous promoters (e.g., constitutive promoters like ubi3 or root specific promoters like tobRB7) results in the reduced infestation of plant roots for either soybean cyst nematodes, root knot nematodes or root lesion nematodes and additionally a root protective effect (i.e., increased root weights) in the presence of lesion nematode infections. Importantly the degree of in planta nematicidal efficacy is not a simple function of the total amounts of methylketone produced or the specific levels of any one methylketone accumulated (e.g., *L. hirsutum* MKT which makes a very large amount of the strongly nematicidal C13 methylketone is not necessarily the most efficacious MKT for broad spectrum nematode control in plants).

Example 4

Nematode Testing in Transgenic Whole Plant Greenhouse Assays

Transgenic Soybean for SCN:

Four inch square plastic pots are filled with a media mixture of 80% sand plus 20% loam soil. Pots are placed in the greenhouse and watered to settle the media firmly into the pot. The next day 1 soybean seed per pot is planted 2 inches deep into the pot. Pots are watered as needed to keep the media moist. Four-five days after planting SCN eggs are added to distilled water to create a concentration of 1000 vermiform eggs per milliliter of water. For each pot a hole near the planting site is punched about 1 cm deep into the pot. One milliliter of the nematode solution is pippetted into the hole and the hole is covered with the media. Watering is then restricted to water only as needed to keep plants from wilting for 24 hours. After the 24 hours normal watering is resumed. The plants are then allowed to grow for 28 days.

After 28 days the plants are collected and the above ground portion of the soybean plant is cut off, weighed and then appropriately discarded. Each plant is harvested individually. The root of the plant is placed in a bucket of water, is swirled around and gently massaged with the hand to remove the growing media and dislodge any cysts attached to the root. The liquid and loose contents are then poured over a 500 micron sieve which is mounted above a 250 micron sieve. More water is then added to the bucket, this water is swirled to create a suspension with the bucket contents and the water is again poured over the sieves. All cysts and any debris between 500 microns and 250 microns are captured in the 250 micron sieved. The contents of the 250 micron sieve are collected and examined under a microscope and the number of cysts per sample are counted and recorded. A test treatment is replicated 4 times.

Transgenic Tobacco for RKN:

Tobacco seeds for each construct are randomly planted into a 6 inch×4 inch germination tray containing Fafard™ germinating mix. The flats are then placed under a mist system to keep them moist for 7 days or until the plants germinate. The flats are then transferred to the greenhouse and the plants are allowed to grow for another 7-10 days until they have 2-3 young leaves. Selected plants are then transplanted into 3 inch square deep-well plastic pots, 1 plant per pot. The plastic pots are ⅔ full of a 60:40 blend of sand:Turface™. The tobacco plant is placed on top of this mix and the last ⅓ of the pot is filled with 100% sand keeping the foliage of the plant on top of the sand and the pot is lightly watered. The pots are then placed in the greenhouse where the plants are allowed to adapt to the new growing media for 3-5 days. RKN eggs are added to distilled water to create a concentration of 1000 vermiform eggs per milliliter of water. For each pot a hole near the planting site is punched about 1 cm deep into the pot. Five milliliters of the nematode solution is pippetted into the hole and the hole is covered with the media. Watering is then restricted to water only as needed to keep plants from wilting for 24 hours. After the 24 hours normal watering is resumed. The plants are then grown for 56 days.

After 56 days the plants are collected and the above ground portion of the tobacco plant is cut off, weighed and then appropriately discarded. Each plant is harvested individually. The root of the plant is placed in a bucket of water, is swirled around and gently massaged with the hand to remove the growing media. The root is the place in a moist towel and transported to the lab for gall rating. Each root is rated separately for galling on a scale of 0-100 where 0=no galls on the root and 100=the entire root is covered with galls. Tests treatments are replicated 5 times.

Transgenic Corn for Lesion:

A mixture of sand and Turface (2:1) is poured into 4 inch pots to fill the bottom ⅔$^{rd}$ of the pot. Inoculum composed of corn roots infected with a lesion nematode such as *P. scribneri* is incorporated into the soil mix and then covered with 100% sand. Pots are watered and allowed to drain completely. A single corn seed is planted per pot. Corn grows for 30 days and then harvested.

Inoculum to be used consists of a lesion (e.g., *P. scribneri*) infected corn roots that have previously been analyzed for nematode population. This population is expressed as nematodes per gram. Infected roots are weighed for each pot to be treated to yield 10,000 nematodes per pot. Inoculum is applied prior to seed planting.

After 30 days, corn plants are topped and the tops weighed and discarded. Roots are gently washed, blotted and weighed. Roots are chopped and thoroughly mixed; three grams of roots are placed in a funnel lined with a screen and a folded Kimwipe. Funnels are placed in a 50 ml conical tube in a mist tent for 6 days. Roots are misted for 30 seconds every 30 minutes; nematodes move from the roots and settle into the bottom of the tube. After 6 days, nematodes are counted.

Transgenic Tobacco for Lesion:

Tobacco seeds are randomly planted into 6 inch×4 inch germination trays containing Fafard™ germination mix. Flats are placed under a mist system to keep them moist for 7 days or until the plants germinate. Seedlings are transferred to the greenhouse and allowed to grow for another 7-10 days until they have 2-3 young leaves. A mixture of sand and Turface (2:1) is poured into 3 inch deep-well plastic pots to ⅔$^{rd}$ full. Corn roots infected with lesion nematodes (e.g., *P. scribneri*) are incorporated into the soil mix and then covered with 100% sand. Pots are watered and allowed to drain completely; selected plants are then transplanted. Inoculated plants are grown for 60 days.

Inoculum to be used consists of lesion nematode (e.g., *P. scribneri*) infected corn roots that have previously been analyzed for nematode population. This population is expressed as nematodes per gram. Infected roots are weighed for each pot to be treated to yield 6,000 nematodes per pot. Inoculum is applied prior to transplanting.

After 60 days, tobacco plants are topped and the tops weighed and discarded. Roots are gently washed, blotted and weighed. Roots are chopped and thoroughly mixed; 2.5 grams of roots are placed in a funnel lined with a screen and a folded Kimwipe. Funnels are placed in a 50 ml conical tube in a mist tent for 6 days. Roots are misted for 30 seconds every 30 minutes; nematodes move from the roots and settle into the bottom of the tube. After 6 days, nematodes are counted.

Example 5

Example Whole Plant Creation Methods

This example describes a plant transformation method useful in producing transgenic soybean plants and transgenic seed. Other methods are known in the art of plant cell transformation that can be applied using the DNA constructs of the present invention.

For *Agrobacterium* mediated transformation, soybean seeds are germinated overnight and the meristem explants excised (see U.S. Pat. No. 7,002,058). The meristems and the explants are placed in a wounding vessel. Soybean explants and induced *Agrobacterium* cells from a strain containing plasmid DNA with the expression cassettes of the present invention and a plant selectable marker cassette are mixed within about 14 hours from the time of initiation of seed germination and wounded using sonication. Following wounding, explants are placed in co-culture for 2-5 days at which point they are transferred to selection media for 6-8 weeks to allow selection and growth of transgenic shoots. Trait positive shoots are harvested after approximately 6-8 weeks and placed into selective rooting media for 2-3 weeks. Shoots producing roots are transferred to the greenhouse and potted in soil. Shoots that remain healthy on selection but that do not produce roots are transferred to non-selective rooting media for an additional two weeks. Roots from any shoots that produce roots off selection are tested for expression of the plant selectable marker before they are transferred to the greenhouse and potted in soil. Additionally, a DNA construct can be transferred into the genome of a soybean cell by particle bombardment and the cell regenerated into a fertile soybean plant as described in U.S. Pat. No. 5,015,580.

Transgenic soybean plant cells are transformed with recombinant DNA of this invention. Progeny transgenic plants and seed of the transformed plant cells are selected that provide pathogen resistance, especially nematode resistance.

Example 6

Optimized Methylketone Thioesterase Sequences and Uses in the Creation of Nematode Resistant Plants This example provides descriptions of compositions in use or contemplated for use in controlling plant parasitic nematodes singularly or in any combination. Table 3 provides a list of the compositions. A crop transformation base vector comprising selection expression cassettes and elements necessary for the maintenance of the plasmid in a bacterial cell is used to assemble DNA segments (e.g., promoters, leaders, introns, 3'UTR such as those shown in Table 4) that provide regulatory activity when operably linked to DNA segments that provide functionality in the present invention. The assembly of these DNA segments can be accomplished using methods known in the art of recombinant DNA technology. DNA coding sequences of the present invention such as any one or more of the DNA molecules identified in SEQ ID NO: 1-56 and SEQ ID NO: 113-169 are cloned and inserted into an expression cassette or inserted into operable linkage with another coding sequence or genetic element of an expression cassette. Other genetic elements can be selected and tested by those skilled in the art that provide functional expression of a methylketone thioesterase in plant tissues.

TABLE 7

| Example Methylketone Thioesterase sequences | | |
|---|---|---|
| SEQ ID NO: 1 | Le MKT cDNA | Native nucleotide sequence of *L. esculentum* methylketone thioesterase |
| SEQ ID NO: 57 | Le MKT ORF | Native amino acid sequence of *L. esculentum* methylketone thioesterase |
| SEQ ID NO: 2 | Pi MKT cDNA | Native nucleotide sequence of *P. integrifolia* methylketone thioesterase |
| SEQ ID NO: 58 | Pi MKT ORF | Native amino acid sequence of *P. integrifolia* methylketone thioesterase |
| SEQ ID NO: 3 | Lh MKT cDNA | Native nucleotide sequence of *L. hirsutum* methylketone thioesterase |
| SEQ ID NO: 59 | Lh MKT ORF | Native amino acid sequence of *L. hirsutum* methylketone thioesterase |
| SEQ ID NO: 4 | St MKT cDNA | Native nucleotide sequence of *S. tuberosum* methylketone thioesterase |
| SEQ ID NO: 60 | St MKT ORF | Native amino acid sequence of *S. tuberosum* methylketone thioesterase |
| SEQ ID NO: 5 | Le MKT mod cDNA | Modified nucleotide sequence of *L. esculentum* methylketone thioesterase |
| SEQ ID NO: 61 | Le MKT mod ORF | Modified amino acid sequence of *L. esculentum* methylketone thioesterase |
| SEQ ID NO: 6 | Pi MKT mod cDNA | Modified nucleotide sequence of *P. integrifolia* methylketone thioesterase |
| SEQ ID NO: 62 | Pi MKT mod ORF | Modified amino acid sequence of *P. integrifolia* methylketone thioesterase |
| SEQ ID NO: 7 | Lh MKT mod cDNA | Modified nucleotide sequence of *L. hirsutum* methylketone thioesterase |
| SEQ ID NO: 63 | Lh MKT mod ORF | Modified amino acid sequence of *L. hirsutum* methylketone thioesterase |
| SEQ ID NO: 8 | St MKT mod cDNA | Modified nucleotide sequence of *S. tuberosum* methylketone thioesterase |
| SEQ ID NO: 64 | St MKT mod ORF | Modified amino acid sequence of *S. tuberosum* methylketone thioesterase |
| SEQ ID NO: 9 | Ctp Le MKT mod cDNA | Modified nucleotide sequence of *L. esculentum* methylketone thioesterase with chloroplast transit peptide from *L. esculentum* DCL1 |

TABLE 7-continued

Example Methylketone Thioesterase sequences

| SEQ ID NO | Name | Description |
|---|---|---|
| SEQ ID NO: 65 | Ctp Le MKT mod ORF | Modified amino acid sequence of *L. esculentum* methylketone thioesterase with chloroplast transit peptide from *L. esculentum* DCL1 |
| SEQ ID NO: 10 | Ctp Lh MKT mod cDNA | Modified nucleotide sequence of *L. hirsutum* methylketone thioesterase with chloroplast transit peptide from *L. esculentum* DCL1 |
| SEQ ID NO: 66 | Ctp Lh MKT mod ORF | Modified amino acid sequence of *L. hirsutum* methylketone thioesterase with chloroplast transit peptide from *L. esculentum* DCL1 |
| SEQ ID NO: 11 | Le MKT opt1 cDNA | Optimization 1 nucleotide sequence of *L. esculentum* methylketone thioesterase |
| SEQ ID NO: 67 | Le MKT opt1 ORF | Optimization 1 amino acid sequence of *L. esculentum* methylketone thioesterase |
| SEQ ID NO: 12 | Pi MKT opt1 cDNA | Optimization 1 nucleotide sequence of *P. integrifolia* methylketone thioesterase |
| SEQ ID NO: 68 | Pi MKT opt1 ORF | Optimization 1 amino acid sequence of *P. integrifolia* methylketone thioesterase |
| SEQ ID NO: 13 | Lh MKT opt1 cDNA | Optimization 1 nucleotide sequence of *L. hirsutum* methylketone thioesterase |
| SEQ ID NO: 69 | Lh MKT opt1 ORF | Optimization 1 amino acid sequence of *L. hirsutum* methylketone thioesterase |
| SEQ ID NO: 14 | St MKT opt1 cDNA | Optimization 1 nucleotide sequence of *S. tuberosum* methylketone thioesterase |
| SEQ ID NO: 70 | St MKT opt1 ORF | Optimization 1 amino acid sequence of *S. tuberosum* methylketone thioesterase |
| SEQ ID NO: 15 | Le MKT opt2 cDNA | Optimization 2 nucleotide sequence of *L. esculentum* methylketone thioesterase |
| SEQ ID NO: 71 | Le MKT opt2 ORF | Optimization 2 amino acid sequence of *L. esculentum* methylketone thioesterase |
| SEQ ID NO: 16 | Pi MKT opt2 cDNA | Optimization 2 nucleotide sequence of *P. integrifolia* methylketone thioesterase |
| SEQ ID NO: 72 | Pi MKT opt2 ORF | Optimization 2 amino acid sequence of *P. integrifolia* methylketone thioesterase |
| SEQ ID NO: 17 | Lh MKT opt2 cDNA | Optimization 2 nucleotide sequence of *L. hirsutum* methylketone thioesterase |
| SEQ ID NO: 73 | Lh MKT opt2 ORF | Optimization 2 amino acid sequence of *L. hirsutum* methylketone thioesterase |
| SEQ ID NO: 18 | St MKT opt2 cDNA | Optimization 2 nucleotide sequence of *S. tuberosum* methylketone thioesterase |
| SEQ ID NO: 74 | St MKT opt2 ORF | Optimization 2 amino acid sequence of *S. tuberosum* methylketone thioesterase |
| SEQ ID NO: 19 | Le MKT opt3 cDNA | Optimization 3 nucleotide sequence of *L. esculentum* methylketone thioesterase |
| SEQ ID NO: 75 | Le MKT opt3 ORF | Optimization 3 amino acid sequence of *L. esculentum* methylketone thioesterase |
| SEQ ID NO: 20 | Le MKT opt4 cDNA | Optimization 4 nucleotide sequence of *L. esculentum* methylketone thioesterase |
| SEQ ID NO: 76 | Le MKT opt4 ORF | Optimization 4 amino acid sequence of *L. esculentum* methylketone thioesterase |
| SEQ ID NO: 21 | Le MKT opt5 cDNA | Optimization 5 nucleotide sequence of *L. esculentum* methylketone thioesterase |
| SEQ ID NO: 77 | Le MKT opt5 ORF | Optimization 5 amino acid sequence of *L. esculentum* methylketone thioesterase |
| SEQ ID NO: 22 | Le MKT opt6 cDNA | Optimization 6 nucleotide sequence of *L. esculentum* methylketone thioesterase |
| SEQ ID NO: 78 | Le MKT opt6 ORF | Optimization 6 amino acid sequence of *L. esculentum* methylketone thioesterase |
| SEQ ID NO: 23 | Pi MKT opt3 cDNA | Optimization 3 nucleotide sequence of *P. integrifolia* methylketone thioesterase |
| SEQ ID NO: 79 | Pi MKT opt3 ORF | Optimization 3 amino acid sequence of *P. integrifolia* methylketone thioesterase |
| SEQ ID NO: 24 | Pi MKT opt4 cDNA | Optimization 4 nucleotide sequence of *P. integrifolia* methylketone thioesterase |
| SEQ ID NO: 80 | Pi MKT opt4 ORF | Optimization 4 amino acid sequence of *P. integrifolia* methylketone thioesterase |
| SEQ ID NO: 25 | Pi MKT opt5 cDNA | Optimization 5 nucleotide sequence of *P. integrifolia* methylketone thioesterase |
| SEQ ID NO: 81 | Pi MKT opt5 ORF | Optimization 5 amino acid sequence of *P. integrifolia* methylketone thioesterase |
| SEQ ID NO: 26 | Lh MKT opt3 cDNA | Optimization 3 nucleotide sequence of *L. hirsutum* methylketone thioesterase |
| SEQ ID NO: 82 | Lh MKT opt3 ORF | Optimization 3 amino acid sequence of *L. hirsutum* methylketone thioesterase |
| SEQ ID NO: 27 | Lh MKT opt4 cDNA | Optimization 4 nucleotide sequence of *L. hirsutum* methylketone thioesterase |
| SEQ ID NO: 83 | Lh MKT opt4 ORF | Optimization 4 amino acid sequence of *L. hirsutum* methylketone thioesterase |

TABLE 7-continued

Example Methylketone Thioesterase sequences

| | | |
|---|---|---|
| SEQ ID NO: 28 | Lh MKT opt5 cDNA | Optimization 5 nucleotide sequence of *L. hirsutum* methylketone thioesterase |
| SEQ ID NO: 84 | Lh MKT opt5 ORF | Optimization 5 amino acid sequence of *L. hirsutum* methylketone thioesterase |
| SEQ ID NO: 29 | St MKT opt3 cDNA | Optimization 3 nucleotide sequence of *S. tuberosum* methylketone thioesterase |
| SEQ ID NO: 85 | St MKT opt3 ORF | Optimization 3 amino acid sequence of *S. tuberosum* methylketone thioesterase |
| SEQ ID NO: 30 | Le/Lh chim1 cDNA | Optimization 1 nucleotide acid sequence of *L. esculentum*/*L. hirsutum* chimeric MKT |
| SEQ ID NO: 86 | Le/Lh chim1 ORF | Optimization 1 amino acid sequence of *L. esculentum*/*L. hirsutum* chimeric MKT |
| SEQ ID NO: 31 | Le/Lh chim2 cDNA | Optimization 2 nucleotide acid sequence of *L. esculentum*/*L. hirsutum* chimeric MKT |
| SEQ ID NO: 87 | Le/Lh chim2 ORF | Optimization 2 amino acid sequence of *L. esculentum*/*L. hirsutum* chimeric MKT |
| SEQ ID NO: 32 | Le/Lh chim3 cDNA | Optimization 3 nucleotide acid sequence of *L. esculentum*/*L. hirsutum* chimeric MKT |
| SEQ ID NO: 88 | Le/Lh chim3 ORF | Optimization 3 amino acid sequence of *L. esculentum*/*L. hirsutum* chimeric MKT |
| SEQ ID NO: 33 | Le/Lh chim4 cDNA | Optimization 4 nucleotide acid sequence of *L. esculentum*/*L. hirsutum* chimeric MKT |
| SEQ ID NO: 89 | Le/Lh chim4 ORF | Optimization 4 amino acid sequence of *L. esculentum*/*L. hirsutum* chimeric MKT |
| SEQ ID NO: 34 | Le/Lh chim5 cDNA | Optimization 5 nucleotide acid sequence of *L. esculentum*/*L. hirsutum* chimeric MKT |
| SEQ ID NO: 90 | Le/Lh chim5 ORF | Optimization 5 amino acid sequence of *L. esculentum*/*L. hirsutum* chimeric MKT |
| SEQ ID NO: 35 | Le/Lh chim6 cDNA | Optimization 6 nucleotide acid sequence of *L. esculentum*/*L. hirsutum* chimeric MKT |
| SEQ ID NO: 91 | Le/Lh chim6 ORF | Optimization 6 amino acid sequence of *L. esculentum*/*L. hirsutum* chimeric MKT |
| SEQ ID NO: 36 | Le/Lh chim7 cDNA | Optimization 7 nucleotide acid sequence of *L. esculentum*/*L. hirsutum* chimeric MKT |
| SEQ ID NO: 92 | Le/Lh chim7 ORF | Optimization 7 amino acid sequence of *L. esculentum*/*L. hirsutum* chimeric MKT |
| SEQ ID NO: 37 | Le/Lh chim8 cDNA | Optimization 8 nucleotide acid sequence of *L. esculentum*/*L. hirsutum* chimeric MKT |
| SEQ ID NO: 93 | Le/Lh chim8 ORF | Optimization 8 amino acid sequence of *L. esculentum*/*L. hirsutum chimeric MKT* |
| SEQ ID NO: 38 | Le/Lh chim9 cDNA | Optimization 9 nucleotide acid sequence of *L. esculentum*/*L. hirsutum* chimeric MKT |
| SEQ ID NO: 94 | Le/Lh chim9 ORF | Optimization 9 amino acid sequence of *L. esculentum*/*L. hirsutum* chimeric MKT |
| SEQ ID NO: 39 | Le/Lh chim10 cDNA | Optimization 10 nucleotide acid sequence of *L. esculentum*/*L. hirsutum* chimeric MKT |
| SEQ ID NO: 95 | Le/Lh chim10 ORF | Optimization 10 amino acid sequence of *L. esculentum*/*L. hirsutum* chimeric MKT |
| SEQ ID NO: 40 | Le/Lh chim11 cDNA | Optimization 11 nucleotide acid sequence of *L. esculentum*/*L. hirsutum* chimeric MKT |
| SEQ ID NO: 96 | Le/Lh chim11 ORF | Optimization 11 amino acid sequence of *L. esculentum*/*L. hirsutum* chimeric MKT |
| SEQ ID NO: 41 | Le/Lh chim12 cDNA | Optimization 12 nucleotide acid sequence of *L. esculentum*/*L. hirsutum* chimeric MKT |
| SEQ ID NO: 97 | Le/Lh chim12 ORF | Optimization 12 amino acid sequence of *L. esculentum*/*L. hirsutum* chimeric MKT |
| SEQ ID NO: 42 | Le/Lh chim13 cDNA | Optimization 13 nucleotide acid sequence of *L. esculentum*/*L. hirsutum* chimeric MKT |
| SEQ ID NO: 98 | Le/Lh chim13 ORF | Optimization 13 amino acid sequence of *L. esculentum*/*L. hirsutum* chimeric MKT |
| SEQ ID NO: 43 | Le/Lh chim14 cDNA | Optimization 14 nucleotide acid sequence of *L. esculentum*/*L. hirsutum* chimeric MKT |
| SEQ ID NO: 99 | Le/Lh chim14 ORF | Optimization 14 amino acid sequence of *L. esculentum*/*L. hirsutum* chimeric MKT |
| SEQ ID NO: 44 | Le/Lh chim15 cDNA | Optimization 15 nucleotide acid sequence of *L. esculentum*/*L. hirsutum* chimeric MKT |
| SEQ ID NO: 100 | Le/Lh chim15 ORF | Optimization 15 amino acid sequence of *L. esculentum*/*L. hirsutum* chimeric MKT |
| SEQ ID NO: 45 | Le/Lh chim16 cDNA | Optimization 16 nucleotide acid sequence of *L. esculentum*/*L. hirsutum* chimeric MKT |
| SEQ ID NO: 101 | Le/Lh chim16 ORF | Optimization 16 amino acid sequence of *L. esculentum*/*L. hirsutum* chimeric MKT |
| SEQ ID NO: 46 | Le/Lh chim17 cDNA | Optimization 17 nucleotide acid sequence of *L. esculentum*/*L. hirsutum* chimeric MKT |
| SEQ ID NO: 102 | Le/Lh chim17 ORF | Optimization 17 amino acid sequence of *L. esculentum*/*L. hirsutum* chimeric MKT |
| SEQ ID NO: 47 | Le/Lh chim18 cDNA | Optimization 18 nucleotide acid sequence of *L. esculentum*/*L. hirsutum* chimeric MKT |

TABLE 7-continued

Example Methylketone Thioesterase sequences

| SEQ ID NO: 103 | Le/Lh chim18 ORF | Optimization 18 amino acid sequence of *L. esculentum*/ *L. hirsutum* chimeric MKT |
|---|---|---|
| SEQ ID NO: 48 | Le/Lh chim19 cDNA | Optimization 19 nucleotide acid sequence of *L. esculentum*/ *L. hirsutum* chimeric MKT |
| SEQ ID NO: 104 | Le/Lh chim19 ORF | Optimization 19 amino acid sequence of *L. esculentum*/ *L. hirsutum* chimeric MKT |
| SEQ ID NO: 49 | Le/Lh chim20 cDNA | Optimization 20 nucleotide acid sequence of *L. esculentum*/ *L. hirsutum* chimeric MKT |
| SEQ ID NO: 105 | Le/Lh chim20 ORF | Optimization 20 amino acid sequence of *L. esculentum*/ *L. hirsutum* chimeric MKT |
| SEQ ID NO: 50 | Le/Lh chim21 cDNA | Optimization 21 nucleotide acid sequence of *L. esculentum*/ *L. hirsutum* chimeric MKT |
| SEQ ID NO: 106 | Le/Lh chim21 ORF | Optimization 21 amino acid sequence of *L. esculentum*/ *L. hirsutum* chimeric MKT |
| SEQ ID NO: 51 | Le/Lh chim22 cDNA | Optimization 22 nucleotide acid sequence of *L. esculentum*/ *L. hirsutum* chimeric MKT |
| SEQ ID NO: 107 | Le/Lh chim22 ORF | Optimization 22 amino acid sequence of *L. esculentum*/ *L. hirsutum* chimeric MKT |
| SEQ ID NO: 52 | Le/Lh chim23 cDNA | Optimization 23 nucleotide acid sequence of *L. esculentum*/ *L. hirsutum* chimeric MKT |
| SEQ ID NO: 108 | Le/Lh chim23 ORF | Optimization 23 amino acid sequence of *L. esculentum*/ *L. hirsutum* chimeric MKT |
| SEQ ID NO: 53 | Le/Lh chim24 cDNA | Optimization 24 nucleotide acid sequence of *L. esculentum*/ *L. hirsutum* chimeric MKT |
| SEQ ID NO: 109 | Le/Lh chim24 ORF | Optimization 24 amino acid sequence of *L. esculentum*/ *L. hirsutum* chimeric MKT |
| SEQ ID NO: 54 | Le/Lh chim25 cDNA | Optimization 25 nucleotide acid sequence of *L. esculentum*/ *L. hirsutum* chimeric MKT |
| SEQ ID NO: 110 | Le/Lh chim25 ORF | Optimization 25 amino acid sequence of *L. esculentum*/ *L. hirsutum* chimeric MKT |
| SEQ ID NO: 55 | Le/Lh chim26 cDNA | Optimization 26 nucleotide acid sequence of *L. esculentum*/ *L. hirsutum* chimeric MKT |
| SEQ ID NO: 111 | Le/Lh chim26 ORF | Optimization 26 amino acid sequence of *L. esculentum*/ *L. hirsutum* chimeric MKT |
| SEQ ID NO: 56 | St MKT opt3 cDNA | Optimization 3 nucleotide sequence of *S. tuberosum* methylketone thioesterase |
| SEQ ID NO: 112 | St MKT opt3 ORF | Optimization 3 amino acid sequence of *S. tuberosum* methylketone thioesterase |
| SEQ ID NO: 113 | Rc MKT cDNA | Native nucleotide sequence of *R. communis* methylketone thioesterase |
| SEQ ID NO: 170 | Rc MKT ORF | Native amino acid sequence of *R. communis* methylketone thioesterase |
| SEQ ID NO: 114 | Pt MKT cDNA | Native nucleotide sequence of *P. trichocarpa* methylketone thioesterase |
| SEQ ID NO: 171 | Pt MKT ORF | Native amino acid sequence of *P. trichocarpa* methylketone thioesterase |
| SEQ ID NO: 115 | Vv a MKT cDNA | Native nucleotide sequence of *V. vinifera* A methylketone thioesterase |
| SEQ ID NO: 172 | Vv a MKT ORF | Native amino acid sequence of *V. vinifera* A methylketone thioesterase |
| SEQ ID NO: 116 | Vv b MKT cDNA | Native nucleotide sequence of *V. vinifera* B methylketone thioesterase |
| SEQ ID NO: 173 | Vv b MKT ORF | Native amino acid sequence of *V. vinifera* B methylketone thioesterase |
| SEQ ID NO: 117 | At a MKT cDNA | Native nucleotide sequence of *A. thaliana* A methylketone thioesterase |
| SEQ ID NO: 174 | At a MKT ORF | Native amino acid sequence of *A. thaliana* A methylketone thioesterase |
| SEQ ID NO: 118 | At b MKT cDNA | Native nucleotide sequence of *A. thaliana* B methylketone thioesterase |
| SEQ ID NO: 175 | At b MKT ORF | Native amino acid sequence of *A. thaliana* B methylketone thioesterase |
| SEQ ID NO: 119 | At c MKT cDNA | Native nucleotide sequence of *A. thaliana* C methylketone thioesterase |
| SEQ ID NO: 176 | At c MKT ORF | Native amino acid sequence of *A. thaliana* C methylketone thioesterase |
| SEQ ID NO: 120 | Ps a MKT cDNA | Native nucleotide sequence of *P. sitchensis* A methylketone thioesterase |
| SEQ ID NO: 177 | Ps a MKT ORF | Native amino acid sequence of *P. sitchensis* A methylketone thioesterase |
| SEQ ID NO: 121 | Ps b MKT cDNA | Native nucleotide sequence of *P. sitchensis* B methylketone thioesterase |
| SEQ ID NO: 178 | Ps b MKT ORF | Native amino acid sequence of *P. sitchensis* B methylketone thioesterase |
| SEQ ID NO: 122 | Osj MKT cDNA | Native nucleotide sequence of *O. sativa japonica* methylketone thioesterase |
| SEQ ID NO: 179 | Osj MKT ORF | Native amino acid sequence of *O. sativa japonica* methylketone thioesterase |

TABLE 7-continued

Example Methylketone Thioesterase sequences

| SEQ ID NO: 123 | Osi MKT cDNA | Native nucleotide sequence of *O. sativa indica* methylketone thioesterase |
| SEQ ID NO: 180 | Osi MKT ORF | Native amino acid sequence of *O. sativa indica* methylketone thioesterase |
| SEQ ID NO: 124 | Zm MKT cDNA | Native nucleotide sequence of *Z. mays* methylketone thioesterase |
| SEQ ID NO: 181 | Zm MKT ORF | Native amino acid sequence of *Z. mays* methylketone thioesterase |
| SEQ ID NO: 125 | Sb MKT cDNA | Native nucleotide sequence of *S. bicolor* methylketone thioesterase |
| SEQ ID NO: 182 | Sb MKT ORF | Native amino acid sequence of *S. bicolor* methylketone thioesterase |
| SEQ ID NO: 126 | Pe MKT cDNA | Native nucleotide sequence of *P. edulis* methylketone thioesterase |
| SEQ ID NO: 183 | Pe MKT ORF | Native amino acid sequence of *P. edulis* methylketone thioesterase |
| SEQ ID NO: 127 | Pg MKT cDNA | Native nucleotide sequence of *P. glauca* methylketone thioesterase |
| SEQ ID NO: 184 | Pg MKT ORF | Native amino acid sequence of *P. glauca* methylketone thioesterase |
| SEQ ID NO: 128 | Gh MKT cDNA | Native nucleotide sequence of *G. hirsutum* methylketone thioesterase |
| SEQ ID NO: 185 | Gh MKT ORF | Native amino acid sequence of *G. hirsutum* methylketone thioesterase |
| SEQ ID NO: 129 | Gm MKT cDNA | Native nucleotide sequence of *G. max* methylketone thioesterase |
| SEQ ID NO: 186 | Gm MKT ORF | Native amino acid sequence of *G. max* methylketone thioesterase |
| SEQ ID NO: 130 | Sh MKT cDNA | Native nucleotide sequence of *Saccharum* hybrid methylketone thioesterase |
| SEQ ID NO: 187 | Sh MKT ORF | Native amino acid sequence of *Saccharum* hybrid methylketone thioesterase |
| SEQ ID NO: 131 | At a MKT mod cDNA | Modified nucleotide sequence of *A. thaliana* A methylketone thioesterase |
| SEQ ID NO: 188 | At a MKT mod ORF | Modified amino acid sequence of *A. thaliana* A methylketone thioesterase |
| SEQ ID NO: 132 | At b MKT mod cDNA | Modified nucleotide sequence of *A. thaliana* B methylketone thioesterase |
| SEQ ID NO: 189 | At b MKT mod ORF | Modified amino acid sequence of *A. thaliana* B methylketone thioesterase |
| SEQ ID NO: 133 | At c MKT mod cDNA | Modified nucleotide sequence of *A. thaliana* C methylketone thioesterase |
| SEQ ID NO: 190 | At c MKT mod ORF | Modified amino acid sequence of *A. thaliana* C methylketone thioesterase |
| SEQ ID NO: 134 | Pt MKT mod cDNA | Modified nucleotide sequence of *P. trichocarpa* methylketone thioesterase |
| SEQ ID NO: 191 | Pt MKT mod ORF | Modified amino acid sequence of *P. trichocarpa* methylketone thioesterase |
| SEQ ID NO: 135 | Rc MKT mod cDNA | Modified nucleotide sequence of *R. communis* methylketone thioesterase |
| SEQ ID NO: 192 | Rc MKT mod ORF | Modified amino acid sequence of *R. communis* methylketone thioesterase |
| SEQ ID NO: 136 | Vv a MKT mod cDNA | Modified nucleotide sequence of *V. vinifera* A methylketone thioesterase |
| SEQ ID NO: 193 | Vv a MKT mod ORF | Modified amino acid sequence of *V. vinifera* A methylketone thioesterase |
| SEQ ID NO: 137 | Vv b MKT mod cDNA | Modified nucleotide sequence of *V. vinifera* B methylketone thioesterase |
| SEQ ID NO: 194 | Vv b MKT mod ORF | Modified amino acid sequence of *V. vinifera* B methylketone thioesterase |
| SEQ ID NO: 138 | Osj MKT mod cDNA | Modified nucleotide sequence of *O. sativa japonica* methylketone thioesterase |
| SEQ ID NO: 195 | Osj MKT mod ORF | Modified amino acid sequence of *O. sativa japonica* methylketone thioesterase |
| SEQ ID NO: 139 | Osi MKT mod cDNA | Modified nucleotide sequence of *O. sativa indica* methylketone thioesterase |
| SEQ ID NO: 196 | Osi MKT mod ORF | Modified amino acid sequence of *O. sativa indica* methylketone thioesterase |
| SEQ ID NO: 140 | Pe MKT mod cDNA | Modified nucleotide sequence of *P. edulis* methylketone thioesterase |
| SEQ ID NO: 197 | Pe MKT mod ORF | Modified amino acid sequence of *P. edulis* methylketone thioesterase |
| SEQ ID NO: 141 | Zm MKT mod cDNA | Modified nucleotide sequence of *Z. mays* methylketone thioesterase |
| SEQ ID NO: 198 | Zm MKT mod ORF | Modified amino acid sequence of *Z. mays* methylketone thioesterase |
| SEQ ID NO: 142 | Sb MKT mod cDNA | Modified nucleotide sequence of *S. bicolor* methylketone thioesterase |

TABLE 7-continued

Example Methylketone Thioesterase sequences

| SEQ ID NO: | Name | Description |
|---|---|---|
| SEQ ID NO: 199 | Sb MKT mod ORF | Modified amino acid sequence of *S. bicolor* methylketone thioesterase |
| SEQ ID NO: 143 | Le MKT imp A cDNA | Improved A nucleotide sequence of *L. esculentum* ethylketone thioesterase |
| SEQ ID NO: 200 | Le MKT imp A ORF | Improved A amino acid sequence of *L. esculentum* methylketone thioesterase |
| SEQ ID NO: 144 | Pi MKT nor A cDNA | Normalized A nucleotide sequence of *P. integrifolia* methylketone thioesterase |
| SEQ ID NO: 201 | Pi MKT nor A ORF | Normalized A amino acid sequence of *P. integrifolia* methylketone thioesterase |
| SEQ ID NO: 145 | Pi MKT Lh ends cDNA | Nucleotide sequence of *P. integrifolia* methylketone thioesterase with Lh ends |
| SEQ ID NO: 202 | Pi MKT Lh ends ORF | Amino acid sequence of *P. integrifolia* methylketone thioesterase with Lh ends |
| SEQ ID NO: 146 | Lh MKT Pi ends cDNA | Nucleotide sequence of *L. hirsutum* methylketone thioesterase with Pi ends |
| SEQ ID NO: 203 | Lh MKT Pi ends ORF | Amino acid sequence of *L. hirsutum* methylketone thioesterase with Pi ends |
| SEQ ID NO: 147 | Le/Lh chim27 cDNA | Optimization 27 nucleotide acid sequence of *L. esculentum*/*L. hirsutum* chimeric MKT |
| SEQ ID NO: 204 | Le/Lh chim27 ORF | Optimization 27 amino acid sequence of *L. esculentum*/*L. hirsutum* chimeric MKT |
| SEQ ID NO: 148 | Le/Lh chim28 cDNA | Optimization 28 nucleotide acid sequence of *L. esculentum*/*L. hirsutum* chimeric MKT |
| SEQ ID NO: 205 | Le/Lh chim28 ORF | Optimization 28 amino acid sequence of *L. esculentum*/*L. hirsutum* chimeric MKT |
| SEQ ID NO: 149 | Le/Lh chim29 cDNA | Optimization 29 nucleotide acid sequence of *L. esculentum*/*L. hirsutum* chimeric MKT |
| SEQ ID NO: 206 | Le/Lh chim29 ORF | Optimization 29 amino acid sequence of *L. esculentum*/*L. hirsutum* chimeric MKT |
| SEQ ID NO: 150 | Le/Lh chim30 cDNA | Optimization 30 nucleotide acid sequence of *L. esculentum*/*L. hirsutum* chimeric MKT |
| SEQ ID NO: 207 | Le/Lh chim30 ORF | Optimization 30 amino acid sequence of *L. esculentum*/*L. hirsutum* chimeric MKT |
| SEQ ID NO: 151 | Lh/St chim1 cDNA | Optimization 1 nucleotide acid sequence of *L. hirsutum*/*S. tuberosum* chimeric MKT |
| SEQ ID NO: 208 | Lh/St chim1 ORF | Optimization 1 amino acid sequence of *L. hirsutum*/*S. tuberosum* chimeric MKT |
| SEQ ID NO: 152 | Lh/St chim2 cDNA | Optimization 2 nucleotide acid sequence of *L. hirsutum*/*S. tuberosum* chimeric MKT |
| SEQ ID NO: 209 | Lh/St chim2 ORF | Optimization 2 amino acid sequence of *L. hirsutum*/*S. tuberosum* chimeric MKT |
| SEQ ID NO: 153 | Lh/St chim3 cDNA | Optimization 3 nucleotide acid sequence of *L. hirsutum*/*S. tuberosum* chimeric MKT |
| SEQ ID NO: 210 | Lh/St chim3 ORF | Optimization 3 amino acid sequence of *L. hirsutum*/*S. tuberosum* chimeric MKT |
| SEQ ID NO: 154 | Lh/St chim4 cDNA | Optimization 4 nucleotide acid sequence of *L. hirsutum*/*S. tuberosum* chimeric MKT |
| SEQ ID NO: 211 | Lh/St chim4 ORF | Optimization 4 amino acid sequence of *L. hirsutum*/*S. tuberosum* chimeric MKT |
| SEQ ID NO: 155 | Lh/St chim5 cDNA | Optimization 5 nucleotide acid sequence of *L. hirsutum*/*S. tuberosum* chimeric MKT |
| SEQ ID NO: 212 | Lh/St chim5 ORF | Optimization 5 amino acid sequence of *L. hirsutum*/*S. tuberosum* chimeric MKT |
| SEQ ID NO: 156 | Lh/St chim6 cDNA | Optimization 6 nucleotide acid sequence of *L. hirsutum*/*S. tuberosum* chimeric MKT |
| SEQ ID NO: 213 | Lh/St chim6 ORF | Optimization 6 amino acid sequence of *L. hirsutum*/*S. tuberosum* chimeric MKT |
| SEQ ID NO: 157 | Lh/St chim7 cDNA | Optimization 7 nucleotide acid sequence of *L. hirsutum*/*S. tuberosum* chimeric MKT |
| SEQ ID NO: 214 | Lh/St chim7 ORF | Optimization 7 amino acid sequence of *L. hirsutum*/*S. tuberosum* chimeric MKT |
| SEQ ID NO: 158 | Lh/St chim8 cDNA | Optimization 8 nucleotide acid sequence of *L. hirsutum*/*S. tuberosum* chimeric MKT |
| SEQ ID NO: 215 | Lh/St chim8 ORF | Optimization 8 amino acid sequence of *L. hirsutum*/*S. tuberosum* chimeric MKT |
| SEQ ID NO: 159 | Lh/St chim9 cDNA | Optimization 9 nucleotide acid sequence of *L. hirsutum*/*S. tuberosum* chimeric MKT |
| SEQ ID NO: 216 | Lh/St chim9 ORF | Optimization 9 amino acid sequence of *L. hirsutum*/*S. tuberosum* chimeric MKT |
| SEQ ID NO: 160 | Lh/St chim10 cDNA | Optimization 10 nucleotide acid sequence of *L. hirsutum*/*S. tuberosum* chimeric MKT |
| SEQ ID NO: 217 | Lh/St chim10 ORF | Optimization 10 amino acid sequence of *L. hirsutum*/*S. tuberosum* chimeric MKT |
| SEQ ID NO: 161 | Lh/St chim11 cDNA | Optimization 11 nucleotide acid sequence of *L. hirsutum*/*S. tuberosum* chimeric MKT |
| SEQ ID NO: 218 | Lh/St chim11 ORF | Optimization 11 amino acid sequence of *L. hirsutum*/*S. tuberosum* chimeric MKT |

TABLE 7-continued

Example Methylketone Thioesterase sequences

| SEQ ID NO: 162 | Lh/St chim12 cDNA | Optimization 12 nucleotide acid sequence of *L. hirsutum/ S. tuberosum* chimeric MKT |
| --- | --- | --- |
| SEQ ID NO: 219 | Lh/St chim12 ORF | Optimization 12 amino acid sequence of *L. hirsutum/ S. tuberosum* chimeric MKT |
| SEQ ID NO: 163 | Lh/St chim13 cDNA | Optimization 13 nucleotide acid sequence of *L. hirsutum/ S. tuberosum* chimeric MKT |
| SEQ ID NO: 220 | Lh/St chim13 ORF | Optimization 13 amino acid sequence of *L. hirsutum/ S. tuberosum* chimeric MKT |
| SEQ ID NO: 164 | Lh/St chim14 cDNA | Optimization 14 nucleotide acid sequence of *L. hirsutum/ S. tuberosum* chimeric MKT |
| SEQ ID NO: 221 | Lh/St chim14 ORF | Optimization 14 amino acid sequence of *L. hirsutum/ S. tuberosum* chimeric MKT |
| SEQ ID NO: 165 | Lh/St chim15 cDNA | Optimization 15 nucleotide acid sequence of *L. hirsutum/ S. tuberosum* chimeric MKT |
| SEQ ID NO: 222 | Lh/St chim15 ORF | Optimization 15 amino acid sequence of *L. hirsutum/ S. tuberosum* chimeric MKT |
| SEQ ID NO: 166 | Lh/St chim16 cDNA | Optimization 16 nucleotide acid sequence of *L. hirsutum/ S. tuberosum* chimeric MKT |
| SEQ ID NO: 223 | Lh/St chim16 ORF | Optimization 16 amino acid sequence of *L. hirsutum/ S. tuberosum* chimeric MKT |
| SEQ ID NO: 167 | Lh/St chim17 cDNA | Optimization 17 nucleotide acid sequence of *L. hirsutum/ S. tuberosum* chimeric MKT |
| SEQ ID NO: 224 | Lh/St chim17 ORF | Optimization 17 amino acid sequence of *L. hirsutum/ S. tuberosum* chimeric MKT |
| SEQ ID NO: 168 | Lh/St chim18 cDNA | Optimization 18 nucleotide acid sequence of *L. hirsutum/ S. tuberosum* chimeric MKT |
| SEQ ID NO: 225 | Lh/St chim18 ORF | Optimization 18 amino acid sequence of *L. hirsutum/ S. tuberosum* chimeric MKT |
| SEQ ID NO: 169 | Ctp Le MKT nat cDNA | Native nucleotide sequence of *L. esculentum* methylketone thioesterase with chloroplast transit peptide from *L. esculentum* DCL1 |
| SEQ ID NO: 226 | Ctp Le MKT nat ORF | Native amino acid sequence of *L. esculentum* methylketone thioesterase with chloroplast transit peptide from *L. esculentum* DCL1 |

TABLE 8

Descriptions of other genetic elements

| SEQ ID NO: 227 | UBI3 promoter | Promoter from ubi3 gene in *Solanum tuberosum* |
| --- | --- | --- |
| SEQ ID NO: 228 | UBI3 terminator | Terminator from ubi3 gene in *Solanum tuberosum* |
| SEQ ID NO: 229 | DCL1 44 cDNA | Optimized nucleotide sequence for 44 amino acid plastid import leader from DCL1 *Lycopersicon esculentum* |
| SEQ ID NO: 230 | DCL1 44 ORF | Amino acid sequence for 44 amino acid plastid import leader from DCL1 from *Lycopersicon esculentum* |
| SEQ ID NO: 231 | DCL1 50 cDNA | Optimized nucleotide sequence for 50 amino acid leader from DCL1 from *Lycopersicon esculentum* |
| SEQ ID NO: 232 | DCL1 50 ORF | Amino acid sequence for 50 amino acid plastid import leader from DCL1 from *Lycopersicon esculentum* |
| SEQ ID NO: 233 | UBQ10 INTRON | 10$^{th}$ intron from *Arabidopsis thaliana* polyubiquitin gene |
| SEQ ID NO: 234 | HIS TAG | Poly histidine peptide tag |
| SEQ ID NO: 235 | HA TAG | Influenza hemagglutinin epitope |
| SEQ ID NO: 236 | HIS + HA TAG | Poly histidine tag appended to influenza hemagglutinin epitope |
| SEQ ID NO: 237 | AcV5 TAG | Baculovirus Autographa californica GP64 envelope fusion protein epitope |
| SEQ ID NO: 238 | FLAG TAG | Epitope tag derived from amino-acid leader peptide of the gene-10 product from bacteriophage T7 |
| SEQ ID NO: 239 | cMyc TAG | Synthetic peptide conjugated to KLH, corresponding to C-terminal amino acids 408-432 of Human c-Myc |
| SEQ ID NO: 240 | RB7 promoter | Root specific promoter from *Nicotiana tabacum* |
| SEQ ID NO: 241 | 35S/ubi3 promoter | Chimeric promoter of 35S enhancer and ubi3 |

Additional optimized methylketone thioesterases contemplated in this invention can be described by the amino sequence profiles below:

(SEQ ID NO: 242)
$X_0X_1X_2X_6X_7X_8$VEL$X_9$VRDYELDQ$X_{10}$GVVNNA$X_{11}$YASYCQH$X_{12}$RH $X_{13}X_{14}$LE$X_{15}$IG$X_{16}X_{17}X_{18}$D$X_{19}$V$X_{20}$R$X_{21}$G$X_{22}$ALA$X_{23}X_{24}$E $X_{25}X_{26}$LK$X_{27}$LAPLRSGDRF$X_{28}$V$X_{29}X_{30}$R$X_{31}$S$X_{32}X_{33}X_{34}X_{35}$AR L$X_{36}$FEHFIFKLP$X_{37}X_{38}$EPILEA$X_{39}X_{40}X_{41}$AV$X_{42}$L$X_{43}X_{44}X_{45}$Y RP$X_{46}$RIP$X_{47}$E$X_{48}X_{49}$SK$X_{50}$V$X_{51}$FL$X_{52}X_{53}$E$X_{54}X_{55}$ (SEQ ID NO: 243)
$X_0X_1X_2X_3X_4X_5X_6X_7X_8$VEL$X_9$VRDYELDQ$X_{10}$GVVNNA$X_{11}$YASYCQH $X_{12}$RH$X_{13}X_{14}$LE$X_{15}$IG$X_{16}X_{17}X_{18}$D$X_{19}$V$X_{20}$R$X_{21}$G$X_{22}$ALA$X_{23}$ $X_{24}$E$X_{25}X_{26}$LK$X_{27}$LAPLRSGDRF$X_{28}$V$X_{29}X_{30}$R$X_{31}$S$X_{32}X_{33}X_{34}$ $X_{35}$ARL$X_{36}$FEHFIFKLP$X_{37}X_{38}$EPILEA$X_{39}X_{40}X_{41}$AV$X_{42}$L$X_{43}$ $X_{44}X_{45}$YRP$X_{46}$RIP$X_{47}$E$X_{48}X_{49}$SK$X_{50}$V$X_{51}$FL$X_{52}X_{53}$KSCG$X_{56}$ QH$X_{57}$L

(SEQ ID NO: 244)
$X_0X_1X_2X_3X_4X_5X_6X_7X_8$VEM$X_9$VRDYELDQ$X_{10}$GVVNNA$X_{11}$YASYCQH $X_{12}$RH$X_{13}X_{14}$LE$X_{15}$VG$X_{16}X_{17}X_{18}$D$X_{19}$V$X_{20}$R$X_{21}$G$X_{22}$SLA$X_{23}$ $X_{24}$E$X_{25}X_{26}$LK$X_{27}$FAPLRSGDRF$X_{28}$V$X_{29}X_{30}$R$X_{31}$A$X_{32}X_{33}X_{34}$

-continued $X_{35}$ARL$X_{36}$FEHFIFKLP$X_{37}X_{38}$EPILEA$X_{39}X_{40}X_{41}$AV$X_{42}$L$X_{43}$
$X_{44}X_{45}$YRP$X_{46}$RIP$X_{47}$E$X_{48}X_{49}$SK$X_{50}$Q$X_{51}$F$X_{58}$S$X_{59}X_{60}$S$X_{61}$
$X_{62}$ Preferred Residues (Underlined) and Other Residue Examples $X_0$=L, M, MA, X where X=1 to 15 amino acids; $X_1$=<u>S</u>, <u>N</u>, <u>R</u>, <u>A</u>, T, G; $X_2$=<u>D</u>, <u>E</u>, <u>G</u>, <u>R</u>, S, L, deletion; $X_3$=<u>Q</u>, L, <u>E</u>, <u>V</u>; $X_4$=<u>V</u>, <u>L</u>, <u>D</u>, <u>E</u>; $X_5$=<u>Y</u>, <u>K</u>, <u>Q</u>; $X_6$=<u>F</u>, <u>H</u>, Q, <u>P</u>, L, V; $X_7$=<u>H</u>, <u>Y</u>, <u>F</u>, L, V; $X_8$=<u>D</u>, <u>E</u>, G; $X_9$=<u>K</u>, <u>T</u>, Q; $X_{10}$=<u>F</u>, <u>Y</u>; $X_{11}$=<u>T</u>, <u>I</u>, <u>V</u>; $X_{12}$=<u>C</u>, <u>G</u>; $X_{13}$=<u>E</u>, <u>A</u>; $X_{14}$=<u>L</u>, <u>F</u>, V; $X_{15}$=<u>K</u>, <u>R</u>, <u>A</u>, <u>S</u>, N, T, C; $X_{16}$=<u>V</u>, <u>I</u>, <u>F</u>, L; $X_{17}$=<u>S</u>, <u>N</u>; $X_{18}$=<u>A</u>, <u>V</u>, <u>C</u>, <u>P</u>; $X_{19}$=<u>E</u>, <u>A</u>, <u>V</u>; $X_{20}$=<u>A</u>, <u>T</u>, C, S; $X_{21}$=<u>S</u>, <u>N</u>, T, I; $X_{22}$=<u>D</u>, <u>E</u>, <u>N</u>; $X_{23}$=<u>L</u>, <u>V</u>, <u>I</u>, T; $X_{24}$=<u>T</u>, <u>S</u>; $X_{25}$=<u>L</u>, M; $X_{26}$=<u>S</u>, <u>T</u>, <u>H</u>, <u>N</u>; $X_{27}$=<u>F</u>, <u>Y</u>; $X_{28}$=<u>V</u>, <u>I</u>; $X_{29}$=<u>T</u>, <u>K</u>, <u>R</u>; $X_{30}$=<u>V</u>, <u>A</u>, <u>T</u>; $X_{31}$=<u>L</u>, <u>I</u>, <u>V</u>; $X_{32}$=<u>H</u>, <u>R</u>, <u>D</u>, <u>G</u>, <u>S</u>, N; $X_{33}$=<u>S</u>, <u>T</u>, <u>I</u>, <u>F</u>, A; $X_{34}$=<u>S</u>, <u>T</u>, <u>K</u>; $X_{35}$=<u>A</u>, <u>G</u>, V, M; $X_{36}$=<u>F</u>, <u>Y</u>, <u>I</u>; $X_{37}$=<u>D</u>, <u>N</u>; $X_{38}$=<u>R</u>, <u>Q</u>, <u>E</u>, <u>H</u>; $X_{39}$=<u>R</u>, <u>K</u>; $X_{40}$=<u>G</u>, <u>A</u>; $X_{41}$=<u>I</u>, <u>T</u>, M; V; $X_{42}$=<u>Y</u>, <u>W</u>, <u>C</u>, R; $X_{43}$=<u>N</u>, <u>D</u>; $X_{44}$=<u>R</u>, <u>K</u>, <u>N</u>; $X_{45}$=<u>I</u>, <u>S</u>, <u>N</u>, <u>K</u>, <u>D</u>, R; $X_{46}$=<u>I</u>, <u>V</u>, <u>T</u>, A; $X_{47}$=<u>S</u>, <u>T</u>, <u>A</u>, <u>P</u>, <u>R</u>; $X_{48}$=<u>F</u>, <u>I</u>, <u>M</u>, <u>L</u>; $X_{49}$=<u>K</u>, <u>R</u>, <u>N</u>, <u>S</u>, <u>L</u>; $X_{50}$=<u>F</u>, <u>L</u>, <u>I</u>, <u>M</u>; $X_{51}$=<u>L</u>, <u>Q</u>, <u>K</u>, <u>H</u>, <u>F</u>; $X_{52}$=<u>H</u>, <u>R</u>, <u>K</u>; $X_{53}$=<u>Q</u>, <u>N</u>, <u>H</u>, C, I; $X_{54}$=<u>A</u>, <u>E</u>, D; $X_{55}$=nothing, S, SH, SN, LN, PS; $X_{56}$=<u>V</u>, <u>T</u>, I; $X_{57}$=<u>H</u>, <u>R</u>, K; $X_{58}$=<u>T</u>, <u>S</u>, L; $X_{59}$=<u>E</u>, K, R, V; $X_{60}$=<u>G</u>, <u>D</u>; $X_{61}$=<u>S</u>, <u>R</u>, K; $X_{62}$=<u>S</u>, <u>G</u>, GX where X=1 to 15 amino acids.

Also contemplated are examples where 1 to 10 of the conserved residues are substituted with another amino acid. Particularly preferred are cases where the conserved residue substitutions are conservative (e.g., D to E, A to G, L to V, K to R, etc). In some embodiments each X independently represents 1, 2, 3, 5, 6, 7, 8, 9, or 10 amino acids.

Example 7

Methods for Construct Detection in Transgenic Plants

This example describes the detection and measurement of the recombinant DNA construct in the transgenic plant cell. Detecting or measuring transcription of the recombinant DNA construct in the transgenic plant cell of the invention can be achieved by any suitable method, including protein detection methods (for example, western blots, ELISAs, and other immunochemical methods), measurements of enzymatic activity, or nucleic acid detection methods (for example, Southern blots, northern blots, PCR, RT-PCR, fluorescent in situ hybridization). Such methods are well known to those of ordinary skill in the art as evidenced by the numerous handbooks available; see, for example, Joseph Sambrook and David W. Russell, "Molecular Cloning: A Laboratory Manual" (third edition), Cold Spring Harbor Laboratory Press, NY, 2001; Frederick M. Ausubel et al. (editors) "Short Protocols in Molecular Biology" (fifth edition), John Wiley and Sons, 2002; John M. Walker (editor) "Protein Protocols Handbook" (second edition), Humana Press, 2002; and Leandro Peña (editor) "Transgenic Plants: Methods and Protocols", Humana Press, 2004.

DNA sequence information provided by the invention allows for the preparation of relatively short DNA (or RNA) sequences having the ability to specifically hybridize to DNA sequences of the selected polynucleotides disclosed herein. The polynucleotides disclosed in the present invention include SEQ ID NO: 5-8, SEQ ID NO: 11-56 and SEQ ID NO: 131-168. In these aspects, nucleic acid probes of an appropriate length are prepared. The ability of the nucleic acid probes to specifically hybridize to one or more of these gene coding sequences lends them particular utility in a variety of embodiments. Most importantly, the probes may be used in a variety of assays for detecting the presence of complementary sequences in a given sample.

In certain embodiments, it is advantageous to use oligonucleotide primers. The sequence of such primers is designed using a portion of a polynucleotide sequence of the present invention to be homologous or complementary to the sequence for use in detecting, amplifying a defined polynucleotide segment using PCR™ technology (A Guide to Methods and Applications, Academic Press: San Diego, 1990). PCR primer pairs can be derived from a known sequence, for example, by using computer programs intended for that purpose such as Primer (Version 0.5,© (1991, Whitehead Institute for Biomedical Research, Cambridge, Mass.). Primers and probes based on the sequences disclosed herein can be used to confirm and, if necessary, to modify the disclosed sequences by conventional methods, for example, by re-cloning and re-sequencing. Exemplary PCR reaction conditions may include: Component Amount/Volume required sub-library aliquot 1 µl Gene-specific primer 1, 1 µl (100 pmol, GenomeWalker™) Adaptor primer 1 (AP1), 1 µl dNTP mix (10 mM of each dNTP), 1 µl DMSO 2.5 µl (or 2-5% final concentration) 10×PCR buffer, 5 µl (final concentration of 1×) Amplitaq Gold™, 0.5 µl distilled water for final reaction volume of 50 µl reaction conditions for primary PCR:

A. 9 minutes at 95° C.;
B. 94° C. for 2 seconds, 70° C. for 3 minutes; repeat 94° C./70° C. cycling for total of 7 times;
C. 94° C. for 2 seconds, 65° C. for 3 minutes; repeat 94° C./65° C. cycling for total of 36 times;
D. 65° C. for 4 minutes as a final extension;
E. 10° C. for an extended incubation
NESTED PCR (secondary PCR reaction) Component Amount/Volume Required 1:50 dilution of the primary PCR reaction; 1 µl Gene-specific primer 2; 1 µl (100 pmol, GenomeWalker™ Adaptor primer 2; 1 µl or 3 (AP2 or AP3), dNTP mix (10 mM of each dNTP); 1 µl DMSO; 2.5 µl 10×PCR buffer containing $MgCl_2$; 5 µl (final concentration of 1×) Amplitaq Gold™; 0.5 µl distilled water to final reaction volume of 50 µA reaction. Conditions for Nested PCR:

A. 9 minutes at 95° C.;
B. 94° C. for 2 seconds, 70° C. for 3 minutes; repeat 94° C./70° C. cycling for total of 5 times;
C. 94° C. for 2 seconds, 65° C. for 3 minutes; repeat 94° C./65° C. cycling for total of 24 times;
D. 65° C. for 4 minutes as a final extension;
E. 10° C. for an extended incubation.
PCR conditions can be modified from the described conditions by those skilled in the method to produce an amplicon.

Detection of foreign gene expression in transgenic plant is monitored by an immunological method for example ELISA (enzyme-linked immunosorbent assays) for a quantitative determination of the level of corresponding protein obtained. Quantitative determination of the encoded protein in the leaves of transgenic plants is performed using ELISA, for example as disclosed in Clark et al.: ELISA Techniques. In: Weissbach A, Weissbach H (eds) *Methods in Enzymology* 118:742-766, Academic Press, Florida (1986).

Certain Useful sequences are described below.

SEQ ID NO 1: *Lycopersicon esculentum* MKT cDNA
ATGGCTGAGTTCCATGAAGTTGAACTCAAAGTCCGGGACTATGAATTGGATCAGTATGGTGTTGTAAACA -continued

```
ATGCTATTTATGCAAGTTATTGCCAACATGGTCGTCATGAGCTTCTAGAAAGGATTGGTATAAGTGCTGA
TGAAGTGGCACGCAGTGGTGACGCACTAGCACTAACAGAGCTGTCACTTAAGTATCTAGCACCTCTAAGG
AGTGGAGATAGATTTGTCGTGAAGGCACGAATATCTGATTCTTCAGCTGCTCGTTTGTTTTTCGAACACT
TCATCTTCAAGCTTCCAGATCAAGAGCCCATCTTGGAGGCAAGAGGAATAGCAGTGTGGCTCAATAAAAG
TTACCGTCCTGTCCGAATCCCGGCAGAGTTCAGATCAAAATTTGTTCAGTTCCTTCGCCAGGAGGCATCC
AAC
``` gi|196122242|gb|EU908050.1|Solanum lycopersicum thioesterase-like protein (MKS2) mRNA, partial cds SEQ ID NO 57: *Lycopersicon esculentum* MKT ORF
MAEFHEVELKVRDYELDQYGVVNNAIYASYCQHGRHELLERIGISADEVARSGDALALTELSLKYLAPLR
SGDRFVVKARISDSSAARLFFEHFIFKLPDQEPILEARGIAVWLNKSYRPVRIPAEFRSKFVQFLRQEAS
N gi|196122243|gb|ACG69783.1|thioesterase-like protein [*Solanum lycopersicum*]

SEQ ID NO 2: *Petunia integrifolia* subsp. *inflata* MKT cDNA
```
CATAAATTGGGATGGAGGGGTACAATCTGTTACCCCTCGTCCATTCATTAAGGGTAAGTTTAATTGTTAA
TTTAATAATGTGTCGTTCTTTTTTGTGAGGAGGTGTGAGTGGCTGGCTGTGCTGGGTCTGCGGAGTGGTA
AAGGCAGACCAAAGAAGAATTGGGGCGAGGTGATTCGACATGATATGGCTCGCCTCCAGGTCACCGAGGA
CACGACCCTTGACAGGAAAGCGTGGAGGTCTAGGATTAGGGTAGAAGGTTAGGTGAAAGGGGCTGATAGA
TCTCGCCCAGTGTTCCCCTCCTTCCCCCGCCGCCTTTCGACCCGCGGGAGTATACAATGTCAGCCCAACA
TAGGTTGTTAACCAAAAAGAGAAGTTCCCGTGAAAACAGAAAAGACCTCCCCCTTAACCCCCCTTACT
TGGCAGATTCAGATTGAGTGCCGTCATTTTAGCGAATGAATGAGTTCTATGAAGTCGAACTCAAAGTCCG
GGACTATGAGTTGGATCAATATGGTGTTGTAAACAATGCTATTTATGCTAGTTATTGCCAACATTGTCGG
CATGAGCTTCTGGAAAAGATTGGCGTAAATGCTGATGCAGTGGCACGCAATGGTGAAGCATTAGCACTAA
CAGAGATGACACTAAAGTATCTAGCACCTCTAAGGAGTGGAGACAGATTCATTGTGAAGGTGCGAATATC
TGACTCTTCAGCTGCTCGTTTGTTCTTTGAACACTTCATCTTCAAGCTTCCAGATCAAGAGCCTATCTTG
GAGGCAAGAGGAACAGCAGTGTGGCTTAATAAAAGTTACCGTCCTGAATTCCTTCAGAGTTCAGAT
CAAAATTCGTTCAGTTCCTTCGCCAGGAGGCATGAACTAGTGTGCTTGTCTACAAAAGTCCAGAAAAGTT
GTCTTGCTCAAGAATTTCATGAGCAAAAGCTCAAACTAATGTATATGAAGAACTCAATTCATACTGCTTC
GCATAGAGGCAAGCGTTGGGGTCAATTAAAAGAAGTAAAAGCCTACACAATTGATTGGGAAAATCAGCTG
TTGGAACTCAAAAGTGGGGAGCTAGAGGACCCTTAAAAAGAGGGCAGAAATTTATTTTTCCATTAGATTG
GTGATGCACTTAGTTTATCTCCTTTGTGAATTGAAAGCACTTATTCAATTGAAAGTTTAGTAATCTGTAT
TTTTTCAGGATAAATTCTAGATATAAGAAATTTCAAATTTATAAAGTTCTCTTAAAAAGGGTCTTTCTTC
AAATGTGACTAAGTTTGAAATGTCAAGGCTCAGGGACTGTGTGTCCAGTGTTCTGTCTCTTCTTCAGTTA
CTCTGAATTTGCTGTGTAGATCCTTG
``` gi|46371864|gb|AY577288.1|Petunia integrifolia subsp. inflata clone Pi061803d putative pollen thioesterase mRNA, complete cds SEQ ID NO 58: *Petunia integrifolia* subsp. *inflata* MKT ORF
MNEFYEVELKVRDYELDQYGVVNNAIYASYCQHCRHELLEKIGVNADAVARNGEALALTEMTLKYLAPLR
SGDRFIVKVRISDSSAARLFFEHFIFKLPDQEPILEARGTAVWLNKSYRPVRIPSEFRSKFVQFLRQEA gi|46371865|gb|AAS90598.1|putative pollen thioesterase [*Petunia integrifolia* subsp. *inflata*]

SEQ ID NO 3: *Lycopersicon hirsutum* f. *glabratum* MKT cDNA
```
ATGAGTGATCAGGTCTATCACCATGACGTTGAACTCACAGTCAGGGACTATGAGTTGGATCAGTTTGGTG
TTGTAAATAATGCTACTTATGCGAGTTATTGTCAACATTGTCGTCATGCGTTTCTAGAAAAAATTGGTGT
TAGTGTTGATGAAGTAACGCGAAATGGTGATGCATTAGCTGTAACAGAGCTCTCACTTAAGTTTCTAGCA
CCACTAAGGAGTGGAGATAGATTCGTGGTGAGGGCGCGATTATCCCACTTTACAGTAGCTCGATTGTTTT
TCGAGCATTTCATCTTCAAGCTTCCAGATCAAGAGCCTATATTGGAGGCAAGAGGAATAGCAGTGTGGCT
TAATAGAAGTTATCGTCCTATTCGAATTCCGTCAGAGTTCAATTCAAAATTTGTTAAATTCCTTCACCAG
AAGAGTTGCGGTGTACAACATCATCTC
``` gi|195979084|gb|EU883793.1|*Lycopersicon hirsutum* f. *glabratum* thioesterase-like protein (Sh-MKS2) mRNA, partial cds SEQ ID NO 59: *Lycopersicon hirsutum* f. *glabratum* MKT ORF
MSDQVYHHDVELTVRDYELDQFGVVNNATYASYCQHCRHAFLEKIGVSVDEVTRNGDALAVTELSLKFLA
PLRSGDRFVVRARLSHFTVARLFFEHFIFKLPDQEPILEARGIAVWLNRSYRPIRIPSEFNSKFVKFLHQ
KSCGVQHHL gi|195979085|gb|ACG63705.1|thioesterase-like protein [*Lycopersicon hirsutum* f. *glabratum*]

SEQ ID NO 4: *Solanum tuberosum* MKT cDNA
```
CCTTAGACAACAGATTTCCCAATATTTACAATTTCCTTCTCTTCTACCTCTGAATTTTTTCGTCAAATGT
CTCATTCCGTCTGCATTGCACCCAACCCACTGTTGCTGAATCATCGGCAACGACCGTCTACATTTCCGTT
CATCCCTCACCGGCAACTCCCGCTCCCAAATTTACAGTTATCGGCCCGTAAATCGAGGAGTTTTGAAGCT
CATAATGCATTCGATCTCAAAGATACCCAAGGAATGGGTGATCAGCTCTATCAACATGAAGTTGAACTCC
AAGTCAGGGACTATGAATTGGATCAGTTTGGTGTTGTAAACAATGCTACTTATGCAAGTTATTGTCAACA
TTGCCGTCATGAGTTTCTTGAAAAGATTGGTGTAAGTGTTGATGAAGTATGTCGCACTGGTGAAGCATTA
GCAACAACAGAGCTTTCACTTAAGTATCTAGCACCTCTAAGGAGTGGAGATAGATTTGTGGTGAAGGTGC
GAATATCCCGCTCTACAGCAGCTCGATTGTTTTTCGAGCATTTCATCTTCAAGCTTCCAGATCAAGAGCC
TATATTGGAGGCAAGAGGAATAGCAGTGTGGCTTAATAGAAGTTACCGTCCTATCCGAATTCCATCAGAG
```

TTCAGTTCAAAATTTGTTCAGTTCCTTCACCAGAAGAGTTGCGGTACACAACACCGTCTCTAGAACCTAC
TCGTGGAATTACATTGGTATTATTTCTGAATTTAGTGCTTGTAATGTCTAACAACATTTGATCTTTCATT
AAATTGAATG gi|13614793|gb|BG596653.1|BG596653 EST495331 cSTS Solanum tuberosum cDNA
clone cSTS15E12 5' sequence, mRNA sequence SEQ ID NO 60: Solanum tuberosum MKT ORF
MSHSVCIAPNPLLLNHRQRPSTFPFIPHRQLPLPNLQLSARKSRSFEAHNAFDLKDTQGMGDQLYQHEVE
LQVRDYELDQFGVVNNATYASYCQHCRHEFLEKIGVSVDEVCRTGEALATTELSLKYLAPLRSGDRFVVK
VRISRSTAARLFFEHFIFKLPDQEPILEARGIAVWLNRSYRPIRIPSEFSSKFVQFLHQKSCGTQHRL SEQ ID NO 5: Lycopersicon esculentum MKT modified cDNA
ATGGCTGAGTTCCATGAAGTTGAACTCAAAGTCaGGGACTATGAATTGGATCAGTATGGTGTTGTAAACAATGCTAT
cTATGCAAGTTATTGCCAACATGGTCGTCATGAGCTcCTtGAAAGGATTGGTATAAGTGCTGATGAAGTGGCACGtA
GTGGTGACGCACTtGCACTtACAGAGtTGTCACTTAAGTATCTtGCACCTCTtAGGAGTGGAGATAGATTTGTCGTG
AAaGCtaGAATATCTGATTCTTCAGCTGCTCGTTTGTTcTTtGAACACTTCATCTTCAaCTTCCtGATCAAGAGCC
CATCTTGGAGGCAAGAGGAATAGCAGTGTGGCTCAAcAAgAGTTACCGTCCTGTCaGAATCCCaGCAGAGTTCAGAT
CAAAATTTGTTCAGTTCCTTCGtCAGGAGGCATCCAACtga SEQ ID NO 61: Lycopersicon esculentum MKT modified ORF
MAEFHEVELKVRDYELDQYGVVNNAIYASYCQHGRHELLERIGISADEVARSGDALALTELSLKYLAPLRSGDRFVV
KARISDSSAARLFFEHFIFKLPDQEPILEARGIAVWLNKSYRPVRIPAEFRSKFVQFLRQEASN SEQ ID NO 6: Petunia integrifolia MKT modified cDNA
ATGgctAATGAGTTCTATGAAGTCGAACTCAAAGTCaGGGACTATGAGTTGGATCAATATGGTGTTGTAAACAATGC
TATcTATGCTAGTTATTGCCAACATTGTAGGCATGAGCTTCTtGAAAAGATTGGCGTAAATGCTGATGCAGTGGCAC
GtAATGGTGAAGCATTAGCACTtACAGAGATGACACTcAAGTATCTtGCACCTCTcAGGAGTGGAGACAGATTCATT
GTGAAaGTtaGAATATCTGACTCTTCAGCTGCTCGTTTGTTCTTTGAACACTTCATCTTCAAaCTTCCtGATCAAGA
GCCTATCTTGGAGGCAAGAGGAACAGCAGTGTGGCTTAAcAAgAGTTACCGTCCTGTCaGAATcCCTTCAGAGTTCA
GATCAAAATTCGTTCAGTTCCTTCGtCAGGAGGCATGA SEQ ID NO 62: Petunia integrifolia MKT modified ORF
MANEFYEVELKVRDYELDQYGVVNNAIYASYCQHCRHELLEKIGVNADAVARNGEALALTEMTLKYLAPLRSGDRFI
VKVRISDSSAARLFFEHFIFKLPDQEPILEARGTAVWLNKSYRPVRIPSEFRSKFVQFLRQEA SEQ ID NO 7: Lycopersicon hirsutum MKT modified cDNA
ATGgctAGTGATCAGGTCTATCACCATGACGTTGAACTCACAGTCAGGGACTATGAGTTGGATCAGTTTGGTGTTGT
AAATAATGCTACTTATGCtAGTTATTGTCAACATTGTCGTCATGCtTTcCTtGAgAAgATTGGTGTTAGTGTTGATG
AAGTAACcCGtAATGGTGATGCATTAGCTGTAACAGAGCTCTCACTTAAGTTTCTtGCACCACTtAGGAGTGGAGAT
AGATTCGTGGTGAGGGCtaGATTgTCCCACTTTACAGTAGCTaGATTGTTcTTtGAGCATTTCATCTTCAaCTTCC
tGATCAAGAGCCTATATTGGAGGCAAGAGGAATAGCAGTGTGGCTTAATAGAAGTTATCGTCCTATTCGtATTCCaT
CAGAGTTCAATTCAAAATTTGTTAAATTCCTTCACCAGAAGAGTTGCGGTGTACAACATCATCTCtga SEQ ID NO 63: Lycopersicon hirsutum MKT modified ORF
MASDQVYHHDVELTVRDYELDQFGVVNNATYASYCQHCRHAFLEKIGVSVDEVTRNGDALAVTELSLKFLAPLRSGD
RFVVRARLSHFTVARLFFEHFIFKLPDQEPILEARGIAVWLNRSYRPIRIPSEFNSKFVKFLHQKSCGVQHHL SEQ ID NO 8: Solanum tuberosum MKT modified cDNA
ATGgctGGTGATCAGCTCTATCAACATGAAGTTGAACTCCAAGTCAGGGACTATGAATTGGATCAGTTTGGTGTTGT
AAACAATGCTACTTATGCAAGTTATTGTCAACATTGCCGTCATGAGTTTCTTGAgAAGATTGGTGTAAGTGTTGATG
AAGTATGTaGAACTGGTGAAGCATTAGCAACAACAGAGCTTTCACTTAAGTATCTtGCACCTCTcAGGAGTGGAGAT
AGATTTGTGGTGAAGGTGaGAATATCCaGGTCTACAGCAGCTCGtTTGTTcTTCGAGCATTTCATCTTCAaCTTCC
AGATCAAGAGCCTATATTGGAGGCAAGAGGAATAGCAGTGTGGCTTAATAGAAGTTACCGTCCTATCaGAATaCCAT
CAGAGTTCAGTTCAAAgTTTGTTCAGTTCCTTCACCAGAAGAGTTGCGGTACACAACACCGTCTCTAG SEQ ID NO 64: Solanum tuberosum MKT modified ORF
MAGDQLYQHEVELQVRDYELDQFGVVNNATYASYCQHCRHEFLEKIGVSVDEVCRTGEALATTELSLKYLAPLRSGD
RFVVKVRISRSTAARLFFEHFIFKLPDQEPILEARGIAVWLNRSYRPIRIPSEFSSKFVQFLHQKSCGTQHRL.

SEQ ID NO 9: Modified L. esculentum MKT cDNA with heterologous plastid transit sequence
Atggcttcaatttgtacttcaaattttcactttctatgcagaaaaaacaattctagccctatttctcatcatctact
gttatctccctcttctttatccttctcacgttgcggcggattgcggttgtgtcgtgcggccgcaGAGTTCCATGAAG
TTGAACTCAAAGTCAGGGACTATGAATTGGATCAGTATGGTGTTGTAAACAATGCTATCTATGCAAGTTATTGCCAA
CATGGTCGTCATGAGCTCCTTGAAAGGATTGGTATAAGTGCTGATGAAGTGGCACGTAGTGGTGACGCACTTGCACT
TACAGAGTTGTCACTTAAGTATCTTGCACCTCTTAGGAGTGGAGATAGATTTGTCGTGAAAGCTAGAATATCTGATT
CTTCAGCTGCTCGTTTGTTCTTTGAACACTTCATCTTCAAACTTCCTGATCAAGAGCCCATCTTGGAGGCAAGAGGA
ATAGCAGTGTGGCTCAACAAGAGTTACCGTCCTGTCAGAATCCCAGCAGAGTTCAGATCAAAATTTGTTCAGTTCCT
TCGTCAGGAGGCATCCAACTGA SEQ ID NO 65: Modified L. esculentum MKT ORF with heterologous plastid transit peptide
masictsnfhflcrknnsspishhlllspsslsfsrcgglrlcraaaEFHEVELKVRDYELDQYGVVNNAIYASYCQ
HGRHELLERIGISADEVARSGDALALTELSLKYLAPLRSGDRFVVKARISDSSAARLFFEHFIFKLPDQEPILEARG
IAVWLNKSYRPVRIPAEFRSKFVQFLRQEASN SEQ ID NO 10: Modified L. hirsutum MKT cDNA with heterologous plastid transit sequence
Atggcttcaatttgtacttcaaattttcactttctttgcaggaagaacaattctagccctatttctcatcatctact
tttatctccctcttctttatccttctcacgttgcggcggattgcgtttgtgtcgtgcggccgcaAGTGATCAGGTCT
ATCACCATGACGTTGAACTCACAGTCAGGGACTATGAGTTGGATCAGTTTGGTGTTGTAAATAATGCTACTTATGCt
AGTTATTGTCAACATTGTCGTCATGCtTTcCTtGAgAAgATTGGTGTTAGTGTTGATGAAGTAACcCGtAATGGTGA
TGCATTAGCTGTAACAGAGCTCTCACTTAAGTTTCTtGCACCACTtAGGAGTGGAGATAGATTCGTGGTGAGGGCta -continued
```
GATTgTCCCACTTTACAGTAGCTaGATTGTTcTTtGAGCATTTCATCTTCAAaCTTCCtGATCAAGAGCCTATATTG
GAGGCAAGAGGAATAGCAGTGTGGCTTAATAGAAGTTATCGTCCTATTCGtATTCCaTCAGAGTTCAATTCAAATTT
TGTTAAATTCCTTCACCAGAAGAGTTGCGGTGTACAACATCATCTCtga
```

SEQ ID NO 66: Modified *L. hirsutum* MKT ORF with heterologous plastid transit peptide
```
masictsnfhflcrknnsspishhlllspsslsfsrcgglrlcraaaSDQVYHHDVELTVRDYELDQFGVVNNATYA
SYCQHCRHAFLEKIGVSVDEVTRNGDALAVTELSLKFLAPLRSGDRFVVRARLSHFTVARLFFEHFIFKLPDQEPIL
EARGIAVWLNRSYRPIRIPSEFNSKFVKFLHQKSCGVQHHL
```

SEQ ID NO 11: *Lycopersicon esculentum* optimization 1 cDNA
```
ATGagtGAGTTCCATGAAGTTGAACTCAAAGTCaGGGACTATGAATTGGATCAGTATGGTGTTGTAAACAATGCTAT
cTATGCAAGTTATTGCCAACATtgcCGTCATGAGCTcCTtGAAAGGATTGGTgtgAGTGCTGATGAAGTGGCACGtA
GTGGTGACGCACTtGCACTtACAGAGtTGTCACTTAAGTATCTtGCACCTCTtAGGAGTGGAGATAGATTTGTCGTG
AAaGCtaGAATATCTGATTCTTCAGCTGCTCGTTTGTTcTTtGAACACTTCATCTTCAAaCTTCCtGATCAAGAGCC
CATCTTGGAGGCAAGAGGAATAGCAGTGTGGCTCAAcAAgAGTTACCGTCCTGTCaGAATCCCatccGAGTTCAGAT
CAAAATTTGTTCAGTTCCTTCGtCAGGAGGCATCCAAC
```

SEQ ID NO 67: *Lycopersicon esculentum* optimization 1 ORF
```
MSEFHEVELKVRDYELDQYGVVNNAIYASYCQHCRHELLERIGVSADEVARSGDALALTELSLKYLAPLR
SGDRFVVKARISDSSAARLFFEHFIFKLPDQEPILEARGIAVWLNKSYRPVRIPSEFRSKFVQFLRQEAS
N
```

SEQ ID NO 12: *Petunia integrifolia* optimization 1 cDNA
```
ATGAATGAGTTCTATGAAGTCGAACTCAAAGTCaGGGACTATGAGTTGGATCAATATGGTGTTGTAAACAATGCTAT
cTATGCTAGTTATTGCCAACATTGTaGGCATGAGCTTCTtGAAAAGATTGGCGTAagtGCTGATgagGTGGCACGtA
ATGGTGAAGCATTAGCACTtACAGAGtTAACACTcAAGTACTTtGCACCTCTcAGGAGTGGAGATAGACAGATTCgttGTG
AAaGTtaGAATATCTGACTCTTCAGCTGCTCGTTTGTTCTTTGAACACTTCATCTTCAAaCTTCCtGATCAAGAGCC
TATCTTGGAGGCAAGAGGAatcGCAGTGTGGCTTAAcAAgAGTTACCGTCCTGTCaGAATcCCTTCAGAGTTCAGAT
CAAAATTCGTTCAGTTCCTTCGtCAGGAGGCAtcaaac
```

SEQ ID NO 68: *Petunia integrifolia* optimization 1 ORF
```
MNEFYEVELKVRDYELDQYGVVNNAIYASYCQHCRHELLEKIGVSADEVARNGEALALTELTLKYLAPLR
SGDRFVVKVRISDSSAARLFFEHFIFKLPDQEPILEARGIAVWLNKSYRPVRIPSEFRSKFVQFLRQEAS
N
```

SEQ ID NO 13: *Lycopersicon hirsutum* optimization 1 cDNA
```
ATGAGTGATCAGGTCTATttcCATGACGTTGAACTCaagGTCAGGGACTATGAGTTGGATCAGTTTGGTGTTGTAAA
TAATGCTACTTATGCtAGTTATTGTCAACATTGTCGTCATgagTTcCTtGAgAAgATTGGTGTTAGTGTTGATGAAG
TAgctCGtAATGGTGATGCATTAGCTcttACAGAGCTCTCACTTAAGTTCTTtGCACCACTtAGGAGTGGAGATAGA
TTCGTGGTGAGGGCtaGAAtcTCCgatagtACAgcaGCTaGATTGTTcTTtGAGCATTTCATCTTCAAaCTTCCtGA
TCAAGAGCCTATATTGGAGGCAAGAGGAATAGCAGTGTGGCTTAATAGAAGTTATCGTCCTATTCGtATTCCaTCAG
AGTTCagaTCAAAATTTGTTcagTTCCTTCACCAGAAGAGTTGCGGTGTACAACATCATCTC
```

SEQ ID NO 69: *Lycopersicon hirsutum* optimization 1 ORF
```
MSDQVYFHDVELKVRDYELDQFGVVNNATYASYCQHCRHEFLEKIGVSVDEVARNGDALALTELSLKFLA
PLRSGDRFVVRARISDSTAARLFFEHFIFKLPDQEPILEARGIAVWLNRSYRPIRIPSEFRSKFVQFLHQ
KSCGVQHHL
```

SEQ ID NO 14: *Solanum tuberosum* optimization 1 cDNA
```
ATGagtGATCAGCTCTATttcCATGAAGTTGAACTCaagGTCAGGGACTATGAATTGGATCAGTTTGGTGTTGTAAA
CAATGCTACTTATGCAAGTTATTGTCAACATTGCCGTCATGAgAAGATTTCTTGAgAAGATTGGTGTAAGTGTTGATGAAG
TAgcaaGaACTGGTGAAGCATTAGCACttACAGAGCTTTCACTTAAGTATCTtGCACCTCTcAGGAGTGGAGATAGA
TTTGTGGTGAAGGTGaGAATATCCgatTCTACAGCAGCTCGtTTGTTcTTCGAGCATTTCATCTTCAAaCTTCCAGA
TCAAGAGCCTATATTGGAGGCAAGAGGAATAGCAGTGTGGCTTAATAGAAGTTACCGTCCTATCaGAATaCCATCAG
AGTTCcgtTCAAgTTTGTTCAGTTCCTTCACCAGAAGAGTTGCGGTACACAACACCGTCTC
```

SEQ ID NO 70: *Solanum tuberosum* optimization 1 ORF
```
MSDQLYFHEVELKVRDYELDQFGVVNNATYASYCQHCRHEFLEKIGVSVDEVARTGEALALTELSLKYLA
PLRSGDRFVVKVRISDSTAARLFFEHFIFKLPDQEPILEARGIAVWLNRSYRPIRIPSEFRSKFVQFLHQ
KSCGTQHRL
```

SEQ ID NO 15: *Lycopersicon esculentum* optimization 2 cDNA
```
ATGagtGATCAGCTCTATttcCATGAAGTTGAACTCaagGTCAGGGACTATGAATTGGATCAGTTTGGTGTTGTAAA
CAATGCTACTTATGCAAGTTATTGTCAACATTGCCGTCATGAGTTTCTTGAgAAGATTGGTGTAAGTGTTGATGAAG
TAgcaaGaACTGGTGAAGCATTAGCACttACAGAGCTTTCACTTAAGTATCTtGCACCTCTcAGGAGTGGAGATAGA
TTTGTGGTGAAGGTGaGAATATCCgatTCTACAGCAGCTCGtTTGTTcTTCGAGCATTTCATCTTCAAaCTTCCAGA
TCAAGAGCCTATATTGGAGGCAAGAGGAATAGCAGTGTGGCTTAATAGAAGTTACCGTCCTATCaGAATaCCATCAG
AGTTCcgtTCAAgTTTGTTCAGTTCCTTCACCAGAAGAGTTGCGGTACACAACACCGTCTC
```

SEQ ID NO 71: *Lycopersicon esculentum* optimization 2 ORF
```
MSDQVYFHEVELKVRDYELDQFGVVNNATYASYCQHCRHEFLERIGISVDEVARSGDALALTELSLKYLA
PLRSGDRFVVKARISDSTAARLFFEHFIFKLPDQEPILEARGIAVWLNRSYRPIRIPSEFRSKFVQFLHQ
KSCGVQHHL
```

SEQ ID NO 16: *Petunia integrifolia* optimization 2 cDNA
```
ATGaatGATCAGCTCTATTTCTATGAAGTCGAACTCAAAGTCaGGGACTATGAGTTGGATCAAttcGGTGTTGTAAA
CAATGCTaccTATGCTAGTTATTGCCAACATTGTaGGCATGAGtttCTtGAAAAGATTGGCGTAAATGttGATGCAG
TGGCACGtAATGGTGAAGCATTAGCACTtACAGAGATGACACTcAAGTATCTtGCACCTCTcAGGAGTGGAGACAGA
TTCATTGTGAAaGTtaGAATATCTGACTCTacaGCTGCTCGTTTGTTCTTTGAACACTTCATCTTCAAaCTTCCtGA
TCAAGAGCCTATCTTGGAGGCAAGAGGAACAGCAGTGTGGCTTAAcaggAGTTACCGTCCTatcaGAATcCCTTCAG
AGTTCAGATCAAAATTCGTTCAGTTCCTTCACCAGAAGAGTTGCGGTACACAACACCGTCTC
```

SEQ ID NO 72: *Petunia integrifolia* optimization 2 ORF
MNDQLYFYEVELKVRDYELDQFGVVNNATYASYCQHCRHEFLEKIGVNVDAVARNGEALALTEMTLKYLA
PLRSGDRFIVKVRISDSTAARLFFEHFIFKLPDQEPILEARGTAVWLNRSYRPIRIPSEFRSKFVQFLHQ
KSCGTQHRL SEQ ID NO 17: *Lycopersicon hirsutum* optimization 2 cDNA
ATGAgtgagcaccatGACGTTGAACTCACAGTCAGGGACTATGAGTTGGATCAGtatGGTGTTGTAAATAATGCTat
tTATGCtAGTTATTGTCAACATTGTCGTCATGCtttgCTtGAgAAgATTGGTGTTGTAAGTgctGATGAAGTAACcCGtA
ATGGTGATGCATTAGCTGTAACAGAGCTCTCACTTAAGTTTCTTCTGCACCACTtAGGAGTGGAGATAGATTCGTGGTG
AGGGCtaGATTgTCCCACTTTagcGTAGCTaGATTGTTcTTtGAGCATTTCATCTTCAAaCTTCCtGATCAAGAGCC
TATATTGGAGGCAAGAGGAATAGCAGTGTGGCTTAATaagAGTTATCGTCCTgttCGtATTCCaTCAGAGTTCAATT
CAAAATTTGTTAAATTCCTTCGtCAGGAGGCATCCAAC SEQ ID NO 73: *Lycopersicon hirsutum* optimization 2 ORF
MSEHHDVELTVRDYELDQYGVVNNAIYASYCQHCRHALLEKIGVSADEVTRNGDALAVTELSLKFLAPLR
SGDRFVVRARLSHFSVARLFFEHFIFKLPDQEPILEARGIAVWLNKSYRPVRIPSEFNSKFVKFLRQEAS
N SEQ ID NO 18: *Solanum tuberosum* optimization 2 cDNA
ATGAgtgagcagcatGAAGTTGAACTCCAAGTCAGGGACTATGAATTGGATCAGtatGGTGTTGTAAACAATGCTat
tTATGCAAGTTATTGTCAACATTGCCGTCATGAGCttCTTGAgAAGATTGGTGTAAGtgctGATGAAGTATGTaGaA
CTGGTGAAGCATTAGCAACAACAGAGCTTTCACTTAAGTATCTTGCACCTCTcAGGAGTGGAGATAGATTTGTGGTG
AAGGTGAgAATATCCAGgTCTtccGCAGCTCGtTTGTTCTTCGAGCATTTCATCTTCAAaCTTCCAGATCAAGAGCC
TATATTGGAGGCAAGAGGAATAGCAGTGTGGCTTAATaagAGTTACCGTCCTgtgaGAATaCCATCAGAGTTCAGTT
CAAAgTTTGTTCAGTTCCTTCGtCAGGAGGCATCCAAC SEQ ID NO 74: *Solanum tuberosum* optimization 2 ORF
MSEQHEVELQVRDYELDQYGVVNNAIYASYCQHCRHELLEKIGVSADEVCRTGEALATTELSLKYLAPLR
SGDRFVVKVRISRSSAARLFFEHFIFKLPDQEPILEARGIAVWLNKSYRPVRIPSEFSSKFVQFLRQEAS
N SEQ ID NO 19: *Lycopersicon esculentum* optimization 3 cDNA
ATGGCTGAGTTCCATGAAGTTGAACTCAAAGTCaGGGACTATGAATTGGATCAGTATGGTGTTGTAAACAATGCTAT
cTATGCAAGTTATTGCCAACATGGTCGTCATGAGCTcCTtGAAAGGATTGGTATAaacGCTGATgcaGTGGCACGta
atGGTGACGCACTtGCACTtGCACTtACAGAGtTGTCACTTAAGTATCTtGCACCTCTtAGGAGTGGAGATAGATTTGTCGTG
AAaGCTaGAATATCTGATTCTTCAGCTGCTCGTTTGTTcTTtGAACACTTCATCTTCAAaCTTCCtGATCAAGAGCC
CATCTTGGAGGCAAGAGGAATAGCAGTGTGGCTCAACAAgAGTTACCGTCCTGTCaGAATCCCaGCAGAGTTCAGAT
CAAAATTTGTTCAGTTCCTTCGtCAGGAGGCATCCAAC SEQ ID NO 75: *Lycopersicon esculentum* optimization 3 ORF
MAEFHEVELKVRDYELDQYGVVNNAIYASYCQHGRHELLERIGINADAVARNGDALALTELSLKYLAPLR
SGDRFVVKARISDSSAARLFFEHFIFKLPDQEPILEARGIAVWLNKSYRPVRIPAEFRSKFVQFLRQEAS
N SEQ ID NO 20: *Lycopersicon esculentum* optimization 4 cDNA
ATGGCTGAGTTCCATGAAGTTGAACTCAAAGTCaGGGACTATGAATTGGATCAGTATGGTGTTGTAAACAATGCTAT
cTATGCAAGTTATTGCCAACATtgcCGTCATGAGCTcCTtGAAAGGATTGGTATAaacGCTGATgcaGTGGCACGta
atGGTGACGCACTtGCACTtACAGAGtTGTCACTTAAGTATCTtGCACCTCTtAGGAGTGGAGATAGATTTGTCGTG
AAaGCTaGAATATCTGATTCTTCAGCTGCTCGTTTGTTcTTtGAACACTTCATCTTCAAaCTTCCtGATCAAGAGCC
CATCTTGGAGGCAAGAGGAATAGCAGTGTGGCTCAACAAgAGTTACCGTCCTGTCaGAATCCCaGCAGAGTTCAGAT
CAAAATTTGTTCAGTTCCTTCGtCAGGAGGCATCCAAC SEQ ID NO 76: *Lycopersicon esculentum* optimization 4 ORF
MAEFHEVELKVRDYELDQYGVVNNAIYASYCQHCRHELLERIGINADAVARNGDALALTELSLKYLAPLR
SGDRFVVKARISDSSAARLFFEHFIFKLPDQEPILEARGIAVWLNKSYRPVRIPAEFRSKFVQFLRQEAS
N SEQ ID NO 21: *Lycopersicon esculentum* optimization 5 cDNA
ATGGCTGAGTTCCATGAAGTTGAACTCAAAGTCaGGGACTATGAATTGGATCAGTATGGTGTTGTAAACAATGCTAT
cTATGCAAGTTATTGCCAACATtgcCGTCATGAGCTcCTtGAAAGGATTGGTATAAGTGCTGATGAAGTGGCACGta
GTGGTGACGCACTtGCACTtACAGAGtTGTCACTTAAGTATCTtGCACCTCTtAGGAGTGGAGATAGATTTGTCGTG
AAaGCTaGAATATCTGATTCTTCAGCTGCTCGTTTGTTcTTtGAACACTTCATCTTCAAaCTTCCtGATCAAGAGCC
CATCTTGGAGGCAAGAGGAATAGCAGTGTGGCTCAACAAgAGTTACCGTCCTGTCaGAATCCCaGCAGAGTTCAGAT
CAAAATTTGTTCAGTTCCTTCGtCAGGAGGCATCCAAC SEQ ID NO 77: *Lycopersicon esculentum* optimization 5 ORF
MAEFHEVELKVRDYELDQYGVVNNAIYASYCQHCRHELLERIGISADEVARSGDALALTELSLKYLAPLR
SGDRFVVKARISDSSAARLFFEHFIFKLPDQEPILEARGIAVWLNKSYRPVRIPAEFRSKFVQFLRQEAS
N SEQ ID NO 22: *Lycopersicon esculentum* optimization 6 cDNA
ATGGCTGAGTTCtatGAAGTTGAACTCAAAGTCaGGGACTATGAATTGGATCAGTATGGTGTTGTAAACAATGCTAT
cTATGCAAGTTATTGCCAACATGGTCGTCATGAGCTcCTtGAAAGGATTGGTATAAGTGCTGATGAAGTGGCACGta
GTGGTGACGCACTtGCACTtACAGAGtTGTCACTTAAGTATCTtGCACCTCTtAGGAGTGGAGATAGATTTGTCGTG
AAaGCTaGAATATCTGATTCTTCAGCTGCTCGTTTGTTcTTtGAACACTTCATCTTCAAaCTTCCtGATCAAGAGCC
CATCTTGGAGGCAAGAGGAATAGCAGTGTGGCTCAACAAgAGTTACCGTCCTGTCaGAATCCCaGCAGAGTTCAGAT
CAAAATTTGTTCAGTTCCTTCGtCAGGAGGCATCCAAC SEQ ID NO 78: *Lycopersicon esculentum* optimization 6 ORF
MAEFYEVELKVRDYELDQYGVVNNAIYASYCQHGRHELLERIGISADEVARSGDALALTELSLKYLAPLR
SGDRFVVKARISDSSAARLFFEHFIFKLPDQEPILEARGIAVWLNKSYRPVRIPAEFRSKFVQFLRQEAS
N SEQ ID NO 23: *Petunia integrifolia* optimization 3 cDNA
ATGAATGAGTTCTATGAAGTCGAACTCAAAGTCaGGGACTATGAGTTGGATCAATATGGTGTTGTAAACAATGCTAT
cTATGCTAGTTATTGCCAACATggtaGGGCATGAGCTTCTtGAAAAGATTGGCGTAAATGCTGATGCAGTGGCACGtA
ATGGTGAAGCATTAGCACTtACAGAGATGACACTcAAGTATCTtGCACCTCTcAGGAGTGGAGACAGATTCATTGTG
AAaGTtaGAATATCTGACTCTTCAGCTGCTCGTTTGTTCTTTGAACACTTCATCTTCAAaCTTCCtGATCAAGAGCC
TATCTTGGAGGCAAGAGGAACAGCAGTGTGGCTTAAcAAgAGTTACCGTCCTGTCaGAATcCCTTCAGAGTTCAGAT
CAAAATTCGTTCAGTTCCTTCGtCAGGAGGCA SEQ ID NO 79: *Petunia integrifolia* optimization 3 ORF
MNEFYEVELKVRDYELDQYGVVNNAIYASYCQHGRHELLEKIGVNADAVARNGEALALTEMTLKYLAPLR
SGDRFIVKVRISDSSAARLFFEHFIFKLPDQEPILEARGTAVWLNKSYRPVRIPSEFRSKFVQFLRQEA SEQ ID NO 24: *Petunia integrifolia* optimization 4 cDNA
ATGAATGAGTTCTATGAAGTCGAACTCAAAGTCaGGGACTATGAGTTGGATCAATATGGTGTTGTAAACAATGCTAT
cTATGCTAGTTATTGCCAACATggtaGGGCATGAGCTTCTtGAAAAGATTGGCGTAagtGCTGATgagGTGGCACGta
gtGGTGAAGCATTAGCACTtACAGAGATGACACTcAAGTATCTtGCACCTCTcAGGAGTGGAGACAGATTCATTGTG
AAaGTtaGAATATCTGACTCTTCAGCTGCTCGTTTGTTCTTTGAACACTTCATCTTCAAaCTTCCtGATCAAGAGCC
TATCTTGGAGGCAAGAGGAACAGCAGTGTGGCTTAAcAAgAGTTACCGTCCTGTCaGAATcCCTTCAGAGTTCAGAT
CAAAATTCGTTCAGTTCCTTCGtCAGGAGGCA SEQ ID NO 80: *Petunia integrifolia* optimization 4 ORF
MNEFYEVELKVRDYELDQYGVVNNAIYASYCQHGRHELLEKIGVSADEVARSGEALALTEMTLKYLAPLR
SGDRFIVKVRISDSSAARLFFEHFIFKLPDQEPILEARGTAVWLNKSYRPVRIPSEFRSKFVQFLRQEA SEQ ID NO 25: *Petunia integrifolia* optimization 5 cDNA
ATGAATGAGTTCTATGAAGTCGAACTCAAAGTCaGGGACTATGAGTTGGATCAATATGGTGTTGTAAACAATGCTAT
cTATGCTAGTTATTGCCAACATTGtAGGCATGAGCTTCTtGAAAAGATTGGCGTAagtGCTGATgagGTGGCACGta
gtGGTGAAGCATTAGCACTtACAGAGATGACACTcAAGTATCTtGCACCTCTcAGGAGTGGAGACAGATTCATTGTG
AAaGTtaGAATATCTGACTCTTCAGCTGCTCGTTTGTTCTTTGAACACTTCATCTTCAAaCTTCCtGATCAAGAGCC
TATCTTGGAGGCAAGAGGAACAGCAGTGTGGCTTAAcAAgAGTTACCGTCCTGTCaGAATcCCTTCAGAGTTCAGAT
CAAAATTCGTTCAGTTCCTTCGtCAGGAGGCA SEQ ID NO 81: *Petunia integrifolia* optimization 5 ORF
MNEFYEVELKVRDYELDQYGVVNNAIYASYCQHCRHELLEKIGVSADEVARSGEALALTEMTLKYLAPLR
SGDRFIVKVRISDSSAARLFFEHFIFKLPDQEPILEARGTAVWLNKSYRPVRIPSEFRSKFVQFLRQEA SEQ ID NO 26: *Lycopersicon hirsutum* optimization 3 cDNA
ATGAATGAGTTCTATGAAGTCGAACTCAAAGTCaGGGACTATGAGTTGGATCAATATGGTGTTGTAAACAATGCTAT
cTATGCTAGTTATTGCCAACATTGtAGGCATGAGCTTCTtGAAAAGATTGGCGTAagtGCTGATgagGTGGCACGta
gtGGTGAAGCATTAGCACTtACAGAGATGACACTcAAGTATCTtGCACCTCTcAGGAGTGGAGACAGATTCATTGTG
AAaGTtaGAATATCTGACTCTTCAGCTGCTCGTTTGTTCTTTGAACACTTCATCTTCAAaCTTCCtGATCAAGAGCC
TATCTTGGAGGCAAGAGGAACAGCAGTGTGGCTTAAcAAgAGTTACCGTCCTGTCaGAATcCCTTCAGAGTTCAGAT
CAAAATTCGTTCAGTTCCTTCGtCAGGAGGCA SEQ ID NO 82: *Lycopersicon hirsutum* optimization 3 ORF
MSDQVYHHDVELTVRDYELDQFGVVNNATYASYCQHGRHELLEKIGVSVDEVTRNGDALAVTELSLKFLA
PLRSGDRFVVRARLSHFTVARLFFEHFIFKLPDQEPILEARGIAVWLNRSYRPIRIPSEFNSKFVKFLHQ
KSCGVQHHL SEQ ID NO 27: *Lycopersicon hirsutum* optimization 4 cDNA
ATGAGTGATCAGGTCTATCACCATGACGTTGAACTCACAGTCAGGGACTATGAGTTGGATCAGTTTGGTGTTGTAAA
TAATGCTACTTATGCtAGTTATTGTCAACATggtCGTCATgagttgCTtGAgAAgATTGGTGTTaatgctGATGAAG
TAACcCGtAATGGTGATGCATTAGCTGTAACAGAGCTCTCACTTAAGTTTCTtGCACCACTtAGGAGTGGAGATAGA
TTCGTGGTGAGGGCtaGATTgTCCCACTTTACAGTAGCTaGATTGTTcTTtGAGCATTTCATCTTCAAaCTTCCtGA
TCAAGAGCCTATATTGGAGGCAAGAGGAATAGCAGTGTGGCTTAATAGAAGTTATCGTCCTATTCGtATTCCaTCAG
AGTTCAATTCAAAATTTGTTAAATTCCTTCACCAGAAGAGTTGCGGTGTACAACATCATCTC SEQ ID NO 83: *Lycopersicon hirsutum* optimization 4 ORF
MSDQVYHHDVELTVRDYELDQFGVVNNATYASYCQHGRHELLEKIGVNADEVTRNGDALAVTELSLKFLA
PLRSGDRFVVRARLSHFTVARLFFEHFIFKLPDQEPILEARGIAVWLNRSYRPIRIPSEFNSKFVKFLHQ
KSCGVQHHL SEQ ID NO 28: *Lycopersicon hirsutum* optimization 5 cDNA
ATGAGTGATCAGGTCTATCACCATGACGTTGAACTCACAGTCAGGGACTATGAGTTGGATCAGTTTGGTGTTGTAAA
TAATGCTACTTATGCtAGTTATTGTCAACATTGTCGTCATGCtTTcCTtGAgAAgATTGGTGTTaatgctGATGAAG
TAACcCGtAATGGTGATGCATTAGCTGTAACAGAGCTCTCACTTAAGTTTCTtGCACCACTtAGGAGTGGAGATAGA
TTCGTGGTGAGGGCtaGATTgTCCCACTTTACAGTAGCTaGATTGTTcTTtGAGCATTTCATCTTCAAaCTTCCtGA
TCAAGAGCCTATATTGGAGGCAAGAGGAATAGCAGTGTGGCTTAATAGAAGTTATCGTCCTATTCGtATTCCaTCAG
AGTTCAATTCAAAATTTGTTAAATTCCTTCACCAGAAGAGTTGCGGTGTACAACATCATCTC SEQ ID NO 84: *Lycopersicon hirsutum* optimization 5 ORF
MSDQVYHHDVELTVRDYELDQFGVVNNATYASYCQHCRHAFLEKIGVNADEVTRNGDALAVTELSLKFLA
PLRSGDRFVVRARLSHFTVARLFFEHFIFKLPDQEPILEARGIAVWLNRSYRPIRIPSEFNSKFVKFLHQ
KSCGVQHHL -continued SEQ ID NO 29: *Solanum tuberosum* optimization 3 cDNA
ATGGGTGATCAGCTCTATCAACATGAAGTTGAACTCCAAGTCAGGGACTATGAATTGGATCAGTTTGGTGTTGTAAA
CAATGCTACTTATGCAAGTTATTGTCAACATggcCGTCATGAGTTTCTTGAgAAGATTGGTGTAAGTGTTGATGAAG
TAgctaGaACTGGTGAAGCATTAGCAACAACAGAGCTTTCACTTAAGTATCTtGCACCTCTcAGGAGTGGAGATAGA
TTTGTGGTGAAGGTGaGAATATCCaGgTCTACAGCAGCTCGtTTGTTcTTCGAGCATTTCATCTTCAaACTTCCAGA
TCAAGAGCCTATATTGGAGGCAAGAGGAATAGCAGTGTGGCTTAATAGAAGTTACCGTCCTATCaGAATaCCATCAG
AGTTCAGTTCAAAgTTTGTTCAGTTCCTTCACCAGAAGAGTTGCGGTACACAACACCGTCTC SEQ ID NO 85: *Solanum tuberosum* optimization 3 ORF
MGDQLYQHEVELQVRDYELDQFGVVNNATYASYCQHGRHEFLEKIGVSVDEVARTGEALATTELSLKYL
APLRSGDRFVVKVRISRSTAARLFFEHFIFKLPDQEPILEARGIAVWLNRSYRPIRIPSEFSSKFVQFLHQKS
CGTQHRL SEQ ID NO 30: *L. esculentum/L. hirsutum* chimeric optimization 1 cDNA
ATGGCTGAGTTCCATGAAGTTGAACTCAAAGTCCGGGACTATGAATTGGATCAGTATGGTGTTGTAAACAATGCTAT
TTATGCAAGTTATTGCCAACATGGTCGTCATGAGCTTCTAGAAAGGATTGGTATAAGTGCTGATGAAGTGGCACGCA
GTGGTGACGCACTAGCACTAACAGAGCTGTCACTTAAGTATCTAGCACCTCTAAGGAGTGGAGATAGATTTGTCGTG
AAGGCACGAATATCTGATTCTTCAGCTGCTCGTTTGTTTTTCGAACACTTCATCTTCAAGCTTCCAGATCAAGAGCC
TATATTGGAGGCAAGAGGAATAGCAGTGTGGCTTAATAGAAGTTATCGTCCTATTCGAATTCCGTCAGAGTTCAATT
CAAAATTTGTTAAATTCCTTCACCAGAAGAGTTGCGGTACAACATCATCTC SEQ ID NO 86: *L. esculentum/L. hirsutum* chimeric optimization 1 ORF
MAEFHEVELKVRDYELDQYGVVNNAIYASYCQHGRHELLERIGISADEVARSGDALALTELSLKYLAPLRSGDRFVV
KARISDSSAARLFFEHFIFKLPDQEPILEARGIAVWLNRSYRPIRIPSEFNSKFVKFLHQKSCGVQHHL SEQ ID NO 31: *L. esculentum/L. hirsutum* chimeric optimization 2 cDNA
ATGGCTGAGTTCCATGAAGTTGAACTCAAAGTCCGGGACTATGAATTGGATCAGTATGGTGTTGTAAACAATGCTAT
TTATGCAAGTTATTGCCAACATGGTCGTCATGAGCTTCTAGAAAGGATTGGTATAAGTGCTGATGAAGTGGCACGCA
GTGGTGACGCACTAGCACTAACAGAGCTGTCACTTAAGTATCTAGCACCTCTAAGGAGTGGAGATAGATTCGTGGTG
AGGGCGCGATTATCCCACTTTACAGTAGCTCGATTGTTTTTCGAGCATTTCATCTTCAAGCTTCCAGATCAAGAGCC
CATCTTGGAGGCAAGAGGAATAGCAGTGTGGCTCAATAAAAGTTACCGTCCTGTCCGAATCCCGGCAGAGTTCAGAT
CAAAATTTGTTCAGTTCCTTCGCCAGGAGGCATCCAAC SEQ ID NO 87: *L. esculentum/L. hirsutum* chimeric optimization 2 ORF
MAEFHEVELKVRDYELDQYGVVNNAIYASYCQHGRHELLERIGISADEVARSGDALALTELSLKYLAPLRSGDRFVV
RARLSHFTVARLFFEHFIFKLPDQEPILEARGIAVWLNKSYRPVRIPAEFRSKFVQFLRQEASN SEQ ID NO 32: *L. esculentum/L. hirsutum* chimeric optimization 3 cDNA
ATGGCTGAGTTCCATGAAGTTGAACTCAAAGTCCGGGACTATGAATTGGATCAGTATGGTGTTGTAAACAATGCTAT
TTATGCAAGTTATTGCCAACATGGTCGTCATGAGCTTCTAGAAAGGATTGGTATAAGTGCTGATGAAGTGGCACGCA
GTGGTGACGCACTAGCACTAACAGAGCTGTCACTTAAGTATCTAGCACCTCTAAGGAGTGGAGATAGATTCGTGGTG
AGGGCGCGATTATCCCACTTTACAGTAGCTCGATTGTTTTTCGAGCATTTCATCTTCAAGCTTCCAGATCAAGAGCC
TATATTGGAGGCAAGAGGAATAGCAGTGTGGCTTAATAGAAGTTATCGTCCTATTCGAATTCCGTCAGAGTTCAATT
CAAAATTTGTTAAATTCCTTCACCAGAAGAGTTGCGGTGTACAACATCATCTC SEQ ID NO 88: *L. esculentum/L. hirsutum* chimeric optimization 3 ORF
MAEFHEVELKVRDYELDQYGVVNNAIYASYCQHGRHELLERIGISADEVARSGDALALTELSLKYLAPLRSGDRFVV
RARLSHFTVARLFFEHFIFKLPDQEPILEARGIAVWLNRSYRPIRIPSEFNSKFVKFLHQKSCGVQHHL SEQ ID NO 33: *L. esculentum/L. hirsutum* chimeric optimization 4 cDNA
ATGGCTGAGTTCCATGAAGTTGAACTCAAAGTCCGGGACTATGAATTGGATCAGTATGGTGTTGTAAACAATGCTAT
TTATGCAAGTTATTGTCAACATTGTCGTCATGCGTTTCTAGAAAAAATTGGTGTTAGTGTTGATGAAGTAACGCGAA
ATGGTGATGCATTAGCTGTAACAGAGCTCTCACTTAAGTTTCTAGCACCACTAAGGAGTGGAGATAGATTTGTCGTG
AAGGCACGAATATCTGATTCTTCAGCTGCTCGTTTGTTTTTCGAACACTTCATCTTCAAGCTTCCAGATCAAGAGCC
CATCTTGGAGGCAAGAGGAATAGCAGTGTGGCTCAATAAAAGTTACCGTCCTGTCCGAATCCCGGCAGAGTTCAGAT
CAAAATTTGTTCAGTTCCTTCGCCAGGAGGCATCCAAC SEQ ID NO 89: *L. esculentum/L. hirsutum* chimeric optimization 4 ORF
MAEFHEVELKVRDYELDQYGVVNNAIYASYCQHCRHAFLEKIGVSVDEVTRNGDALAVTELSLKFLAPLRSGDRFVV
KARISDSSAARLFFEHFIFKLPDQEPILEARGIAVWLNKSYRPVRIPAEFRSKFVQFLRQEASN SEQ ID NO 34: *L. esculentum/L. hirsutum* chimeric optimization 5 cDNA
ATGGCTGAGTTCCATGAAGTTGAACTCAAAGTCCGGGACTATGAATTGGATCAGTATGGTGTTGTAAACAATGCTAT
TTATGCAAGTTATTGTCAACATTGTCGTCATGCGTTTCTAGAAAAAATTGGTGTTAGTGTTGATGAAGTAACGCGAA
ATGGTGATGCATTAGCTGTAACAGAGCTCTCACTTAAGTTTCTAGCACCACTAAGGAGTGGAGATAGATTTGTCGTG
AAGGCACGAATATCTGATTCTTCAGCTGCTCGTTTGTTTTTCGAACACTTCATCTTCAAGCTTCCAGATCAAGAGCC
TATATTGGAGGCAAGAGGAATAGCAGTGTGGCTTAATAGAAGTTATCGTCCTATTCGAATTCCGTCAGAGTTCAATT
CAAAATTTGTTAAATTCCTTCACCAGAAGAGTTGCGGTGTACAACATCATCTC SEQ ID NO 90: *L. esculentum/L. hirsutum* chimeric optimization 5 ORF
MAEFHEVELKVRDYELDQYGVVNNAIYASYCQHCRHAFLEKIGVSVDEVTRNGDALAVTELSLKFLAPLRSGDRFVV
KARISDSSAARLFFEHFIFKLPDQEPILEARGIAVWLNRSYRPIRIPSEFNSKFVKFLHQKSCGVQHHL SEQ ID NO 35: *L. esculentum/L. hirsutum* chimeric optimization 6 cDNA
ATGGCTGAGTTCCATGAAGTTGAACTCAAAGTCCGGGACTATGAATTGGATCAGTATGGTGTTGTAAACAATGCTAT
TTATGCAAGTTATTGTCAACATTGTCGTCATGCGTTTCTAGAAAAAATTGGTGTTAGTGTTGATGAAGTAACGCGAA
ATGGTGATGCATTAGCTGTAACAGAGCTCTCACTTAAGTTTCTAGCACCACTAAGGAGTGGAGATAGATTCGTGGTG
AGGGCGCGATTATCCCACTTTACAGTAGCTCGATTGTTTTTCGAGCATTTCATCTTCAAGCTTCCAGATCAAGAGCC
CATCTTGGAGGCAAGAGGAATAGCAGTGTGGCTCAATAAAAGTTACCGTCCTGTCCGAATCCCGGCAGAGTTCAGAT
CAAAATTTGTTCAGTTCCTTCGCCAGGAGGCATCCAAC -continued SEQ ID NO 91: *L. esculentum/L. hirsutum* chimeric optimization 6 ORF
MAEFHEVELKVRDYELDQYGVVNNAIYASYCQHCRHAFLEKIGVSVDEVTRNGDALAVTELSLKFLAPLRSGDRFVV
RARLSHFTVARLFFEHFIFKLPDQEPILEARGIAVWLNKSYRPVRIPAEFRSKFVQFLRQEASN SEQ ID NO 36: *L. esculentum/L. hirsutum* chimeric optimization 7 cDNA
ATGGCTGAGTTCCATGAAGTTGAACTCAAAGTCCGGGACTATGAATTGGATCAGTATGGTGTTGTAAACAATGCTAT
TTATGCAAGTTATTGTCAACATTGTCGTCATGCGTTTCTAGAAAAAATTGGTGTTAGTGTTGATGAAGTAACGCGAA
ATGGTGATGCATTAGCTGTAACAGAGCTCTCACTTAAGTTTCTAGCACCACTAAGGAGTGGAGATAGATTCGTGGTG
AGGGCGCGATTATCCCACTTTACAGTAGCTCGATTGTTTTTCGAGCATTTCATCTTCAAGCTTCCAGATCAAGAGCC
TATATTGGAGGCAAGAGGAATAGCAGTGTGGCTTAATAGAAGTTATCGTCCTATTCGAATTCCGTCAGAGTTCAATT
CAAAATTTGTTAAATTCCTTCACCAGAAGAGTTGCGGTGTACAACATCATCTC SEQ ID NO 92: *L. esculentum/L. hirsutum* chimeric optimization 7 ORF
MAEFHEVELKVRDYELDQYGVVNNAIYASYCQHCRHAFLEKIGVSVDEVTRNGDALAVTELSLKFLAPLRSGDRFVV
RARLSHFTVARLFFEHFIFKLPDQEPILEARGIAVWLNRSYRPIRIPSEFNSKFVKFLHQKSCGVQHHL SEQ ID NO 37: *L. esculentum/L. hirsutum* chimeric optimization 8 cDNA
ATGAGTGATCAGGTCTATCACCATGACGTTGAACTCACAGTCAGGGACTATGAGTTGGATCAGTTTGGTGTTGTAAA
TAATGCTACTTATGCGAGTTATTGCCAACATGGTCGTCATGAGCTTCTAGAAAGGATTGGTATAAGTGCTGATGAAG
TGGCACGCAGTGGTGACGCACTAGCACTAACAGAGCTGTCACTTAAGTATCTAGCACCTCTAAGGAGTGGAGATAGA
TTTGTCGTGAAGGCACGAATATCTGATTCTTCAGCTGCTCGTTTGTTTTCGAACACTTCATCTTCAAGCTTCCAGA
TCAAGAGCCCATCTTGGAGGCAAGAGGAATAGCAGTGTGGCTCAATAAAAGTTACCGTCCTGTCCGAATCCCGGCAG
AGTTCAGATCAAAATTTGTTCAGTTCCTTCGCCAGGAGGCATCCAAC SEQ ID NO 93: *L. esculentum/L. hirsutum* chimeric optimization 8 ORF
MSDQVYHHDVELTVRDYELDQFGVVNNATYASYCQHGRHELLERIGISADEVARSGDALALTELSLKYLAPLRSGDR
FVVKARISDSSAARLFFEHFIFKLPDQEPILEARGIAVWLNKSYRPVRIPAEFRSKFVQFLRQEASN SEQ ID NO 38: *L. esculentum/L. hirsutum* chimeric optimization 9 cDNA
ATGAGTGATCAGGTCTATCACCATGACGTTGAACTCACAGTCAGGGACTATGAGTTGGATCAGTTTGGTGTTGTAAA
TAATGCTACTTATGCGAGTTATTGCCAACATGGTCGTCATGAGCTTCTAGAAAGGATTGGTATAAGTGCTGATGAAG
TGGCACGCAGTGGTGACGCACTAGCACTAACAGAGCTGTCACTTAAGTATCTAGCACCTCTAAGGAGTGGAGATAGA
TTTGTCGTGAAGGCACGAATATCTGATTCTTCAGCTGCTCGTTTGTTTTCGAACACTTCATCTTCAAGCTTCCAGA
TCAAGAGCCTATATTGGAGGCAAGAGGAATAGCAGTGTGGCTTAATAGAAGTTATCGTCCTATTCGAATTCCGTCAG
AGTTCAATTCAAAATTTGTTAAATTCCTTCACCAGAAGAGTTGCGGTGTACAACATCATCTC SEQ ID NO 94: *L. esculentum/L. hirsutum* chimeric optimization 9 ORF
MSDQVYHHDVELTVRDYELDQFGVVNNATYASYCQHGRHELLERIGISADEVARSGDALALTELSLKYLAPLRSGDR
FVVKARISDSSAARLFFEHFIFKLPDQEPILEARGIAVWLNRSYRPIRIPSEFNSKFVKFLHQKSCGVQHHL SEQ ID NO 39: *L. esculentum/L. hirsutum* chimeric optimization 10 cDNA
ATGAGTGATCAGGTCTATCACCATGACGTTGAACTCACAGTCAGGGACTATGAGTTGGATCAGTTTGGTGTTGTAAA
TAATGCTACTTATGCGAGTTATTGCCAACATGGTCGTCATGAGCTTCTAGAAAGGATTGGTATAAGTGCTGATGAAG
TGGCACGCAGTGGTGACGCACTAGCACTAACAGAGCTGTCACTTAAGTATCTAGCACCTCTAAGGAGTGGAGATAGA
TTCGTGGTGAGGGCGCGATTATCCCACTTTACAGTAGCTCGATTGTTTTCGAGCATTTCATCTTCAAGCTTCCAGA
TCAAGAGCCCATCTTGGAGGCAAGAGGAATAGCAGTGTGGCTCAATAAAAGTTACCGTCCTGTCCGAATCCCGGCAG
AGTTCAGATCAAAATTTGTTCAGTTCCTTCGCCAGGAGGCATCCAAC SEQ ID NO 95: *L. esculentum/L. hirsutum* chimeric optimization 10 ORF
MSDQVYHHDVELTVRDYELDQFGVVNNATYASYCQHGRHELLERIGISADEVARSGDALALTELSLKYLAPLRSGDR
FVVRARLSHFTVARLFFEHFIFKLPDQEPILEARGIAVWLNKSYRPVRIPAEFRSKFVQFLRQEASN SEQ ID NO 40: *L. esculentum/L. hirsutum* chimeric optimization 11 cDNA
ATGAGTGATCAGGTCTATCACCATGACGTTGAACTCACAGTCAGGGACTATGAGTTGGATCAGTTTGGTGTTGTAAA
TAATGCTACTTATGCGAGTTATTGCCAACATGGTCGTCATGAGCTTCTAGAAAGGATTGGTATAAGTGCTGATGAAG
TGGCACGCAGTGGTGACGCACTAGCACTAACAGAGCTGTCACTTAAGTATCTAGCACCTCTAAGGAGTGGAGATAGA
TTCGTGGTGAGGGCGCGATTATCCCACTTTACAGTAGCTCGATTGTTTTCGAGCATTTCATCTTCAAGCTTCCAGA
TCAAGAGCCTATATTGGAGGCAAGAGGAATAGCAGTGTGGCTTAATAGAAGTTATCGTCCTATTCGAATTCCGTCAG
AGTTCAATTCAAAATTTGTTAAATTCCTTCACCAGAAGAGTTGCGGTGTACAACATCATCTC SEQ ID NO 96: *L. esculentum/L. hirsutum* chimeric optimization 11 ORF
MSDQVYHHDVELTVRDYELDQFGVVNNATYASYCQHGRHELLERIGISADEVARSGDALALTELSLKYLAPLRSGDR
FVVRARLSHFTVARLFFEHFIFKLPDQEPILEARGIAVWLNRSYRPIRIPSEFNSKFVKFLHQKSCGVQHHL SEQ ID NO 41: *L. esculentum/L. hirsutum* chimeric optimization 12 cDNA
ATGAGTGATCAGGTCTATCACCATGACGTTGAACTCACAGTCAGGGACTATGAGTTGGATCAGTTTGGTGTTGTAAA
TAATGCTACTTATGCGAGTTATTGTCAACATTGTCGTCATGCGTTTCTAGAAAAAATTGGTGTTAGTGTTGATGAAG
TAACGCGAAATGGTGATGCATTAGCTGTAACAGAGCTCTCACTTAAGTTTCTAGCACCACTAAGGAGTGGAGATAGA
TTTGTCGTGAAGGCACGAATATCTGATTCTTCAGCTGCTCGTTTGTTTTCGAACACTTCATCTTCAAGCTTCCAGA
TCAAGAGCCCATCTTGGAGGCAAGAGGAATAGCAGTGTGGCTCAATAAAAGTTACCGTCCTGTCCGAATCCCGGCAG
AGTTCAGATCAAAATTTGTTCAGTTCCTTCGCCAGGAGGCATCCAAC SEQ ID NO 97: *L. esculentum/L. hirsutum* chimeric optimization 12 ORF
MSDQVYHHDVELTVRDYELDQFGVVNNATYASYCQHCRHAFLEKIGVSVDEVTRNGDALAVTELSLKFLAPLRSGDR
FVVKARISDSSAARLFFEHFIFKLPDQEPILEARGIAVWLNKSYRPVRIPAEFRSKFVQFLRQEASN SEQ ID NO 42: *L. esculentum/L. hirsutum* chimeric optimization 13 cDNA
ATGAGTGATCAGGTCTATCACCATGACGTTGAACTCACAGTCAGGGACTATGAGTTGGATCAGTTTGGTGTTGTAAA
TAATGCTACTTATGCGAGTTATTGTCAACATTGTCGTCATGCGTTTCTAGAAAAAATTGGTGTTAGTGTTGATGAAG
TAACGCGAAATGGTGATGCATTAGCTGTAACAGAGCTCTCACTTAAGTTTCTAGCACCACTAAGGAGTGGAGATAGA
TTTGTCGTGAAGGCACGAATATCTGATTCTTCAGCTGCTCGTTTGTTTTCGAACACTTCATCTTCAAGCTTCCAGA -continued TCAAGAGCCTATATTGGAGGCAAGAGGAATAGCAGTGTGGCTTAATAGAAGTTATCGTCCTATTCGAATTCCGTCAG
AGTTCAATTCAAAATTTGTTAAATTCCTTCACCAGAAGAGTTGCGGTGTACAACATCATCTC SEQ ID NO 98: *L. esculentum/L. hirsutum* chimeric optimization 13 ORF
MSDQVYHHDVELTVRDYELDQFGVVNNATYASYCQHCRHAFLEKIGVSVDEVTRNGDALAVTELSLKFLAPLRSGDR
FVVKARISDSSAARLFFEHFIFKLPDQEPILEARGIAVWLNRSYRPIRIPSEFNSKFVKFLHQKSCGVQHHL SEQ ID NO 43: *L. esculentum/L. hirsutum* chimeric optimization 14 cDNA
ATGAGTGATCAGGTCTATCACCATGACGTTGAACTCACAGTCAGGGACTATGAGTTGGATCAGTTTGGTGTTGTAAA
TAATGCTACTTATGCGAGTTATTGTCAACATTGTCGTCATGCGTTTCTAGAAAAAATTGGTGTTAGTGTTGATGAAG
TAACGCGAAATGGTGATGCATTAGCTGTAACAGAGCTCTCACTTAAGTTTCTAGCACCACTAAGGAGTGGAGATAGA
TTCGTGGTGAGGGCGCGATTATCCCACTTTACAGTAGCTCGATTGTTTTTCGAGCATTTCATCTTCAAGCTTCCAGA
TCAAGAGCCCATCTTGGAGGCAAGAGGAATAGCAGTGTGGCTCAATAAAAGTTACCGTCCTGTCCGAATCCCGGCAG
AGTTCAGATCAAAATTTGTTCAGTTCCTTCGCCAGGAGGCATCCAAC SEQ ID NO 99: *L. esculentum/L. hirsutum* chimeric optimization 14 ORF
MSDQVYHHDVELTVRDYELDQFGVVNNATYASYCQHCRHAFLEKIGVSVDEVTRNGDALAVTELSLKFLAPLRSGDR
FVVRARLSHFTVARLFFEHFIFKLPDQEPILEARGIAVWLNSYRPVRIPAEFRSKFVQFLRQEASN SEQ ID NO 44: *L. esculentum/L. hirsutum* chimeric optimization 15 cDNA
ATGAGTGATCAGGTCTATCACCATGAAGTTGAACTCAAAGTCCGGGACTATGAATTGGATCAGTATGGTGTTGTAAA
CAATGCTATTTATGCAAGTTATTGCCAACATGGTCGTCATGAGCTTCTAGAAAGGATTGGTATAAGTGCTGACACGCA
TGGCACGCAGTGGTGACGCACTAGCACTAACAGAGCTGTCACTTAAGTATCTAGCACCTCTAAGGAGTGGAGATAGA
TTTGTCGTGAAGGCACGAATATCTGATTCTTCAGCTGCTCGTTTGTTTTTCGAACACTTCATCTTCAAGCTTCCAGA
TCAAGAGCCCATCTTGGAGGCAAGAGGAATAGCAGTGTGGCTCAATAAAAGTTACCGTCCTGTCCGAATCCCGGCAG
AGTTCAGATCAAAATTTGTTCAGTTCCTTCGCCAGGAGGCATCCAAC SEQ ID NO 100: *L. esculentum/L. hirsutum* chimeric optimization 15 ORF
MSDQVYHHEVELKVRDYELDQYGVVNNAIYASYCQHGRHELLERIGISADEVARSGDALALTELSLKYLAPLRSGDR
FVVKARISDSSAARLFFEHFIFKLPDQEPILEARGIAVWLNKSYRPVRIPAEFRSKFVQFLRQEASN SEQ ID NO 45: *L. esculentum/L. hirsutum* chimeric optimization 16 cDNA
ATGGCTGAGTTCCATGAAGTTGAACTCAAAGTCCGGGACTATGAATTGGATCAGTATGGTGTTGTAAACAATGCTAT
TTATGCAAGTTATTGCCAACATGGTCGTCATGAGCTTCTAGAAAGGATTGGTATAAGTGCTGATGAAGTGGCACGCA
GTGGTGACGCACTAGCACTAACAGAGCTGTCACTTAAGTATCTAGCACCTCTAAGGAGTGGAGATAGATTTGTCGTG
AAGGCACGAATATCTGATTCTTCAGCTGCTCGTTTGTTTTTCGAACACTTCATCTTCAAGCTTCCAGATCAAGAGCC
CATCTTGGAGGCAAGAGGAATAGCAGTGTGGCTCAATAAAAGTTACCGTCCTGTCCGAATCCCGGCAGAGTTCAGAT
CAAAATTTGTTCAGTTCCTTCGCCAGAAGAGTTGCGGTGTACAACATCATCTC SEQ ID NO 101: *L. esculentum/L. hirsutum* chimeric optimization 16 ORF
MAEFHEVELKVRDYELDQYGVVNNAIYASYCQHGRHELLERIGISADEVARSGDALALTELSLKYLAPLRSGDRFVV
KARISDSSAARLFFEHFIFKLPDQEPILEARGIAVWLNKSYRPVRIPAEFRSKFVQFLRQKSCGVQHHL SEQ ID NO 46: *L. esculentum/L. hirsutum* chimeric optimization 17 cDNA
ATGAGTGATCAGGTCTATCACCATGAAGTTGAACTCAAAGTCCGGGACTATGAATTGGATCAGTATGGTGTTGTAAA
CAATGCTATTTATGCAAGTTATTGCCAACATGGTCGTCATGAGCTTCTAGAAAGGATTGGTATAAGTGCTGATGAAG
TGGCACGCAGTGGTGACGCACTAGCACTAACAGAGCTGTCACTTAAGTATCTAGCACCTCTAAGGAGTGGAGATAGA
TTTGTCGTGAAGGCACGAATATCTGATTCTTCAGCTGCTCGTTTGTTTTTCGAACACTTCATCTTCAAGCTTCCAGA
TCAAGAGCCCATCTTGGAGGCAAGAGGAATAGCAGTGTGGCTCAATAAAAGTTACCGTCCTGTCCGAATCCCGGCAG
AGTTCAGATCAAAATTTGTTCAGTTCCTTCGCCAGAAGAGTTGCGGTGTACAACATCATCTC SEQ ID NO 102: *L. esculentum/L. hirsutum* chimeric optimization 17 ORF
MSDQVYHHEVELKVRDYELDQYGVVNNAIYASYCQHGRHELLERIGISADEVARSGDALALTELSLKYLAPLRSGDR
FVVKARISDSSAARLFFEHFIFKLPDQEPILEARGIAVWLNKSYRPVRIPAEFRSKFVQFLRQKSCGVQHHL SEQ ID NO 47: *L. esculentum/L. hirsutum* chimeric optimization 18 cDNA
ATGAGTGATCAGGTCTATCACCATGAAGTTGAACTCAAAGTCCGGGACTATGAATTGGATCAGTATGGTGTTGTAAA
CAATGCTATTTATGCAAGTTATTGCCAACATGGTCGTCATGAGCTTCTAGAAAGGATTGGTATAAGTGCTGATGAAG
TGGCACGCAGTGGTGACGCACTAGCACTAACAGAGCTGTCACTTAAGTATCTAGCACCTCTAAGGAGTGGAGATAGA
TTCGTGGTGAGGGCGCGATTATCCCACTTTACAGTAGCTCGATTGTTTTTCGAGCATTTCATCTTCAAGCTTCCAGA
TCAAGAGCCCATCTTGGAGGCAAGAGGAATAGCAGTGTGGCTCAATAAAAGTTACCGTCCTGTCCGAATCCCGGCAG
AGTTCAGATCAAAATTTGTTCAGTTCCTTCGCCAGGAGGCATCCAAC SEQ ID NO 103: *L. esculentum/L. hirsutum* chimeric optimization 18 ORF
MSDQVYHHEVELKVRDYELDQYGVVNNAIYASYCQHGRHELLERIGISADEVARSGDALALTELSLKYLAPLRSGDR
FVVRARLSHFTVARLFFEHFIFKLPDQEPILEARGIAVWLNSYRPVRIPAEFRSKFVQFLRQEASN SEQ ID NO 48: *L. esculentum/L. hirsutum* chimeric optimization 19 cDNA
ATGGCTGAGTTCCATGAAGTTGAACTCAAAGTCCGGGACTATGAATTGGATCAGTATGGTGTTGTAAACAATGCTAT
TTATGCAAGTTATTGCCAACATGGTCGTCATGAGCTTCTAGAAAGGATTGGTATAAGTGCTGATGAAGTGGCACGCA
GTGGTGACGCACTAGCACTAACAGAGCTGTCACTTAAGTATCTAGCACCTCTAAGGAGTGGAGATAGATTCGTGGTG
AGGGCGCGATTATCCCACTTTACAGTAGCTCGATTGTTTTTCGAGCATTTCATCTTCAAGCTTCCAGATCAAGAGCC
CATCTTGGAGGCAAGAGGAATAGCAGTGTGGCTCAATAAAAGTTACCGTCCTGTCCGAATCCCGGCAGAGTTCAGAT
CAAAATTTGTTCAGTTCCTTCGCCAGAAGAGTTGCGGTGTACAACATCATCTC SEQ ID NO 104: *L. esculentum/L. hirsutum* chimeric optimization 19 ORF
MAEFHEVELKVRDYELDQYGVVNNAIYASYCQHGRHELLERIGISADEVARSGDALALTELSLKYLAPLRSGDRFVV
RARLSHFTVARLFFEHFIFKLPDQEPILEARGIAVWLNSYRPVRIPAEFRSKFVQFLRQKSCGVQHHL SEQ ID NO 49: *L. esculentum/L. hirsutum* chimeric optimization 20 cDNA
ATGAGTGATCAGGTCTATCACCATGAAGTTGAACTCAAAGTCCGGGACTATGAATTGGATCAGTATGGTGTTGTAAA SEQ ID NO 105: *L. esculentum/L. hirsutum* chimeric optimization 20 ORF
MSDQVYHHEVELKVRDYELDQYGVVNNAIYASYCQHGRHELLERIGISADEVARSGDALALTELSLKYLAPLRSGDR
FVVRARLSHFTVARLFFEHFIFKLPDQEPILEARGIAVWLNKSYRPVRIPAEFRSKFVQFLRQKSCGVQHHL SEQ ID NO 50: *L. esculentum/L. hirsutum* chimeric optimization 21 cDNA
ATGGCTGAGTTCCATGACGTTGAACTCACAGTCAGGGACTATGAGTTGGATCAGTTTGGTGTTGTAAATAATGCTAC
TTATGCGAGTTATTGTCAACATTGTCGTCATGCGTTTCTAGAAAAAATTGGTGTTAGTGTTGATGAAGTAACGCGAA
ATGGTGATGCATTAGCTGTAACAGAGCTCTCACTTAAGTTTCTAGCACCACTAAGGAGTGGAGATAGATTCGTGGTG
AGGGCGCGATTATCCCACTTTACAGTAGCTCGATTGTTTTTCGAGCATTTCATCTTCAAGCTTCCAGATCAAGAGCC
TATATTGGAGGCAAGAGGAATAGCAGTGTGGCTTAATAGAAGTTATCGTCCTATTCGAATTCCGTCAGAGTTCAATT
CAAAATTTGTTAAATTCCTTCACCAGAAGAGTTGCGGTGTACAACATCATCTC SEQ ID NO 106: *L. esculentum/L. hirsutum* chimeric optimization 21 ORF
MAEFHDVELTVRDYELDQFGVVNNATYASYCQHCRHAFLEKIGVSVDEVTRNGDALAVTELSLKFLAPLRSGDRFVV
RARLSHFTVARLFFEHFIFKLPDQEPILEARGIAVWLNRSYRPIRIPSEFNSKFVKFLHQKSCGVQHHL SEQ ID NO 51: *L. esculentum/L. hirsutum* chimeric optimization 22 cDNA
ATGAGTGATCAGGTCTATCACCATGACGTTGAACTCACAGTCAGGGACTATGAGTTGGATCAGTTTGGTGTTGTAAA
TAATGCTACTTATGCGAGTTATTGTCAACATTGTCGTCATGCGTTTCTAGAAAAAATTGGTGTTAGTGTTGATGAAG
TAACGCGAAATGGTGATGCATTAGCTGTAACAGAGCTCTCACTTAAGTTTCTAGCACCACTAAGGAGTGGAGATAGA
TTCGTGGTGAGGGCGCGATTATCCCACTTTACAGTAGCTCGATTGTTTTTCGAGCATTTCATCTTCAAGCTTCCAGA
TCAAGAGCCTATATTGGAGGCAAGAGGAATAGCAGTGTGGCTTAATAGAAGTTATCGTCCTATTCGAATTCCGTCAG
AGTTCAATTCAAAATTTGTTAAATTCCTTCACCAGGAGGCATCCAAC SEQ ID NO 107: *L. esculentum/L. hirsutum* chimeric optimization 22 ORF
MAEFHDVELTVRDYELDQFGVVNNATYASYCQHCRHAFLEKIGVSVDEVTRNGDALAVTELSLKFLAPLRSGDRFVV
RARLSHFTVARLFFEHFIFKLPDQEPILEARGIAVWLNRSYRPIRIPSEFNSKFVKFLHQEASN SEQ ID NO 52: *L. esculentum/L. hirsutum* chimeric optimization 23 cDNA
ATGGCTGAGTTCCATGACGTTGAACTCACAGTCAGGGACTATGAGTTGGATCAGTTTGGTGTTGTAAATAATGCTAC
TTATGCGAGTTATTGTCAACATTGTCGTCATGCGTTTCTAGAAAAAATTGGTGTTAGTGTTGATGAAGTAACGCGAA
ATGGTGATGCATTAGCTGTAACAGAGCTCTCACTTAAGTTTCTAGCACCACTAAGGAGTGGAGATAGATTCGTGGTG
AGGGCGCGATTATCCCACTTTACAGTAGCTCGATTGTTTTTCGAGCATTTCATCTTCAAGCTTCCAGATCAAGAGCC
TATATTGGAGGCAAGAGGAATAGCAGTGTGGCTTAATAGAAGTTATCGTCCTATTCGAATTCCGTCAGAGTTCAATT
CAAAATTTGTTAAATTCCTTCACCAGGAGGCATCCAAC SEQ ID NO 108: *L. esculentum/L. hirsutum* chimeric optimization 23 ORF
MAEFHDVELTVRDYELDQFGVVNNATYASYCQHCRHAFLEKIGVSVDEVTRNGDALAVTELSLKFLAPLRSGDRFVV
RARLSHFTVARLFFEHFIFKLPDQEPILEARGIAVWLNRSYRPIRIPSEFNSKFVKFLHQEASN SEQ ID NO 53: *L. esculentum/L. hirsutum* chimeric optimization 24 cDNA
ATGGCTGAGTTCCATGACGTTGAACTCACAGTCAGGGACTATGAGTTGGATCAGTTTGGTGTTGTAAATAATGCTAC
TTATGCGAGTTATTGTCAACATTGTCGTCATGCGTTTCTAGAAAAAATTGGTGTTAGTGTTGATGAAGTAACGCGAA
ATGGTGATGCATTAGCTGTAACAGAGCTCTCACTTAAGTTTCTAGCACCACTAAGGAGTGGAGATAGATTTGTCGTG
AAGGCACGAATATCTGATTCTTCAGCTGCTCGTTTGTTTTTCGAACACTTCATCTTCAAGCTTCCAGATCAAGAGCC
TATATTGGAGGCAAGAGGAATAGCAGTGTGGCTTAATAGAAGTTATCGTCCTATTCGAATTCCGTCAGAGTTCAATT
CAAAATTTGTTAAATTCCTTCACCAGAAGAGTTGCGGTGTACAACATCATCTC SEQ ID NO 109: *L. esculentum/L. hirsutum* chimeric optimization 24 ORF
MAEFHDVELTVRDYELDQFGVVNNATYASYCQHCRHAFLEKIGVSVDEVTRNGDALAVTELSLKFLAPLRSGDRFVV
KARISDSSAARLFFEHFIFKLPDQEPILEARGIAVWLNRSYRPIRIPSEFNSKFVKFLHQKSCGVQHHL SEQ ID NO 54: *L. esculentum/L. hirsutum* chimeric optimization 25 cDNA
ATGAGTGATCAGGTCTATCACCATGACGTTGAACTCACAGTCAGGGACTATGAGTTGGATCAGTTTGGTGTTGTAAA
TAATGCTACTTATGCGAGTTATTGTCAACATTGTCGTCATGCGTTTCTAGAAAAAATTGGTGTTAGTGTTGATGAAG
TAACGCGAAATGGTGATGCATTAGCTGTAACAGAGCTCTCACTTAAGTTTCTAGCACCACTAAGGAGTGGAGATAGA
TTTGTCGTGAAGGCACGAATATCTGATTCTTCAGCTGCTCGTTTGTTTTTCGAACACTTCATCTTCAAGCTTCCAGA
TCAAGAGCCTATATTGGAGGCAAGAGGAATAGCAGTGTGGCTTAATAGAAGTTATCGTCCTATTCGAATTCCGTCAG
AGTTCAATTCAAAATTTGTTAAATTCCTTCACCAGGAGGCATCCAAC SEQ ID NO 110: *L. esculentum/L. hirsutum* chimeric optimization 25 ORF
MSDQVYHHDVELTVRDYELDQFGVVNNATYASYCQHCRHAFLEKIGVSVDEVTRNGDALAVTELSLKFLAPLRSGDR
FVVKARISDSSAARLFFEHFIFKLPDQEPILEARGIAVWLNRSYRPIRIPSEFNSKFVKFLHQEASN SEQ ID NO 55: *L. esculentum/L. hirsutum* chimeric optimization 26 cDNA
ATGGCTGAGTTCCATGACGTTGAACTCACAGTCAGGGACTATGAGTTGGATCAGTTTGGTGTTGTAAATAATGCTAC
TTATGCGAGTTATTGTCAACATTGTCGTCATGCGTTTCTAGAAAAAATTGGTGTTAGTGTTGATGAAGTAACGCGAA
ATGGTGATGCATTAGCTGTAACAGAGCTCTCACTTAAGTTTCTAGCACCACTAAGGAGTGGAGATAGATTTGTCGTG
AAGGCACGAATATCTGATTCTTCAGCTGCTCGTTTGTTTTTCGAACACTTCATCTTCAAGCTTCCAGATCAAGAGCC
TATATTGGAGGCAAGAGGAATAGCAGTGTGGCTTAATAGAAGTTATCGTCCTATTCGAATTCCGTCAGAGTTCAATT
CAAAATTTGTTAAATTCCTTCACCAGGAGGCATCCAAC SEQ ID NO 111: *L. esculentum/L. hirsutum* chimeric optimization 26 ORF
MAEFHDVELTVRDYELDQFGVVNNATYASYCQHCRHAFLEKIGVSVDEVTRNGDALAVTELSLKFLAPLRSGDRFVV
KARISDSSAARLFFEHFIFKLPDQEPILEARGIAVWLNRSYRPIRIPSEFNSKFVKFLHQEASN SEQ ID NO 56: *Solanum tuberosum* optimization 4 cDNA
ATGGGTGATCAGCTCTATCAACATGAAGTTGAACTCCAAGTCAGGGACTATGAATTGGATCAGTTTGGTGTTGTAAA
CAATGCTACTTATGCAAGTTATTGTCAACATTGCCGTCATGAGTTTCTTGAgAAGATTGGTGTAAGTGTTGATGAAG
TAactaGaACTGGTGAAGCATTAGCAACAACAGAGCTTTCACTTAAGTATCTtGCACCTCTcAGGAGTGGAGATAGA
TTTGTGGTGAAGGTGaGAATATCCaGgTCTACAGCAGCTCGtTTGTTcTTCGAGCATTTCATCTTCAaCTTCCAGA
TCAAGAGCCTATATTGGAGGCAAGAGGAATAGCAGTGTGGCTTAATAGAAGTTACCGTCCTATCaGAATaCCATCAG
AGTTCAGTTCAAAgTTTGTTCAGTTCCTTCACCAGAAGAGTTGCGGTACACAACACCGTCTC SEQ ID NO 112: *Solanum tuberosum* optimization 4 ORF
MGDQLYQHEVELQVRDYELDQFGVVNNATYASYCQHCRHEFLEKIGVSVDEVTRTGEALATTELSLKYL
APLRSGDRFVVKVRISRSTAARLFFEHFIFKLPDQEPILEARGIAVWLNRSYRPIRIPSEFSSKFVQFLHQKS
CGTQHRL SEQ ID NO 113: *Ricinus communis* MKT cDNA
ATGGCATTGCAGCAGGCATTTATCTACCCAATGCAAGTGACTACTCCCCTCTCACGTGCCAACACAACAT
GGATCAATCTCCACCGTCCATCAGCATCACTACTATTTCGAGTTTCCGGCCGCCCATGTCGCCAGTCGT
CCGGTCACTCCCTACCGTGAAGAGCTGCCGTGGGTTATCATTTCTTGATATCAGAGGCGGTAAAGGAATG
AATAGTTTTGTTGGTGTTGAGCTAAAAGTGCGTGATTATGAGCTTGATCAGTACGGAGTTGTCAATAATG
CTGTCTATGCCAGTTATTGTCAGCATGGTCGTCATGAACTTTTGGAGAGGATTGGGGTCAGTGCTGATGC
TGTTGCTCGCACAGGTGATGCATTGGCACTCTCCGAGTTGTCACTCAAGTTCCTTGCACCTCTAAGAAGT
GGGAGACAGGTTTGTTGTAAAGGTGAGGATCTCTGGCTCCTCAGCTGCCCGCTTATACTTTGATCACTTCA
TCTTCAAGCTGCCAAATGAAGAGCCTATTTTGGAAGCAAAAGCCACAGCAGTATGGCTTGACAAAAATTA
TCGTCCTGTCCGTATTCCATCTGATATGAGGTCTAAATTGGTTCAGTTTCTCAAACACGAGGAGTCTAAT gi|255572095|ref|XM_002526942.1|*Ricinus communis* acyl-CoA thioesterase,
putative, mRNA SEQ ID NO 170: *Ricinus communis* MKT ORF
MALQQAFIYPMQVTTPLSRANTTWINLHRPSASLLFRVSRPPMSPVVRSLPTVKSCRGLSFLDIRGGKGM
NSFVGVELKVRDYELDQYGVVNNAVYASYCQHGRHELLERIGVSADAVARTGDALALSELSLKFLAPLRS
GDRFVVKVRISGSSAARLYFDHFIFKLPNEEPILEAKATAVWLDKNYRPVRIPSDMRSKLVQFLKHEESN SEQ ID NO 114: *Populus trichocarpa* MKT cDNA
ATGATTTTGCAGGCATTGGCAATAACCCCGCCGCCACACGTGACGTTTCCTACCACCTCACGTGCCTGCG
CAAAATGGATGATCCATCTTCCCCGTCAATCCTCATCTGCTCCGTTTCCAACATCCCGGCCGCCACATGT
GCGGTCACTGCCCCTCATCAGAAACTGCACGTCGTTACCATTTATCGATCTCAAAGCTGGCAAAGGAATG
AGTGGGTTAGTGGAAGTGGAGCTAAAAGTGCGTGATTACGAGCTGGATCAATTCGGAGTTGTCAACAATG
CTGTTTACGCAAGTTATTGCCAACATGGTCGTCATGAGCTTTTGGAGAGGATTGGTGTCAGTGCTGATGT
GGTTGCTCGCACTGGCGATGCTTTGGCACTGTCAGAATTGTCACTCAAATTCCTCGCCCCGCTAAGAAGT
GGGAGACAGGTTTGTTGTAAAGGTAAGGATCTCTGGTTCCTCTGCTGCTCGCCTATACTTTGAACACTTCA
TTTTCAGACTGCCAAATGAAGAGCCTATTCTGGAAGCAAAAGCAACGGCTGTCTGGCTTGACAAAAAATA
TCATCCAGTTCGCATTCCACCTGAATTCAGATCTAAATTTGTTCAGTTCCTTCGGCATGAGGAGTCT gi|73934722|gb|DT518032.1|DT518032 WS02436.B21_A02 PTxD-ICC-N-A-14 *Populus
trichocarpa* x *Populus deltoides* cDNA clone WS02436_A02 3', mRNA sequence SEQ ID NO 171: *Populus trichocarpa* MKT ORF
MILQALAITPPPHVTFPTTSRACAKWMIHLPRQSSSAPFPTSRPPHVRSLPLIRNCTSLPFIDLKAGKGM
SGLVEVELKVRDYELDQFGVVNNAVYASYCQHGRHELLERIGVSADVVARTGDALALSELSLKFLAPLRS
GDRFVVKVRISGSSAARLYFEHFIFRLPNEEPILEAKATAVWLDKKYHPVRIPPEFRSKFVQFLRHEES SEQ ID NO 115: *Vitis vinifera* "A" MKT cDNA
ATGTTGCAGGCTCTCCTCTCCCCCACGCACATGGCGGTTCCCGCCTCACGTGCCCACACAAGGGGCCTCC
GTCTCTATCGTCCACCACTTCTTCTCCCGGCACCTCAGCCTCCTAGCAATTGTCGCTCCCCACGACTCCG
ATCAGTCCCGCCGTGAGGAGCGCCAGTGGACTCGCTTTTGATTTCAAAGGCGGAAAAGGAATGAGTGGG
TTCCTTGATGTTGAGCTCAAAGTCCGGGATTATGAATTGGATCAATATGGTGTTGTAAACAATGCTGTTT
ATGCAAGTTATTGTCAACATGGTCGGCATGAGCTTCTGGAAAAGATTGGTGTCAATGCTGATGCTGTTGC
TCGCACTGGTGATGCATTAGCACTTTCAGAGCTGACACTCAAATTCCTTGCACCTCTGAGAAGTGGAGAC
AGGTTTGTGGTGAAGGTGAGGGTCTCTGATTCCTCAGCTGCCCGCTTATACTTTGAACACTTCATCTTCA
AGCTCCCAAATGAAGAGCCCATCTTGGAAGCTAGGGCCACAGCAGTATGTCTCGACAAAAACTACCGTCC
CGTTCGAATACCAACAGAGATAAGATCTAAATTGGTTCAATTCCTACGACATGAGGAATCCCAT SEQ ID NO 172: *Vitis vinifera* "A" MKT ORF
MLQALLSPTHMAVPASRAHTRGLRLYRPPLLLPAPQPPSNCRSPRLRSVPAVRSASGLAFDFKGGKGMSG
FLDVELKVRDYELDQYGVVNNAVYASYCQHGRHELLEKIGVNADAVARTGDALALSELTLKFLAPLRSGD
RFVVKVRVSDSSAARLYFEHFIFKLPNEEPILEARATAVCLDKNYRPVRIPTEIRSKLVQFLRHEESH gi|225424011|ref|XP_002283543.1|PREDICTED: hypothetical protein [*Vitis
vinifera*]

SEQ ID NO 116: *Vitis vinifera* "B" MKT cDNA
ATGTTGCAGGCTCTCCTCTCCCCCACGCACATGGCGGTTCCCGCCTCACGTGCCGACACAAGGGGCCTCC
GTCTCTACTGTCCACCACTTCTTCTCCCGGCACCTCAGCCTCCTAGCAATTGTCGCTCCCCACGTCTCCG
ATCAGTCCCGCCGTGAGGAGCGCCAGTGGACTTGCTTTTGATTTCAAAGGCGGAAAAGGAATGAGTGGG
TTCCTTGATGTTGAGCTCAAAGTCCGGGATTATGAATTGGATCAATATGGTGTTGTAAACAATGCTGTTT
ATGCAAGTTATTGTCAACATGGTCGGCATGAGCTTCTGGAAAAGATTGGTCTCAATGCTGATGCTGTTGC
TTGCATTGGTGACGCTGTAGCACTTTCAGAGCTGACACTCAAATTCCTTGCACCTCTGAGAAGTGGAGAC
AGGTTTGTGGTGAAGGTGAGGGTCTCTGATGCCTCAGCTGCTCGCTTATACTTTGAACACTTCATCTTCA
AGCTCCCAAATGAAGAGCCCATCTTGGAAGCTAGGGCCACAGGAGTATGTCTCGACAAAAACTACCGTCC
CGTTCGAATACCAACAGAGATAAGATCTATATTGGTTCAATTCCTACGACATGAGGAATCCCAT SEQ ID NO 173: *Vitis vinifera* "B" MKT ORF
MLQALLSPTHMAVPASRADTRGLRLYCPPLLLPAPQPPSNCRSPRLRSVPAVRSASGLAFDFKGGKGMSG
FLDVELKVRDYELDQYGVVNNAVYASYCQHGRHELLEKIGLNADAVACIGDAVALSELTLKFLAPLRSGD
RFVVKVRVSDASAARLYFEHFIFKLPNEEPILEARATGVCLDKNYRPVRIPTEIRSILVQFLRHEESH gi|225424015|ref|XP_002283545.1|PREDICTED: hypothetical protein [*Vitis vinifera*]

SEQ ID NO 117: *Arabidopsis thaliana* "A" MKT cDNA
ATGTTTCTTCAGGTTACCGGCACGGCGACTCCGGCTATGCCTGCGGTAGTGTTTCTCAATTCATGGAGAC
GACCACTTAGTATTCCTCTCCGGAGCGTAAAAACCTTCAAGCCTCTAGCATTCTTCGATCTCAAAGGAGG
CAAAGGAATGAGTGAGTTCCATGAGGTTGAACTCAAAGTTCGTGATTATGAATTGGATCAGTTTGGTGTT
GTGAACAATGCTGTTTACGCAAACTACTGTCAACACGGTCGACATGAGTTTCTAGAGAGTATCGGTATCA
ACTGCGACGAAGTAGCACGTTCTGGGGAAGCCTTAGCAATTTCAGAGTTGACAATGAAGTTCCTTTCACC
TTTACGTAGCGGAGACAAATTCGTGGTGAAAGCGAGGATATCGGGGACATCTGCTGCGCGTATTTACTTC
GATCATTTCATCTTTAAACTTCCAAATCAAGAGCCTATATTGGAGGCAAAAGGAATAGCTGTGTGGCTCG
ACAACAAGTACCGTCCTGTTCGCATCCCATCTTCTATACGTTCTAAATTTGTTCACTTCCTACGCCAAGA
CGACGCCGTT SEQ ID NO 174: *Arabidopsis thaliana* "A" MKT ORF
MFLQVTGTATPAMPAVVFLNSWRRPLSIPLRSVKTFKPLAFFDLKGGKGMSEFHEVELKVRDYELDQFGV
VNNAVYANYCQHGRHEFLESIGINCDEVARSGEALAISELTMKFLSPLRSGDKFVVKARISGTSAARIYF
DHFIFKLPNQEPILEAKGIAVWLDNKYRPVRIPSSIRSKFVHFLRQDDAV gi|18408985|ref|NP_564926.1|thioesterase family protein [*Arabidopsis thaliana*]

SEQ ID NO 118: *Arabidopsis thaliana* "B" MKT cDNA
ATGATTCGGGTTACCGGCACGGCGGCTCCGGCTATGTCTGTGGTGTTTCCGACTTCATGGAGACAACCGG
TTATGCTTCCTCTCCGGAGCGCAAAGACCTTCAAGCCTCACATTTCTTGATCTTAAAGGAGGCAAAGA
AATGAGTGAGTTCCATGAGGTTGAGCTTAAAGTTCGTGATTATGAATTGGATCAGTTTGGTGTTGTGAAC
AATGCTGTTTACGCAAACTACTGCCAACACGGCATGCACGAATTTCTAGAGAGTATTGGTATCAACTGTG
ATGAAGTTGCCCGTTCTGGTGAAGCCTTAGCAATATCAGAGTTGACAATGAATTTCCTTGCACCTTTACG
TAGCGGAGACAAGTTTGTAGTGAAAGTGAACATATCTAGAACATCTGCTGCGCGTATTTACTTCGATCAT
TCCATCTTGAAACTTCCAAATCAAGAGGTTATATTGGAGGCGAAAGCAACAGTTGTATGGCTTGACAACA
AGCACCGTCCTGTTCGTATCCCATCTTCGATACGCTCTAAATTTGTTCACTTCCTACGCCAAAACGACAC
AGTT SEQ ID NO 175: *Arabidopsis thaliana* "B" MKT ORF
MIRVTGTAAPAMSVVFPTSWRQPVMLPLRSAKTFKPHTFLDLKGGKEMSEFHEVELKVRDYELDQFGVVN
NAVYANYCQHGMHEFLESIGINCDEVARSGEALAISELTMNFLAPLRSGDKFVVKVNISRTSAARIYFDH
SILKLPNQEVILEAKATVVWLDNKHRPVRIPSSIRSKFVHFLRQNDTV gi|42563045|ref|NP_176995.2|thioesterase-related [*Arabidopsis thaliana*]

SEQ ID NO 119: *Arabidopsis thaliana* "C" MKT cDNA
ATGCTTAAAGCTACCGGCACAGTGGCTCCGGCTATGCACGTGGTGTTTCCCTGTTTTTCGAGTCGACCGC
TTATCCTACCTCTCCGGAGCACAAAGACCTTCAAACCTCTCTCATGTTTCAAACAGCAAGGAGGCAAAGG
AATGAATGGAGTCCATGAGATTGAACTTAAAGTTCGTGATTATGAATTAGACCAATTTGGTGTTGTGAAC
AACGCTGTTTATGCAAACTACTGCCAACACGGTCAACACGAGTTTATGGAGACTATCGGTATCAACTGTG
ATGAAGTGTCCCGTTCTGGTGAAGCATTGGCAGTTTCTGAATTGACAATAAAGTTTCTTGCACCTTTACG
TAGTGGATGCAAGTTTGTGGTGAAAACGAGGATATCGGGGACATCTATGACGCGCATTTACTTTGAACAG
TTCATCTTTAAACTTCCAAATCAAGAGCCTATTTTGGAGGCAAAAGGAATGGCTGTGTGGCTTGACAAGA
GGTACCGTCCTGTTTGTATCCCGTCTTACATACGCTCTAATTTCGGTCACTTCCAACGTCAACACGTTGT
CGAATATTGA SEQ ID NO 176: *Arabidopsis thaliana* "C" MKT ORF
MLKATGTVAPAMHVVFPCFSSRPLILPLRSTKTFKPLSCFKQQGGKGMNGVHEIELKVRDYELDQFGVVN
NAVYANYCQHGQHEFMETIGINCDEVSRSGEALAVSELTIKFLAPLRSGCKFVVKTRISGTSMTRIYFEQ
FIFKLPNQEPILEAKGMAVWLDKRYRPVCIPSYIRSNFGHFQRQHVVEY gi|18399594|ref|NP_564457.1|thioesterase family protein [*Arabidopsis thaliana*]

SEQ ID NO 120: *Picea sitchensis* "A" MKT cDNA
ATGTACAACATGGATCTTTTCGGAGCCAAAGGTATGGCTAGGCCTTTTGAGCTCGAGTTAAAAGTGCGTG
ATTATGAATTGGACCAATATGGAGTTGTCAACAATGCAACTTATGCAAGTTATTGCCAACATTGTCGTCA
TGAACTCTGTGAAGCAATTGGGTTTAGCCCAGATGTAATAGCGCGTACTGGGAATGCCCTTGCATTGTCA
GAATTGTCTTTGAAGTACCTTGCACCTCTAAGAAGTGGTGATAGTTTTGTTGTCACTGCAAGGATCTCTG
GTTCATCTGCTGTACGCCTGTTTTTTGAGCACTTCATCTATAAGTTACCTAATAGAGAGCCTGTCTTGGA
AGCAAAGGCCACAGCTGTTTATCTTGATAAAATCTATCGACCTGTTCGACTTCCAGCTGATTTTAAATCT
AAGATCACGCTATTTCTTCGTAATGAAGAATTGAAC SEQ ID NO 177: *Picea sitchensis* "A" MKT ORF
MYNMDLFGAKGMARPFELELKVRDYELDQYGVVNNATYASYCQHCRHELCEAIGFSPDVIARTGNALALS
ELSLKYLAPLRSGDSFVVTARISGSSAVRLFFEHFIYKLPNREPVLEAKATAVYLDKIYRPVRLPADFKS
KITLFLRNEELN gi|294464460|gb|ADE77741.1|[*Picea sitchensis*]

SEQ ID NO 121: *Picea sitchensis* "B" MKT cDNA
ATGACCACAGCAATGGGTGCAATATCAGGTGGGATTTCAGTGGGAGTAAGCGCCAGGTATCCTCATGTTC
AGTGCAGCAGCTTCATTCAAAATCCCACCAAAAAATTGTCGAGAGCCCTTGCATTTCCTTCTCTTCGCAC
AGCGTCTTGTAATCCCGTTTTTAGAAGGGCATTGCCTCCCATTGCCAACATGTACAACATGGATCTTTTC
GGAGCCAAAGGTATGGCTAGACCTTTTGAGCTCGAGTTAAAAGTGCGTGATTATGAATTGGACCAATATG
GAGTTGTCAACAATGCAACTTATGCAAGTTATTGCGAACATTGTCTTCATGAACTCTTTGAAGCAATTGG
GTTTAGCCCAGATGCAATAGCGCGTACTGGGAATGCCCTTGCATTGTCAGAATTGTCTTTGAAGTACCTT
GCACCTCTAAGAAGTGGTGATAGTTTTGTTGTCACTGCAAGGATCTCCGGTTCATCTGCTGTACGCCTGT
TTATTGAGCACTTCATCTATAAGTTACCTAATAGAGAGCCTGTCTTGGAAGCAAAGGCCACAGCTGTTTA
TCTTGATAAAATCTATCGACCTGTTCGACTTCCAGCTGATTTTAAATCTAAGATCACGCTATTTCTTCGT
AATGAAGAATTGAAC SEQ ID NO 178: *Picea sitchensis* "B" MKT ORF
MTTAMGAISGGISVGVSARYPHVQCSSFIQNPTKKLSRALAFPSLRTASCNPVFRRALPPIANMYNMDLF
GAKGMARPFELELKVRDYELDQYGVVNNATYASYCEHCLHELFEAIGFSPDAIARTGNALALSELSLKYL
APLRSGDSFVVTARISGSSAVRLFIEHFIYKLPNREPVLEAKATAVYLDKIYRPVRLPADFKSKITLFLR
NEELN >gi|294464416|gb|ADE77720.1|[*Picea sitchensis*]

SEQ ID NO 122: *Oryza sativa japonica* MKT cDNA
ATGCACCACCAGATTTGGCGCCTCCTCCCCAGCGCCCTCTCGCCGATCCACGCCGGAGCTCCCCGGCCGA
GCCGCCGCCGGCGCGGCTAGGCCGCCCTTCACCGCAACGACGGCGGGCGCTCGCGCTCACGCACCTCGC
CACCCGGCGCACATGTCGCCTCCTCGCTGTCTCCGCCCAGTCCGCCAGCCCCACGCCGGCTTGAGGTTG
GATCAGTTTTTCGAGGTGGAGATGAAGGTACGAGATTATGAACTCGACCAATATGGGGTTGTCAACAATG
CCATCTATGCTAGTTACTGCCAACATGGTCGTCATGAGCTACTTGAAAGTGTAGGCATAAGTGCAGATGC
AGTAGCAGCAGCGGTGAGTCGCTGGCCCTCTCTGAACTGCACCTCAAGTACTACGCGCCTTTGAGAAGT
GGTGACAAGTTCGTCGTTAAGGTCAGGCTTGCGAGCACAAAAGGTATAAGGATGATATTCGAGCACTTCA
TTGAAAAGCTGCCTAATCGTGAGCTCATTTTGGAAGCGAAGGCAACAGCGGTTTGTTTGAACAAAGACTA
CCGCCCCACCCGTATATCTCCAGAGTTCCTGTCCAAGCTGCAGTTCTTCACTTCTGAAGGCAGTAGCAGT SEQ ID NO 179: *Oryza sativa japonica* MKT ORF
MHHQIWRLLPSALSPIHAGAPRPSRPPARLGRPSPQRRRALALTHLATRRTCRLLAVSAQSASPHAGLRL
DQFFEVEMKVRDYELDQYGVVNNAIYASYCQHGRHELLESVGISADAVARSGESLALSELHLKYYAPLRS
GDKFVVKVRLASTKGIRMIFEHFIEKLPNRELILEAKATAVCLNKDYRPTRISPEFLSKLQFFTSEGSSS >gi|38345477|emb|CAE01692.2|OSJNBa0010H02.15 [*Oryza sativa (japonica cultivar-group)*]

SEQ ID NO 123: *Oryza sativa indica* MKT cDNA
ATGCACCACCAGATTTGGCGCCTCCTCCCCAGCGCCCTCTCGCCGATCCACGCCGGAGCTCCCCGGCCGA
GCCGCCGCCGGCGCGGCTAGGCCGCCCCTTCACCGCAACGACGGCGGGCGCTCGCGCTCGCGCTCGCGCA
CCTCGCCACCCGGCGCACATGCCGCCTCCTCGCTGTCTCCGCCCAGTCCGCCAGCCCCACGCCGGCTTG
AGGTTGGATCAGTTTTTCGAGGTGGAGATGAAGGTACGAGATTATGAACTCGACCAATATGGGGTTGTCA
ACAATGCCATCTATGCTAGTTACTGCCAACATGGTCGTCATGAGCTACTTGAATGTGTAGGCATAAGTGC
AGATGCAGTAGCACGCAGCGGTGAGTCGCTGGCCCTCTCTGAACTGCACCTCAAGTACTACGCGCCTTTG
AGAAGTGGTGACAAGTTCGTCGTTAAGGTCAGGCTTGCGAGCACAAAAGGTATAAGGATGATATTCGAGC
ACTTCATTGAAAAGCTGCCTAATCGTGAGCTCATTTTGGAAGCGAAGGCAACAGCGGTTTGTTTGAACAA
AGACTACCGCCCCACCCGTATATCTCCAGAGTTCCTGTCCAAGCTGCAGTTCTTCACTTCTGAAGGCAGT
AGCAGTTAA SEQ ID NO 180: *Oryza sativa indica* MKT ORF
MHHQIWRLLPSALSPIHAGAPRPSRPPARLGRPSPQRRRALALALAHLATRRTCRLLAVSAQSASPHAGL
RLDQFFEVEMKVRDYELDQYGVVNNAIYASYCQHGRHELLECVGISADAVARSGESLALSELHLKYYAPL
RSGDKFVVKVRLASTKGIRMIFEHFIEKLPNRELILEAKATAVCLNKDYRPTRISPEFLSKLQFFTSEGS
SS gi|116310405|emb|CAH67414.1|OSIGBa0143N19.8 [*Oryza sativa (indica cultivar-group)*]

SEQ ID NO 124: *Zea mays* MKT cDNA
ATGCATCACCGGTTCGCGGGCTCGTGCCCACCGCCCGCCCCGCTCTGCCGCCGATCCACGGCGGAGTCG
TCGGCCGGAGCTATCCGCCCGTCCACCGGTCCTTGGCGCTTCGCCTGGCGCCGTTTGCCTCCGCGTCTGT
CCGACGCGCGTGCCGCCCCTCGCCGTCTCCGCCCAATCCACCAGCCTCCGGCCGGAGAAGTTTTTTGAA
GTGGAGATGAAGGTGCGCGACTATGAAATTGACCAGTATGGTGTCGTCAACAATGCAATCTATGCTAGCT
ACTGCCAACATGGTCGTCACGAGCTGCTTGAGAGCGTAGGCATCAGTGCAGATGCAGTGGCGCGCAGTGG
GGAATCCCTGGCTCTCTCTGAGTTGAACCTCAAGTACTTTGCCCCTTTGAGGAGTGGCGATAAGTTTGTT
GTTAAGGTGAGGCTTGCAGGCATCAAAGGTGTACGGATGATATTCGACCACATCATTACAAAACTGCCTA
ATCATGAGCTAATTCTGGAGGCAAAGGCAACGGCTGTTTGCCTGAACAAAGACTACTATCCTACCCGTAT
TCCTCGTGAACTATTGTCCAAGATGCAGCTCTTCTTACCCGTGGACAGCAGAGGGTCAAATGAAGACGTT
AATAATCGGAATAACAGCTGCAAC SEQ ID NO 181: *Zea mays* MKT ORF
MHHRFAGLVPTARPALPPIHGGVVGRSYPPVHRSLALRLAPFASASVRRACRPLAVSAQSTSLRPEKFFE
VEMKVRDYEIDQYGVVNNAIYASYCQHGRHELLESVGISADAVARSGESLALSELNKYFAPLRSGDKFV
VKVRLAGIKGVRMIFDHIITKLPNHELILEAKATAVCLNKDYYPTRIPRELLSKMQLFLPVDSRGSNEDV
NNRNNSCN gi|238014368|gb|ACR38219.1|unknown [Zea mays]

SEQ ID NO 125: *Sorghum bicolor* MKT cDNA
ATGCATCACCAGTTCGCGCGCCTCGTGCCCACCGCCCGCCCCGCGCTGCCGCCGATCCACGGCGGAGCCG
TCGGCCGGAGCTCTCCGCACGTCCACCGGGCCGTGGCGCTTCGACGGCGCGCTCGCCTCCGCGGCTGG
CCGGCGCGCGTGCCGCCCCCTCGCCGTCTCCGCCCAATCCACCAGCCCCCAGGCCGGCTTGAGGCTGGAG
GAGAAGTTTTTTGAAGTGGAGATGAAGGTGCGTGACTATGAACTTGACCAGTATGGTGTTGTCAACAATG
CCGTCTATGCTAGCTACTGCCAACATGGTCGTCACGAGCTACTTGAGAGTGTAGGCATCAGTGCGGATGC
AGTGGCGCGCAGTGGGGAGTCGCTGGCCCTCTCTGAGCTAAACCTAAAGTACTTTGGCCCTTTGAGGAGC
GGCGACAAGTTTGTTGTTAAGGTGAGGCTTGTGGGCATCAAAGGTGTACGGATGATATTCGAGCACATCA
TTGAGAAACTTCCTAATCACGAGCTAATTCTGGAGGCAAAGGCAACAGCTGTTTGCCTGAACAAAGACTA
CTATCCTACCCGCATTCCTCGTGAACTATTGTCCAAGATGCAGCTCTTCTCATCCGAGGACAGCAGAGGG
TCAAATAAAGACGTTAATAATCGGAATAACAGCTGCAAC SEQ ID NO 182: *Sorghum bicolor* MKT cDNA
MHHQFARLVPTARPALPPIHGGAVGRSSPHVHRAVALRRAPLASAAGRRACRPLAVSAQSTSPQAGLRLE
EKFFEVEMKVRDYELDQYGVVNNAVYASYCQHGRHELLESVGISADAVARSGESLALSELNLKYFGPLRS
GDKFVVKVRLVGIKGVRMIFEHIIEKLPNHELILEAKATAVCLNKDYYPTRIPRELLSKMQLFSSEDSRG
SNKDVNNRNNSCN gi|242076712|ref|XP_002448292.1|hypothetical protein SORBIDRAFT_06g024720
[*Sorghum bicolor*]

SEQ ID NO 126: *Phyllostachys edulis* MKT cDNA
ATGCTGGCACTCCGGCGCGCCGCACCAGTCCACTCCACCGCGATGCGCCACCAGATTTGGCGCCTCGTGC
CCAACGCCCAGTCGCCGCTCCCGCCGATCCACGCCGATGCTGCCGCGGAGCTGCTCCCGGACCGTCAACCC
TACACCGCTCCGCCTGCCGGCGCTCGCCTCCGCCGCCACCCGAGGCATATGCCGCCCCTCGCCGTCTCC
GCTCAGTCAGCCAGCCCCCACGCCGGCCTGAGGGTGGATAAGTTTTTCGAAGTGGCCGATGAAGGTGCGCG
ACTATGAACTCGACCAGTATGGAGTTGTCAACAATGCTGTCTATGCTAGCTACTGCCAACATGGCCGTCA
TGAGCTACTTGAGAGTGTAGGCATAAGTGCAGATGCAGTAGCGCAGTGGTGAGTCGCTGGCCCTCTCT
GATCTGCACCTCAAGTTCTTCGCGCCTTTGAAGTGGTGACGAGTTTGTCGTTAAGGTGAGACTTGCAA
GCATCAAAGGTGTAAGGATGATATTCGAGCACTCCATTGAGAAGCTGCCTAACCGCGAGTTGATTTTGGA
AGCAAAGGCAACAGCTGTTTGTCTCAACAAGGACTACCGTCAACCCGTGTATCCCCAGAGTTCCTGTCC
AGGCTGCAGCTCTTCTCATCCAAGGACAGCAAGGGT gi|242389648|emb|FP100679.1|*Phyllostachys edulis* cDNA clone: bphylf027g11

SEQ ID NO 183: *Phyllostachys edulis* MKT ORF
MLALRRAAPVHSTAMRHQIWRLVPNAQSPLPPIHADARRSCSRTVNPTPLRLPALASAATRGICRPLAVS
AQSASPHAGLRVDKFFEVAMKVRDYELDQYGVVNNAVYASYCQHGRHELLESVGISADAVARSGESLALS
DLHLKFFAPLRSGDEFVVKVRLASIKGVRMIFEHSIEKLPNRELILEAKATAVCLNKDYRPTRVSPEFLS
RLQLFSSKDSKG SEQ ID NO 127: *Picea glauca* MKT cDNA
ATGGCCACAGCAATGGGTGCAATATCAGGTGGGATTTCAGTGGGAGTAAACGCCAGGTATCCTCATGTTC
AGTGCAGCAGTTTCATTCAAAATCCCACCAAAAAATTGTCGAGAGCCCTTGCATTTCCTTCTCTTCGCAC
AGCGTCTTTGTAATCCCGTATTTAGAAGGGCATTGCCTCCCATTGCCGACATGTACAACATGGAACTTTTC
GGAGCCAAAGGTATGGCTAGACCTTTTGAGCTCGAGTTAAAAGTGCGTGATTATGAATTGGACCAATATG
GAGTTGTCAACAATGCAACTTATGCAAGTTATTGCCAACATTGTCGTCATGAACTCTGTGAAGCAATTGG
GTTTAGCCCAGATGCAATAGCGCGTACTGGGAATGCCCTTGCATTGTCAGAATTGTCTTTGAAGTACCTT
GCACCTCTCAAGAAGTGGTGATAGTTTTGTTGTCACTGCAAGGATCTCCGGTTCATCTGCTGTACGCCTGT
TTTTTGAGCACTTCATCTATAAGTTACCTAATAGAGAGCCTGTCTTGGAAGCAAAGGCCACAGCTGTTTA
TCTTGATAAATCTATCGACCTGTTCGACTTCCAGCTGATTTTAAATCTAAGATCACGCTATTTCTTCGT
AATGAAGAATTGAACTAG gi|270148361|gb|BT115313.1|*Picea glauca* clone GQ03614_A18

SEQ ID NO 184: *Picea glauca* MKT ORF
MATAMGAISGGISVGVNARYPHVQCSSFIQNPTKKLSRALAFPSLRTASCNPVFRRALPPIADMYNMELF
GAKGMARPFELELKVRDYELDQYGVVNNATYASYCQHCRHELCEAIGFSPDAIARTGNALALSELSLKYL
APLRSGDSFVVTARISGSSAVRLFFEHFIYKLPNREPVLEAKATAVYLDKIYRPVRLPADFKSKITLFLR
NEELN SEQ ID NO 128: *Gossypium hirsutum* MKT cDNA
ATGCTCCAGGCTTCGGTTTTCCCGGCGCACGCCGCCTTGCCTTCCCCTCGTCCAAATGCTACTTTTCTCA
ATCTTCACCGTCCATCTTCATCCTTTCCAATCTCTCCGCTGTTGATGCCGCTGCGTGTCCCTACGCTCTC
CACCTCAAGGAGCTTCACTGTCGGAGCACTTTTTGATCTCAAAGGCGGCCAAGGAATGACTTCGTTCCAT
GAGGTTGAGCTCAAAGTCCGTGACTACGAACTGGATCAGTATGGAGTTGTTAATAATGCTGTTTATGCAA
GTTATTGTCAACACGGTCGCCATGAACTACTTGAAAGTATTGGTATCAGCTGTGATGAAGTTGCCCGCAC
TGGTGATTCATTAGCACTGTCAGAGTTGTCGCTCAAATTCTTGGACCTTTAAGGAGTGGAGACAATTTT
GTTGTTAAGGTGAGGGTTTCCAACTCCTCAGGGGCTCGCCTGTACTTTGAGCATTTCATCTTTAAGATGC
CAAATGAAGTGCCTATTCTGGAGGCAAAGGCCACAGCTGTATGGCTTGACAAAAATTATCGTCCTGCTCG
TATCCCTCCAGAATTCAGATCAAAATTTGTTCAATTCCTTCGTTGTGAGGAACCTAGT gi|78333905|gb|DT554179.1|DT554179 EST1064819 GH_TMO *Gossypium hirsutum* cDNA SEQ ID NO 185: *Gossypium hirsutum* MKT ORF
MLQASVFPAHAALPSPRPNATFLNLHRPSSSFPISPLLMPLRVPTLSTSRSFTVGALFDLKGGQGMTSFH
EVELKVRDYELDQYGVVNNAVYASYCQHGRHELLESIGISCDEVARTGDSLALSELSLKFLGPLRSGDNF
VVKVRVSNSSGARLYFEHFIFKMPNEVPILEAKATAVWLDKNYRPARIPPEFRSKFVQFLRCEEPS SEQ ID NO 129: *Glycine max* MKT cDNA
ATGCTCTACAACCACACTTCCTCGATGTCATTGCCTTCCCCATTGTACCTGAATACTACGTCGTTTCGCC
TCACGCGCCAATCTCCTTTTCCTTTTCCCCGCCGGCGCTTCAATCCACCGGCTTTCCGATCAGTTTCGCC
GTTGAGTTCCAGCCCCTCTGCATCACTCTTCGATCTCAGAGGGGGCAAAGGAATGAGTGGATTCCATGAC
GTTGAACTGAAGGTGCGCGACTATGAGTTGGATCAGTACGGTGGTGTTAACAATGCAGTTTATGCTAGTT
ATTGCCAGCACGGTCGTCATGAACTCTTGCAAAACATTGGTATTAATTGCGATGCTGTGGCTCGCAGTGG
TGATGCATTGGCATTGTCTGAACTATCGCTCAAATTCCTTGCACCTCTAAGAAGTGGAGACAAATTTGTT
GTAAGAGTTAGGATTTCTGGCTCTTCAGCTGCTCGTTTATACTTTGATCACTTCATCTATAAGCTGCCAA
ACCAAGAGCCTATTTTGGAAGCCAAGGCCATAGCGGTGCGGCTTGACAAAAACTATCGTCCTATACGAAT
TCCAGCAGAGATGAAGTCTAAATTTGTAAAGTTTATTCGAATTGAGGACTCT gi|16283114|gb|BI945379.1|BI945379 sb60f02.y1 Gm-c1010 *Glycine max*

SEQ ID NO 186: *Glycine max* MKT ORF
MLYNHTSSMSLPSPLYLNTTSFRLTRQSPFPFPPRRRFNPPAFRSVSPLSSSPSASLFDLRGGKGMSGFHD
VELKVRDYELDQYGVVNNAVYASYCQHGRHELLQNIGINCDAVARSGDALALSELSLKFLAPLRSGDKFV
VRVRISGSSAARLYFDHFIYKLPNQEPILEAKAIAVRLDKNYRPIRIPAEMKSKFVKFIRIEDS SEQ ID NO 130: *Saccharum* hybrid MKT cDNA
ATGCATCACCAGTTCGCGCGCCTCGTGCCCGCCGCCCGCCCCGCGCTGCCGCCGATCCACGGCGGAGCCG
TTGGGCGGAGCTCTCCGCCCGTCCACCGGGCCGTGGCGCTTCGCCGGGCGCCGCTCGCCTCCGCGGCTGG
CCGGCGCGCGTACCGCCCCCTGGCCGTCTCCGCCCAATCCACCAGCCCCCAAGCCGGCTTGAGGCTGGAG
GAGAAGTTTTTTGAAGTGGAGATGAAGGTGCGTGACTATGAACTTGACCAGTATGGTGTTGTCAACAATG
CAGTCTATGCTAGCTACTGCCAACATGGTCGTCACGAGGTGCTTGAGAGTGTAGGCATCAGTGCGGATGC
AGTGGCTCGCAGTGGGGAGTCGCTGGCCCTCTCTGAGCTAAACCTAAAGTACTTTGCCCCTTTGAGGAGT
GGCGACAAGTTTGTTGTTAAGGTAAGGCTTGTGGGCATCAAAGGCATGAGGATTATGTTCGAGCACATCA
TTGAGAAGCTGCCTAATCACGAGCTAATTCTGGAGGCAAAGGCAACAGCTGTTTGCCTGAACAAAGACTA
CTATCCTACCCGCATTCCTCGTGAACTACTGGCCAAGATGCAGCTCTTCTCATNCCGAGGCAGCAGAGGG
ACAAATGACGACATTAATAATCGGAATAACAGCTGCAAC

*Saccharum* hybrid cultivar SP80-3280

SEQ ID NO 187: *Saccharum* hybrid MKT ORF
MHHQFARLVPAARPALPPIHGGAVGRSSPPVHRAVALRRAPLASAAGRRAYRPLAVSAQSTSPQAGLRLE
EKFFEVEMKVRDYELDQYGVVNNAVYASYCQHGRHEVLESVGISADAVARSGESLALSELNLKYFAPLRS
GDKFVVKVRLVGIKGIRMIFEHIIEKLPNHELILEAKATAVCLNKDYYPTRIPRELLAKMQLFSXRGSRG
TNDDINNRNNSCN SEQ ID NO 131: *Arabidopsis thaliana* "A" modified cDNA
ATGgctTCAGAATTTCACGAAGTTGAATTGAAGGTTAGAGATTATGAACTCGATCAGTTCGGCGTCGTTAATAACGC
AGTTTATGCTAACTACTGCCAGCACGGCAGACACGAGTTTCTCGAGTCCATTGGCATTAACTGTGACGAGGTCGCAA
GGTCAGGAGAAGCACTTGCAATTTCCGAGCTTACTATGAAGTTCTTGTCTCCTCTTAGGAGTGGTGATAAGTTTGTC
GTTAAAGCTAGAATATCCGGGACTTCTGCTGCTAGGATTTATTTCGATCACTTTATATTCAAACTCCCAAACCAAGA
ACCAATTCTTGAGGCTAAAGGTATAGCAGTTTGGCTTGATAATAAGTACAGACCTGTACGTATCCCAAGCTCTATTA
GGTCAAAGTTTGTACACTTTCTTCGTCAGGATGATGCAGTG SEQ ID NO 188: *Arabidopsis thaliana* "A" modified ORF
MASEFHEVELKVRDYELDQFGVVNNAVYANYCQHGRHEFLESIGINCDEVARSGEALAISELTMKFLSPLRSGDKFV
VKARISGTSAARIYFDHFIFKLPNQEPILEAKGIAVWLDNKYRPVRIPSSIRSKFVHFLRQDDAV SEQ ID NO 132: *Arabidopsis thaliana* "B" modified cDNA
ATGgctTCAGAATTTCACGAAGTTGAATTGAAGGTTAGAGATTATGAACTCGATCAGTTCGGCGTCGTTAATAACGC
AGTTTATGCTAATTATTGTCAACATGGTATGCATGAGTTTCTCGAATCCATTGGCATCAACTGTGATGAAGTGGCCA
GAAGTGGTGAGGCTTTAGCAATTTCAGAACTCACAATGAATTTCCTTGCACCTCTTAGGAGTGGTGATAAATTCGTA
GTGAAGGTTAACATAAGTAGAACAAGTGCAGCCAGAATCTACTTTGATCATTCAATATTGAAACTTCCCAATCAGGA
GGTGATTCTTGAGGCTAAGGCCACCGTTGTTTGGTTGGATAACAAGCATAGGCCTGTGCGTATTCCATCTTCAATCA
GGTCAAAGTTCGTCCACTTCTTGAGACAGAACGACACTGTT SEQ ID NO189: *Arabidopsis thaliana* "B" modified ORF
MASEFHEVELKVRDYELDQFGVVNNAVYANYCQHGMHEFLESIGINCDEVARSGEALAISELTMNFLAPLRSGDKFV
VKVNISRTSAARIYFDHSILKLPNQEVILEAKATVVWLDNKHRPVRIPSSIRSKFVHFLRQNDTV SEQ ID NO 133: *Arabidopsis thaliana* "C" modified cDNA
ATGgctAATGGTGTACATGAAATTGAATTGAAGGTTAGAGATTATGAACTCGATCAGTTCGGCGTCGTTAATAACGC
AGTTTATGCCAATTACTGCCAGCATGGCCAGCATGAGTTCATGGAAACAATCGGAATTAACTGCGACGAAGTTTCAA
GGTCTGGTGAAGCACTTGCAGTCTCAGAACTCACTATAAAGTTCCTTGCACCTCTTAGGAGTGGTTGCAAATTTGTC
GTCAAGACTAGGATATCCGGTACCTCTATGACTCGTATCTATTTCGAACAATTCATCTTCAAGTTACCTAACCAAGA
ACCAATTCTTGAGGCTAAGGGTATGGCTGTATGGTTGGACAAGAGATACAGGCCTGTTTGTATTCCATCTTACATCc
gtAGCAATTTCGGTCATTTCCAAAGGCAGCACGTGGTCGAATAT SEQ ID NO 190: *Arabidopsis thaliana* "C" modified ORF
MANGVHEIELKVRDYELDQFGVVNNAVYANYCQHGQHEFMETIGINCDEVSRSGEALAVSELTIKFLAPLRSGCKFV
VKTRISGTSMTRIYFEQFIFKLPNQEPILEAKGMAVWLDKRYRPVCIPSYIRSNFGHFQRQHVVEY SEQ ID NO 134: *Populus trichocarpa* modified cDNA
ATGgctTCTggtcttGTTGAAGTCGAATTGAAGGTTAGAGATTATGAACTCGATCAGTTCGGCGTCGTTAATAACGC
AGTTTATGCTAACTATTGCCAACATGGAAGACATGAGCTCTTGGAAAGAATAGGCGTGTCCGCAGATGTCGTCGCTA
GGACAGGCGATGCATTGGCTTTGTCAGAGctTAGTCTCAAATTCTTGGCTCCTCTTAGGAGTGGTGATCGTTTTGTT
GTTAAGGTTCgtATATCTGGAAGCTCTGCCCGCAAGGCTTTACTTTGAACATTTCATCTTCcgtTTGCCTAATGAGGA
ACCCATTCTTGAGGCTAAAGCTACCGCCGTCTGGCTTGACAAGAAGTATCATCCAGTGAGAATACCACCTGAGTTCA
GATCTAAGTTCGTCCAGTTCTTGAGGCATGAAGAGTCT SEQ ID NO 191: *Populus trichocarpa* modified ORF
MASGLVEVELKVRDYELDQFGVVNNAVYASYCQHGRHELLERIGVSADVVARTGDALALSELSLKFLAPLRSGDRFV
VKVRISGSSAARLYFEHFIFRLPNEEPILEAKATAVWLDKKYHPVRIPPEFRSKFVQFLRHEES SEQ ID NO 135: *Ricinus communis* modified cDNA
atgGCTaatagcttcgttggagtaGAATTGAAGGTTAGAGATTATGAACTCGATCAGtacGGCGTCGTTAATAACGC
Agtctacgcaagctattgtcagcatggaaggcatgagttacttgaaaggattggagtgtcagctgacgctgttgccc
gtacaggcgatgcacttgcattgagtgagctttccttgaagtttctcgcaCCTCTTAGGAGTGGTgacagatttgtc
gtgaaggttagaatctccggctcaagcgccgctaggttgtacttcgacactttatattcaaactccctaacgagga
accaATTCTTGAGGCTaaggccactgccgtatggctcgacaagaattacaggcctgtcaggatcccttctgatatga
ggtctaaacttgttcaattccttaaacacgaggaaagtaac SEQ ID NO 192: *Ricinus communis* modified ORF
MANSFVGVELKVRDYELDQYGVVNNAVYASYCQHGRHELLERIGVSADAVARTGDALALSELSLKFLAPLRSGDRFV
VKVRISGSSAARLYFDHFIFKLPNEEPILEAKATAVWLDKNYRPVRIPSDMRSKLVQFLKHEESN SEQ ID NO 136: *Vitis vinifera* "A" modified cDNA
ATGgctTCAGGGTTCTTGGATGTTGAATTGAAGGTTAGAGATTATGAACTCGATCAGTACGGCGTCGTTAATAACGC
AGTCTATGCCAGTTACTGTCAACATGGAAGGCACGAGCTCcttGAgAAGATAGGAGTGAATGCAGATGCTGTTGCAC
GTACCGGCGATGCCcttGCACTCAGCGAGTTAACTCTTAAGTTcTTGGCTCCTCTTAGGAGTGGTGATAGGTTTGTG
GTGAAGGTTAGAGTGTCCGACTCATCCGCTGCCAGGCTCTACTTCGAGCACTTTATATTCAAGctcCCaAATGAGGA
GCCTATTCTTGAGGCTAGAGCAACAGCAGTCTGTCTCGATAAGAACTACCgtCCTGTTAGGATACCTACTGAAATTA
GAAGCAAACTCGTCCAGTTTctcAGGCACGAAGAATCACAT SEQ ID NO 193: *Vitis vinifera* "A" modified ORF
MASGFLDVELKVRDYELDQYGVVNNAVYASYCQHGRHELLEKIGVNADAVARTGDALALSELTLKFLAPLRSGDRFV
VKVRVSDSSAARLYFEHFIFKLPNEEPILEARATAVCLDKNYRPVRIPTEIRSKLVQFLRHEESH SEQ ID NO 137: *Vitis vinifera* "B" modified cDNA
ATGgctTCAGGGTTCTTGGATGTTGAATTGAAGGTTAGAGATTATGAACTCGATCAGTACGGCGTCGTTAATAACGC
AGTCTACGCATCATATTGCCAGCATGGGAGGCATGAATTGCTCGAAAAGATAGGTTTGAATGCAGATGCCGTTGCCT
GTATCGGCGACGCTGTTGCActtCCGAGCTTACTTTGAAGTTTTTAGCTCCTCTTAGGAGTGGTGACAGATTCGTT
GTTAAGGTGAGAGTGTCCGACGCTTCCGCAGCCAGGctcTACTTCGAGCACTTTATCTTCAAGTTGCCTAATGAAGA
ACCTATTCTTGAGGCTAGGGCCACTGGCGTTTGTCTCGATAAGAACTATAGACCTGTTAGAATCCCTACCGAAATCA
GATCTATATTGGTTCAATTCCTTAGGCACGAAGAATCCCAT SEQ ID NO 194: *Vitis vinifera* "B" modified ORF
MASGFLDVELKVRDYELDQYGVVNNAVYASYCQHGRHELLEKIGLNADAVACIGDAVALSELTLKFLAPLRSGDRFV
VKVRVSDASAARLYFEHFIFKLPNEEPILEARATGVCLDKNYRPVRIPTEIRSILVQFLRHEESH SEQ ID NO 138: *Oryza sativa japonica* modified cDNA
ATGGCTGGTCTTAGATTGGATCAGTTCTTCGAAGTTGAAATGAAGGTGAGGGATTACGAATTGGATCAGTACGGCGT
CGTTAATAACGCAATCTACGCTagcTATTGCCAGCATGGCAGGCATGAGCTTCTTGAATCAGTTGGAATTTCCGCTG
ATGCTGTTGCTAGAAGTGGTGAGTCATTGGCCTTATCAGAGTTGCACTTAAAGTACTATGCACCTCTTAGGAGTGGT
GATAAGTTCGTTGTGAAGGTTAGGCTCGCCTCTACCAAGGGTATTAGAATGATATTTGAGCACTTTATAGAGAAGCT
CCCTAACAGAGAGCTTATACTTGAAGCCAAGGCTACTGCTGTTTGCTTGAACAAGGACTACAGACCTACACGTATTT
CACCAGAGTTCTTGTCCAAGCTCCAATTCTTCACCTCTGAGGGTTCTAGTTCA SEQ ID NO 195: *Oryza sativa japonica* modified ORF
MAGLRLDQFFEVEMKVRDYELDQYGVVNNAIYASYCQHGRHELLESVGISADAVARSGESLALSELHLKYYAPLRSG
DKFVVKVRLASTKGIRMIFEHFIEKLPNRELILEAKATAVCLNKDYRPTRISPEFLSKLQFFTSEGSSS SEQ ID NO 139: *Oryza sativa indica* modified cDNA
ATGGCTGGTCTTAGATTGGATCAGTTCTTCGAAGTTGAAATGAAGGTGAGGGATTACGAATTGGATCAGTACGGCGT
CGTTAATAACGCAATCTACGCTugcTATTGCCAGCATGGCAGGCATGAGCTTCTTGAATCAGTTGGAATTTCCGCTG
ATGCTGTTGCTAGAAGTGGTGAGTCATTGGCCTTATCAGAGTTGCACTTAAAGTACTATGCACCTCTTAGGAGTGGT
GATAAGTTCGTTGTGAAGGTTAGGCTCGCCTCTACCAAGGGTATTAGAATGATATTTGAGCACTTTATAGAGAAGCT
CCCTAACAGAGAGCTTATACTTGAAGCCAAGGCTACTGCTGTTTGCTTGAACAAGGACTACAGACCTACACGTATTT
CACCAGAGTTCTTGTCCAAGCTCCAATTCTTCACCTCTGAGGGTTCTAGTTCA SEQ ID NO 196: *Oryza sativa indica* modified ORF
MAGLRLDQFFEVEMKVRDYELDQYGVVNNAIYACYCQHGRHELLESVGISADAVARSGESLALSELHLKYYAPLRSG
DKFVVKVRLASTKGIRMIFEHFIEKLPNRELILEAKATAVCLNKDYRPTRISPEFLSKLQFFTSEGSSS SEQ ID NO 140: *Phyllostachys edulis* modified cDNA
ATGGCTGGTCTTAGAgTGGATaAGTTCTTCGAAGTTGcAATGAAGGTGAGGGATTACGAATTGGATCAGTACGGCGT
CGTTAATAACGCAgTCTACGCTAGCTATTGCCAGCATGGCAGGCATGAGCTTCTTGAATCAGTTGGAATTTCCGCTG
ATGCTGTTGCTAGAAGTGGTGAGTCATTGGCCTTATCAGAtTTGCACTTAAAGTcCTtGCACCTCTTAGGAGTGGT
GATgAGTTCGTTGTGAAGGTTAGGCTCGCCTCTAtCAAGGGTgTTAGAATGATATTTGAGCACTcTATAGAGAAGCT
CCCTAACAGAGAGCTTATACTTGAAGCCAAGGCTACTGCTGTTTGCTTGAACAAGGACTACAGACCTACACGTgTTT
CACCAGAGTTCTTGTCCAgGCTCCAgTTgTTCAgCTCTaAGGaTTCTAaaggAtga SEQ ID NO 197: *Phyllostachys edulis* modified ORF
MAGLRVDKFFEVAMKVRDYELDQYGVVNNAVYASYCQHGRHELLESVGISADAVARSGESLALSDLHLKFFAPLRSG
DEFVVKVRLASIKGVRMIFEHSIEKLPNRELILEAKATAVCLNKDYRPTRVSPEFLSRLQLFSSKDSKG SEQ ID NO 141: *Zea mays* modified cDNA
ATGGCAGAGAAGTTCTTTGAAGTCGAGATGAAAGTTAGAGATTACGAGATAGATCAGTATGGAGTCGTTAATAATGC
AATCTATGCCAGCTATTGTCAGCATGGTAGACACGAGTTGCTCGAATCCGTGGGCATATCTGCCGATGCTGTTGCTA
GGTCTGGAGAGTCACTTGCATTGTCTGAACTCAACCTCAAATACTTCGCACCTCTTCGTTCTGGAGACAAGTTTGTT -continued GTCAAAGTTAGGCTCGCTGGAATTAAGGGTGTTCGTATGATATTTGATCACATTATCACCAAACTTCCTAATCATGA
GTTGATCTTGGAGGCTAAAGCTACAGCTGTTTGCCTCAATAAGGATTATTATCCTACAAGGATACCAAGGGAACTTC
TTAGTAAGATGCAGCTCTTCCTTCCAGTCGACAGCAGAGGTAGTAATGAAGACGTGAACAATCGTAATAATTCATGC
AATtga SEQ ID NO 198: *Zea mays* modified ORF
MAEKFFEVEMKVRDYEIDQYGVVNNAIYASYCQHGRHELLESVGISADAVARSGESLALSELNLKYFAPLRSGDKFV
VKVRLAGIKGVRMIFDHIITKLPNHELILEAKATAVCLNKDYYPTRIPRELLSKMQLFLPVDSRGSNEDVNNRNNSC
N SEQ ID NO 142: *Sorghum bicolor* modified cDNA
ATGGCAggtttgagacttgagGAGAAGTTCTTTGAAGTCGAGATGAAAGTTAGAGATTACGAGtTAGATCAGTATGG
AGTCGTTAATAATGCAgTCTATGCCAGCTATTGTCAGCATGGTAGACACGAGTTGCTCGAATCCGTGGGCATATCTG
CCGATGCTGTTGCTAGGTCTGGAGAGTCACTTGCATTGTCTGAACTCAACCTCAAATACTTCGgACCTCTTCGTTCT
GGAGACAAGTTTGTTGTCAAAGTTAGGCTCGtTGGAATTAAGGGTGTTCGTATGATATTTGAgCACATTATCgagAA
ACTTCCTAATCATGAGTTGATCTTGGAGGCTAAAGCTACAGCTGTTTGCCTCAATAAGGATTATTATCCTACAAGGA
TACCAAGGGAACTTCTTAGTAAGATGCAGCTCTTCtcTtCAGagGACAGCAGAGGTAGTAAtaAAGACGTGAACAAT
CGTAATAATTCATGCAAT SEQ ID NO 199: *Sorghum bicolor* modified ORF
MAGLRLEEKFFEVEMKVRDYELDQYGVVNNAVYASYCQHGRHELLESVGISADAVARSGESLALSELNLKYFGPLRS
GDKFVVKVRLVGIKGVRMIFEHIIEKLPNHELILEAKATAVCLNKDYYPTRIPRELLSKMQLFSSEDSRGSNKDVNN
RNNSCN SEQ ID NO 143: *Lycopersicon esculentum* "improved A" cDNA
ATGaacGAGTTCCATGAAGTTGAACTCAAAGTCaGGGACTATGAGTTGGATCAGTATGGTGTTGTAAACAATGCTAT
cTATGCAAGTTATTGCCAACATtgcCGTCATGAGCTcCCTtGAAAGGATTGGTATAAGTGCTGATGAAGTGGCACGta
atGGTGACGCACTtGCACTtACAGAGtTGTCACTTAAGTATCTtGCACCTCTtAGGAGTGGAGATAGATTTGTCGTG
AAaGCtaGAATATCTGATTCTTCAGCTGCTCGTTTGTTcTTtGAACACTTCATCTTCAaACTTCCtGATCAAGAGCC
CATCTTGGAGGCAAGAGGAATAGCAGTGTGGCTCAacAAgAGTTACCGTCCTGTCAgAATCCCatctGAGTTCAGAT
CAAAATTTGTTCAGTTCCTTCGtCAGGAGGCATCCAAC SEQ ID NO 200: *Lycopersicon esculentum* "improved A" ORF
MNEFHEVELKVRDYELDQYGVVNNAIYASYCQHCRHELLERIGISADEVARNGDALALTELSLKYLAPLRSGDRFVV
KARISDSSAARLFFEHFIFKLPDQEPILEARGIAVWLNKSYRPVRIPSEFRSKFVQFLRQEASN SEQ ID NO 144: *Petunia integrifolia* "normalized A" cDNA
ATGAATGAGTTCcatGAAGTCGAACTCAAAGTCaGGGACTATGAGTTGGATCAATATGGTGTTGTAAACAATGCTAT
cTATGCTAGTTATTGCCAACATTGTaGGCATGAGCTTCTtGAAAAGATTGGCGTAAATGCTGATGCAGTGGCACGtA
ATGGTGAAGCATTAGCACTtACAGAGcttACACTcAAGTATCTtGCACCTCTcAGGAGTGGAGACAGATTCGttGTG
AAaGTtaGAATATCTGACTCTTCAGCTGCTCGTTTGTTCTTTGAACACTTCATCTTCAaACTTCCtGATCAAGAGCC
TATCTTGGAGGCAAGAGGAACAGCAGTGTGGCTTAAcAAgAGTTACCGTCCTGTCAgAATcCCTTCAGAGTTCAGAT
CAAAATTCGTTCAGTTCCTTCGtCAGGAGGCAtccaac SEQ ID NO 201: *Petunia integrifolia* "normalized A" ORF
MNEFHEVELKVRDYELDQYGVVNNAIYASYCQHCRHELLEKIGVNADAVARNGEALALTELTLKYLAPLRSGDRFVV
KVRISDSSAARLFFEHFIFKLPDQEPILEARGTAVWLNKSYRPVRIPSEFRSKFVQFLRQEASN SEQ ID NO 145: *Petunia integrifolia* with *Lycopersicon hirsutum* ends cDNA
ATGagtgatcaggtctatcaccatGAAGTCGAACTCAAAGTCaGGGACTATGAGTTGGATCAATATGGTGTTGTAAA
CAATGCTATcTATGCTAGTTATTGCCAACATTGTaGGCATGAGCTTCTtGAAAAGATTGGCGTAAATGCTGATGCAG
TGGCACGtAATGGTGAAGCATTAGCACTtACAGAGATGACACTcAAGTATCTtGCACCTCTcAGGAGTGGAGACAGA
TTCATTGTGAAaGTtaGAATATCTGACTCTTCAGCTGCTCGTTTGTTCTTTGAACACTTCATCTTCAaACTTCCtGA
TCAAGAGCCTATCTTGGAGGCAAGAGGAACAGCAGTGTGGCTTAAcAAgAGTTACCGTCCTGTCAgAATcCCTTCAG
AGTTCAGATCAAAATTCGTTCAGTTCCTTcaccagaagagttgcggtgtacaacatcatctcTGA SEQ ID NO 202: *Petunia integrifolia* with *Lycopersicon hirsutum* ends ORF
MSDQVYHHEVELKVRDYELDQYGVVNNAIYASYCQHCRHELLEKIGVNADAVARNGEALALTEMTLKYLAPLRSGDR
FIVKVRISDSSAARLFFEHFIFKLPDQEPILEARGTAVWLNKSYRPVRIPSEFRSKFVQFLHQKSCGVQHHL SEQ ID NO 146: *Lycopersicon hirsutum* with *Petunia integrifolia* ends cDNA
ATGaatgagttcCATGACGTTGAACTCACAGTCAGGGACTATGAGTTGGATCAGTTTGGTGTTGTAAATAATGCTAC
TTATGCtAGTTATTGTCAACATTGTCGTCATGCtTTcCTtGAgAAgATTGGTGTTAGTGTTGATGAAGTAACcCGtA
ATGGTGATGCATTAGCTGTAACAGAGCTCTCACTTAAGTTTCTtGCACCACTtAGGAGTGGAGATAGATTCGTGGTG
AGGGCtaGATTgTCCCACTTTACAGTAGCTaGATTGTTcTTtGAGCATTTCATtTTCAaACTTCCtGATCAAGAGCC
TATATTGGAGGCAAGAGGAATAGCAGTGTGGCTTAATAGAAGTTATCGTCCTATTCGtATTCCaTCAGAGTTCAATT
CAAAATTTGTTAAATTCCTTcgtcaggaggcatga SEQ ID NO 203: *Lycopersicon hirsutum* with *Petunia integrifolia* ends ORF
MNEFHDVELTVRDYELDQFGVVNNATYASYCQHCRHAFLEKIGVSVDEVTRNGDALAVTELSLKFLAPLRSGDRFVV
RARLSHFTVARLFFEHFIFKLPDQEPILEARGIAVWLNRSYRPIRIPSEFNSKFVKFLRQEA SEQ ID NO 147: *L. esculentum/L. hirsutum* chimeric optimization 27 cDNA
ATGgctAGTGATCAGGTCTATCACcatgaagttgaactcaaagtccgggactatgaattggatcagtatggtgttgt
aaacaatgctatttatgcaagtTATTGTCAACATTGTCGTCATGCGTTTCTAGAAAAAATTGGTGTTAGTGTTGATG
AAGTAACGCGAAATGGTGATGCATTAGCCGTAACAGAGCTCTCACTTAAGTTTCTAGCACCACTAAGGAGTGGAGAT
AGATTCGTGGTGAGGGCGCGATTATCCCACTTTACAGTAGCTCGATTGTTTTTCGAGCATTTCATCTTCAAACTTCC
AGATCAAGAGCCTATATTGGAGGCAAGAGGAATAGCAGTGTGGCTTAATAGAAGTTATCGTCCTATTCGAATTCCGT
CAGAGTTCAATTCAAAATTTGTTAAATTCCTTCACCAGAAGAGTTGCGGTGTACAACATCATCTC H0111H = CHIM 7 with switch to 5' "H" tail SEQ ID NO 204: *L. esculentum/L. hirsutum* chimeric optimization 27 ORF
MASDQVYHHEVELKVRDYELDQYGVVNNAIYASYCQHCRHAFLEKIGVSVDEVTRNGDALAVTELSLKFLAPLRSGD
RFVVRARLSHFTVARLFFEHFIFKLPDQEPILEARGIAVWLNRSYRPIRIPSEFNSKFVKFLHQKSCGVQHHL SEQ ID NO 148: *L. esculentum/L. hirsutum* chimeric optimization 28 cDNA
ATGgctAGTGATCAGGTCTATCACCATGACGTTGAACTCACAGTCAGGGACTATGAGTTGGATCAGTTTGGTGTTGT
AAATAATGCTACTTTATGCGAGTTATTGTCAACATTGTCGTCATGCGTTTCTAGAAAAAATTGGTGTTAGTGTTGATG
AAGTAACGCGAAATGGTGATGCATTAGCCGTAACAGAGCTCTCACTTAAGTTTCTAGCACCACTAAGGAGTGGAGAT
AGATTCGTGGTGAGGGCGCGATTATCCCACTTTACAGTAGCTCGATTGTTTTCGAGCATTTCATCTTCAAACTTCC
Agatcaagagcctatattggaggcaagaggaatagcagtgtggctcaataaaagttaccgtcctgtccgaatcccgg
cagagttcagatcaaaatttgttcagttccttcgccagAAGAGTTGCGGTGTACAACATCATCTC H1110H = CHIM14 with switch to 3' "H" tail SEQ ID NO 205: *L. esculentum/L. hirsutum* chimeric optimization 28 ORF
:
MASDQVYHHDVELTVRDYELDQFGVVNNATYASYCQHCRHAFLEKIGVSVDEVTRNGDALAVTELSLKFLAPLRSGD
RFVVRARLSHFTVARLFFEHFIFKLPDQEPILEARGIAVWLNKSYRPVRIPAEFRSKFVQFLRQKSCGVQHHL SEQ ID NO 149: *L. esculentum/L. hirsutum* chimeric optimization 29 cDNA
atggctgagttcCATGACGTTGAACTCACAGTCAGGGACTATGAGTTGGATCAGTTTGGTGTTGTAAATAATGCTAC
TTATGCGAGTtattgccaacatggtcgtcatgagcttctagaaaggattggtataagtgctgatgaagtggcacgca
Gtggtgacgcactagcactaacagagctgtcacttaagtatctagcacctctaaggagtggagatagatttgtcgtg
Aaggcacgaatatctgattcttcagctgctcgtttgttttcgaacacttcatcttcaaacttccagatcaagagcc
Catcttggaggcaagaggaatagcagtgtggctcaataaaagttaccgtcctgtccgaatcccggcagagttcagat
caaaatttgttcagttccttcgccaggaggcatccaac e1000e = CHIM 8 with switch to 5' "e" tail SEQ ID NO 206: *L. esculentum/L. hirsutum* chimeric optimization 29 ORF
MAEFHDVELTVRDYELDQFGVVNNATYASYCQHGRHELLERIGISADEVARSGDALALTELSLKYLAPLRSGDRFVV
KARISDSSAARLFFEHFIFKLPDQEPILEARGIAVWLNKSYRPVRIPAEFRSKFVQFLRQEASN SEQ ID NO 150: *L. esculentum/L. hirsutum* chimeric optimization 30 cDNA
Atgctgagttccatgaagttgaactcaaagtccgggactatgaattggatcagtatggtgttgtaaacaatgctat
Ttatgcaagttattgccaacatggtcgtcatgagcttctagaaaggattggtataagtgctgatgaagtggcacgca
Gtggtgacgcactagcactaacagagctgtcacttaagtatctagcacctctaaggagtggagatagatttgtcgtg
aaggcacgaatatctgattcttcagctgctcgtttgttttcgaacacttcatcttcaaacttccaGATCAAGAGCC
CATCTTGGAGGCAAGAGGAATAGCAGTGTGGCTTAATAGAAGTTATCGTCCTATTCGAATTCCGTCAGAGTTCAATT
CAAAATTTGTTAAATTCCTTCACCAGgaggcatccaac e0001e = CHIM 1 with switch to 3' "e" tail SEQ ID NO 207: *L. esculentum/L. hirsutum* chimeric optimization 30 ORF
MAEFHEVELKVRDYELDQYGVVNNAIYASYCQHGRHELLERIGISADEVARSGDALALTELSLKYLAPLRSGDRFVV
KARISDSSAARLFFEHFIFKLPDQEPILEARGIAVWLNRSYRPIRIPSEFNSKFVKFLHQEASN SEQ ID NO 151: *L. hirsutum/S. tuberosum* chimeric optimization 1 cDNA
ATGggtGATCAGctcTATCACCATGACGTTGAACTCACAGTCAGGGACTATGAGTTGGATCAGTTTGGTGTTGTAAA
TAATGCTACTTATGCTAGTTATTGTCAACATTGTCGTCATGCTTTCCTTGAGAAGATTGGTGTTAGTGTTGATGAAG
TAACCCGTAATGGTGATGCATTAGCTGTAACAGAGCTCTCACTTAAGTTTCTTGCACCACTTAGGAGTGGAGATAGA
TTCGTGGTGAGGGCTAGATTGTCCCACTTTACAGTAGCTAGATTGTTCTTTGAGCATTTCATTTTCAAACTTCCTGA
TCAAGAGCCTATATTGGAGGCAAGAGGAATAGCAGTGTGGCTTAATAGAAGTTATCGTCCTATTCGTATTCCATCAG
AGTTCAATTCAAAATTTGTTAAATTCCTTCACCAGAAGAGTTGCGGTGTACAACATCATCTCTGA LhS01 = Lh with St N-term SEQ ID NO 208: *L. hirsutum/S. tuberosum* chimeric optimization 1 ORF
MGDQLYHHDVELTVRDYELDQFGVVNNATYASYCQHCRHAFLEKIGVSVDEVTRNGDALAVTELSLKFLAPLRSGDR
FVVRARLSHFTVARLFFEHFIFKLPDQEPILEARGIAVWLNRSYRPIRIPSEFNSKFVKFLHQKSCGVQHHL SEQ ID NO 152: *L. hirsutum/S. tuberosum* chimeric optimization 2 cDNA
ATgAGTGATCAGGTCTATcagCATgagGTTGAACTCcaaGTCAGGGACTATGAGTTGGATCAGTTTGGTGTTGTAAA
TAATGCTACTTATGCTAGTTATTGTCAACATTGTCGTCATGCTTTCCTTGAGAAGATTGGTGTTAGTGTTGATGAAG
TAACCCGTAATGGTGATGCATTAGCTGTAACAGAGCTCTCACTTAAGTTTCTTGCACCACTTAGGAGTGGAGATAGA
TTCGTGGTGAGGGCTAGATTGTCCCACTTTACAGTAGCTAGATTGTTCTTTGAGCATTTCATTTTCAAACTTCCTGA
TCAAGAGCCTATATTGGAGGCAAGAGGAATAGCAGTGTGGCTTAATAGAAGTTATCGTCCTATTCGTATTCCATCAG
AGTTCAATTCAAAATTTGTTAAATTCCTTCACCAGAAGAGTTGCGGTGTACAACATCATCTC Lh with St beta1

SEQ ID NO 209: *L. hirsutum/S. tuberosum* chimeric optimization 2 ORF
MSDQVYQHEVELQVRDYELDQFGVVNNATYASYCQHCRHAFLEKIGVSVDEVTRNGDALAVTELSLKFLAPLRSGDR
FVVRARLSHFTVARLFFEHFIFKLPDQEPILEARGIAVWLNRSYRPIRIPSEFNSKFVKFLHQKSCGVQHHL SEQ ID NO 153: *L. hirsutum/S. tuberosum* chimeric optimization 3 cDNA
ATGAGTGATCAGGTCTATCACCATGACGTTGAACTCACAGTCAGGGACTATGAGTTGGATCAGTTTGGTGTTGTAAA
TAATGCTACTTATGCTAGTTATTGTCAACATTGTCGTCATgagTTCCTTGAGAAGATTGGTGTTAGTGTTGATGAAG

```
TAACCCGTAATGGTGATGCATTAGCTGTAACAGAGCTCTCACTTAAGTTTCTTGCACCACTTAGGAGTGGAGATAGA
TTCGTGGTGAGGGCTAGATTGTCCCACTTTACAGTAGCTAGATTGTTCTTTGAGCATTTCATTTTCAAACTTCCTGA
TCAAGAGCCTATATTGGAGGCAAGAGGAATAGCAGTGTGGCTTAATAGAAGTTATCGTCCTATTCGTATTCCATCAG
AGTTCAATTCAAAATTTGTTAAATTCCTTCACCAGAAGAGTTGCGGTGTACAACATCATCTC
```

Lh with St alpha2

SEQ ID NO 210: L. hirsutum/S. tuberosum chimeric optimization 3 ORF
MSDQVYHHDVELTVRDYELDQFGVVNNATYASYCQHCRHEFLEKIGVSVDEVTRNGDALAVTELSLKFLAPLRSGDR
FVVRARLSHFTVARLFFEHFIFKLPDQEPILEARGIAVWLNRSYRPIRIPSEFNSKFVKFLHQKSCGVQHHL SEQ ID NO 154: L. hirsutum/S. tuberosum chimeric optimization 4 cDNA
```
ATGAGTGATCAGGTCTATCACCATGACGTTGAACTCACAGTCAGGGACTATGAGTTGGATCAGTTTGGTGTTGTAAA
TAATGCTACTTATGCTAGTTATTGTCAACATTGTCGTCATGCTTTCCTTGAGAAGATTGGTGTTAGTGTTGATGAAG
TAtgcCGTactGGTGATGCATTAGCTGTAACAGAGCTCTCACTTAAGTTTCTTGCACCACTTAGGAGTGGAGATAGA
TTCGTGGTGAGGGCTAGATTGTCCCACTTTACAGTAGCTAGATTGTTCTTTGAGCATTTCATTTTCAAACTTCCTGA
TCAAGAGCCTATATTGGAGGCAAGAGGAATAGCAGTGTGGCTTAATAGAAGTTATCGTCCTATTCGTATTCCATCAG
AGTTCAATTCAAAATTTGTTAAATTCCTTCACCAGAAGAGTTGCGGTGTACAACATCATCTC
```

Lh with St a2/b2 loop helix

SEQ ID NO 211: L. hirsutum/S. tuberosum chimeric optimization 4 ORF
MSDQVYHHDVELTVRDYELDQFGVVNNATYASYCQHCRHAFLEKIGVSVDEVCRTGDALAVTELSLKFLAPLRSGDR
FVVRARLSHFTVARLFFEHFIFKLPDQEPILEARGIAVWLNRSYRPIRIPSEFNSKFVKFLHQKSCGVQHHL SEQ ID NO 155: L. hirsutum/S. tuberosum chimeric optimization 5 cDNA
```
ATGAGTGATCAGGTCTATCACCATGACGTTGAACTCACAGTCAGGGACTATGAGTTGGATCAGTTTGGTGTTGTAAA
TAATGCTACTTATGCTAGTTATTGTCAACATTGTCGTCATGCTTTCCTTGAGAAGATTGGTGTTAGTGTTGATGAAG
TAACCCGTAATGGTgagGCATTAGCTacaACAGAGCTCTCACTTAAGtatCTTGCACCACTTAGGAGTGGAGATAGA
TTCGTGGTGAGGGCTAGATTGTCCCACTTTACAGTAGCTAGATTGTTCTTTGAGCATTTCATTTTCAAACTTCCTGA
TCAAGAGCCTATATTGGAGGCAAGAGGAATAGCAGTGTGGCTTAATAGAAGTTATCGTCCTATTCGTATTCCATCAG
AGTTCAATTCAAAATTTGTTAAATTCCTTCACCAGAAGAGTTGCGGTGTACAACATCATCTC
```

Lh with St beta2

SEQ ID NO 212: L. hirsutum/S. tuberosum chimeric optimization 5 ORF
MSDQVYHHDVELTVRDYELDQFGVVNNATYASYCQHCRHAFLEKIGVSVDEVTRNGEALATTELSLKYLAPLRSGDR
FVVRARLSHFTVARLFFEHFIFKLPDQEPILEARGIAVWLNRSYRPIRIPSEFNSKFVKFLHQKSCGVQHHL SEQ ID NO 156: L. hirsutum/S. tuberosum chimeric optimization 6 cDNA
```
ATGAGTGATCAGGTCTATCACCATGACGTTGAACTCACAGTCAGGGACTATGAGTTGGATCAGTTTGGTGTTGTAAA
TAATGCTACTTATGCTAGTTATTGTCAACATTGTCGTCATGCTTTCCTTGAGAAGATTGGTGTTAGTGTTGATGAAG
TAACCCGTAATGGTGATGCATTAGCTGTAACAGAGCTCTCACTTAAGTTTCTTGCACCACTTAGGAGTGGAGATAGA
TTCGTGGTGaaggttAGAatcTCCcgctctACAgcaGCTAGATTGTTCTTTGAGCATTTCATTTTCAAACTTCCTGA
TCAAGAGCCTATATTGGAGGCAAGAGGAATAGCAGTGTGGCTTAATAGAAGTTATCGTCCTATTCGTATTCCATCAG
AGTTCAATTCAAAATTTGTTAAATTCCTTCACCAGAAGAGTTGCGGTGTACAACATCATCTC
```

Lh with St beta3

SEQ ID NO 213: L. hirsutum/S. tuberosum chimeric optimization 6 ORF
MSDQVYHHDVELTVRDYELDQFGVVNNATYASYCQHCRHAFLEKIGVSVDEVTRNGDALAVTELSLKFLAPLRSGDR
FVVKVRISRSTAARLFFEHFIFKLPDQEPILEARGIAVWLNRSYRPIRIPSEFNSKFVKFLHQKSCGVQHHL SEQ ID NO 157: L. hirsutum/S. tuberosum chimeric optimization 7 cDNA
```
ATGAGTGATCAGGTCTATCACCATGACGTTGAACTCACAGTCAGGGACTATGAGTTGGATCAGTTTGGTGTTGTAAA
TAATGCTACTTATGCTAGTTATTGTCAACATTGTCGTCATGCTTTCCTTGAGAAGATTGGTGTTAGTGTTGATGAAG
TAACCCGTAATGGTGATGCATTAGCTGTAACAGAGCTCTCACTTAAGTTTCTTGCACCACTTAGGAGTGGAGATAGA
TTCGTGGTGAGGGCTAGATTGTCCCACTTTACAGTAGCTAGATTGTTCTTTGAGCATTTCATTTTCAAACTTCCTGA
TCAAGAGCCTATATTGGAGGCAAGAGGAATAGCAGTGTGGCTTAATAGAAGTTATCGTCCTATTCGTATTCCATCAG
AGTTCagtTCAAAATTTGTTcaaTTCCTTCACCAGAAGAGTTGCGGTGTACAACATCATCTC
```

Lh with St alpha3

SEQ ID NO 214: L. hirsutum/S. tuberosum chimeric optimization 7 cDNA
MSDQVYHHDVELTVRDYELDQFGVVNNATYASYCQHCRHAFLEKIGVSVDEVTRNGDALAVTELSLKFLAPLRSGDR
FVVRARLSHFTVARLFFEHFIFKLPDQEPILEARGIAVWLNRSYRPIRIPSEFSSKFVQFLHQKSCGVQHHL SEQ ID NO 158: L. hirsutum/S. tuberosum chimeric optimization 8 cDNA
```
ATGAGTGATCAGGTCTATCACCATGACGTTGAACTCACAGTCAGGGACTATGAGTTGGATCAGTTTGGTGTTGTAAA
TAATGCTACTTATGCTAGTTATTGTCAACATTGTCGTCATGCTTTCCTTGAGAAGATTGGTGTTAGTGTTGATGAAG
TAACCCGTAATGGTGATGCATTAGCTGTAACAGAGCTCTCACTTAAGTTTCTTGCACCACTTAGGAGTGGAGATAGA
TTCGTGGTGAGGGCTAGATTGTCCCACTTTACAGTAGCTAGATTGTTCTTTGAGCATTTCATTTTCAAACTTCCTGA
TCAAGAGCCTATATTGGAGGCAAGAGGAATAGCAGTGTGGCTTAATAGAAGTTATCGTCCTATTCGTATTCCATCAG
AGTTCAATTCAAAATTTGTTAAATTCCTTCACCAGAAGAGTTGCGGTacaCAACATCgtCTC
```

Lh with St C-term

SEQ ID NO 215: L. hirsutum/S. tuberosum chimeric optimization 8 ORF
MSDQVYHHDVELTVRDYELDQFGVVNNATYASYCQHCRHAFLEKIGVSVDEVTRNGDALAVTELSLKFLAPLRSGDR
FVVRARLSHFTVARLFFEHFIFKLPDQEPILEARGIAVWLNRSYRPIRIPSEFNSKFVKFLHQKSCGTQHRL SEQ ID NO 159: L. hirsutum/S. tuberosum chimeric optimization 9 cDNA
atgggtgatcagctctatcaacatgaagttgaactccaagtcagggACTATGAGTTGGATCAGTTTGGTGTTGTAAA
TAATGCTACTTATGCTAGTTATTGTCAACATTGTCGCCATGCTTTCCTTGAGAAGATTGGTGTTAGTGTTGATGAAG
TAACCCGTAATGGTGATGCATTAGCTGTAACAGAGCTCTCACTTAAGTTTCTTGCACCACTTAGGAGTGGAGATAGA
TTCGTGGTGAGGGCTAGATTGTCCCACTTTACAGTAGCTAGATTGTTCTTTGAGCATTTCATTTTCAAACTTCCTGA
TCAAGAGCCTATATTGGAGGCAAGAGGAATAGCAGTGTGGCTTAATAGAAGTTATCGTCCTATTCGTATTCCATCAG
AGTTCagttcaaagtttgttcagttccttcaccagaagagttgcggtacacaacaccgtctc Lh with St N-term, beta1, alpha3, C-term SEQ ID NO 216: L. hirsutum/S. tuberosum chimeric optimization 9 ORF
MGDQLYQHEVELQVRDYELDQFGVVNNATYASYCQHCRHAFLEKIGVSVDEVTRNGDALAVTELSLKFLAPLRSGDR
FVVRARLSHFTVARLFFEHFIFKLPDQEPILEARGIAVWLNRSYRPIRIPSEFSSKFVQFLHQKSCGTQHRL SEQ ID NO 160: L. hirsutum/S. tuberosum chimeric optimization 10 cDNA
ATGagtGATCAGgtcTATCAACATGAAGTTGAACTCCAAGTCAGGGACTATGAATTGGATCAGTTTGGTGTTGTAAA
CAATGCTACTTATGCAAGTTATTGTCAACATTGCCGTCATGAGTTTCTTGAgAAGATTGGTGTAAGTGTTGATGAAG
TATGTaGaACTGGTGAAGCATTAGCAACAACAGAGCTTTCACTTAAGTATCTtGCACCTCTcAGGAGTGGAGATAGA
TTTGTGGTGAAGGTGaGAATATCCaGgTCTACAGCAGCTCGtTTGTTcTTCGAGCATTTCATCTTCAaCTTCCAGA
TCAAGAGCCTATATTGGAGGCAAGAGGAATAGCAGTGTGGCTTAATAGAAGTTACCGTCCTATCaGAATaCCATCAG
AGTTCAGTTCAAAgTTTGTTCAGTTCCTTCACCAGAAGAGTTGCGGTACACAACACCGTCTC St with Lh N-term SEQ ID NO 217: L. hirsutum/S. tuberosum chimeric optimization 10 ORF
MSDQVYQHEVELQVRDYELDQFGVVNNATYASYCQHCRHEFLEKIGVSVDEVCRTGEALATTELSLKYLAPLRSGDR
FVVKVRISRSTAARLFFEHFIFKLPDQEPILEARGIAVWLNRSYRPIRIPSEFSSKFVQFLHQKSCGTQHRL SEQ ID NO 161: L. hirsutum/S. tuberosum chimeric optimization 11 cDNA
ATGGGTGATCAGCTCTATcacCATgatGTTGAACTCacaGTCAGGGACTATGAATTGGATCAGTTTGGTGTTGTAAA
CAATGCTACTTATGCAAGTTATTGTCAACATTGCCGTCATGAGTTTCTTGAgAAGATTGGTGTAAGTGTTGATGAAG
TATGTaGaACTGGTGAAGCATTAGCAACAACAGAGCTTTCACTTAAGTATCTtGCACCTCTcAGGAGTGGAGATAGA
TTTGTGGTGAAGGTGaGAATATCCaGgTCTACAGCAGCTCGtTTGTTcTTCGAGCATTTCATCTTCAaCTTCCAGA
TCAAGAGCCTATATTGGAGGCAAGAGGAATAGCAGTGTGGCTTAATAGAAGTTACCGTCCTATCaGAATaCCATCAG
AGTTCAGTTCAAAgTTTGTTCAGTTCCTTCACCAGAAGAGTTGCGGTACACAACACCGTCTC St with Lh Beta1

SEQ ID NO 218: L. hirsutum/S. tuberosum chimeric optimization 11 ORF
MGDQLYHHDVELTVRDYELDQFGVVNNATYASYCQHCRHEFLEKIGVSVDEVCRTGEALATTELSLKYLAPLRSGDR
FVVKVRISRSTAARLFFEHFIFKLPDQEPILEARGIAVWLNRSYRPIRIPSEFSSKFVQFLHQKSCGTQHRL SEQ ID NO 162: L. hirsutum/S. tuberosum chimeric optimization 12 cDNA
ATGGGTGATCAGCTCTATCAACATGAAGTTGAACTCCAAGTCAGGGACTATGAATTGGATCAGTTTGGTGTTGTAAA
CAATGCTACTTATGCAAGTTATTGTCAACATTGCCGTCATGcaTTTCTTGAgAAGATTGGTGTAAGTGTTGATGAAG
TATGTaGaACTGGTGAAGCATTAGCAACAACAGAGCTTTCACTTAAGTATCTtGCACCTCTcAGGAGTGGAGATAGA
TTTGTGGTGAAGGTGaGAATATCCaGgTCTACAGCAGCTCGtTTGTTcTTCGAGCATTTCATCTTCAaCTTCCAGA
TCAAGAGCCTATATTGGAGGCAAGAGGAATAGCAGTGTGGCTTAATAGAAGTTACCGTCCTATCaGAATaCCATCAG
AGTTCAGTTCAAAgTTTGTTCAGTTCCTTCACCAGAAGAGTTGCGGTACACAACACCGTCTC St with Lh alpha2

SEQ ID NO 219: L. hirsutum/S. tuberosum chimeric optimization 12 ORF
MGDQLYQHEVELQVRDYELDQFGVVNNATYASYCQHCRHAFLEKIGVSVDEVCRTGEALATTELSLKYLAPLRSGDR
FVVKVRISRSTAARLFFEHFIFKLPDQEPILEARGIAVWLNRSYRPIRIPSEFSSKFVQFLHQKSCGTQHRL SEQ ID NO 163: L. hirsutum/S. tuberosum chimeric optimization 13 cDNA
ATGGGTGATCAGCTCTATCAACATGAAGTTGAACTCCAAGTCAGGGACTATGAATTGGATCAGTTTGGTGTTGTAAA
CAATGCTACTTATGCAAGTTATTGTCAACATTGCCGTCATGAGTTTCTTGAgAAGATTGGTGTAAGTGTTGATGAAG
TAactAGAaatGGTGAAGCATTAGCAACAACAGAGCTTTCACTTAAGTATCTtGCACCTCTcAGGAGTGGAGATAGA
TTTGTGGTGAAGGTGaGAATATCCaGgTCTACAGCAGCTCGtTTGTTcTTCGAGCATTTCATCTTCAaCTTCCAGA
TCAAGAGCCTATATTGGAGGCAAGAGGAATAGCAGTGTGGCTTAATAGAAGTTACCGTCCTATCaGAATACCATCAG
AGTTCAGTTCAAAgTTTGTTCAGTTCCTTCACCAGAAGAGTTGCGGTACACAACACCGTCTC St with Lh alpha2/beta2 loop helix SEQ ID NO 220: L. hirsutum/S. tuberosum chimeric optimization 13 ORF
MGDQLYQHEVELQVRDYELDQFGVVNNATYASYCQHCRHEFLEKIGVSVDEVTRNGEALATTELSLKYLAPLRSGDR
FVVKVRISRSTAARLFFEHFIFKLPDQEPILEARGIAVWLNRSYRPIRIPSEFSSKFVQFLHQKSCGTQHRL SEQ ID NO 164: L. hirsutum/S. tuberosum chimeric optimization 14 cDNA
ATGGGTGATCAGCTCTATCAACATGAAGTTGAACTCCAAGTCAGGGACTATGAATTGGATCAGTTTGGTGTTGTAAA
CAATGCTACTTATGCAAGTTATTGTCAACATTGCCGTCATGAGTTTCTTGAGAAGATTGGTGTAAGTGTTGATGAAG
TATGTAGAACTGGTgatGCATTAGCAgttACAGAGCTTTCACTTAAGtttCTtGCACCTCTcAGGAGTGGAGATAGA
TTTGTGGTGAAGGTGaGAATATCCaGgTCTACAGCAGCTCGtTTGTTcTTCGAGCATTTCATCTTCAaCTTCCAGA
TCAAGAGCCTATATTGGAGGCAAGAGGAATAGCAGTGTGGCTTAATAGAAGTTACCGTCCTATCaGAATaCCATCAG
AGTTCAGTTCAAAgTTTGTTCAGTTCCTTCACCAGAAGAGTTGCGGTACACAACACCGTCTC St with Lh beta2

SEQ ID NO 221: L. hirsutum/S. tuberosum chimeric optimization 14 ORF
translation:
MGDQLYQHEVELQVRDYELDQFGVVNNATYASYCQHCRHEFLEKIGVSVDEVCRTGDALAVTELSLKFLAPLRSGDR
FVVKVRISRSTAARLFFEHFIFKLPDQEPILEARGIAVWLNRSYRPIRIPSEFSSKFVQFLHQKSCGTQHRL SEQ ID NO 165: L. hirsutum/S. tuberosum chimeric optimization 15 cDNA
ATGGGTGATCAGCTCTATCAACATGAAGTTGAACTCCAAGTCAGGGACTATGAATTGGATCAGTTTGGTGTTGTAAA
CAATGCTACTTATGCAAGTTATTGTCAACATTGCCGTCATGAGTTTCTTGAgAAGATTGGTGTAAGTGTTGATGAAG
TATGTaGaACTGGTGAAGCATTAGCAACAACAGAGCTTTCACTTAAGTATCTtGCACCTCTcAGGAGTGGAGATAGA
TTTGTGGTGagggcgAGAttaTCCcatttcACAgtaGCTCGtTTGTTcTTCGAGCATTTCATCTTCAAaCTTCCAGA
TCAAGAGCCTATATTGGAGGCAAGAGGAATAGCAGTGTGGCTTAATAGAAGTTACCGTCCTATCaGAATaCCATCAG
AGTTCAGTTCAAAgTTTGTTCAGTTCCTTCACCAGAAGAGTTGCGGTACACAACACCGTCTC St with Lh beta3

SEQ ID NO 222: L. hirsutum/S. tuberosum chimeric optimization 15 ORF
MGDQLYQHEVELQVRDYELDQFGVVNNATYASYCQHCRHEFLEKIGVSVDEVCRTGEALATTELSLKYLAPLRSGDR
FVVRARLSHFTVARLFFEHFIFKLPDQEPILEARGIAVWLNRSYRPIRIPSEFSSKFVQFLHQKSCGTQHRL SEQ ID NO 166: L. hirsutum/S. tuberosum chimeric optimization 16 cDNA
ATGGGTGATCAGCTCTATCAACATGAAGTTGAACTCCAAGTCAGGGACTATGAATTGGATCAGTTTGGTGTTGTAAA
CAATGCTACTTATGCAAGTTATTGTCAACATTGCCGTCATGAGTTTCTTGAgAAGATTGGTGTAAGTGTTGATGAAG
TATGTaGaACTGGTGAAGCATTAGCAACAACAGAGCTTTCACTTAAGTATCTtGCACCTCTcAGGAGTGGAGATAGA
TTTGTGGTGAAGGTGaGAATATCCaGgTCTACAGCAGCTCGtTTGTTcTTCGAGCATTTCATCTTCAAaCTTCCAGA
TCAAGAGCCTATATTGGAGGCAAGAGGAATAGCAGTGTGGCTTAATAGAAGTTACCGTCCTATCaGAATaCCATCAG
AGTTCaatTCAAAGTTTGTTaagTTCCTTCACCAGAAGAGTTGCGGTACACAACACCGTCTC St with Lh alpha3

SEQ ID NO 223: L. hirsutum/S. tuberosum chimeric optimization 16 ORF
MGDQLYQHEVELQVRDYELDQFGVVNNATYASYCQHCRHEFLEKIGVSVDEVCRTGEALATTELSLKYLAPLRSGDR
FVVKVRISRSTAARLFFEHFIFKLPDQEPILEARGIAVWLNRSYRPIRIPSEFNSKFVKFLHQKSCGTQHRL SEQ ID NO 167: L. hirsutum/S. tuberosum chimeric optimization 17 cDNA
ATGGGTGATCAGCTCTATCAACATGAAGTTGAACTCCAAGTCAGGGACTATGAATTGGATCAGTTTGGTGTTGTAAA
CAATGCTACTTATGCAAGTTATTGTCAACATTGCCGTCATGAGTTTCTTGAgAAGATTGGTGTAAGTGTTGATGAAG
TATGTaGaACTGGTGAAGCATTAGCAACAACAGAGCTTTCACTTAAGTATCTtGCACCTCTcAGGAGTGGAGATAGA
TTTGTGGTGAAGGTGaGAATATCCaGgTCTACAGCAGCTCGtTTGTTcTTCGAGCATTTCATCTTCAAaCTTCCAGA
TCAAGAGCCTATATTGGAGGCAAGAGGAATAGCAGTGTGGCTTAATAGAAGTTACCGTCCTATCaGAATaCCATCAG
AGTTCAGTTCAAAgTTTGTTCAGTTCCTTCACCAGAAGAGTTGCGGTgtaCAACACcatCTC St with Lh C-term SEQ ID NO 224: L. hirsutum/S. tuberosum chimeric optimization 17 ORF
MGDQLYQHEVELQVRDYELDQFGVVNNATYASYCQHCRHEFLEKIGVSVDEVCRTGEALATTELSLKYLAPLRSGDR
FVVKVRISRSTAARLFFEHFIFKLPDQEPILEARGIAVWLNRSYRPIRIPSEFSSKFVQFLHQKSCGVQHHL SEQ ID NO 168: L. hirsutum/S. tuberosum chimeric optimization 18 cDNA
atgagtgatcaggtctatcaccatgacgttgaactcacagtcaggGACTATGAATTGGATCAGTTTGGTGTTGTAAA
CAATGCTACTTATGCAAGTTATTGTCAACATTGCCGTCATGAGTTTCTTGAgAAGATTGGTGTAAGTGTTGATGAAG
TATGTaGaACTGGTGAAGCATTAGCAACAACAGAGCTTTCACTTAAGTATCTtGCACCTCTcAGGAGTGGAGATAGA
TTTGTGGTGAAGGTGaGAATATCCaGgTCTACAGCAGCTCGtTTGTTcTTCGAGCATTTCATCTTCAAaCTTCCAGA
TCAAGAGCCTATATTGGAGGCAAGAGGAATAGCAGTGTGGCTTAATAGAAGTTACCGTCCTATCaGAATaCCATCAG
AGTTCaattcaaaatttgttaaattccttcaccagaagagttgcggtgtacaacatcatctc St with Lh N-term, beta1, alpha3, C-term SEQ ID NO 225: L. hirsutum/S. tuberosum chimeric optimization 18 ORF
MSDQVYHHDVELTVRDYELDQFGVVNNATYASYCQHCRHEFLEKIGVSVDEVCRTGEALATTELSLKYLAPLRSGDR
FVVKVRISRSTAARLFFEHFIFKLPDQEPILEARGIAVWLNRSYRPIRIPSEFNSKFVKFLHQKSCGVQHHL SEQ ID NO 169: L. esculentum MKT cDNA with heterologous plastid transit sequence
atggcttcaatttgtacttcaaattttcactttctatgcagaaaaaacaattctagccctatttctcatcatctact
gttatctccctcttctttatccttctcacgttgcggcggattgcggttgtgtcgtgcggccgcaGAGTTCCATGAAG
TTGAACTCAAAGTCCGGGACTATGAATTGGATCAGTATGGTGTTGTAAACAATGCTACTATTTATGCAAGTTATTGCCAA
CATGGTCGTCATGAGCTTCTAGAAAAGGATTGGTATAAGTGCTGATGAAGTGGCACGCAGTGGTGACGCACTAGCACT
AACAGAGCTGTCACTTAAGTATCTAGCACCTCTAAGGAGTGGAGATAGATTTGTCGTGAAGGCACGAATATCTGATT
CTTCAGCTGCTCGTTTGTTTTTCGAACACTTCATCTTCAAACTTCCAGATCAAGAGCCCATCTTGGAGGCAAGAGGA
ATAGCAGTGTGGCTCAATAAAAGTTACCGTCCTGTCCGAATCCCGGCAGAGTTCAGATCAAAATTTGTTCAGTTCCT
TCGCCAGGAGGCATCCAACTGA SEQ ID NO 226: L. esculentum MKT ORF with heterologous plastid transit sequence
masictsnfhflcrknnsspishhlllspsslsfsrcgglrlcraaaEFHEVELKVRDYELDQYGVVNNAIYASYCQ
HGRHELLERIGISADEVARSGDALALTELSLKYLAPLRSGDRFVVKARISDSSAARLFFEHFIFKLPDQEPILEARG
IAVWLNKSYRPVRIPAEFRSKFVQFLRQEASN SEQ ID NO 227: Ubi3 promoter Solanum tuberosum
GGCCGGCCAAAGCACATACTTATCGATTTAAATTTCATCGAAGAGATTAATATCGAATAATCATATACAT -continued ACTTTAAATACATAACAAATTTTAAATACATATATCTGGTATATAATTAATTTTTTAAAGTCATGAAGTA
TGTATCAAATACACATATGGAAAAAATTAACTATTCATAATTTAAAAAATAGAAAAGATACATCTAGTGA
AATTAGGTGCATGTATCAAATACATTAGGAAAAGGGCATATATCTTGATCTAGATAATTAACGATTTTGA
TTTATGTATAATTTCCAAATGAAGGTTTATATCTACTTCAGAAATAACAATATACTTTTATCAGAACATT
CAACAAAGCAACAACCAACTAGAGTGAAAAATACACATTGTTCTCTAGACATACAAAATTGAGAAAAGAA
TCTCAAAATTTAGAGAAACAAATCTGAATTTCTAGAAGAAAAAAATAATTATGCACTTTGCTATTGCTCG
AAAAATAAATGAAAGAAATTAGACTTTTTTAAAAGATGTTAGACTAGATATACTCAAAAGCTATTAAAGG
AGTAATATTCTTCTTACATTAAGTATTTTAGTTACAGTCCTGTAATTAAAGACACATTTTAGATTGTATC
TAAACTTAAATGTATCTAGAATACATATATTTGAATGCATCATATACATGTATCCGACACACCAATTCTC
ATAAAAAACGTAATATCCTAAACTAATTTATCCTTCAAGTCAACTTAAGCCCAATATACATTTTCATCTC
TAAAGGCCCAAGTGGCACAAAATGTCAGGCCCAATTACGAAGAAAAGGGCTTGTAAAACCCTAATAAAGT
GGCACTGGCAGAGCTTACACTCTCATTCCATCAACAAAGAAACCCTAAAAGCCGCAGCGCCACTGATTTC
TCTCCTCCAGGCGAAG SEQ ID NO 228: Ubi3 terminator Solanum tuberosum
Gtttaaactgatttaatgtttagcaaatgtcttatcagttttctcttttgtcgaacggtaatttagagt
Tttttttgctatatggattttcgttttgatgtatgtgacaaccctcgggattgttgatttatttcaaaac
Taagagtttttgtcttattgttctcgtctattttggatatcaatcttagttttatatctttctagttctc
Tacgtgttaaatgttcaacacactagcaatttggcctgccagcgtatggattatggaactatcaagtgtgt
Gggatcgataaatatgcttctcaggaatttgagattttacagtctttatgctcattgggtgagtataata
tagtaaaaaaatagtaaatttaagcaataatgttaggtgctatgtgtctgtcgagactatt SEQ ID NO 229: DCL1 44 optimized nucleotide cDNA
ATGGCTTCAATTTGTACTTCAAATTTTCACTTTCTtTGCAGgAAgAACAATTCTAGCCCTATTTCTCATCA
TCTACTtTTATCTCCCTCTTCTTTATCCTTCTCACGTTGCGGCGGATTGCGtTTGTGTCGT SEQ ID NO 230: DCL1 44 AMINO ACID TRANSIT PEPTIDE
MASICTSNFHFLCRKNNSSPISHHLLLSPSSLSFSRCGGLRLCR SEQ ID NO 231: DCL1 50 optimized nucleotide cDNA
ATGGCTTCAATTTGTACTTCAAATTTTCACTTTCTtTGCAGgAAgAACAATTCTAGCCCTATTTCTCATCA
TCTACTtTTATCTCCCTCTTCTTTATCCTTCTCACGTTGCGGCGGATTGCGtTTGTGTCGTTGCGCtGCaG
TGAAGACC SEQ ID NO 232: DCL1 50 AMINO ACID TRANSIT PEPTIDE
MASICTSNFHFLCRKNNSSPISHHLLLSPSSLSFSRCGGLRLCRCAAVKT SEQ ID NO 233: UBQ10 INTRON:
CGTGATCAAGgtaaatttctgtgttccttattctctcaaaatcttcgatttgttttcgttcgatcccaatttcgta
tatgttcttggtttagattctgttaatcttagatcgaagacgattttctgggtttgatcgttagatatcatcttaa
ttctcgattagggtttcatagatatcatccgatttgttcaaataatttgagttttgtcgaataattactcttcgatt
tgtgatttctaTCTtGAtctggtgttagtttctagtttgtgcgatcgaatttgtcgattaatctgagttttctgat
taacag 1-10 = context for 5' splice. 11-314 is intron (gt . . . ag)

SEQ ID NOs: 247 and 234: HIS TAG:
GCTGCACATCACCATCATCACCAC
translation: AAHHHHHH SEQ ID NOs: 248 and 235: HA TAG:
gctgcagcctatccatacgatgtgcctgactatgct
translation: AAAYPYDVPDYA SEQ ID NOs: 249 and 236: HIS + HA TAG:
gctgcagcctatccatacgatgtgcctgactatgctgctgcaCATCACCATCATCACCAC
translation: AAAYPYDVPDYAAAHHHHHH SEQ ID NOs: 250 and 237: AcV5 TAG:
gcagcctcttggaaagatgcgagcggctggtct
translation: AASWKDASGWS SEQ ID NOs: 251 and 238: FLAG TAG:
gcagccgactacaaagacgatgacgacaaa
translation: AADYKDDDDK SEQ ID NOs: 252 and 239: cMyc TAG:
gcagccgaacagaaactgatctctgaagaagatctg
translation: AAEQKLISEEDL SEQ ID NO 240: RB7 promoter from Nicotiana tabacum:
CCCATATGTCCTACACAATGTGAATTTGAATTAGTTTGGTCATACGGTATATCATATGATTATAAATAAAAAAAATT
AGCAAAAGAATATAATTTATTAAATATTTTACACCATACCAAACACAACCGCATTATATATAATCTTAATTATCATT
ATCACCAGCATCAACATTATAATGATTCCCCTATGCGTTGGAACGTCATTATAGTTATTCTAAACAAGAAAGAAATT
TGTTCTTGACATCAGACATCTAGTATTATAACTCTAGTGGAGCTTACCTTTTCTTTTCCTTCTTTTTTTTCTTCTTA
AAAAAATTATCACTTTTTAAATCTTGTATATTAGTTAAGCTTATCTAAACAAAGTTTTAAATTCATTTCTTAAACGT
CCATTACAATGTAATAACTTAGTCGTCTCAATTAAACCATTAATGTGAAATATAAATCAAAAAAAGCCAAAGGGC
GGTGGGACGGCGCCAATCATTTGTCCTAGTCCACTCAAATAAGGCCCATGGTCGGCAAAACCAAACACAAATGTGT
TATTTTTAATTTTTTCCTCTTTTATTGTTAAAGTTGCAAAATGTGTTATTTTTGGTAAGACCCTATGGATATATAAA
GACAGGTTATGTGAAACTTGGAAAACCATCAAGTTTTAAGCAAAACCCTCTTAAGAACTTAAATTGAGCTTCTTTTG
GGGCATTTTTCTAGTGAGAA

```
SEQ ID NO 241: E35S/ubi3 chimeric promoter:
ggtccgattGAGACTTTTCAACAAAGGGTAATATCCGGAAACCTCCTCGGATTCCATTGCCCAGCTATCTGTCACTT
TATTGTGAAGATAGTGGAAAAGGAAGGTGGCTCCTACAAATGCCATCATTGCGATAAAGGAAAGGCCATCGTTGAAG
ATGCCTCTGCCGACAGTGGTCCCAAAGATGGACCCCCACCCACGAGGAGCATCGTGGAAAAAGAAGACGTTCCAACC
ACGTCTTCAAAGCAAGTGGATTGATGTGATatctccactgacgtaagggatgacgcacaatcccactatccttcgca
attcCCAAAGCACATACTTATCGATTTAAATTTCATCGAAGAGATTAATATCGAATAATCATATACATACTTTAAAT
ACATAACAAATTTTAAATACATATATCTGGTATATAATTAATTTTTTAAAGTCATGAAGTATGTATCAAATACACAT
ATGGAAAAAATTAACTATTCATAATTTAAAAAATAGAAAAGATACATCTAGTGAAATTAGGTGCATGTATCAAATAC
ATTAGGAAAAGGGCATATATCTTGATCTAGATAATTAACGATTTTGATTTATGTATAATTTCCAAATGAAGGTTTAT
ATCTACTTCAGAAATAACAATATACTTTTATCAGAACATTCAACAAAGCAACAACCAACTAGAGTGAAAAATACACA
TTGTTCTCTAGACATACAAAATTGAGAAAAGAATCTCAAAATTTAGAGAAACAAATCTGAATTTCTAGAAGAAAAA
ATAATTATGCACTTTGCTATTGCTCGAAAAATAAATGAAAGAAATTAGACTTTTTTAAAAGATGTTAGACTAGATAT
ACTCAAAAGCTATTAAAGGAGTAATATTCTTCTTACATTAAGTATTTTAGTTACAGTCCTGTAATTAAAGACACATT
TTAGATTGTATCTAAACTTAAATGTATCTAGAATACATATATTTGAATGCATCATATACATGTATCCGACACACCAA
TTCTCATAAAAAACGTAATATCCTAAACTAATTTATCCTTCAAGTCAACTTAAGCCCAATATACATTTTCATCTCTA
AAGGCCCAAGTGGCACAAAATGTCAGGCCCAATTACGAAGAAAAGGGCTTGTAAAACCCTAATAAAGTGGCACTGGC
AGAGCTTACACTCTCATTCCATCAACAAAGAAACCCTAAAAGCCGCAGCGCCACTGATTTCTCTCCTCCAGGCGAAG 35S(BA)+ ubi3 promoter DESIGN: 1232 nt; 1-306 = 35S(BA)element, 313-1232 =
divu promoter region. Chimeric promoter of 35S BA domain and ubi3 promoter
from Solanum tuberosum
```

All publications and patents referenced herein are intended to be herein incorporated by reference in their entirety.

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

The invention claimed is:

1. A DNA molecule operably linked to a heterologous promoter, wherein said DNA molecule encodes a polypeptide comprising an amino acid sequence that is at least 95% identical to SEQ ID NO:64, wherein said polypeptide has methylketone thioesterase activity.

2. The DNA molecule of claim 1, wherein said DNA molecule comprises SEQ ID NO:8.

3. The DNA molecule of claim 1, wherein the polypeptide further comprises the amino acid sequence of a plastid transit peptide.

4. A vector comprising the DNA molecule operably linked to a heterologous promoter of claim 1, wherein said heterologous promoter is functional in a plant cell or a bacterial cell.

5. A host cell comprising the DNA molecule operably linked to a heterologous promoter of claim 1, wherein said host cell is a plant cell or a bacterial cell.

6. The host cell of claim 5, wherein the plant cell is from a seed, root, leaf, shoot, flower, pollen, or ovule.

7. The host cell of claim 5, wherein the plant cell is a crop plant cell selected from the group consisting of a cotton, soybean, canola, corn, wheat, rice, sunflower, sorghum, sugarcane, potato, and tomato plant cell.

8. A plant, or a part thereof, comprising the DNA molecule operably linked to a heterologous promoter of claim 1.

9. The plant, or part thereof, of claim 8, wherein the part thereof is selected from the group consisting of a seed, pollen, a root, a leaf, a shoot, a flower and an ovule.

10. A product processed from the plant, or part thereof, of claim 8, said product comprising a detectable amount of said DNA molecule.

11. The product of claim 10, wherein said product is selected from the group consisting of meal, flour, oil, hay, starch, juice, protein extract, and fiber.

12. A method for controlling a pathogen or pest in a plant, said method comprising expressing in the plant the DNA molecule operably linked to a heterologous promoter of claim 1.

13. The method of claim 12, wherein the pest is a nematode selected from the group consisting of *Heterodera* species, *Globodera* species, *Meloidogyne* species, *Rotylenchulus* species, *Hoplolaimus* species, *Belonolaimus* species, *Pratylenchus* species, *Longidorus* species, *Paratrichodorus* species, *Ditylenchus* species, *Xiphinema* species, *Dolichodorus* species, *Helicotylenchus* species, *Radopholus* species, *Hirschmanniella* species, *Tylenchorhynchus* species, and *Trichodorus* species, or an insect selected from the orders consisting of *Coleoptera, Diptera, Hemiptera* (including *Homoptera* and *Heteroptera*), *Hymenoptera* and *Lepidoptera*.

14. The plant, or part thereof, of claim 8, further comprising a nucleic acid sequence encoding an acyl carrier protein.

15. A plant material admixed or coated with a composition comprising the host cell of claim 5, wherein said host cell is a bacterial cell.

16. The plant material of claim 15, wherein the plant material is selected from the group consisting of plant propagation material, shoot, seedling, tuber and sprout.

17. A method for controlling a pathogen or pest in a plant, said method comprising providing the roots of the plant with a composition comprising the host cell of claim 5, wherein said host cell is a bacterial cell.

18. The method of claim 17, wherein the pest or pathogen is a nematode selected from the group consisting of *Heterodera* species, *Globodera* species, *Meloidogyne* species, *Rotylenchulus* species, *Hoplolaimus* species, *Belonolaimus* species, *Pratylenchus* species, *Longidorus* species, *Paratrichodorus* species, *Ditylenchus* species, *Xiphinema* species, *Dolichodorus* species, *Helicotylenchus* species, *Radopholus* species, *Hirschmanniella* species, *Tylenchorhynchus* species, and *Trichodorus* species, or an insect selected from the orders consisting of *Coleoptera, Diptera, Hemiptera* (including *Homoptera* and *Heteroptera*), *Hymenoptera* and *Lepidoptera*.

19. The host cell of claim 5, further comprising a nucleotide sequence encoding a methylketone synthase.

20. The plant, or part thereof, of claim 8, further comprising a nucleotide sequence encoding a methylketone synthase.

\* \* \* \* \*

SEQUENCE LISTING

```
<160> NUMBER OF SEQ ID NOS: 279

<210> SEQ ID NO 1
<211> LENGTH: 423
<212> TYPE: DNA
<213> ORGANISM: Lycopersicon esculentum

<400> SEQUENCE: 1
atggctgagt tccatgaagt tgaactcaaa gtccgggact atgaattgga tcagtatggt        60
gttgtaaaca atgctattta tgcaagttat tgccaacatg gtcgtcatga gcttctagaa       120
aggattggta taagtgctga tgaagtggca cgcagtggtg acgcactagc actaacagag       180
ctgtcactta agtatctagc acctctaagg agtggagata gatttgtcgt gaaggcacga       240
atatctgatt cttcagctgc tcgtttgttt ttcgaacact tcatcttcaa gcttccagat       300
caagagccca tcttggaggc aagaggaata gcagtgtggc tcaataaaag ttaccgtcct       360
gtccgaatcc cggcagagtt cagatcaaaa tttgttcagt tccttcgcca ggaggcatcc       420
aac                                                                    423

<210> SEQ ID NO 2
<211> LENGTH: 1356
<212> TYPE: DNA
<213> ORGANISM: Petunia integrifolia

<400> SEQUENCE: 2
cataaattgg gatggagggg tacaatctgt taccctcgt ccattcatta agggtaagtt         60
taattgttaa tttaataatg tgtcgttctt ttttgtgagg aggtgtgagt ggctggctgt       120
gctgggtctg cggagtggta aaggcagacc aaagaagaat tggggcgagg tgattcgaca       180
tgatatggct cgcctccagg tcaccgagga cacgacccctt gacaggaaag cgtggaggtc      240
```

-continued

```
taggattagg gtagaaggtt aggtgaaagg ggctgataga tctcgcccag tgttcccctc      300
cttcccccgc cgcctttcga cccgcgggag tatacaatgt cagcccaaca taggttgtta      360
accaaaaaag agaagttccc gtgaaaacag aaaaagacct ccccttaac ccccttact        420 tggcagattc agattgagtg ccgtcatttt agcgaatgaa tgagttctat gaagtcgaac      480
tcaaagtccg ggactatgag ttggatcaat atggtgttgt aaacaatgct atttatgcta      540
gttattgcca acattgtcgg catgagcttc tggaaaagat tggcgtaaat gctgatgcag      600
tggcacgcaa tggtgaagca ttagcactaa cagagatgac actaaagtat ctagcacctc      660
taaggagtgg agacagattc attgtgaagg tgcgaatatc tgactcttca gctgctcgtt      720
tgttctttga acacttcatc ttcaagcttc cagatcaaga gcctatcttg gaggcaagag      780
gaacagcagt gtggcttaat aaaagttacc gtcctgtccg aattccttca gagttcagat      840
caaaattcgt tcagttcctt cgccaggagg catgaactag tgtgcttgtc tacaaaagtc      900
cagaaaagtt gtcttgctca agaatttcat gagcaaaagc tcaaactaat gtatatgaag      960
aactcaattc atactgcttc gcatagaggc aagcgttggg gtcaattaaa agaagtaaaa     1020
gcctacacaa ttgattggga aaatcagctg ttggaactca aaagtgggga gctagaggac     1080
ccttaaaaag agggcagaaa tttatttttc cattagattg gtgatgcact agtttatct     1140 cctttgtgaa ttgaaagcac ttattcaatt gaaagtttag taatctgtat tttttcagga    1200
taaattctag atataagaaa tttcaaattt ataaagttct cttaaaaagg gtctttcttc    1260
aaatgtgact aagtttgaaa tgtcaaggct cagggactgt gtgtccagtg ttctgtctct    1320
tcttcagtta ctctgaattt gctgtgtaga tccttg                              1356
```

<210> SEQ ID NO 3
<211> LENGTH: 447
<212> TYPE: DNA
<213> ORGANISM: Lycopersicon hirsutum

<400> SEQUENCE: 3

```
atgagtgatc aggtctatca ccatgacgtt gaactcacag tcagggacta tgagttggat       60
cagtttggtg ttgtaaataa tgctacttat gcgagttatt gtcaacattg tcgtcatgcg      120
tttctagaaa aaattggtgt tagtgttgat gaagtaacgc gaaatggtga tgcattagct      180
gtaacagagc tctcacttaa gtttctagca ccactaagga gtggagatag attcgtggtg      240
agggcgcgat tatcccactt tacagtagct cgattgtttt tcgagcattt catcttcaag      300
cttccagatc aagagcctat attggaggca agaggaatag cagtgtggct taatagaagt      360
tatcgtccta ttcgaattcc gtcagagttc aattcaaaat ttgttaaatt ccttcaccag      420
aagagttgcg gtgtacaaca tcatctc                                          447
```

<210> SEQ ID NO 4
<211> LENGTH: 780
<212> TYPE: DNA
<213> ORGANISM: Solanum tuberosum

<400> SEQUENCE: 4

```
ccttagacaa cagatttccc aatatttaca atttccttct cttctacctc tgaattttt        60 cgtcaaatgt ctcattccgt ctgcattgca cccaacccac tgttgctgaa tcatcggcaa      120
cgaccgtcta catttccgtt catccctcac cggcaactcc cgctcccaaa tttacagtta      180
tcggcccgta aatcgaggag ttttgaagct cataatgcat tcgatctcaa agatacccaa      240
```

```
ggaatgggtg atcagctcta tcaacatgaa gttgaactcc aagtcaggga ctatgaattg      300
gatcagtttg gtgttgtaaa caatgctact tatgcaagtt attgtcaaca ttgccgtcat      360
gagtttcttg aaaagattgg tgtaagtgtt gatgaagtat gtcgcactgg tgaagcatta      420
gcaacaacag agctttcact taagtatcta gcacctctaa ggagtggaga tagatttgtg      480
gtgaaggtgc gaatatcccg ctctacagca gctcgattgt ttttcgagca tttcatcttc      540
aagcttccag atcaagagcc tatattggag caagaggaa tagcagtgtg gcttaataga       600
agttaccgtc ctatccgaat ccatcagag ttcagttcaa aatttgttca gttccttcac       660
cagaagagtt gcggtacaca acaccgtctc tagaacctac tcgtggaatt acattggtat      720
tatttctgaa tttagtgctt gtaatgtcta acaacatttg atctttcatt aaattgaatg      780
```

<210> SEQ ID NO 5
<211> LENGTH: 426
<212> TYPE: DNA
<213> ORGANISM: Artificial Sequence
<220> FEATURE:
<223> OTHER INFORMATION: Synthetic polynucleotide

<400> SEQUENCE: 5

```
atggctgagt tccatgaagt tgaactcaaa gtcagggact atgaattgga tcagtatggt       60
gttgtaaaca atgctatcta tgcaagttat tgccaacatg gtcgtcatga gctccttgaa      120
aggattggta agtgctga tgaagtggca cgtagtggtg acgcacttgc acttacagag        180
ttgtcactta agtatcttgc acctcttagg agtggagata gatttgtcgt gaaagctaga      240
atatctgatt cttcagctgc tcgtttgttc tttgaacact tcatcttcaa acttcctgat      300
caagagccca tcttggaggc aagaggaata gcagtgtggc tcaacaagag ttaccgtcct      360
gtcagaatcc cagcagagtt cagatcaaaa tttgttcagt tccttcgtca ggaggcatcc      420
aactga                                                                426
```

<210> SEQ ID NO 6
<211> LENGTH: 423
<212> TYPE: DNA
<213> ORGANISM: Artificial Sequence
<220> FEATURE:
<223> OTHER INFORMATION: Synthetic polynucleotide

<400> SEQUENCE: 6

```
atggctaatg agttctatga agtcgaactc aaagtcaggg actatgagtt ggatcaatat       60
ggtgttgtaa acaatgctat ctatgctagt tattgccaac attgtaggca tgagcttctt      120
gaaaagattg gcgtaaatgc tgatgcagtg gcacgtaatg gtgaagcatt agcacttaca      180
gagatgacac tcaagtatct tgcacctctc aggagtggag acagattcat gtgaaagtt       240 agaatatctg actcttcagc tgctcgtttg ttctttgaac acttcatctt caaacttcct      300
gatcaagagc ctatcttgga ggcaagagga acagcagtgt ggcttaacaa gagttaccgt      360
cctgtcagaa tcccttcaga gttcagatca aaattcgttc agttccttcg tcaggaggca      420
tga                                                                    423
```

<210> SEQ ID NO 7
<211> LENGTH: 453
<212> TYPE: DNA
<213> ORGANISM: Artificial Sequence
<220> FEATURE:
<223> OTHER INFORMATION: Synthetic polynucleotide

<400> SEQUENCE: 7

```
atggctagtg atcaggtcta tcaccatgac gttgaactca cagtcaggga ctatgagttg      60
gatcagtttg gtgttgtaaa taatgctact tatgctagtt attgtcaaca ttgtcgtcat     120
gctttccttg agaagattgg tgttagtgtt gatgaagtaa cccgtaatgg tgatgcatta     180
gctgtaacag agctctcact taagtttctt gcaccactta ggagtggaga tagattcgtg     240
gtgagggcta gattgtccca ctttacagta gctagattgt tctttgagca tttcatcttc     300
aaacttcctg atcaagagcc tatattggag gcaagaggaa tagcagtgtg gcttaataga     360
agttatcgtc ctattcgtat tccatcagag ttcaattcaa aatttgttaa attccttcac     420
cagaagagtt gcggtgtaca acatcatctc tga                                  453
```

<210> SEQ ID NO 8
<211> LENGTH: 453
<212> TYPE: DNA
<213> ORGANISM: Artificial Sequence
<220> FEATURE:
<223> OTHER INFORMATION: Synthetic polynucleotide

<400> SEQUENCE: 8

```
atggctggtg atcagctcta tcaacatgaa gttgaactcc aagtcaggga ctatgaattg      60
gatcagtttg gtgttgtaaa caatgctact tatgcaagtt attgtcaaca ttgccgtcat     120
gagtttcttg agaagattgg tgtaagtgtt gatgaagtat gtagaactgg tgaagcatta     180
gcaacaacag agctttcact taagtatctt gcacctctca ggagtggaga tagatttgtg     240
gtgaaggtga gaatatccag gtctacagca gctcgtttgt tcttgagca tttcatcttc     300 aaacttccag atcaagagcc tatattggag gcaagaggaa tagcagtgtg gcttaataga     360
agttaccgtc ctatcagaat accatcagag ttcagttcaa agtttgttca gttccttcac     420
cagaagagtt gcggtacaca acaccgtctc tag                                  453
```

<210> SEQ ID NO 9
<211> LENGTH: 561
<212> TYPE: DNA
<213> ORGANISM: Artificial Sequence
<220> FEATURE:
<223> OTHER INFORMATION: Synthetic polynucleotide

<400> SEQUENCE: 9

```
atggcttcaa tttgtacttc aaattttcac tttctatgca gaaaaaacaa ttctagccct      60
atttctcatc atctactgtt atctccctct tctttatcct tctcacgttg cggcggattg     120
cggttgtgtc gtgcggccgc agagttccat gaagttgaac tcaaagtcag ggactatgaa     180
ttggatcagt atggtgttgt aaacaatgct atctatgcaa gttattgcca acatggtcgt     240
catgagctcc ttgaaaggat tggtataagt gctgatgaag tggcacgtag tggtgacgca     300
cttgcactta cagagttgtc acttaagtat cttgcacctc ttaggagtgg agatagattt     360
gtcgtgaaag ctagaatatc tgattcttca gctgctcgtt tgttctttga acacttcatc     420
ttcaaacttc ctgatcaaga gcccatcttg gaggcaagag gaatagcagt gtggctcaac     480
aagagttacc gtcctgtcag aatcccagca gagttcagat caaaatttgt tcagttcctt     540
cgtcaggagg catccaactg a                                               561
```

<210> SEQ ID NO 10
<211> LENGTH: 588
<212> TYPE: DNA
<213> ORGANISM: Artificial Sequence
<220> FEATURE:

<223> OTHER INFORMATION: Synthetic polynucleotide

<400> SEQUENCE: 10

| | | |
|---|---|---|
| atggcttcaa tttgtacttc aaattttcac tttctttgca ggaagaacaa ttctagccct | 60 |
| atttctcatc atctactttt atctccctct tctttatcct tctcacgttg cggcggattg | 120 |
| cgtttgtgtc gtgcggccgc aagtgatcag gtctatcacc atgacgttga actcacagtc | 180 |
| agggactatg agttggatca gtttggtgtt gtaaataatg ctacttatgc tagttattgt | 240 |
| caacattgtc gtcatgcttt ccttgagaag attggtgtta gtgttgatga agtaacccgt | 300 |
| aatggtgatg cattagctgt aacagagctc tcacttaagt ttcttgcacc acttaggagt | 360 |
| ggagatagat tcgtggtgag ggctagattg tcccactttia cagtagctag attgttcttt | 420 |
| gagcatttca tcttcaaact tcctgatcaa gagcctatat tggaggcaag aggaatagca | 480 |
| gtgtggctta atagaagtta tcgtcctatt cgtattccat cagagttcaa ttcaaaattt | 540 |
| gttaaattcc ttcaccagaa gagttgcggt gtacaacatc atctctga | 588 |

<210> SEQ ID NO 11
<211> LENGTH: 423
<212> TYPE: DNA
<213> ORGANISM: Artificial Sequence
<220> FEATURE:
<223> OTHER INFORMATION: Synthetic polynucleotide

<400> SEQUENCE: 11

| | | |
|---|---|---|
| atgagtgagt tccatgaagt tgaactcaaa gtcagggact atgaattgga tcagtatggt | 60 |
| gttgtaaaca atgctatcta tgcaagttat tgccaacatt gccgtcatga gctccttgaa | 120 |
| aggattggtg tgagtgctga tgaagtggca cgtagtggtg acgcacttgc acttacagag | 180 |
| ttgtcactta gtatcttgc acctcttagg agtggagata gatttgtcgt gaaagctaga | 240 |
| atatctgatt cttcagctgc tcgtttgttc tttgaacact tcatcttcaa acttcctgat | 300 |
| caagagccca tcttggaggc aagaggaata gcagtgtggc tcaacaagag ttaccgtcct | 360 |
| gtcagaatcc catccgagtt cagatcaaaa tttgttcagt tccttcgtca ggaggcatcc | 420 |
| aac | 423 |

<210> SEQ ID NO 12
<211> LENGTH: 423
<212> TYPE: DNA
<213> ORGANISM: Artificial Sequence
<220> FEATURE:
<223> OTHER INFORMATION: Synthetic polynucleotide

<400> SEQUENCE: 12

| | | |
|---|---|---|
| atgaatgagt tctatgaagt cgaactcaaa gtcagggact atgagttgga tcaatatggt | 60 |
| gttgtaaaca atgctatcta tgctagttat tgccaacatt gtaggcatga gcttcttgaa | 120 |
| aagattggcg taagtgctga tgaggtggca cgtaatggtg aagcattagc acttacagag | 180 |
| ttaacactca agtatcttgc acctctcagg agtggagaca gattcgttgt gaaagttaga | 240 |
| atatctgact cttcagctgc tcgtttgttc tttgaacact tcatcttcaa acttcctgat | 300 |
| caagagccta tcttggaggc aagaggaatc gcagtgtggc ttaacaagag ttaccgtcct | 360 |
| gtcagaatcc cttcagagtt cagatcaaaa ttcgttcagt tccttcgtca ggaggcatca | 420 |
| aac | 423 |

<210> SEQ ID NO 13
<211> LENGTH: 447

```
<212> TYPE: DNA
<213> ORGANISM: Artificial Sequence
<220> FEATURE:
<223> OTHER INFORMATION: Synthetic polynucleotide

<400> SEQUENCE: 13
atgagtgatc aggtctattt ccatgacgtt gaactcaagg tcagggacta tgagttggat      60
cagtttggtg ttgtaaataa tgctacttat gctagttatt gtcaacattg tcgtcatgag     120
ttccttgaga agattggtgt tagtgttgat gaagtagctc gtaatggtga tgcattagct     180
cttacagagc tctcacttaa gtttcttgca ccacttagga gtggagatag attcgtggtg     240
agggctagaa tctccgatag tacagcagct agattgttct tgagcatttt catcttcaaa     300
cttcctgatc aagagcctat attggaggca agaggaatag cagtgtggct taatagaagt     360
tatcgtccta ttcgtattcc atcagagttc agatcaaaat tgttcagtt ccttcaccag      420 aagagttgcg gtgtacaaca tcatctc                                         447

<210> SEQ ID NO 14
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 14
atgagtgatc agctctattt ccatgaagtt gaactcaagg tcagggacta tgaattggat      60
cagtttggtg ttgtaaacaa tgctacttat gcaagttatt gtcaacattg ccgtcatgag     120
tttcttgaga agattggtgt aagtgttgat gaagtagcaa gaactggtga agcattagca     180
cttacagagc tttcacttaa gtatcttgca cctctcagga gtggagatag atttgtggtg     240
aaggtgagaa tatccgattc tacagcagct cgtttgttct tcgagcattt catcttcaaa     300
cttccagatc aagagcctat attggaggca agaggaatag cagtgtggct taatagaagt     360
taccgtccta tcagaatacc atcagagttc cgttcaaagt tgttcagtt ccttcaccag      420 aagagttgcg gtacacaaca ccgtctc                                         447

<210> SEQ ID NO 15
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 15
atgagtgatc agctctattt ccatgaagtt gaactcaagg tcagggacta tgaattggat      60
cagtttggtg ttgtaaacaa tgctacttat gcaagttatt gtcaacattg ccgtcatgag     120
tttcttgaga agattggtgt aagtgttgat gaagtagcaa gaactggtga agcattagca     180
cttacagagc tttcacttaa gtatcttgca cctctcagga gtggagatag atttgtggtg     240
aaggtgagaa tatccgattc tacagcagct cgtttgttct tcgagcattt catcttcaaa     300
cttccagatc aagagcctat attggaggca agaggaatag cagtgtggct taatagaagt     360
taccgtccta tcagaatacc atcagagttc cgttcaaagt tgttcagtt ccttcaccag      420 aagagttgcg gtacacaaca ccgtctc                                         447

<210> SEQ ID NO 16
<211> LENGTH: 447
<212> TYPE: DNA
```

<213> ORGANISM: Artificial Sequence
<220> FEATURE:
<223> OTHER INFORMATION: Synthetic polynucleotide

<400> SEQUENCE: 16

```
atgaatgatc agctctattt ctatgaagtc gaactcaaag tcagggacta tgagttggat      60
caattcggtg ttgtaaacaa tgctacctat gctagttatt gccaacattg taggcatgag     120
tttcttgaaa agattggcgt aaatgttgat gcagtggcac gtaatggtga agcattagca     180
cttacagaga tgacactcaa gtatcttgca cctctcagga gtggagacag attcattgtg     240
aaagttagaa tatctgactc tacagctgct cgtttgttct tgaacactt catcttcaaa      300
cttcctgatc aagagcctat cttggaggca agaggaacag cagtgtggct taacaggagt     360
taccgtccta tcagaatccc ttcagagttc agatcaaaat tcgttcagtt ccttcaccag     420
aagagttgcg gtacacaaca ccgtctc                                         447
```

<210> SEQ ID NO 17
<211> LENGTH: 423
<212> TYPE: DNA
<213> ORGANISM: Artificial Sequence
<220> FEATURE:
<223> OTHER INFORMATION: Synthetic polynucleotide

<400> SEQUENCE: 17

```
atgagtgagc accatgacgt tgaactcaca gtcagggact atgagttgga tcagtatggt      60
gttgtaaata tgctatttta tgctagttat tgtcaacatt gtcgtcatgc tttgcttgag     120
aagattggtg ttagtgctga tgaagtaacc cgtaatggtg atgcattagc tgtaacagag     180
ctctcactta gtttcttgc accacttagg agtggagata gattcgtggt gagggctaga     240
ttgtcccact ttagcgtagc tagattgttc tttgagcatt tcatcttcaa acttcctgat     300
caagagccta tattggaggc aagaggaata gcagtgtggc ttaataagag ttatcgtcct     360
gttcgtattc catcagagtt caattcaaaa tttgttaaat tccttcgtca ggaggcatcc     420
aac                                                                   423
```

<210> SEQ ID NO 18
<211> LENGTH: 423
<212> TYPE: DNA
<213> ORGANISM: Artificial Sequence
<220> FEATURE:
<223> OTHER INFORMATION: Synthetic polynucleotide

<400> SEQUENCE: 18

```
atgagtgagc agcatgaagt tgaactccaa gtcagggact atgaattgga tcagtatggt      60
gttgtaaaca atgctatttta tgcaagttat tgtcaacatt gccgtcatga gcttcttgag    120
aagattggtg taagtgctga tgaagtatgt agaactggtg aagcattagc aacaacagag     180
ctttcactta gtatcttgc acctctcagg agtggagata gatttgtggt gaaggtgaga     240
atatccaggt cttccgcagc tcgtttgttc ttcgagcatt tcatcttcaa acttccagat     300
caagagccta tattggaggc aagaggaata gcagtgtggc ttaataagag ttaccgtcct     360
gtgagaatac catcagagtt cagttcaaag tttgttcagt tccttcgtca ggaggcatcc     420
aac                                                                   423
```

<210> SEQ ID NO 19
<211> LENGTH: 423
<212> TYPE: DNA
<213> ORGANISM: Artificial Sequence
<220> FEATURE:
<223> OTHER INFORMATION: Synthetic polynucleotide

<400> SEQUENCE: 19

```
atggctgagt tccatgaagt tgaactcaaa gtcagggact atgaattgga tcagtatggt      60
gttgtaaaca atgctatcta tgcaagttat tgccaacatg gtcgtcatga gctccttgaa     120
aggattggta taaacgctga tgcagtggca cgtaatggtg acgcacttgc acttacagag     180
ttgtcactta agtatcttgc acctcttagg agtggagata gatttgtcgt gaaagctaga     240
atatctgatt cttcagctgc tcgtttgttc tttgaacact tcatcttcaa acttcctgat     300
caagagccca tcttggaggc aagaggaata gcagtgtggc tcaacaagag ttaccgtcct     360
gtcagaatcc cagcagagtt cagatcaaaa tttgttcagt tccttcgtca ggaggcatcc     420
aac                                                                   423
```

<210> SEQ ID NO 20
<211> LENGTH: 423
<212> TYPE: DNA
<213> ORGANISM: Artificial Sequence
<220> FEATURE:
<223> OTHER INFORMATION: Synthetic polynucleotide

<400> SEQUENCE: 20

```
atggctgagt tccatgaagt tgaactcaaa gtcagggact atgaattgga tcagtatggt      60
gttgtaaaca atgctatcta tgcaagttat tgccaacatt gccgtcatga gctccttgaa     120
aggattggta taaacgctga tgcagtggca cgtaatggtg acgcacttgc acttacagag     180
ttgtcactta agtatcttgc acctcttagg agtggagata gatttgtcgt gaaagctaga     240
atatctgatt cttcagctgc tcgtttgttc tttgaacact tcatcttcaa acttcctgat     300
caagagccca tcttggaggc aagaggaata gcagtgtggc tcaacaagag ttaccgtcct     360
gtcagaatcc cagcagagtt cagatcaaaa tttgttcagt tccttcgtca ggaggcatcc     420
aac                                                                   423
```

<210> SEQ ID NO 21
<211> LENGTH: 423
<212> TYPE: DNA
<213> ORGANISM: Artificial Sequence
<220> FEATURE:
<223> OTHER INFORMATION: Synthetic polynucleotide

<400> SEQUENCE: 21

```
atggctgagt tccatgaagt tgaactcaaa gtcagggact atgaattgga tcagtatggt      60
gttgtaaaca atgctatcta tgcaagttat tgccaacatt gccgtcatga gctccttgaa     120
aggattggta taagtgctga tgaagtggca cgtagtggtg acgcacttgc acttacagag     180
ttgtcactta agtatcttgc acctcttagg agtggagata gatttgtcgt gaaagctaga     240
atatctgatt cttcagctgc tcgtttgttc tttgaacact tcatcttcaa acttcctgat     300
caagagccca tcttggaggc aagaggaata gcagtgtggc tcaacaagag ttaccgtcct     360
gtcagaatcc cagcagagtt cagatcaaaa tttgttcagt tccttcgtca ggaggcatcc     420
aac                                                                   423
```

<210> SEQ ID NO 22
<211> LENGTH: 423
<212> TYPE: DNA
<213> ORGANISM: Artificial Sequence
<220> FEATURE:

<223> OTHER INFORMATION: Synthetic polynucleotide

<400> SEQUENCE: 22

```
atggctgagt tctatgaagt tgaactcaaa gtcagggact atgaattgga tcagtatggt    60
gttgtaaaca atgctatcta tgcaagttat tgccaacatg gtcgtcatga gctccttgaa   120
aggattggta taagtgctga tgaagtggca cgtagtggtg acgcacttgc acttacagag   180
ttgtcactta agtatcttgc acctcttagg agtggagata gatttgtcgt gaaagctaga   240
atatctgatt cttcagctgc tcgtttgttc tttgaacact tcatcttcaa acttcctgat   300
caagagccca tcttggaggc aagaggaata gcagtgtggc tcaacaagag ttaccgtcct   360
gtcagaatcc cagcagagtt cagatcaaaa tttgttcagt tccttcgtca ggaggcatcc   420
aac                                                                 423
```

<210> SEQ ID NO 23
<211> LENGTH: 417
<212> TYPE: DNA
<213> ORGANISM: Artificial Sequence
<220> FEATURE:
<223> OTHER INFORMATION: Synthetic polynucleotide

<400> SEQUENCE: 23

```
atgaatgagt tctatgaagt cgaactcaaa gtcagggact atgagttgga tcaatatggt    60
gttgtaaaca atgctatcta tgctagttat tgccaacatg gtaggcatga gcttcttgaa   120
aagattggcg taaatgctga tgcagtggca cgtaatggtg aagcattagc acttacagag   180
atgacactca agtatcttgc acctctcagg agtggagaca gattcattgt gaaagttaga   240
atatctgact cttcagctgc tcgtttgttc tttgaacact tcatcttcaa acttcctgat   300
caagagccta tcttggaggc aagaggaaca gcagtgtggc ttaacaagag ttaccgtcct   360
gtcagaatcc cttcagagtt cagatcaaaa ttcgttcagt tccttcgtca ggaggca      417
```

<210> SEQ ID NO 24
<211> LENGTH: 417
<212> TYPE: DNA
<213> ORGANISM: Artificial Sequence
<220> FEATURE:
<223> OTHER INFORMATION: Synthetic polynucleotide

<400> SEQUENCE: 24

```
atgaatgagt tctatgaagt cgaactcaaa gtcagggact atgagttgga tcaatatggt    60
gttgtaaaca atgctatcta tgctagttat tgccaacatg gtaggcatga gcttcttgaa   120
aagattggcg taagtgctga tgaggtggca cgtagtggtg aagcattagc acttacagag   180
atgacactca agtatcttgc acctctcagg agtggagaca gattcattgt gaaagttaga   240
atatctgact cttcagctgc tcgtttgttc tttgaacact tcatcttcaa acttcctgat   300
caagagccta tcttggaggc aagaggaaca gcagtgtggc ttaacaagag ttaccgtcct   360
gtcagaatcc cttcagagtt cagatcaaaa ttcgttcagt tccttcgtca ggaggca      417
```

<210> SEQ ID NO 25
<211> LENGTH: 417
<212> TYPE: DNA
<213> ORGANISM: Artificial Sequence
<220> FEATURE:
<223> OTHER INFORMATION: Synthetic polynucleotide

<400> SEQUENCE: 25

```
atgaatgagt tctatgaagt cgaactcaaa gtcagggact atgagttgga tcaatatggt    60
```

```
gttgtaaaca atgctatcta tgctagttat tgccaacatt gtaggcatga gcttcttgaa        120
aagattggcg taagtgctga tgaggtggca cgtagtggtg aagcattagc acttacagag        180
atgacactca gtatcttgc acctctcagg agtggagaca gattcattgt gaaagttaga         240
atatctgact cttcagctgc tcgtttgttc tttgaacact tcatcttcaa acttcctgat        300
caagagccta tcttggaggc aagaggaaca gcagtgtggc ttaacaagag ttaccgtcct        360
gtcagaatcc cttcagagtt cagatcaaaa ttcgttcagt tccttcgtca ggaggca          417
```

<210> SEQ ID NO 26
<211> LENGTH: 417
<212> TYPE: DNA
<213> ORGANISM: Artificial Sequence
<220> FEATURE:
<223> OTHER INFORMATION: Synthetic polynucleotide

<400> SEQUENCE: 26

```
atgaatgagt ctatgaagt cgaactcaaa gtcagggact atgagttgga tcaatatggt         60
gttgtaaaca atgctatcta tgctagttat tgccaacatt gtaggcatga gcttcttgaa        120
aagattggcg taagtgctga tgaggtggca cgtagtggtg aagcattagc acttacagag        180
atgacactca gtatcttgc acctctcagg agtggagaca gattcattgt gaaagttaga         240
atatctgact cttcagctgc tcgtttgttc tttgaacact tcatcttcaa acttcctgat        300
caagagccta tcttggaggc aagaggaaca gcagtgtggc ttaacaagag ttaccgtcct        360
gtcagaatcc cttcagagtt cagatcaaaa ttcgttcagt tccttcgtca ggaggca          417
```

<210> SEQ ID NO 27
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 27

```
atgagtgatc aggtctatca ccatgacgtt gaactcacag tcagggacta tgagttggat         60
cagtttggtg ttgtaaataa tgctacttat gctagttatt gtcaacatgg tcgtcatgag        120
ttgcttgaga agattggtgt taatgctgat gaagtaaccc gtaatggtga tgcattagct        180
gtaacagagc tctcacttaa gtttcttgca ccacttagga gtggagatag attcgtggtg        240
agggctagat tgtcccactt tacagtagct agattgttct ttgagcattt catcttcaaa        300
cttcctgatc aagagcctat attggaggca agaggaatag cagtgtggct aatagaagt         360 tatcgtccta ttcgtattcc atcagagttc aattcaaaat ttgttaaatt ccttcaccag        420
aagagttgcg gtgtacaaca tcatctc                                            447
```

<210> SEQ ID NO 28
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 28

```
atgagtgatc aggtctatca ccatgacgtt gaactcacag tcagggacta tgagttggat         60
cagtttggtg ttgtaaataa tgctacttat gctagttatt gtcaacattg tcgtcatgct        120
ttccttgaga agattggtgt taatgctgat gaagtaaccc gtaatggtga tgcattagct        180
```

```
gtaacagagc tctcacttaa gtttcttgca ccacttagga gtggagatag attcgtggtg    240
agggctagat tgtcccactt tacagtagct agattgttct ttgagcattt catcttcaaa    300
cttcctgatc aagagcctat attggaggca agaggaatag cagtgtggct taatagaagt    360
tatcgtccta ttcgtattcc atcagagttc aattcaaaat ttgttaaatt ccttcaccag    420
aagagttgcg gtgtacaaca tcatctc                                        447

<210> SEQ ID NO 29
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 29
atgggtgatc agctctatca acatgaagtt gaactccaag tcagggacta tgaattggat     60
cagtttggtg ttgtaaacaa tgctacttat gcaagttatt gtcaacatgg ccgtcatgag    120
tttcttgaga agattggtgt aagtgttgat gaagtagcta gaactggtga agcattagca    180
acaacagagc tttcacttaa gtatcttgca cctctcagga gtggagatag atttgtggtg    240
aaggtgagaa tatccaggtc tacagcagct cgtttgttct tcgagcattt catcttcaaa    300
cttccagatc aagagcctat attggaggca agaggaatag cagtgtggct taatagaagt    360
taccgtccta tcagaatacc atcagagttc agttcaaagt tgttcagtt ccttcaccag    420 aagagttgcg gtacacaaca ccgtctc                                        447

<210> SEQ ID NO 30
<211> LENGTH: 438
<212> TYPE: DNA
<213> ORGANISM: Artificial Sequence
<220> FEATURE:
<223> OTHER INFORMATION: Synthetic polynucleotide

<400> SEQUENCE: 30
atggctgagt tccatgaagt tgaactcaaa gtccgggact atgaattgga tcagtatggt     60
gttgtaaaca atgctatttta tgcaagttat tgccaacatg gtcgtcatga gcttctagaa    120
aggattggta taagtgctga tgaagtggca cgcagtggtg acgcactagc actaacagag    180
ctgtcactta agtatctagc acctctaagg agtggagata gatttgtcgt gaaggcacga    240
atatctgatt cttcagctgc tcgtttgttt ttcgaacact tcatcttcaa gcttccagat    300
caagagccta tattggaggc aagaggaata gcagtgtggc ttaatagaag ttatcgtcct    360
attcgaattc cgtcagagtt caattcaaaa tttgttaaat tccttcacca aaagagttgc    420
ggtgtacaac atcatctc                                                  438

<210> SEQ ID NO 31
<211> LENGTH: 423
<212> TYPE: DNA
<213> ORGANISM: Artificial Sequence
<220> FEATURE:
<223> OTHER INFORMATION: Synthetic polynucleotide

<400> SEQUENCE: 31
atggctgagt tccatgaagt tgaactcaaa gtccgggact atgaattgga tcagtatggt     60
gttgtaaaca atgctatttta tgcaagttat tgccaacatg gtcgtcatga gcttctagaa    120
aggattggta taagtgctga tgaagtggca cgcagtggtg acgcactagc actaacagag    180
ctgtcactta agtatctagc acctctaagg agtggagata gattcgtggt gagggcgcga    240
```

```
ttatcccact ttacagtagc tcgattgttt ttcgagcatt tcatcttcaa gcttccagat      300
caagagccca tcttggaggc aagaggaata gcagtgtggc tcaataaaag ttaccgtcct      360
gtccgaatcc cggcagagtt cagatcaaaa tttgttcagt tccttcgcca ggaggcatcc      420
aac                                                                   423
```

<210> SEQ ID NO 32
<211> LENGTH: 438
<212> TYPE: DNA
<213> ORGANISM: Artificial Sequence
<220> FEATURE:
<223> OTHER INFORMATION: Synthetic polynucleotide

<400> SEQUENCE: 32

```
atggctgagt ccatgaagt tgaactcaaa gtccgggact atgaattgga tcagtatggt       60
gttgtaaaca atgctattta tgcaagttat tgccaacatg gtcgtcatga gcttctagaa     120
aggattggta taagtgctga tgaagtggca cgcagtggtg acgcactagc actaacagag     180
ctgtcactta agtatctagc acctctaagg agtggagata gattcgtggt gagggcgcga     240
ttatcccact ttacagtagc tcgattgttt ttcgagcatt tcatcttcaa gcttccagat     300
caagagccta tattggaggc aagaggaata gcagtgtggc ttaatagaag ttatcgtcct     360
attcgaattc cgtcagagtt caattcaaaa tttgttaaat tccttcacca gaagagttgc     420
ggtgtacaac atcatctc                                                   438
```

<210> SEQ ID NO 33
<211> LENGTH: 423
<212> TYPE: DNA
<213> ORGANISM: Artificial Sequence
<220> FEATURE:
<223> OTHER INFORMATION: Synthetic polynucleotide

<400> SEQUENCE: 33

```
atggctgagt ccatgaagt tgaactcaaa gtccgggact atgaattgga tcagtatggt       60
gttgtaaaca atgctattta tgcaagttat tgtcaacatt gtcgtcatgc gtttctagaa     120
aaaattggtg ttagtgttga tgaagtaacg cgaaatggtg atgcattagc tgtaacagag     180
ctctcactta agtttctagc accactaagg agtggagata gatttgtcgt gaaggcacga     240
atatctgatt cttcagctgc tcgtttgttt ttcgaacact tcatcttcaa gcttccagat     300
caagagccca tcttggaggc aagaggaata gcagtgtggc tcaataaaag ttaccgtcct     360
gtccgaatcc cggcagagtt cagatcaaaa tttgttcagt tccttcgcca ggaggcatcc     420
aac                                                                   423
```

<210> SEQ ID NO 34
<211> LENGTH: 438
<212> TYPE: DNA
<213> ORGANISM: Artificial Sequence
<220> FEATURE:
<223> OTHER INFORMATION: Synthetic polynucleotide

<400> SEQUENCE: 34

```
atggctgagt ccatgaagt tgaactcaaa gtccgggact atgaattgga tcagtatggt       60
gttgtaaaca atgctattta tgcaagttat tgtcaacatt gtcgtcatgc gtttctagaa     120
aaaattggtg ttagtgttga tgaagtaacg cgaaatggtg atgcattagc tgtaacagag     180
ctctcactta agtttctagc accactaagg agtggagata gatttgtcgt gaaggcacga     240
```

```
atatctgatt cttcagctgc tcgtttgttt ttcgaacact tcatcttcaa gcttccagat    300
caagagccta tattggaggc aagaggaata gcagtgtggc ttaatagaag ttatcgtcct    360
attcgaattc cgtcagagtt caattcaaaa tttgttaaat tccttcacca gaagagttgc    420
ggtgtacaac atcatctc                                                  438

<210> SEQ ID NO 35
<211> LENGTH: 423
<212> TYPE: DNA
<213> ORGANISM: Artificial Sequence
<220> FEATURE:
<223> OTHER INFORMATION: Synthetic polynucleotide

<400> SEQUENCE: 35
atggctgagt ccatgaagt tgaactcaaa gtccgggact atgaattgga tcagtatggt     60
gttgtaaaca atgctattta tgcaagttat tgtcaacatt gtcgtcatgc gtttctagaa    120
aaaattggtg ttagtgttga tgaagtaacg cgaaatggtg atgcattagc tgtaacagag    180
ctctcactta agtttctagc accactaagg agtggagata gattcgtggt gagggcgcga    240
ttatcccact ttacagtagc tcgattgttt ttcgagcatt tcatcttcaa gcttccagat    300
caagagccca tcttggaggc aagaggaata gcagtgtggc tcaataaaag ttaccgtcct    360
gtccgaatcc cggcagagtt cagatcaaaa tttgttcagt ccttcgcca ggaggcatcc     420 aac                                                                  423

<210> SEQ ID NO 36
<211> LENGTH: 438
<212> TYPE: DNA
<213> ORGANISM: Artificial Sequence
<220> FEATURE:
<223> OTHER INFORMATION: Synthetic polynucleotide

<400> SEQUENCE: 36
atggctgagt ccatgaagt tgaactcaaa gtccgggact atgaattgga tcagtatggt     60
gttgtaaaca atgctattta tgcaagttat tgtcaacatt gtcgtcatgc gtttctagaa    120
aaaattggtg ttagtgttga tgaagtaacg cgaaatggtg atgcattagc tgtaacagag    180
ctctcactta agtttctagc accactaagg agtggagata gattcgtggt gagggcgcga    240
ttatcccact ttacagtagc tcgattgttt ttcgagcatt tcatcttcaa gcttccagat    300
caagagccta tattggaggc aagaggaata gcagtgtggc ttaatagaag ttatcgtcct    360
attcgaattc cgtcagagtt caattcaaaa tttgttaaat tccttcacca gaagagttgc    420
ggtgtacaac atcatctc                                                  438

<210> SEQ ID NO 37
<211> LENGTH: 432
<212> TYPE: DNA
<213> ORGANISM: Artificial Sequence
<220> FEATURE:
<223> OTHER INFORMATION: Synthetic polynucleotide

<400> SEQUENCE: 37
atgagtgatc aggtctatca ccatgacgtt gaactcacag tcagggacta tgagttggat     60
cagtttggtg ttgtaaataa tgctacttat gcgagttatt gccaacatgg tcgtcatgag    120
cttctagaaa ggattggtat aagtgctgat gaagtggcac gcagtggtga cgcactagca    180
ctaacagagc tgtcacttaa gtatctagca cctctaagga gtggagatag atttgtcgtg    240
aaggcacgaa tatctgattc ttcagctgct cgtttgtttt tcgaacactt catcttcaag    300
```

```
cttccagatc aagagcccat cttggaggca agaggaatag cagtgtggct caataaaagt    360
taccgtcctg tccgaatccc ggcagagttc agatcaaaat ttgttcagtt ccttcgccag    420
gaggcatcca ac                                                        432
```

```
<210> SEQ ID NO 38
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 38
atgagtgatc aggtctatca ccatgacgtt gaactcacag tcagggacta tgagttggat     60
cagtttggtg ttgtaaataa tgctacttat gcgagttatt gccaacatgg tcgtcatgag    120
cttctagaaa ggattggtat aagtgctgat gaagtggcac gcagtggtga cgcactagca    180
ctaacagagc tgtcacttaa gtatctagca cctctaagga gtggagatag atttgtcgtg    240
aaggcacgaa tatctgattc ttcagctgct cgtttgtttt tcgaacactt catcttcaag    300
cttccagatc aagagcctat attggaggca agaggaatag cagtgtggct aatagaagt     360 tatcgtccta ttcgaattcc gtcagagttc aattcaaaat ttgttaaatt ccttcaccag    420
aagagttgcg gtgtacaaca tcatctc                                       447
```

```
<210> SEQ ID NO 39
<211> LENGTH: 432
<212> TYPE: DNA
<213> ORGANISM: Artificial Sequence
<220> FEATURE:
<223> OTHER INFORMATION: Synthetic polynucleotide

<400> SEQUENCE: 39
atgagtgatc aggtctatca ccatgacgtt gaactcacag tcagggacta tgagttggat     60
cagtttggtg ttgtaaataa tgctacttat gcgagttatt gccaacatgg tcgtcatgag    120
cttctagaaa ggattggtat aagtgctgat gaagtggcac gcagtggtga cgcactagca    180
ctaacagagc tgtcacttaa gtatctagca cctctaagga gtggagatag attcgtggtg    240
agggcgcgat tatcccactt tacagtagct cgattgtttt tcgagcattt catcttcaag    300
cttccagatc aagagcccat cttggaggca agaggaatag cagtgtggct caataaaagt    360
taccgtcctg tccgaatccc ggcagagttc agatcaaaat ttgttcagtt ccttcgccag    420
gaggcatcca ac                                                        432
```

```
<210> SEQ ID NO 40
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 40
atgagtgatc aggtctatca ccatgacgtt gaactcacag tcagggacta tgagttggat     60
cagtttggtg ttgtaaataa tgctacttat gcgagttatt gccaacatgg tcgtcatgag    120
cttctagaaa ggattggtat aagtgctgat gaagtggcac gcagtggtga cgcactagca    180
ctaacagagc tgtcacttaa gtatctagca cctctaagga gtggagatag attcgtggtg    240
agggcgcgat tatcccactt tacagtagct cgattgtttt tcgagcattt catcttcaag    300
```

```
cttccagatc aagagcctat attggaggca agaggaatag cagtgtggct taatagaagt    360
tatcgtccta ttcgaattcc gtcagagttc aattcaaaat ttgttaaatt ccttcaccag    420
aagagttgcg gtgtacaaca tcatctc                                        447
```

```
<210> SEQ ID NO 41
<211> LENGTH: 432
<212> TYPE: DNA
<213> ORGANISM: Artificial Sequence
<220> FEATURE:
<223> OTHER INFORMATION: Synthetic polynucleotide

<400> SEQUENCE: 41
```

```
atgagtgatc aggtctatca ccatgacgtt gaactcacag tcagggacta tgagttggat     60
cagtttggtg ttgtaaataa tgctacttat gcgagttatt gtcaacattg tcgtcatgcg    120
tttctagaaa aaattggtgt tagtgttgat gaagtaacgc gaaatggtga tgcattagct    180
gtaacagagc tctcacttaa gtttctagca ccactaagga gtggagatag atttgtcgtg    240
aaggcacgaa tatctgattc ttcagctgct cgtttgtttt tcgaacactt catcttcaag    300
cttccagatc aagagcccat cttggaggca agaggaatag cagtgtggct caataaaagt    360
taccgtcctg tccgaatccc ggcagagttc agatcaaaat ttgttcagtt ccttcgccag    420
gaggcatcca ac                                                        432
```

```
<210> SEQ ID NO 42
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 42
```

```
atgagtgatc aggtctatca ccatgacgtt gaactcacag tcagggacta tgagttggat     60
cagtttggtg ttgtaaataa tgctacttat gcgagttatt gtcaacattg tcgtcatgcg    120
tttctagaaa aaattggtgt tagtgttgat gaagtaacgc gaaatggtga tgcattagct    180
gtaacagagc tctcacttaa gtttctagca ccactaagga gtggagatag atttgtcgtg    240
aaggcacgaa tatctgattc ttcagctgct cgtttgtttt tcgaacactt catcttcaag    300
cttccagatc aagagcctat attggaggca agaggaatag cagtgtggct taatagaagt    360
tatcgtccta ttcgaattcc gtcagagttc aattcaaaat ttgttaaatt ccttcaccag    420
aagagttgcg gtgtacaaca tcatctc                                        447
```

```
<210> SEQ ID NO 43
<211> LENGTH: 432
<212> TYPE: DNA
<213> ORGANISM: Artificial Sequence
<220> FEATURE:
<223> OTHER INFORMATION: Synthetic polynucleotide

<400> SEQUENCE: 43
```

```
atgagtgatc aggtctatca ccatgacgtt gaactcacag tcagggacta tgagttggat     60
cagtttggtg ttgtaaataa tgctacttat gcgagttatt gtcaacattg tcgtcatgcg    120
tttctagaaa aaattggtgt tagtgttgat gaagtaacgc gaaatggtga tgcattagct    180
gtaacagagc tctcacttaa gtttctagca ccactaagga gtggagatag attcgtggtg    240
agggcgcgat tatcccactt tacagtagct cgattgtttt tcgagcattt catcttcaag    300
cttccagatc aagagcccat cttggaggca agaggaatag cagtgtggct caataaaagt    360
```

```
taccgtcctg tccgaatccc ggcagagttc agatcaaaat tgttcagtt ccttcgccag    420 gaggcatcca ac                                                       432

<210> SEQ ID NO 44
<211> LENGTH: 432
<212> TYPE: DNA
<213> ORGANISM: Artificial Sequence
<220> FEATURE:
<223> OTHER INFORMATION: Synthetic polynucleotide

<400> SEQUENCE: 44
atgagtgatc aggtctatca ccatgaagtt gaactcaaag tccgggacta tgaattggat    60
cagtatggtg ttgtaaacaa tgctatttat gcaagttatt gccaacatgg tcgtcatgag   120
cttctagaaa ggattggtat aagtgctgat gaagtggcac gcagtggtga cgcactagca   180
ctaacagagc tgtcacttaa gtatctagca cctctaagga gtggagatag atttgtcgtg   240
aaggcacgaa tatctgattc ttcagctgct cgtttgtttt tcgaacactt catcttcaag   300
cttccagatc aagagcccat cttggaggca agaggaatag cagtgtggct caataaaagt   360
taccgtcctg tccgaatccc ggcagagttc agatcaaaat tgttcagtt ccttcgccag    420 gaggcatcca ac                                                       432

<210> SEQ ID NO 45
<211> LENGTH: 438
<212> TYPE: DNA
<213> ORGANISM: Artificial Sequence
<220> FEATURE:
<223> OTHER INFORMATION: Synthetic polynucleotide

<400> SEQUENCE: 45
atggctgagt ccatgaagt tgaactcaaa gtccgggact atgaattgga tcagtatggt     60
gttgtaaaca atgctattta tgcaagttat gccaacatg gtcgtcatga gcttctagaa    120
aggattggta taagtgctga tgaagtggca cgcagtggtg acgcactagc actaacagag   180
ctgtcactta agtatctagc acctctaagg agtggagata gatttgtcgt gaaggcacga   240
atatctgatt cttcagctgc tcgtttgttt ttcgaacact tcatcttcaa gcttccagat   300
caagagccca tcttggaggc aagaggaata gcagtgtggc tcaataaaag ttaccgtcct   360
gtccgaatcc cggcagagtt cagatcaaaa tttgttcagt tccttcgcca agagttgc    420 ggtgtacaac atcatctc                                                 438

<210> SEQ ID NO 46
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 46
atgagtgatc aggtctatca ccatgaagtt gaactcaaag tccgggacta tgaattggat    60
cagtatggtg ttgtaaacaa tgctatttat gcaagttatt gccaacatgg tcgtcatgag   120
cttctagaaa ggattggtat aagtgctgat gaagtggcac gcagtggtga cgcactagca   180
ctaacagagc tgtcacttaa gtatctagca cctctaagga gtggagatag atttgtcgtg   240
aaggcacgaa tatctgattc ttcagctgct cgtttgtttt tcgaacactt catcttcaag   300
cttccagatc aagagcccat cttggaggca agaggaatag cagtgtggct caataaaagt   360
```
taccgtcctg tccgaatccc ggcagagttc agatcaaaat ttgttcagtt ccttcgccag        420
aagagttgcg gtgtacaaca tcatctc                                            447

<210> SEQ ID NO 47
<211> LENGTH: 432
<212> TYPE: DNA
<213> ORGANISM: Artificial Sequence
<220> FEATURE:
<223> OTHER INFORMATION: Synthetic polynucleotide

<400> SEQUENCE: 47
atgagtgatc aggtctatca ccatgaagtt gaactcaaag tccgggacta tgaattggat         60
cagtatggtg ttgtaaacaa tgctatttat gcaagttatt gccaacatgg tcgtcatgag        120
cttctagaaa ggattggtat aagtgctgat gaagtggcac gcagtggtga cgcactagca        180
ctaacagagc tgtcacttaa gtatctagca cctctaagga gtggagatag attcgtggtg        240
agggcgcgat tatcccactt tacagtagct cgattgtttt tcgagcattt catcttcaag        300
cttccagatc aagagcccat cttggaggca agaggaatag cagtgtggct caataaaagt        360
taccgtcctg tccgaatccc ggcagagttc agatcaaaat ttgttcagtt ccttcgccag        420
gaggcatcca ac                                                            432

<210> SEQ ID NO 48
<211> LENGTH: 438
<212> TYPE: DNA
<213> ORGANISM: Artificial Sequence
<220> FEATURE:
<223> OTHER INFORMATION: Synthetic polynucleotide

<400> SEQUENCE: 48
atggctgagt ccatgaagt tgaactcaaa gtccgggact atgaattgga tcagtatggt         60
gttgtaaaca atgctattta tgcaagttat tgccaacatg gtcgtcatga gcttctagaa        120
aggattggta taagtgctga tgaagtggca cgcagtggtg acgcactagc actaacagag        180
ctgtcactta agtatctagc acctctaagg agtggagata gattcgtggt gagggcgcga        240
ttatcccact ttacagtagc tcgattgttt tcgagcatt tcatcttcaa gcttccagat        300
caagagccca tcttggaggc aagaggaata gcagtgtggc tcaataaaag ttaccgtcct        360
gtccgaatcc cggcagagtt cagatcaaaa tttgttcagt tccttcgcca gaagagttgc        420
ggtgtacaac atcatctc                                                      438

<210> SEQ ID NO 49
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 49
atgagtgatc aggtctatca ccatgaagtt gaactcaaag tccgggacta tgaattggat         60
cagtatggtg ttgtaaacaa tgctatttat gcaagttatt gccaacatgg tcgtcatgag        120
cttctagaaa ggattggtat aagtgctgat gaagtggcac gcagtggtga cgcactagca        180
ctaacagagc tgtcacttaa gtatctagca cctctaagga gtggagatag attcgtggtg        240
agggcgcgat tatcccactt tacagtagct cgattgtttt tcgagcattt catcttcaag        300
cttccagatc aagagcccat cttggaggca agaggaatag cagtgtggct caataaaagt        360
taccgtcctg tccgaatccc ggcagagttc agatcaaaat ttgttcagtt ccttcgccag        420

```
aagagttgcg gtgtacaaca tcatctc                                          447
```

<210> SEQ ID NO 50
<211> LENGTH: 438
<212> TYPE: DNA
<213> ORGANISM: Artificial Sequence
<220> FEATURE:
<223> OTHER INFORMATION: Synthetic polynucleotide

<400> SEQUENCE: 50

```
atggctgagt tccatgacgt tgaactcaca gtcagggact atgagttgga tcagtttggt       60
gttgtaaata atgctactta tgcgagttat tgtcaacatt gtcgtcatgc gtttctagaa      120
aaaattggtg ttagtgttga tgaagtaacg cgaaatggtg atgcattagc tgtaacagag      180
ctctcactta gtttctagc accactaagg agtggagata gattcgtggt gagggcgcga       240
ttatcccact ttacagtagc tcgattgttt tcgagcatt tcatcttcaa gcttccagat       300
caagagccta tattggaggc aagaggaata gcagtgtggc ttaatagaag ttatcgtcct      360
attcgaattc cgtcagagtt caattcaaaa tttgttaaat tccttcacca gaagagttgc      420
ggtgtacaac atcatctc                                                    438
```

<210> SEQ ID NO 51
<211> LENGTH: 432
<212> TYPE: DNA
<213> ORGANISM: Artificial Sequence
<220> FEATURE:
<223> OTHER INFORMATION: Synthetic polynucleotide

<400> SEQUENCE: 51

```
atgagtgatc aggtctatca ccatgacgtt gaactcacag tcaggggacta tgagttggat      60
cagtttggtg ttgtaaataa tgctacttat gcgagttatt gtcaacattg tcgtcatgcg     120
tttctagaaa aaattggtgt tagtgttgat gaagtaacgc gaaatggtga tgcattagct     180
gtaacagagc tctcacttaa gtttctagca ccactaagga gtggagatag attcgtggtg     240
agggcgcgat tatcccactt tacagtagct cgattgtttt tcgagcattt catcttcaag     300
cttccagatc aagagcctat attggaggca agaggaatag cagtgtggct taatagaagt     360
tatcgtccta ttcgaattcc gtcagagttc aattcaaaat ttgttaaatt ccttcaccag     420
gaggcatcca ac                                                         432
```

<210> SEQ ID NO 52
<211> LENGTH: 423
<212> TYPE: DNA
<213> ORGANISM: Artificial Sequence
<220> FEATURE:
<223> OTHER INFORMATION: Synthetic polynucleotide

<400> SEQUENCE: 52

```
atggctgagt tccatgacgt tgaactcaca gtcagggact atgagttgga tcagtttggt       60
gttgtaaata atgctactta tgcgagttat tgtcaacatt gtcgtcatgc gtttctagaa      120
aaaattggtg ttagtgttga tgaagtaacg cgaaatggtg atgcattagc tgtaacagag      180
ctctcactta gtttctagc accactaagg agtggagata gattcgtggt gagggcgcga       240
ttatcccact ttacagtagc tcgattgttt tcgagcatt tcatcttcaa gcttccagat       300
caagagccta tattggaggc aagaggaata gcagtgtggc ttaatagaag ttatcgtcct      360
attcgaattc cgtcagagtt caattcaaaa tttgttaaat tccttcacca ggaggcatcc      420
``` aac                                                                        423

<210> SEQ ID NO 53
<211> LENGTH: 438
<212> TYPE: DNA
<213> ORGANISM: Artificial Sequence
<220> FEATURE:
<223> OTHER INFORMATION: Synthetic polynucleotide

<400> SEQUENCE: 53
atggctgagt tccatgacgt tgaactcaca gtcagggact atgagttgga tcagtttggt      60
gttgtaaata atgctactta tgcgagttat tgtcaacatt gtcgtcatgc gtttctagaa     120
aaaattggtg ttagtgttga tgaagtaacg cgaaatggtg atgcattagc tgtaacagag     180
ctctcactta gtttctagc accactaagg agtggagata gatttgtcgt gaaggcacga      240
atatctgatt cttcagctgc tcgtttgttt ttcgaacact tcatcttcaa gcttccagat     300
caagagccta tattggaggc aagaggaata gcagtgtggc ttaatagaag ttatcgtcct     360
attcgaattc cgtcagagtt caattcaaaa tttgttaaat tccttcacca gaagagttgc     420
ggtgtacaac atcatctc                                                    438

<210> SEQ ID NO 54
<211> LENGTH: 432
<212> TYPE: DNA
<213> ORGANISM: Artificial Sequence
<220> FEATURE:
<223> OTHER INFORMATION: Synthetic polynucleotide

<400> SEQUENCE: 54
atgagtgatc aggtctatca ccatgacgtt gaactcacag tcagggacta tgagttggat      60
cagtttggtg ttgtaaataa tgctacttat gcgagttatt gtcaacattg tcgtcatgcg     120
tttctagaaa aaattggtgt tagtgttgat gaagtaacgc gaaatggtga tgcattagct     180
gtaacagagc tctcacttaa gtttctagca ccactaagga gtggagatag atttgtcgtg     240
aaggcacgaa tatctgattc ttcagctgct cgtttgtttt tcgaacactt catcttcaag     300
cttccagatc aagagcctat attggaggca agaggaatag cagtgtggct taatagaagt     360
tatcgtccta ttcgaattcc gtcagagttc aattcaaaat ttgttaaatt ccttcaccag     420
gaggcatcca ac                                                          432

<210> SEQ ID NO 55
<211> LENGTH: 423
<212> TYPE: DNA
<213> ORGANISM: Artificial Sequence
<220> FEATURE:
<223> OTHER INFORMATION: Synthetic polynucleotide

<400> SEQUENCE: 55
atggctgagt tccatgacgt tgaactcaca gtcagggact atgagttgga tcagtttggt      60
gttgtaaata atgctactta tgcgagttat tgtcaacatt gtcgtcatgc gtttctagaa     120
aaaattggtg ttagtgttga tgaagtaacg cgaaatggtg atgcattagc tgtaacagag     180
ctctcactta gtttctagc accactaagg agtggagata gatttgtcgt gaaggcacga      240
atatctgatt cttcagctgc tcgtttgttt ttcgaacact tcatcttcaa gcttccagat     300
caagagccta tattggaggc aagaggaata gcagtgtggc ttaatagaag ttatcgtcct     360
attcgaattc cgtcagagtt caattcaaaa tttgttaaat tccttcacca ggaggcatcc     420
aac                                                                    423

<210> SEQ ID NO 56
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 56

```
atgggtgatc agctctatca acatgaagtt gaactccaag tcagggacta tgaattggat      60
cagtttggtg ttgtaaacaa tgctacttat gcaagttatt gtcaacattg ccgtcatgag     120
tttcttgaga agattggtgt aagtgttgat gaagtaacta gaactggtga agcattagca     180
acaacagagc tttcacttaa gtatcttgca cctctcagga gtggagatag atttgtggtg     240
aaggtgagaa tatccaggtc tacagcagct cgtttgttct tcgagcattt catcttcaaa     300
cttccagatc aagagcctat attggaggca agaggaatag cagtgtggct aatagaagt      360
taccgtccta tcagaatacc atcagagttc agttcaaagt tgttcagtt ccttcaccag      420
aagagttgcg gtacacaaca ccgtctc                                          447
```

<210> SEQ ID NO 57
<211> LENGTH: 141
<212> TYPE: PRT
<213> ORGANISM: Lycopersicon esculentum

<400> SEQUENCE: 57

```
Met Ala Glu Phe His Glu Val Glu Leu Lys Val Arg Asp Tyr Glu Leu
1               5                   10                  15
Asp Gln Tyr Gly Val Val Asn Asn Ala Ile Tyr Ala Ser Tyr Cys Gln
                20                  25                  30
His Gly Arg His Glu Leu Leu Glu Arg Ile Gly Ile Ser Ala Asp Glu
            35                  40                  45
Val Ala Arg Ser Gly Asp Ala Leu Ala Leu Thr Glu Leu Ser Leu Lys
        50                  55                  60
Tyr Leu Ala Pro Leu Arg Ser Gly Asp Arg Phe Val Val Lys Ala Arg
65                  70                  75                  80
Ile Ser Asp Ser Ser Ala Ala Arg Leu Phe Phe Glu His Phe Ile Phe
                85                  90                  95
Lys Leu Pro Asp Gln Glu Pro Ile Leu Glu Ala Arg Gly Ile Ala Val
            100                 105                 110
Trp Leu Asn Lys Ser Tyr Arg Pro Val Arg Ile Pro Ala Glu Phe Arg
        115                 120                 125
Ser Lys Phe Val Gln Phe Leu Arg Gln Glu Ala Ser Asn
    130                 135                 140
```

<210> SEQ ID NO 58
<211> LENGTH: 139
<212> TYPE: PRT
<213> ORGANISM: Petunia integrifolia

<400> SEQUENCE: 58

```
Met Asn Glu Phe Tyr Glu Val Glu Leu Lys Val Arg Asp Tyr Glu Leu
1               5                   10                  15
Asp Gln Tyr Gly Val Val Asn Asn Ala Ile Tyr Ala Ser Tyr Cys Gln
                20                  25                  30
His Cys Arg His Glu Leu Leu Glu Lys Ile Gly Val Asn Ala Asp Ala
            35                  40                  45
```

```
Val Ala Arg Asn Gly Glu Ala Leu Ala Leu Thr Glu Met Thr Leu Lys
 50                  55                  60

Tyr Leu Ala Pro Leu Arg Ser Gly Asp Arg Phe Ile Val Lys Val Arg
 65                  70                  75                  80

Ile Ser Asp Ser Ser Ala Ala Arg Leu Phe Phe Glu His Phe Ile Phe
                 85                  90                  95

Lys Leu Pro Asp Gln Glu Pro Ile Leu Glu Ala Arg Gly Thr Ala Val
                100                 105                 110

Trp Leu Asn Lys Ser Tyr Arg Pro Val Arg Ile Pro Ser Glu Phe Arg
                115                 120                 125

Ser Lys Phe Val Gln Phe Leu Arg Gln Glu Ala
                130                 135
```

<210> SEQ ID NO 59
<211> LENGTH: 149
<212> TYPE: PRT
<213> ORGANISM: Lycopersicon hirsutum

<400> SEQUENCE: 59

```
Met Ser Asp Gln Val Tyr His His Asp Val Glu Leu Thr Val Arg Asp
 1               5                  10                  15

Tyr Glu Leu Asp Gln Phe Gly Val Val Asn Asn Ala Thr Tyr Ala Ser
                 20                  25                  30

Tyr Cys Gln His Cys Arg His Ala Phe Leu Glu Lys Ile Gly Val Ser
                 35                  40                  45

Val Asp Glu Val Thr Arg Asn Gly Asp Ala Leu Ala Val Thr Glu Leu
 50                  55                  60

Ser Leu Lys Phe Leu Ala Pro Leu Arg Ser Gly Asp Arg Phe Val Val
 65                  70                  75                  80

Arg Ala Arg Leu Ser His Phe Thr Val Ala Arg Leu Phe Phe Glu His
                 85                  90                  95

Phe Ile Phe Lys Leu Pro Asp Gln Glu Pro Ile Leu Glu Ala Arg Gly
                100                 105                 110

Ile Ala Val Trp Leu Asn Arg Ser Tyr Arg Pro Ile Arg Ile Pro Ser
                115                 120                 125

Glu Phe Asn Ser Lys Phe Val Lys Phe Leu His Gln Lys Ser Cys Gly
                130                 135                 140

Val Gln His His Leu
145
```

<210> SEQ ID NO 60
<211> LENGTH: 208
<212> TYPE: PRT
<213> ORGANISM: Solanum tuberosum

<400> SEQUENCE: 60

```
Met Ser His Ser Val Cys Ile Ala Pro Asn Pro Leu Leu Asn His
 1               5                  10                  15

Arg Gln Arg Pro Ser Thr Phe Pro Phe Ile Pro His Arg Gln Leu Pro
                 20                  25                  30

Leu Pro Asn Leu Gln Leu Ser Ala Arg Lys Ser Arg Ser Phe Glu Ala
                 35                  40                  45

His Asn Ala Phe Asp Leu Lys Asp Thr Gln Gly Met Gly Asp Gln Leu
 50                  55                  60

Tyr Gln His Glu Val Glu Leu Gln Val Arg Asp Tyr Glu Leu Asp Gln
 65                  70                  75                  80
```

```
Phe Gly Val Val Asn Asn Ala Thr Tyr Ala Ser Tyr Cys Gln His Cys
                85                  90                  95
Arg His Glu Phe Leu Glu Lys Ile Gly Val Ser Val Asp Glu Val Cys
            100                 105                 110
Arg Thr Gly Glu Ala Leu Ala Thr Thr Glu Leu Ser Leu Lys Tyr Leu
            115                 120                 125
Ala Pro Leu Arg Ser Gly Asp Arg Phe Val Val Lys Val Arg Ile Ser
        130                 135                 140
Arg Ser Thr Ala Ala Arg Leu Phe Phe Glu His Phe Ile Phe Lys Leu
145                 150                 155                 160
Pro Asp Gln Glu Pro Ile Leu Glu Ala Arg Gly Ile Ala Val Trp Leu
                165                 170                 175
Asn Arg Ser Tyr Arg Pro Ile Arg Ile Pro Ser Glu Phe Ser Ser Lys
            180                 185                 190
Phe Val Gln Phe Leu His Gln Lys Ser Cys Gly Thr Gln His Arg Leu
            195                 200                 205

<210> SEQ ID NO 61
<211> LENGTH: 141
<212> TYPE: PRT
<213> ORGANISM: Artificial Sequence
<220> FEATURE:
<223> OTHER INFORMATION: Synthetic polypeptide

<400> SEQUENCE: 61

Met Ala Glu Phe His Glu Val Glu Leu Lys Val Arg Asp Tyr Glu Leu
1               5                   10                  15
Asp Gln Tyr Gly Val Val Asn Asn Ala Ile Tyr Ala Ser Tyr Cys Gln
            20                  25                  30
His Gly Arg His Glu Leu Leu Glu Arg Ile Gly Ile Ser Ala Asp Glu
        35                  40                  45
Val Ala Arg Ser Gly Asp Ala Leu Ala Leu Thr Glu Leu Ser Leu Lys
    50                  55                  60
Tyr Leu Ala Pro Leu Arg Ser Gly Asp Arg Phe Val Val Lys Ala Arg
65                  70                  75                  80
Ile Ser Asp Ser Ser Ala Ala Arg Leu Phe Phe Glu His Phe Ile Phe
                85                  90                  95
Lys Leu Pro Asp Gln Glu Pro Ile Leu Glu Ala Arg Gly Ile Ala Val
            100                 105                 110
Trp Leu Asn Lys Ser Tyr Arg Pro Val Arg Ile Pro Ala Glu Phe Arg
        115                 120                 125
Ser Lys Phe Val Gln Phe Leu Arg Gln Glu Ala Ser Asn
    130                 135                 140

<210> SEQ ID NO 62
<211> LENGTH: 140
<212> TYPE: PRT
<213> ORGANISM: Artificial Sequence
<220> FEATURE:
<223> OTHER INFORMATION: Synthetic polypeptide

<400> SEQUENCE: 62

Met Ala Asn Glu Phe Tyr Glu Val Glu Leu Lys Val Arg Asp Tyr Glu
1               5                   10                  15
Leu Asp Gln Tyr Gly Val Val Asn Asn Ala Ile Tyr Ala Ser Tyr Cys
            20                  25                  30
Gln His Cys Arg His Glu Leu Leu Glu Lys Ile Gly Val Asn Ala Asp
        35                  40                  45
```

```
Ala Val Ala Arg Asn Gly Glu Ala Leu Ala Leu Thr Glu Met Thr Leu
        50                  55                  60

Lys Tyr Leu Ala Pro Leu Arg Ser Gly Asp Arg Phe Ile Val Lys Val
65                  70                  75                  80

Arg Ile Ser Asp Ser Ser Ala Ala Arg Leu Phe Phe Glu His Phe Ile
                85                  90                  95

Phe Lys Leu Pro Asp Gln Glu Pro Ile Leu Glu Ala Arg Gly Thr Ala
                100                 105                 110

Val Trp Leu Asn Lys Ser Tyr Arg Pro Val Arg Ile Pro Ser Glu Phe
                115                 120                 125

Arg Ser Lys Phe Val Gln Phe Leu Arg Gln Glu Ala
                130                 135                 140

<210> SEQ ID NO 63
<211> LENGTH: 150
<212> TYPE: PRT
<213> ORGANISM: Artificial Sequence
<220> FEATURE:
<223> OTHER INFORMATION: Synthetic polypeptide

<400> SEQUENCE: 63

Met Ala Ser Asp Gln Val Tyr His His Asp Val Glu Leu Thr Val Arg
1               5                   10                  15

Asp Tyr Glu Leu Asp Gln Phe Gly Val Val Asn Asn Ala Thr Tyr Ala
                20                  25                  30

Ser Tyr Cys Gln His Cys Arg His Ala Phe Leu Glu Lys Ile Gly Val
                35                  40                  45

Ser Val Asp Glu Val Thr Arg Asn Gly Asp Ala Leu Ala Val Thr Glu
        50                  55                  60

Leu Ser Leu Lys Phe Leu Ala Pro Leu Arg Ser Gly Asp Arg Phe Val
65                  70                  75                  80

Val Arg Ala Arg Leu Ser His Phe Thr Val Ala Arg Leu Phe Phe Glu
                85                  90                  95

His Phe Ile Phe Lys Leu Pro Asp Gln Glu Pro Ile Leu Glu Ala Arg
                100                 105                 110

Gly Ile Ala Val Trp Leu Asn Arg Ser Tyr Arg Pro Ile Arg Ile Pro
                115                 120                 125

Ser Glu Phe Asn Ser Lys Phe Lys Phe Leu His Gln Lys Ser Cys
                130                 135                 140

Gly Val Gln His His Leu
145                 150

<210> SEQ ID NO 64
<211> LENGTH: 150
<212> TYPE: PRT
<213> ORGANISM: Artificial Sequence
<220> FEATURE:
<223> OTHER INFORMATION: Synthetic polypeptide

<400> SEQUENCE: 64

Met Ala Gly Asp Gln Leu Tyr Gln His Glu Val Glu Leu Gln Val Arg
1               5                   10                  15

Asp Tyr Glu Leu Asp Gln Phe Gly Val Val Asn Asn Ala Thr Tyr Ala
                20                  25                  30

Ser Tyr Cys Gln His Cys Arg His Glu Phe Leu Glu Lys Ile Gly Val
                35                  40                  45

Ser Val Asp Glu Val Cys Arg Thr Gly Glu Ala Leu Ala Thr Thr Glu
```

```
                      50                  55                  60
Leu Ser Leu Lys Tyr Leu Ala Pro Leu Arg Ser Gly Asp Arg Phe Val
 65                  70                  75                  80

Val Lys Val Arg Ile Ser Arg Ser Thr Ala Ala Arg Leu Phe Phe Glu
                     85                  90                  95

His Phe Ile Phe Lys Leu Pro Asp Gln Glu Pro Ile Leu Glu Ala Arg
                100                 105                 110

Gly Ile Ala Val Trp Leu Asn Arg Ser Tyr Arg Pro Ile Arg Ile Pro
            115                 120                 125

Ser Glu Phe Ser Ser Lys Phe Val Gln Phe Leu His Gln Lys Ser Cys
            130                 135                 140

Gly Thr Gln His Arg Leu
145                 150

<210> SEQ ID NO 65
<211> LENGTH: 186
<212> TYPE: PRT
<213> ORGANISM: Artificial Sequence
<220> FEATURE:
<223> OTHER INFORMATION: Synthetic polypeptide

<400> SEQUENCE: 65

Met Ala Ser Ile Cys Thr Ser Asn Phe His Phe Leu Cys Arg Lys Asn
  1               5                  10                  15

Asn Ser Ser Pro Ile Ser His His Leu Leu Ser Pro Ser Ser Leu
                 20                  25                  30

Ser Phe Ser Arg Cys Gly Gly Leu Arg Leu Cys Arg Ala Ala Ala Glu
             35                  40                  45

Phe His Glu Val Glu Leu Lys Val Arg Asp Tyr Glu Leu Asp Gln Tyr
         50                  55                  60

Gly Val Val Asn Asn Ala Ile Tyr Ala Ser Tyr Cys Gln His Gly Arg
 65                  70                  75                  80

His Glu Leu Leu Glu Arg Ile Gly Ile Ser Ala Asp Glu Val Ala Arg
                 85                  90                  95

Ser Gly Asp Ala Leu Ala Leu Thr Glu Leu Ser Leu Lys Tyr Leu Ala
            100                 105                 110

Pro Leu Arg Ser Gly Asp Arg Phe Val Val Lys Ala Arg Ile Ser Asp
            115                 120                 125

Ser Ser Ala Ala Arg Leu Phe Phe Glu His Phe Ile Phe Lys Leu Pro
        130                 135                 140

Asp Gln Glu Pro Ile Leu Glu Ala Arg Gly Ile Ala Val Trp Leu Asn
145                 150                 155                 160

Lys Ser Tyr Arg Pro Val Arg Ile Pro Ala Glu Phe Arg Ser Lys Phe
                165                 170                 175

Val Gln Phe Leu Arg Gln Glu Ala Ser Asn
            180                 185

<210> SEQ ID NO 66
<211> LENGTH: 195
<212> TYPE: PRT
<213> ORGANISM: Artificial Sequence
<220> FEATURE:
<223> OTHER INFORMATION: Synthetic polypeptide

<400> SEQUENCE: 66

Met Ala Ser Ile Cys Thr Ser Asn Phe His Phe Leu Cys Arg Lys Asn
  1               5                  10                  15
```

Asn Ser Ser Pro Ile Ser His His Leu Leu Ser Pro Ser Ser Leu
                20                  25                  30

Ser Phe Ser Arg Cys Gly Gly Leu Arg Leu Cys Arg Ala Ala Ala Ser
            35                  40                  45

Asp Gln Val Tyr His His Asp Val Glu Leu Thr Val Arg Asp Tyr Glu
 50                  55                  60

Leu Asp Gln Phe Gly Val Val Asn Asn Ala Thr Tyr Ala Ser Tyr Cys
 65                  70                  75                  80

Gln His Cys Arg His Ala Phe Leu Glu Lys Ile Gly Val Ser Val Asp
                 85                  90                  95

Glu Val Thr Arg Asn Gly Asp Ala Leu Ala Val Thr Glu Leu Ser Leu
                100                 105                 110

Lys Phe Leu Ala Pro Leu Arg Ser Gly Asp Arg Phe Val Val Arg Ala
            115                 120                 125

Arg Leu Ser His Phe Thr Val Ala Arg Leu Phe Phe Glu His Phe Ile
130                 135                 140

Phe Lys Leu Pro Asp Gln Glu Pro Ile Leu Glu Ala Arg Gly Ile Ala
145                 150                 155                 160

Val Trp Leu Asn Arg Ser Tyr Arg Pro Ile Arg Ile Pro Ser Glu Phe
                165                 170                 175

Asn Ser Lys Phe Val Lys Phe Leu His Gln Lys Ser Cys Gly Val Gln
            180                 185                 190

His His Leu
        195

<210> SEQ ID NO 67
<211> LENGTH: 141
<212> TYPE: PRT
<213> ORGANISM: Artificial Sequence
<220> FEATURE:
<223> OTHER INFORMATION: Synthetic polypeptide

<400> SEQUENCE: 67

Met Ser Glu Phe His Glu Val Glu Leu Lys Val Arg Asp Tyr Glu Leu
 1               5                  10                  15

Asp Gln Tyr Gly Val Val Asn Asn Ala Ile Tyr Ala Ser Tyr Cys Gln
                20                  25                  30

His Cys Arg His Glu Leu Leu Glu Arg Ile Gly Val Ser Ala Asp Glu
            35                  40                  45

Val Ala Arg Ser Gly Asp Ala Leu Ala Leu Thr Glu Leu Ser Leu Lys
 50                  55                  60

Tyr Leu Ala Pro Leu Arg Ser Gly Asp Arg Phe Val Val Lys Ala Arg
 65                  70                  75                  80

Ile Ser Asp Ser Ser Ala Ala Arg Leu Phe Phe Glu His Phe Ile Phe
                 85                  90                  95

Lys Leu Pro Asp Gln Glu Pro Ile Leu Glu Ala Arg Gly Ile Ala Val
            100                 105                 110

Trp Leu Asn Lys Ser Tyr Arg Pro Val Arg Ile Pro Ser Glu Phe Arg
        115                 120                 125

Ser Lys Phe Val Gln Phe Leu Arg Gln Glu Ala Ser Asn
130                 135                 140

<210> SEQ ID NO 68
<211> LENGTH: 141
<212> TYPE: PRT
<213> ORGANISM: Artificial Sequence
<220> FEATURE:

<223> OTHER INFORMATION: Synthetic polypeptide

<400> SEQUENCE: 68

Met Asn Glu Phe Tyr Glu Val Glu Leu Lys Val Arg Asp Tyr Glu Leu
1               5                   10                  15

Asp Gln Tyr Gly Val Val Asn Asn Ala Ile Tyr Ala Ser Tyr Cys Gln
            20                  25                  30

His Cys Arg His Glu Leu Leu Glu Lys Ile Gly Val Ser Ala Asp Glu
        35                  40                  45

Val Ala Arg Asn Gly Glu Ala Leu Ala Leu Thr Glu Leu Thr Leu Lys
    50                  55                  60

Tyr Leu Ala Pro Leu Arg Ser Gly Asp Arg Phe Val Lys Val Arg
65                  70                  75                  80

Ile Ser Asp Ser Ser Ala Ala Arg Leu Phe Phe Glu His Phe Ile Phe
                85                  90                  95

Lys Leu Pro Asp Gln Glu Pro Ile Leu Glu Ala Arg Gly Ile Ala Val
            100                 105                 110

Trp Leu Asn Lys Ser Tyr Arg Pro Val Arg Ile Pro Ser Glu Phe Arg
        115                 120                 125

Ser Lys Phe Val Gln Phe Leu Arg Gln Glu Ala Ser Asn
    130                 135                 140

<210> SEQ ID NO 69
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 69

Met Ser Asp Gln Val Tyr Phe His Asp Val Glu Leu Lys Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Glu Phe Leu Glu Lys Ile Gly Val Ser
        35                  40                  45

Val Asp Glu Val Ala Arg Asn Gly Asp Ala Leu Ala Leu Thr Glu Leu
    50                  55                  60

Ser Leu Lys Phe Leu Ala Pro Leu Arg Ser Gly Asp Arg Phe Val Val
65                  70                  75                  80

Arg Ala Arg Ile Ser Asp Ser Thr Ala Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Arg Ser Tyr Arg Pro Ile Arg Ile Pro Ser
        115                 120                 125

Glu Phe Arg Ser Lys Phe Val Gln Phe Leu His Gln Lys Ser Cys Gly
    130                 135                 140

Val Gln His His Leu
145

<210> SEQ ID NO 70
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 70

```
Met Ser Asp Gln Leu Tyr Phe His Glu Val Glu Leu Lys Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Glu Phe Leu Glu Lys Ile Gly Val Ser
        35                  40                  45

Val Asp Glu Val Ala Arg Thr Gly Glu Ala Leu Ala Leu Thr Glu Leu
    50                  55                  60

Ser Leu Lys Tyr Leu Ala Pro Leu Arg Ser Gly Asp Arg Phe Val Val
65                  70                  75                  80

Lys Val Arg Ile Ser Asp Ser Thr Ala Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Arg Ser Tyr Arg Pro Ile Arg Ile Pro Ser
        115                 120                 125

Glu Phe Arg Ser Lys Phe Val Gln Phe Leu His Gln Lys Ser Cys Gly
    130                 135                 140

Thr Gln His Arg Leu
145
```

<210> SEQ ID NO 71
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 71

```
Met Ser Asp Gln Val Tyr Phe His Glu Val Glu Leu Lys Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Glu Phe Leu Glu Arg Ile Gly Ile Ser
        35                  40                  45

Val Asp Glu Val Ala Arg Ser Gly Asp Ala Leu Ala Leu Thr Glu Leu
    50                  55                  60

Ser Leu Lys Tyr Leu Ala Pro Leu Arg Ser Gly Asp Arg Phe Val Val
65                  70                  75                  80

Lys Ala Arg Ile Ser Asp Ser Thr Ala Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Arg Ser Tyr Arg Pro Ile Arg Ile Pro Ser
        115                 120                 125

Glu Phe Arg Ser Lys Phe Val Gln Phe Leu His Gln Lys Ser Cys Gly
    130                 135                 140

Val Gln His His Leu
145
```

<210> SEQ ID NO 72
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 72

Met Asn Asp Gln Leu Tyr Phe Tyr Glu Val Glu Leu Lys Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Glu Phe Leu Glu Lys Ile Gly Val Asn
        35                  40                  45

Val Asp Ala Val Ala Arg Asn Gly Glu Ala Leu Ala Leu Thr Glu Met
    50                  55                  60

Thr Leu Lys Tyr Leu Ala Pro Leu Arg Ser Gly Asp Arg Phe Ile Val
65                  70                  75                  80

Lys Val Arg Ile Ser Asp Ser Thr Ala Ala Arg Leu Phe Phe Glu His
                85                  90                  95

Phe Ile Phe Lys Leu Pro Asp Gln Glu Pro Ile Leu Glu Ala Arg Gly
            100                 105                 110

Thr Ala Val Trp Leu Asn Arg Ser Tyr Arg Pro Ile Arg Ile Pro Ser
        115                 120                 125

Glu Phe Arg Ser Lys Phe Val Gln Phe Leu His Gln Lys Ser Cys Gly
130                 135                 140

Thr Gln His Arg Leu
145

<210> SEQ ID NO 73
<211> LENGTH: 141
<212> TYPE: PRT
<213> ORGANISM: Artificial Sequence
<220> FEATURE:
<223> OTHER INFORMATION: Synthetic polypeptide

<400> SEQUENCE: 73

Met Ser Glu His His Asp Val Glu Leu Thr Val Arg Asp Tyr Glu Leu
1               5                   10                  15

Asp Gln Tyr Gly Val Val Asn Asn Ala Ile Tyr Ala Ser Tyr Cys Gln
            20                  25                  30

His Cys Arg His Ala Leu Leu Glu Lys Ile Gly Val Ser Ala Asp Glu
        35                  40                  45

Val Thr Arg Asn Gly Asp Ala Leu Ala Val Thr Glu Leu Ser Leu Lys
    50                  55                  60

Phe Leu Ala Pro Leu Arg Ser Gly Asp Arg Phe Val Val Arg Ala Arg
65                  70                  75                  80

Leu Ser His Phe Ser Val Ala Arg Leu Phe Phe Glu His Phe Ile Phe
                85                  90                  95

Lys Leu Pro Asp Gln Glu Pro Ile Leu Glu Ala Arg Gly Ile Ala Val
            100                 105                 110

Trp Leu Asn Lys Ser Tyr Arg Pro Val Arg Ile Pro Ser Glu Phe Asn
        115                 120                 125

Ser Lys Phe Val Lys Phe Leu Arg Gln Glu Ala Ser Asn
130                 135                 140

<210> SEQ ID NO 74
<211> LENGTH: 141
<212> TYPE: PRT
<213> ORGANISM: Artificial Sequence
<220> FEATURE:
<223> OTHER INFORMATION: Synthetic polypeptide

<400> SEQUENCE: 74

```
Met Ser Glu Gln His Glu Val Glu Leu Gln Val Arg Asp Tyr Glu Leu
1               5                   10                  15

Asp Gln Tyr Gly Val Val Asn Asn Ala Ile Tyr Ala Ser Tyr Cys Gln
            20                  25                  30

His Cys Arg His Glu Leu Leu Glu Lys Ile Gly Val Ser Ala Asp Glu
            35                  40                  45

Val Cys Arg Thr Gly Glu Ala Leu Ala Thr Thr Glu Leu Ser Leu Lys
    50                  55                  60

Tyr Leu Ala Pro Leu Arg Ser Gly Asp Arg Phe Val Val Lys Val Arg
65                  70                  75                  80

Ile Ser Arg Ser Ser Ala Ala Arg Leu Phe Phe Glu His Phe Ile Phe
                85                  90                  95

Lys Leu Pro Asp Gln Glu Pro Ile Leu Glu Ala Arg Gly Ile Ala Val
                100                 105                 110

Trp Leu Asn Lys Ser Tyr Arg Pro Val Arg Ile Pro Ser Glu Phe Ser
            115                 120                 125

Ser Lys Phe Val Gln Phe Leu Arg Gln Glu Ala Ser Asn
        130                 135                 140
```

<210> SEQ ID NO 75
<211> LENGTH: 141
<212> TYPE: PRT
<213> ORGANISM: Artificial Sequence
<220> FEATURE:
<223> OTHER INFORMATION: Synthetic polypeptide

<400> SEQUENCE: 75

```
Met Ala Glu Phe His Glu Val Glu Leu Lys Val Arg Asp Tyr Glu Leu
1               5                   10                  15

Asp Gln Tyr Gly Val Val Asn Asn Ala Ile Tyr Ala Ser Tyr Cys Gln
            20                  25                  30

His Gly Arg His Glu Leu Leu Glu Arg Ile Gly Ile Asn Ala Asp Ala
            35                  40                  45

Val Ala Arg Asn Gly Asp Ala Leu Ala Leu Thr Glu Leu Ser Leu Lys
    50                  55                  60

Tyr Leu Ala Pro Leu Arg Ser Gly Asp Arg Phe Val Val Lys Ala Arg
65                  70                  75                  80

Ile Ser Asp Ser Ser Ala Ala Arg Leu Phe Phe Glu His Phe Ile Phe
                85                  90                  95

Lys Leu Pro Asp Gln Glu Pro Ile Leu Glu Ala Arg Gly Ile Ala Val
                100                 105                 110

Trp Leu Asn Lys Ser Tyr Arg Pro Val Arg Ile Pro Ala Glu Phe Arg
            115                 120                 125

Ser Lys Phe Val Gln Phe Leu Arg Gln Glu Ala Ser Asn
        130                 135                 140
```

<210> SEQ ID NO 76
<211> LENGTH: 141
<212> TYPE: PRT
<213> ORGANISM: Artificial Sequence
<220> FEATURE:
<223> OTHER INFORMATION: Synthetic polypeptide

<400> SEQUENCE: 76

```
Met Ala Glu Phe His Glu Val Glu Leu Lys Val Arg Asp Tyr Glu Leu
1               5                   10                  15

Asp Gln Tyr Gly Val Val Asn Asn Ala Ile Tyr Ala Ser Tyr Cys Gln
```

```
                20                  25                  30
His Cys Arg His Glu Leu Leu Glu Arg Ile Gly Ile Asn Ala Asp Ala
            35                  40                  45

Val Ala Arg Asn Gly Asp Ala Leu Ala Leu Thr Glu Leu Ser Leu Lys
 50                  55                  60

Tyr Leu Ala Pro Leu Arg Ser Gly Asp Arg Phe Val Val Lys Ala Arg
 65                  70                  75                  80

Ile Ser Asp Ser Ser Ala Ala Arg Leu Phe Phe Glu His Phe Ile Phe
                85                  90                  95

Lys Leu Pro Asp Gln Glu Pro Ile Leu Glu Ala Arg Gly Ile Ala Val
               100                 105                 110

Trp Leu Asn Lys Ser Tyr Arg Pro Val Arg Ile Pro Ala Glu Phe Arg
               115                 120                 125

Ser Lys Phe Val Gln Phe Leu Arg Gln Glu Ala Ser Asn
               130                 135                 140

<210> SEQ ID NO 77
<211> LENGTH: 141
<212> TYPE: PRT
<213> ORGANISM: Artificial Sequence
<220> FEATURE:
<223> OTHER INFORMATION: Synthetic polypeptide

<400> SEQUENCE: 77

Met Ala Glu Phe His Glu Val Glu Leu Lys Val Arg Asp Tyr Glu Leu
 1               5                  10                  15

Asp Gln Tyr Gly Val Val Asn Asn Ala Ile Tyr Ala Ser Tyr Cys Gln
                20                  25                  30

His Cys Arg His Glu Leu Leu Glu Arg Ile Gly Ile Ser Ala Asp Glu
            35                  40                  45

Val Ala Arg Ser Gly Asp Ala Leu Ala Leu Thr Glu Leu Ser Leu Lys
 50                  55                  60

Tyr Leu Ala Pro Leu Arg Ser Gly Asp Arg Phe Val Val Lys Ala Arg
 65                  70                  75                  80

Ile Ser Asp Ser Ser Ala Ala Arg Leu Phe Phe Glu His Phe Ile Phe
                85                  90                  95

Lys Leu Pro Asp Gln Glu Pro Ile Leu Glu Ala Arg Gly Ile Ala Val
               100                 105                 110

Trp Leu Asn Lys Ser Tyr Arg Pro Val Arg Ile Pro Ala Glu Phe Arg
               115                 120                 125

Ser Lys Phe Val Gln Phe Leu Arg Gln Glu Ala Ser Asn
               130                 135                 140

<210> SEQ ID NO 78
<211> LENGTH: 141
<212> TYPE: PRT
<213> ORGANISM: Artificial Sequence
<220> FEATURE:
<223> OTHER INFORMATION: Synthetic polypeptide

<400> SEQUENCE: 78

Met Ala Glu Phe Tyr Glu Val Glu Leu Lys Val Arg Asp Tyr Glu Leu
 1               5                  10                  15

Asp Gln Tyr Gly Val Val Asn Asn Ala Ile Tyr Ala Ser Tyr Cys Gln
                20                  25                  30

His Gly Arg His Glu Leu Leu Glu Arg Ile Gly Ile Ser Ala Asp Glu
            35                  40                  45
```

```
Val Ala Arg Ser Gly Asp Ala Leu Ala Leu Thr Glu Leu Ser Leu Lys
 50                  55                  60

Tyr Leu Ala Pro Leu Arg Ser Gly Asp Arg Phe Val Lys Ala Arg
 65                  70                  75                  80

Ile Ser Asp Ser Ser Ala Ala Arg Leu Phe Phe Glu His Phe Ile Phe
                 85                  90                  95

Lys Leu Pro Asp Gln Glu Pro Ile Leu Glu Ala Arg Gly Ile Ala Val
                100                 105                 110

Trp Leu Asn Lys Ser Tyr Arg Pro Val Arg Ile Pro Ala Glu Phe Arg
                115                 120                 125

Ser Lys Phe Val Gln Phe Leu Arg Gln Glu Ala Ser Asn
        130                 135                 140

<210> SEQ ID NO 79
<211> LENGTH: 139
<212> TYPE: PRT
<213> ORGANISM: Artificial Sequence
<220> FEATURE:
<223> OTHER INFORMATION: Synthetic polypeptide

<400> SEQUENCE: 79

Met Asn Glu Phe Tyr Glu Val Glu Leu Lys Val Arg Asp Tyr Glu Leu
 1               5                  10                  15

Asp Gln Tyr Gly Val Val Asn Asn Ala Ile Tyr Ala Ser Tyr Cys Gln
                20                  25                  30

His Gly Arg His Glu Leu Leu Glu Lys Ile Gly Val Asn Ala Asp Ala
            35                  40                  45

Val Ala Arg Asn Gly Glu Ala Leu Ala Leu Thr Glu Met Thr Leu Lys
 50                  55                  60

Tyr Leu Ala Pro Leu Arg Ser Gly Asp Arg Phe Ile Val Lys Val Arg
 65                  70                  75                  80

Ile Ser Asp Ser Ser Ala Ala Arg Leu Phe Phe Glu His Phe Ile Phe
                 85                  90                  95

Lys Leu Pro Asp Gln Glu Pro Ile Leu Glu Ala Arg Gly Thr Ala Val
                100                 105                 110

Trp Leu Asn Lys Ser Tyr Arg Pro Val Arg Ile Pro Ser Glu Phe Arg
                115                 120                 125

Ser Lys Phe Val Gln Phe Leu Arg Gln Glu Ala
        130                 135

<210> SEQ ID NO 80
<211> LENGTH: 139
<212> TYPE: PRT
<213> ORGANISM: Artificial Sequence
<220> FEATURE:
<223> OTHER INFORMATION: Synthetic polypeptide

<400> SEQUENCE: 80

Met Asn Glu Phe Tyr Glu Val Glu Leu Lys Val Arg Asp Tyr Glu Leu
 1               5                  10                  15

Asp Gln Tyr Gly Val Val Asn Asn Ala Ile Tyr Ala Ser Tyr Cys Gln
                20                  25                  30

His Gly Arg His Glu Leu Leu Glu Lys Ile Gly Val Ser Ala Asp Glu
            35                  40                  45

Val Ala Arg Ser Gly Glu Ala Leu Ala Leu Thr Glu Met Thr Leu Lys
 50                  55                  60

Tyr Leu Ala Pro Leu Arg Ser Gly Asp Arg Phe Ile Val Lys Val Arg
 65                  70                  75                  80
```

```
Ile Ser Asp Ser Ser Ala Ala Arg Leu Phe Phe Glu His Phe Ile Phe
                85                  90                  95

Lys Leu Pro Asp Gln Glu Pro Ile Leu Glu Ala Arg Gly Thr Ala Val
            100                 105                 110

Trp Leu Asn Lys Ser Tyr Arg Pro Val Arg Ile Pro Ser Glu Phe Arg
        115                 120                 125

Ser Lys Phe Val Gln Phe Leu Arg Gln Glu Ala
    130                 135
```

<210> SEQ ID NO 81
<211> LENGTH: 139
<212> TYPE: PRT
<213> ORGANISM: Artificial Sequence
<220> FEATURE:
<223> OTHER INFORMATION: Synthetic polypeptide

<400> SEQUENCE: 81

```
Met Asn Glu Phe Tyr Glu Val Glu Leu Lys Val Arg Asp Tyr Glu Leu
1               5                   10                  15

Asp Gln Tyr Gly Val Val Asn Asn Ala Ile Tyr Ala Ser Tyr Cys Gln
            20                  25                  30

His Cys Arg His Glu Leu Leu Glu Lys Ile Gly Val Ser Ala Asp Glu
        35                  40                  45

Val Ala Arg Ser Gly Ala Leu Ala Leu Thr Glu Met Thr Leu Lys
    50                  55                  60

Tyr Leu Ala Pro Leu Arg Ser Gly Asp Arg Phe Ile Val Lys Val Arg
65                  70                  75                  80

Ile Ser Asp Ser Ser Ala Ala Arg Leu Phe Phe Glu His Phe Ile Phe
                85                  90                  95

Lys Leu Pro Asp Gln Glu Pro Ile Leu Glu Ala Arg Gly Thr Ala Val
            100                 105                 110

Trp Leu Asn Lys Ser Tyr Arg Pro Val Arg Ile Pro Ser Glu Phe Arg
        115                 120                 125

Ser Lys Phe Val Gln Phe Leu Arg Gln Glu Ala
    130                 135
```

<210> SEQ ID NO 82
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 82

```
Met Ser Asp Gln Val Tyr His His Asp Val Glu Leu Thr Val Arg Asp
1               5                   10                  15

Tyr Glu Leu Asp Gln Phe Gly Val Val Asn Asn Ala Thr Tyr Ala Ser
            20                  25                  30

Tyr Cys Gln His Gly Arg His Glu Leu Leu Glu Lys Ile Gly Val Ser
        35                  40                  45

Val Asp Glu Val Thr Arg Asn Gly Asp Ala Leu Ala Val Thr Glu Leu
    50                  55                  60

Ser Leu Lys Phe Leu Ala Pro Leu Arg Ser Gly Asp Arg Phe Val Val
65                  70                  75                  80

Arg Ala Arg Leu Ser His Phe Thr Val Ala Arg Leu Phe Phe Glu His
                85                  90                  95

Phe Ile Phe Lys Leu Pro Asp Gln Glu Pro Ile Leu Glu Ala Arg Gly
```

```
            100                 105                 110
Ile Ala Val Trp Leu Asn Arg Ser Tyr Arg Pro Ile Arg Ile Pro Ser
            115                 120                 125

Glu Phe Asn Ser Lys Phe Val Lys Phe Leu His Gln Lys Ser Cys Gly
        130                 135                 140

Val Gln His His Leu
145

<210> SEQ ID NO 83
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 83

Met Ser Asp Gln Val Tyr His His Asp Val Glu Leu Thr Val Arg Asp
1               5                   10                  15

Tyr Glu Leu Asp Gln Phe Gly Val Val Asn Asn Ala Thr Tyr Ala Ser
            20                  25                  30

Tyr Cys Gln His Gly Arg His Glu Leu Leu Glu Lys Ile Gly Val Asn
        35                  40                  45

Ala Asp Glu Val Thr Arg Asn Gly Asp Ala Leu Ala Val Thr Glu Leu
    50                  55                  60

Ser Leu Lys Phe Leu Ala Pro Leu Arg Ser Gly Asp Arg Phe Val Val
65                  70                  75                  80

Arg Ala Arg Leu Ser His Phe Thr Val Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Arg Ser Tyr Arg Pro Ile Arg Ile Pro Ser
            115                 120                 125

Glu Phe Asn Ser Lys Phe Val Lys Phe Leu His Gln Lys Ser Cys Gly
        130                 135                 140

Val Gln His His Leu
145

<210> SEQ ID NO 84
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 84

Met Ser Asp Gln Val Tyr His His Asp Val Glu Leu Thr Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Ala Phe Leu Glu Lys Ile Gly Val Asn
        35                  40                  45

Ala Asp Glu Val Thr Arg Asn Gly Asp Ala Leu Ala Val Thr Glu Leu
    50                  55                  60

Ser Leu Lys Phe Leu Ala Pro Leu Arg Ser Gly Asp Arg Phe Val Val
65                  70                  75                  80

Arg Ala Arg Leu Ser His Phe Thr Val Ala Arg Leu Phe Phe Glu His
                85                  90                  95
```

```
Phe Ile Phe Lys Leu Pro Asp Gln Glu Pro Ile Leu Glu Ala Arg Gly
                100                 105                 110

Ile Ala Val Trp Leu Asn Arg Ser Tyr Arg Pro Ile Arg Ile Pro Ser
            115                 120                 125

Glu Phe Asn Ser Lys Phe Val Lys Phe Leu His Gln Lys Ser Cys Gly
        130                 135                 140

Val Gln His His Leu
145

<210> SEQ ID NO 85
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 85

Met Gly Asp Gln Leu Tyr Gln His Glu Val Glu Leu Gln Val Arg Asp
1               5                   10                  15

Tyr Glu Leu Asp Gln Phe Gly Val Val Asn Asn Ala Thr Tyr Ala Ser
                20                  25                  30

Tyr Cys Gln His Gly Arg His Glu Phe Leu Glu Lys Ile Gly Val Ser
            35                  40                  45

Val Asp Glu Val Ala Arg Thr Gly Glu Ala Leu Ala Thr Thr Glu Leu
        50                  55                  60

Ser Leu Lys Tyr Leu Ala Pro Leu Arg Ser Gly Asp Arg Phe Val Val
65                  70                  75                  80

Lys Val Arg Ile Ser Arg Ser Thr Ala Ala Arg Leu Phe Phe Glu His
                85                  90                  95

Phe Ile Phe Lys Leu Pro Asp Gln Glu Pro Ile Leu Glu Ala Arg Gly
                100                 105                 110

Ile Ala Val Trp Leu Asn Arg Ser Tyr Arg Pro Ile Arg Ile Pro Ser
            115                 120                 125

Glu Phe Ser Ser Lys Phe Val Gln Phe Leu His Gln Lys Ser Cys Gly
        130                 135                 140

Thr Gln His Arg Leu
145

<210> SEQ ID NO 86
<211> LENGTH: 146
<212> TYPE: PRT
<213> ORGANISM: Artificial Sequence
<220> FEATURE:
<223> OTHER INFORMATION: Synthetic polypeptide

<400> SEQUENCE: 86

Met Ala Glu Phe His Glu Val Glu Leu Lys Val Arg Asp Tyr Glu Leu
1               5                   10                  15

Asp Gln Tyr Gly Val Val Asn Asn Ala Ile Tyr Ala Ser Tyr Cys Gln
                20                  25                  30

His Gly Arg His Glu Leu Leu Glu Arg Ile Gly Ile Ser Ala Asp Glu
            35                  40                  45

Val Ala Arg Ser Gly Asp Ala Leu Ala Leu Thr Glu Leu Ser Leu Lys
        50                  55                  60

Tyr Leu Ala Pro Leu Arg Ser Gly Asp Arg Phe Val Val Lys Ala Arg
65                  70                  75                  80

Ile Ser Asp Ser Ser Ala Ala Arg Leu Phe Phe Glu His Phe Ile Phe
                85                  90                  95
```

```
Lys Leu Pro Asp Gln Glu Pro Ile Leu Glu Ala Arg Gly Ile Ala Val
                100                 105                 110

Trp Leu Asn Arg Ser Tyr Arg Pro Ile Arg Ile Pro Ser Glu Phe Asn
            115                 120                 125

Ser Lys Phe Val Lys Phe Leu His Gln Lys Ser Cys Gly Val Gln His
        130                 135                 140

His Leu
145

<210> SEQ ID NO 87
<211> LENGTH: 141
<212> TYPE: PRT
<213> ORGANISM: Artificial Sequence
<220> FEATURE:
<223> OTHER INFORMATION: Synthetic polypeptide

<400> SEQUENCE: 87

Met Ala Glu Phe His Glu Val Glu Leu Lys Val Arg Asp Tyr Glu Leu
1               5                   10                  15

Asp Gln Tyr Gly Val Val Asn Asn Ala Ile Tyr Ala Ser Tyr Cys Gln
            20                  25                  30

His Gly Arg His Glu Leu Leu Glu Arg Ile Gly Ile Ser Ala Asp Glu
        35                  40                  45

Val Ala Arg Ser Gly Asp Ala Leu Ala Leu Thr Glu Leu Ser Leu Lys
    50                  55                  60

Tyr Leu Ala Pro Leu Arg Ser Gly Asp Arg Phe Val Val Arg Ala Arg
65                  70                  75                  80

Leu Ser His Phe Thr Val Ala Arg Leu Phe Phe Glu His Phe Ile Phe
                85                  90                  95

Lys Leu Pro Asp Gln Glu Pro Ile Leu Glu Ala Arg Gly Ile Ala Val
                100                 105                 110

Trp Leu Asn Lys Ser Tyr Arg Pro Val Arg Ile Pro Ala Glu Phe Arg
            115                 120                 125

Ser Lys Phe Val Gln Phe Leu Arg Gln Glu Ala Ser Asn
        130                 135                 140

<210> SEQ ID NO 88
<211> LENGTH: 146
<212> TYPE: PRT
<213> ORGANISM: Artificial Sequence
<220> FEATURE:
<223> OTHER INFORMATION: Synthetic polypeptide

<400> SEQUENCE: 88

Met Ala Glu Phe His Glu Val Glu Leu Lys Val Arg Asp Tyr Glu Leu
1               5                   10                  15

Asp Gln Tyr Gly Val Val Asn Asn Ala Ile Tyr Ala Ser Tyr Cys Gln
            20                  25                  30

His Gly Arg His Glu Leu Leu Glu Arg Ile Gly Ile Ser Ala Asp Glu
        35                  40                  45

Val Ala Arg Ser Gly Asp Ala Leu Ala Leu Thr Glu Leu Ser Leu Lys
    50                  55                  60

Tyr Leu Ala Pro Leu Arg Ser Gly Asp Arg Phe Val Val Arg Ala Arg
65                  70                  75                  80

Leu Ser His Phe Thr Val Ala Arg Leu Phe Phe Glu His Phe Ile Phe
                85                  90                  95

Lys Leu Pro Asp Gln Glu Pro Ile Leu Glu Ala Arg Gly Ile Ala Val
```

```
                    100                 105                 110
Trp Leu Asn Arg Ser Tyr Arg Pro Ile Arg Ile Pro Ser Glu Phe Asn
                115                 120                 125

Ser Lys Phe Val Lys Phe Leu His Gln Lys Ser Cys Gly Val Gln His
        130                 135                 140

His Leu
145

<210> SEQ ID NO 89
<211> LENGTH: 141
<212> TYPE: PRT
<213> ORGANISM: Artificial Sequence
<220> FEATURE:
<223> OTHER INFORMATION: Synthetic polypeptide

<400> SEQUENCE: 89

Met Ala Glu Phe His Glu Val Glu Leu Lys Val Arg Asp Tyr Glu Leu
1               5                   10                  15

Asp Gln Tyr Gly Val Val Asn Asn Ala Ile Tyr Ala Ser Tyr Cys Gln
                20                  25                  30

His Cys Arg His Ala Phe Leu Glu Lys Ile Gly Val Ser Val Asp Glu
            35                  40                  45

Val Thr Arg Asn Gly Asp Ala Leu Ala Val Thr Glu Leu Ser Leu Lys
        50                  55                  60

Phe Leu Ala Pro Leu Arg Ser Gly Asp Arg Phe Val Val Lys Ala Arg
65                  70                  75                  80

Ile Ser Asp Ser Ser Ala Ala Arg Leu Phe Phe Glu His Phe Ile Phe
                85                  90                  95

Lys Leu Pro Asp Gln Glu Pro Ile Leu Glu Ala Arg Gly Ile Ala Val
                100                 105                 110

Trp Leu Asn Lys Ser Tyr Arg Pro Val Arg Ile Pro Ala Glu Phe Arg
                115                 120                 125

Ser Lys Phe Val Gln Phe Leu Arg Gln Glu Ala Ser Asn
        130                 135                 140

<210> SEQ ID NO 90
<211> LENGTH: 146
<212> TYPE: PRT
<213> ORGANISM: Artificial Sequence
<220> FEATURE:
<223> OTHER INFORMATION: Synthetic polypeptide

<400> SEQUENCE: 90

Met Ala Glu Phe His Glu Val Glu Leu Lys Val Arg Asp Tyr Glu Leu
1               5                   10                  15

Asp Gln Tyr Gly Val Val Asn Asn Ala Ile Tyr Ala Ser Tyr Cys Gln
                20                  25                  30

His Cys Arg His Ala Phe Leu Glu Lys Ile Gly Val Ser Val Asp Glu
            35                  40                  45

Val Thr Arg Asn Gly Asp Ala Leu Ala Val Thr Glu Leu Ser Leu Lys
        50                  55                  60

Phe Leu Ala Pro Leu Arg Ser Gly Asp Arg Phe Val Val Lys Ala Arg
65                  70                  75                  80

Ile Ser Asp Ser Ser Ala Ala Arg Leu Phe Phe Glu His Phe Ile Phe
                85                  90                  95

Lys Leu Pro Asp Gln Glu Pro Ile Leu Glu Ala Arg Gly Ile Ala Val
                100                 105                 110
```

Trp Leu Asn Arg Ser Tyr Arg Pro Ile Arg Ile Pro Ser Glu Phe Asn
            115                 120                 125

Ser Lys Phe Val Lys Phe Leu His Gln Lys Ser Cys Gly Val Gln His
        130                 135                 140

His Leu
145

<210> SEQ ID NO 91
<211> LENGTH: 141
<212> TYPE: PRT
<213> ORGANISM: Artificial Sequence
<220> FEATURE:
<223> OTHER INFORMATION: Synthetic polypeptide

<400> SEQUENCE: 91

Met Ala Glu Phe His Glu Val Glu Leu Lys Val Arg Asp Tyr Glu Leu
1               5                   10                  15

Asp Gln Tyr Gly Val Val Asn Asn Ala Ile Tyr Ala Ser Tyr Cys Gln
            20                  25                  30

His Cys Arg His Ala Phe Leu Glu Lys Ile Gly Val Ser Val Asp Glu
        35                  40                  45

Val Thr Arg Asn Gly Asp Ala Leu Ala Val Thr Glu Leu Ser Leu Lys
    50                  55                  60

Phe Leu Ala Pro Leu Arg Ser Gly Asp Arg Phe Val Val Arg Ala Arg
65                  70                  75                  80

Leu Ser His Phe Thr Val Ala Arg Leu Phe Phe Glu His Phe Ile Phe
                85                  90                  95

Lys Leu Pro Asp Gln Glu Pro Ile Leu Glu Ala Arg Gly Ile Ala Val
            100                 105                 110

Trp Leu Asn Lys Ser Tyr Arg Pro Val Arg Ile Pro Ala Glu Phe Arg
        115                 120                 125

Ser Lys Phe Val Gln Phe Leu Arg Gln Glu Ala Ser Asn
    130                 135                 140

<210> SEQ ID NO 92
<211> LENGTH: 146
<212> TYPE: PRT
<213> ORGANISM: Artificial Sequence
<220> FEATURE:
<223> OTHER INFORMATION: Synthetic polypeptide

<400> SEQUENCE: 92

Met Ala Glu Phe His Glu Val Glu Leu Lys Val Arg Asp Tyr Glu Leu
1               5                   10                  15

Asp Gln Tyr Gly Val Val Asn Asn Ala Ile Tyr Ala Ser Tyr Cys Gln
            20                  25                  30

His Cys Arg His Ala Phe Leu Glu Lys Ile Gly Val Ser Val Asp Glu
        35                  40                  45

Val Thr Arg Asn Gly Asp Ala Leu Ala Val Thr Glu Leu Ser Leu Lys
    50                  55                  60

Phe Leu Ala Pro Leu Arg Ser Gly Asp Arg Phe Val Val Arg Ala Arg
65                  70                  75                  80

Leu Ser His Phe Thr Val Ala Arg Leu Phe Phe Glu His Phe Ile Phe
                85                  90                  95

Lys Leu Pro Asp Gln Glu Pro Ile Leu Glu Ala Arg Gly Ile Ala Val
            100                 105                 110

Trp Leu Asn Arg Ser Tyr Arg Pro Ile Arg Ile Pro Ser Glu Phe Asn
        115                 120                 125

```
Ser Lys Phe Val Lys Phe Leu His Gln Lys Ser Cys Gly Val Gln His
    130                 135                 140

His Leu
145

<210> SEQ ID NO 93
<211> LENGTH: 144
<212> TYPE: PRT
<213> ORGANISM: Artificial Sequence
<220> FEATURE:
<223> OTHER INFORMATION: Synthetic polypeptide

<400> SEQUENCE: 93

Met Ser Asp Gln Val Tyr His His Asp Val Glu Leu Thr Val Arg Asp
1               5                   10                  15

Tyr Glu Leu Asp Gln Phe Gly Val Val Asn Asn Ala Thr Tyr Ala Ser
            20                  25                  30

Tyr Cys Gln His Gly Arg His Glu Leu Leu Glu Arg Ile Gly Ile Ser
        35                  40                  45

Ala Asp Glu Val Ala Arg Ser Gly Asp Ala Leu Ala Leu Thr Glu Leu
    50                  55                  60

Ser Leu Lys Tyr Leu Ala Pro Leu Arg Ser Gly Asp Arg Phe Val Val
65                  70                  75                  80

Lys Ala Arg Ile Ser Asp Ser Ser Ala Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Lys Ser Tyr Arg Pro Val Arg Ile Pro Ala
        115                 120                 125

Glu Phe Arg Ser Lys Phe Val Gln Phe Leu Arg Gln Glu Ala Ser Asn
    130                 135                 140

<210> SEQ ID NO 94
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 94

Met Ser Asp Gln Val Tyr His His Asp Val Glu Leu Thr Val Arg Asp
1               5                   10                  15

Tyr Glu Leu Asp Gln Phe Gly Val Val Asn Asn Ala Thr Tyr Ala Ser
            20                  25                  30

Tyr Cys Gln His Gly Arg His Glu Leu Leu Glu Arg Ile Gly Ile Ser
        35                  40                  45

Ala Asp Glu Val Ala Arg Ser Gly Asp Ala Leu Ala Leu Thr Glu Leu
    50                  55                  60

Ser Leu Lys Tyr Leu Ala Pro Leu Arg Ser Gly Asp Arg Phe Val Val
65                  70                  75                  80

Lys Ala Arg Ile Ser Asp Ser Ser Ala Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Arg Ser Tyr Arg Pro Ile Arg Ile Pro Ser
        115                 120                 125

Glu Phe Asn Ser Lys Phe Val Lys Phe Leu His Gln Lys Ser Cys Gly
```

130                 135                 140

Val Gln His His Leu
145

<210> SEQ ID NO 95
<211> LENGTH: 144
<212> TYPE: PRT
<213> ORGANISM: Artificial Sequence
<220> FEATURE:
<223> OTHER INFORMATION: Synthetic polypeptide

<400> SEQUENCE: 95

Met Ser Asp Gln Val Tyr His His Asp Val Glu Leu Thr Val Arg Asp
1               5                   10                  15

Tyr Glu Leu Asp Gln Phe Gly Val Val Asn Asn Ala Thr Tyr Ala Ser
            20                  25                  30

Tyr Cys Gln His Gly Arg His Glu Leu Leu Glu Arg Ile Gly Ile Ser
        35                  40                  45

Ala Asp Glu Val Ala Arg Ser Gly Asp Ala Leu Ala Leu Thr Glu Leu
    50                  55                  60

Ser Leu Lys Tyr Leu Ala Pro Leu Arg Ser Gly Asp Arg Phe Val Val
65                  70                  75                  80

Arg Ala Arg Leu Ser His Phe Thr Val Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Lys Ser Tyr Arg Pro Val Arg Ile Pro Ala
        115                 120                 125

Glu Phe Arg Ser Lys Phe Val Gln Phe Leu Arg Gln Glu Ala Ser Asn
    130                 135                 140

<210> SEQ ID NO 96
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 96

Met Ser Asp Gln Val Tyr His His Asp Val Glu Leu Thr Val Arg Asp
1               5                   10                  15

Tyr Glu Leu Asp Gln Phe Gly Val Val Asn Asn Ala Thr Tyr Ala Ser
            20                  25                  30

Tyr Cys Gln His Gly Arg His Glu Leu Leu Glu Arg Ile Gly Ile Ser
        35                  40                  45

Ala Asp Glu Val Ala Arg Ser Gly Asp Ala Leu Ala Leu Thr Glu Leu
    50                  55                  60

Ser Leu Lys Tyr Leu Ala Pro Leu Arg Ser Gly Asp Arg Phe Val Val
65                  70                  75                  80

Arg Ala Arg Leu Ser His Phe Thr Val Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Arg Ser Tyr Arg Pro Ile Arg Ile Pro Ser
        115                 120                 125

Glu Phe Asn Ser Lys Phe Val Lys Phe Leu His Gln Lys Ser Cys Gly
    130                 135                 140

Val Gln His His Leu
145

<210> SEQ ID NO 97
<211> LENGTH: 144
<212> TYPE: PRT
<213> ORGANISM: Artificial Sequence
<220> FEATURE:
<223> OTHER INFORMATION: Synthetic polypeptide

<400> SEQUENCE: 97

```
Met Ser Asp Gln Val Tyr His His Asp Val Glu Leu Thr Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Ala Phe Leu Glu Lys Ile Gly Val Ser
        35                  40                  45

Val Asp Glu Val Thr Arg Asn Gly Asp Ala Leu Ala Val Thr Glu Leu
    50                  55                  60

Ser Leu Lys Phe Leu Ala Pro Leu Arg Ser Gly Asp Arg Phe Val Val
65                  70                  75                  80

Lys Ala Arg Ile Ser Asp Ser Ser Ala Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Lys Ser Tyr Arg Pro Val Arg Ile Pro Ala
        115                 120                 125

Glu Phe Arg Ser Lys Phe Val Gln Phe Leu Arg Gln Glu Ala Ser Asn
    130                 135                 140
```

<210> SEQ ID NO 98
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 98

```
Met Ser Asp Gln Val Tyr His His Asp Val Glu Leu Thr Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Ala Phe Leu Glu Lys Ile Gly Val Ser
        35                  40                  45

Val Asp Glu Val Thr Arg Asn Gly Asp Ala Leu Ala Val Thr Glu Leu
    50                  55                  60

Ser Leu Lys Phe Leu Ala Pro Leu Arg Ser Gly Asp Arg Phe Val Val
65                  70                  75                  80

Lys Ala Arg Ile Ser Asp Ser Ser Ala Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Arg Ser Tyr Arg Pro Ile Arg Ile Pro Ser
        115                 120                 125

Glu Phe Asn Ser Lys Phe Val Lys Phe Leu His Gln Lys Ser Cys Gly
    130                 135                 140

Val Gln His His Leu
145
```

<210> SEQ ID NO 99
<211> LENGTH: 144
<212> TYPE: PRT
<213> ORGANISM: Artificial Sequence
<220> FEATURE:
<223> OTHER INFORMATION: Synthetic polypeptide

<400> SEQUENCE: 99

```
Met Ser Asp Gln Val Tyr His His Asp Val Glu Leu Thr Val Arg Asp
1               5                   10                  15

Tyr Glu Leu Asp Gln Phe Gly Val Val Asn Asn Ala Thr Tyr Ala Ser
                20                  25                  30

Tyr Cys Gln His Cys Arg His Ala Phe Leu Glu Lys Ile Gly Val Ser
            35                  40                  45

Val Asp Glu Val Thr Arg Asn Gly Asp Ala Leu Ala Val Thr Glu Leu
        50                  55                  60

Ser Leu Lys Phe Leu Ala Pro Leu Arg Ser Gly Asp Arg Phe Val Val
65                  70                  75                  80

Arg Ala Arg Leu Ser His Phe Thr Val Ala Arg Leu Phe Phe Glu His
                85                  90                  95

Phe Ile Phe Lys Leu Pro Asp Gln Glu Pro Ile Leu Glu Ala Arg Gly
                100                 105                 110

Ile Ala Val Trp Leu Asn Lys Ser Tyr Arg Pro Val Arg Ile Pro Ala
            115                 120                 125

Glu Phe Arg Ser Lys Phe Val Gln Phe Leu Arg Gln Glu Ala Ser Asn
        130                 135                 140
```

<210> SEQ ID NO 100
<211> LENGTH: 144
<212> TYPE: PRT
<213> ORGANISM: Artificial Sequence
<220> FEATURE:
<223> OTHER INFORMATION: Synthetic polypeptide

<400> SEQUENCE: 100

```
Met Ser Asp Gln Val Tyr His His Glu Val Glu Leu Lys Val Arg Asp
1               5                   10                  15

Tyr Glu Leu Asp Gln Tyr Gly Val Val Asn Asn Ala Ile Tyr Ala Ser
                20                  25                  30

Tyr Cys Gln His Gly Arg His Glu Leu Leu Glu Arg Ile Gly Ile Ser
            35                  40                  45

Ala Asp Glu Val Ala Arg Ser Gly Asp Ala Leu Ala Leu Thr Glu Leu
        50                  55                  60

Ser Leu Lys Tyr Leu Ala Pro Leu Arg Ser Gly Asp Arg Phe Val Val
65                  70                  75                  80

Lys Ala Arg Ile Ser Asp Ser Ala Ala Arg Leu Phe Phe Glu His
                85                  90                  95

Phe Ile Phe Lys Leu Pro Asp Gln Glu Pro Ile Leu Glu Ala Arg Gly
                100                 105                 110

Ile Ala Val Trp Leu Asn Lys Ser Tyr Arg Pro Val Arg Ile Pro Ala
            115                 120                 125

Glu Phe Arg Ser Lys Phe Val Gln Phe Leu Arg Gln Glu Ala Ser Asn
        130                 135                 140
```

<210> SEQ ID NO 101
<211> LENGTH: 146
<212> TYPE: PRT

<213> ORGANISM: Artificial Sequence
<220> FEATURE:
<223> OTHER INFORMATION: Synthetic polypeptide

<400> SEQUENCE: 101

Met Ala Glu Phe His Glu Val Glu Leu Lys Val Arg Asp Tyr Glu Leu
1               5                   10                  15

Asp Gln Tyr Gly Val Val Asn Asn Ala Ile Tyr Ala Ser Tyr Cys Gln
            20                  25                  30

His Gly Arg His Glu Leu Leu Glu Arg Ile Gly Ile Ser Ala Asp Glu
        35                  40                  45

Val Ala Arg Ser Gly Asp Ala Leu Ala Leu Thr Glu Leu Ser Leu Lys
    50                  55                  60

Tyr Leu Ala Pro Leu Arg Ser Gly Asp Arg Phe Val Val Lys Ala Arg
65                  70                  75                  80

Ile Ser Asp Ser Ser Ala Ala Arg Leu Phe Phe Glu His Phe Ile Phe
                85                  90                  95

Lys Leu Pro Asp Gln Glu Pro Ile Leu Glu Ala Arg Gly Ile Ala Val
            100                 105                 110

Trp Leu Asn Lys Ser Tyr Arg Pro Val Arg Ile Pro Ala Glu Phe Arg
        115                 120                 125

Ser Lys Phe Val Gln Phe Leu Arg Gln Lys Ser Cys Gly Val Gln His
    130                 135                 140

His Leu
145

<210> SEQ ID NO 102
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 102

Met Ser Asp Gln Val Tyr His His Glu Val Glu Leu Lys Val Arg Asp
1               5                   10                  15

Tyr Glu Leu Asp Gln Tyr Gly Val Val Asn Asn Ala Ile Tyr Ala Ser
            20                  25                  30

Tyr Cys Gln His Gly Arg His Glu Leu Leu Glu Arg Ile Gly Ile Ser
        35                  40                  45

Ala Asp Glu Val Ala Arg Ser Gly Asp Ala Leu Ala Leu Thr Glu Leu
    50                  55                  60

Ser Leu Lys Tyr Leu Ala Pro Leu Arg Ser Gly Asp Arg Phe Val Val
65                  70                  75                  80

Lys Ala Arg Ile Ser Asp Ser Ser Ala Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Lys Ser Tyr Arg Pro Val Arg Ile Pro Ala
        115                 120                 125

Glu Phe Arg Ser Lys Phe Val Gln Phe Leu Arg Gln Lys Ser Cys Gly
    130                 135                 140

Val Gln His His Leu
145

<210> SEQ ID NO 103
<211> LENGTH: 144

<212> TYPE: PRT
<213> ORGANISM: Artificial Sequence
<220> FEATURE:
<223> OTHER INFORMATION: Synthetic polypeptide

<400> SEQUENCE: 103

```
Met Ser Asp Gln Val Tyr His His Glu Val Glu Leu Lys Val Arg Asp
1               5                  10                  15

Tyr Glu Leu Asp Gln Tyr Gly Val Val Asn Asn Ala Ile Tyr Ala Ser
            20                  25                  30

Tyr Cys Gln His Gly Arg His Glu Leu Leu Glu Arg Ile Gly Ile Ser
        35                  40                  45

Ala Asp Glu Val Ala Arg Ser Gly Asp Ala Leu Ala Leu Thr Glu Leu
    50                  55                  60

Ser Leu Lys Tyr Leu Ala Pro Leu Arg Ser Gly Asp Arg Phe Val Val
65                  70                  75                  80

Arg Ala Arg Leu Ser His Phe Thr Val Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Lys Ser Tyr Arg Pro Val Arg Ile Pro Ala
        115                 120                 125

Glu Phe Arg Ser Lys Phe Val Gln Phe Leu Arg Gln Glu Ala Ser Asn
    130                 135                 140
```

<210> SEQ ID NO 104
<211> LENGTH: 146
<212> TYPE: PRT
<213> ORGANISM: Artificial Sequence
<220> FEATURE:
<223> OTHER INFORMATION: Synthetic polypeptide

<400> SEQUENCE: 104

```
Met Ala Glu Phe His Glu Val Glu Leu Lys Val Arg Asp Tyr Glu Leu
1               5                  10                  15

Asp Gln Tyr Gly Val Val Asn Asn Ala Ile Tyr Ala Ser Tyr Cys Gln
            20                  25                  30

His Gly Arg His Glu Leu Leu Glu Arg Ile Gly Ile Ser Ala Asp Glu
        35                  40                  45

Val Ala Arg Ser Gly Asp Ala Leu Ala Leu Thr Glu Leu Ser Leu Lys
    50                  55                  60

Tyr Leu Ala Pro Leu Arg Ser Gly Asp Arg Phe Val Val Arg Ala Arg
65                  70                  75                  80

Leu Ser His Phe Thr Val Ala Arg Leu Phe Phe Glu His Phe Ile Phe
                85                  90                  95

Lys Leu Pro Asp Gln Glu Pro Ile Leu Glu Ala Arg Gly Ile Ala Val
            100                 105                 110

Trp Leu Asn Lys Ser Tyr Arg Pro Val Arg Ile Pro Ala Glu Phe Arg
        115                 120                 125

Ser Lys Phe Val Gln Phe Leu Arg Gln Lys Ser Cys Gly Val Gln His
    130                 135                 140

His Leu
145
```

<210> SEQ ID NO 105
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 105

Met Ser Asp Gln Val Tyr His His Glu Val Glu Leu Lys Val Arg Asp
1               5                   10                  15

Tyr Glu Leu Asp Gln Tyr Gly Val Val Asn Asn Ala Ile Tyr Ala Ser
            20                  25                  30

Tyr Cys Gln His Gly Arg His Glu Leu Leu Glu Arg Ile Gly Ile Ser
        35                  40                  45

Ala Asp Glu Val Ala Arg Ser Gly Asp Ala Leu Ala Leu Thr Glu Leu
    50                  55                  60

Ser Leu Lys Tyr Leu Ala Pro Leu Arg Ser Gly Asp Arg Phe Val Val
65                  70                  75                  80

Arg Ala Arg Leu Ser His Phe Thr Val Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Lys Ser Tyr Arg Pro Val Arg Ile Pro Ala
        115                 120                 125

Glu Phe Arg Ser Lys Phe Val Gln Phe Leu Arg Gln Lys Ser Cys Gly
    130                 135                 140

Val Gln His His Leu
145

<210> SEQ ID NO 106
<211> LENGTH: 146
<212> TYPE: PRT
<213> ORGANISM: Artificial Sequence
<220> FEATURE:
<223> OTHER INFORMATION: Synthetic polypeptide

<400> SEQUENCE: 106

Met Ala Glu Phe His Asp Val Glu Leu Thr Val Arg Asp Tyr Glu Leu
1               5                   10                  15

Asp Gln Phe Gly Val Val Asn Asn Ala Thr Tyr Ala Ser Tyr Cys Gln
            20                  25                  30

His Cys Arg His Ala Phe Leu Glu Lys Ile Gly Val Ser Val Asp Glu
        35                  40                  45

Val Thr Arg Asn Gly Asp Ala Leu Ala Val Thr Glu Leu Ser Leu Lys
    50                  55                  60

Phe Leu Ala Pro Leu Arg Ser Gly Asp Arg Phe Val Val Arg Ala Arg
65                  70                  75                  80

Leu Ser His Phe Thr Val Ala Arg Leu Phe Phe Glu His Phe Ile Phe
                85                  90                  95

Lys Leu Pro Asp Gln Glu Pro Ile Leu Glu Ala Arg Gly Ile Ala Val
            100                 105                 110

Trp Leu Asn Arg Ser Tyr Arg Pro Ile Arg Ile Pro Ser Glu Phe Asn
        115                 120                 125

Ser Lys Phe Val Lys Phe Leu His Gln Lys Ser Cys Gly Val Gln His
    130                 135                 140

His Leu
145

<210> SEQ ID NO 107
<211> LENGTH: 141
<212> TYPE: PRT

```
<213> ORGANISM: Artificial Sequence
<220> FEATURE:
<223> OTHER INFORMATION: Synthetic polypeptide

<400> SEQUENCE: 107

Met Ala Glu Phe His Asp Val Glu Leu Thr Val Arg Asp Tyr Glu Leu
1               5                   10                  15

Asp Gln Phe Gly Val Val Asn Asn Ala Thr Tyr Ala Ser Tyr Cys Gln
                20                  25                  30

His Cys Arg His Ala Phe Leu Glu Lys Ile Gly Val Ser Val Asp Glu
            35                  40                  45

Val Thr Arg Asn Gly Asp Ala Leu Ala Val Thr Glu Leu Ser Leu Lys
        50                  55                  60

Phe Leu Ala Pro Leu Arg Ser Gly Asp Arg Phe Val Val Arg Ala Arg
65                  70                  75                  80

Leu Ser His Phe Thr Val Ala Arg Leu Phe Glu His Phe Ile Phe
                85                  90                  95

Lys Leu Pro Asp Gln Glu Pro Ile Leu Glu Ala Arg Gly Ile Ala Val
                100                 105                 110

Trp Leu Asn Arg Ser Tyr Arg Pro Ile Arg Ile Pro Ser Glu Phe Asn
                115                 120                 125

Ser Lys Phe Val Lys Phe Leu His Gln Glu Ala Ser Asn
    130                 135                 140

<210> SEQ ID NO 108
<211> LENGTH: 141
<212> TYPE: PRT
<213> ORGANISM: Artificial Sequence
<220> FEATURE:
<223> OTHER INFORMATION: Synthetic polypeptide

<400> SEQUENCE: 108

Met Ala Glu Phe His Asp Val Glu Leu Thr Val Arg Asp Tyr Glu Leu
1               5                   10                  15

Asp Gln Phe Gly Val Val Asn Asn Ala Thr Tyr Ala Ser Tyr Cys Gln
                20                  25                  30

His Cys Arg His Ala Phe Leu Glu Lys Ile Gly Val Ser Val Asp Glu
            35                  40                  45

Val Thr Arg Asn Gly Asp Ala Leu Ala Val Thr Glu Leu Ser Leu Lys
        50                  55                  60

Phe Leu Ala Pro Leu Arg Ser Gly Asp Arg Phe Val Val Arg Ala Arg
65                  70                  75                  80

Leu Ser His Phe Thr Val Ala Arg Leu Phe Glu His Phe Ile Phe
                85                  90                  95

Lys Leu Pro Asp Gln Glu Pro Ile Leu Glu Ala Arg Gly Ile Ala Val
                100                 105                 110

Trp Leu Asn Arg Ser Tyr Arg Pro Ile Arg Ile Pro Ser Glu Phe Asn
                115                 120                 125

Ser Lys Phe Val Lys Phe Leu His Gln Glu Ala Ser Asn
    130                 135                 140

<210> SEQ ID NO 109
<211> LENGTH: 146
<212> TYPE: PRT
<213> ORGANISM: Artificial Sequence
<220> FEATURE:
<223> OTHER INFORMATION: Synthetic polypeptide

<400> SEQUENCE: 109
```

```
Met Ala Glu Phe His Asp Val Glu Leu Thr Val Arg Asp Tyr Glu Leu
1               5                   10                  15

Asp Gln Phe Gly Val Val Asn Asn Ala Thr Tyr Ala Ser Tyr Cys Gln
                20                  25                  30

His Cys Arg His Ala Phe Leu Glu Lys Ile Gly Val Ser Val Asp Glu
            35                  40                  45

Val Thr Arg Asn Gly Asp Ala Leu Ala Val Thr Glu Leu Ser Leu Lys
        50                  55                  60

Phe Leu Ala Pro Leu Arg Ser Gly Asp Arg Phe Val Val Lys Ala Arg
65                  70                  75                  80

Ile Ser Asp Ser Ser Ala Ala Arg Leu Phe Phe Glu His Phe Ile Phe
                85                  90                  95

Lys Leu Pro Asp Gln Glu Pro Ile Leu Glu Ala Arg Gly Ile Ala Val
                100                 105                 110

Trp Leu Asn Arg Ser Tyr Arg Pro Ile Arg Ile Pro Ser Glu Phe Asn
            115                 120                 125

Ser Lys Phe Val Lys Phe Leu His Gln Lys Ser Cys Gly Val Gln His
        130                 135                 140

His Leu
145

<210> SEQ ID NO 110
<211> LENGTH: 144
<212> TYPE: PRT
<213> ORGANISM: Artificial Sequence
<220> FEATURE:
<223> OTHER INFORMATION: Synthetic polypeptide

<400> SEQUENCE: 110

Met Ser Asp Gln Val Tyr His His Asp Val Glu Leu Thr Val Arg Asp
1               5                   10                  15

Tyr Glu Leu Asp Gln Phe Gly Val Val Asn Asn Ala Thr Tyr Ala Ser
                20                  25                  30

Tyr Cys Gln His Cys Arg His Ala Phe Leu Glu Lys Ile Gly Val Ser
            35                  40                  45

Val Asp Glu Val Thr Arg Asn Gly Asp Ala Leu Ala Val Thr Glu Leu
        50                  55                  60

Ser Leu Lys Phe Leu Ala Pro Leu Arg Ser Gly Asp Arg Phe Val Val
65                  70                  75                  80

Lys Ala Arg Ile Ser Asp Ser Ser Ala Ala Arg Leu Phe Phe Glu His
                85                  90                  95

Phe Ile Phe Lys Leu Pro Asp Gln Glu Pro Ile Leu Glu Ala Arg Gly
                100                 105                 110

Ile Ala Val Trp Leu Asn Arg Ser Tyr Arg Pro Ile Arg Ile Pro Ser
            115                 120                 125

Glu Phe Asn Ser Lys Phe Val Lys Phe Leu His Gln Glu Ala Ser Asn
        130                 135                 140

<210> SEQ ID NO 111
<211> LENGTH: 141
<212> TYPE: PRT
<213> ORGANISM: Artificial Sequence
<220> FEATURE:
<223> OTHER INFORMATION: Synthetic polypeptide

<400> SEQUENCE: 111

Met Ala Glu Phe His Asp Val Glu Leu Thr Val Arg Asp Tyr Glu Leu
```

-continued

```
1               5                   10                  15

Asp Gln Phe Gly Val Val Asn Asn Ala Thr Tyr Ala Ser Tyr Cys Gln
            20                  25                  30

His Cys Arg His Ala Phe Leu Glu Lys Ile Gly Val Ser Val Asp Glu
        35                  40                  45

Val Thr Arg Asn Gly Asp Ala Leu Ala Val Thr Glu Leu Ser Leu Lys
    50                  55                  60

Phe Leu Ala Pro Leu Arg Ser Gly Asp Arg Phe Val Val Lys Ala Arg
65                  70                  75                  80

Ile Ser Asp Ser Ser Ala Ala Arg Leu Phe Phe Glu His Phe Ile Phe
                85                  90                  95

Lys Leu Pro Asp Gln Glu Pro Ile Leu Glu Ala Arg Gly Ile Ala Val
            100                 105                 110

Trp Leu Asn Arg Ser Tyr Arg Pro Ile Arg Ile Pro Ser Glu Phe Asn
        115                 120                 125

Ser Lys Phe Val Lys Phe Leu His Gln Glu Ala Ser Asn
    130                 135                 140

<210> SEQ ID NO 112
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 112

Met Gly Asp Gln Leu Tyr Gln His Glu Val Glu Leu Gln Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Glu Phe Leu Glu Lys Ile Gly Val Ser
        35                  40                  45

Val Asp Glu Val Thr Arg Thr Gly Glu Ala Leu Ala Thr Thr Glu Leu
    50                  55                  60

Ser Leu Lys Tyr Leu Ala Pro Leu Arg Ser Gly Asp Arg Phe Val Val
65                  70                  75                  80

Lys Val Arg Ile Ser Arg Ser Thr Ala Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Arg Ser Tyr Arg Pro Ile Arg Ile Pro Ser
        115                 120                 125

Glu Phe Ser Ser Lys Phe Val Gln Phe Leu His Gln Lys Ser Cys Gly
    130                 135                 140

Thr Gln His Arg Leu
145

<210> SEQ ID NO 113
<211> LENGTH: 630
<212> TYPE: DNA
<213> ORGANISM: Ricinus communis

<400> SEQUENCE: 113
atggcattgc agcaggcatt tatctaccca atgcaagtga ctactcccct ctcacgtgcc      60
aacacaacat ggatcaatct ccaccgtcca tcagcatcac tactatttcg agtttcccgg     120
ccgcccatgt cgccagtcgt ccggtcactc cctaccgtga agagctgccg tgggttatca     180
```

```
tttcttgata tcagaggcgg taaaggaatg aatagttttg ttggtgttga gctaaaagtg      240
cgtgattatg agcttgatca gtacggagtt gtcaataatg ctgtctatgc cagttattgt      300
cagcatggtc gtcatgaact tttggagagg attggggtca gtgctgatgc tgttgctcgc      360
acaggtgatg cattggcact ctccgagttg tcactcaagt tccttgcacc tctaagaagt      420
ggagacaggt tgttgtaaa ggtgaggatc tctggctcct cagctgcccg cttatacttt       480
gatcacttca tcttcaagct gccaaatgaa gagcctattt ggaagcaaa agccacagca       540 gtatggcttg acaaaaatta tcgtcctgtc cgtattccat ctgatatgag gtctaaattg      600
gttcagtttc tcaaacacga ggagtctaat                                       630

<210> SEQ ID NO 114
<211> LENGTH: 627
<212> TYPE: DNA
<213> ORGANISM: Populus trichocarpa

<400> SEQUENCE: 114
atgattttgc aggcattggc aataaccccg ccgccacacg tgacgtttcc taccacctca       60
cgtgcctgcg caaatggat gatccatctt ccccgtcaat cctcatctgc tccgtttcca       120
acatcccggc cgccacatgt gcggtcactg cccctcatca gaaactgcac gtcgttacca      180
tttatcgatc tcaaagctgg caaaggaat agtgggttag tggaagtgga gctaaaagtg       240
cgtgattacg agctggatca attcggagtt gtcaacaatg ctgtttacgc aagttattgc      300
caacatggtc gtcatgagct tttggagagg attggtgtca gtgctgatgt ggttgctcgc      360 actgcgatg ctttggcact gtcagaattg tcactcaaat tcctcgcccc gctaagaagt       420
ggagacaggt tgttgtaaa ggtaaggatc tctggttcct ctgctgctcg cctatacttt       480
gaacacttca ttttcagact gccaaatgaa gagcctattc tggaagcaaa agcaacggct      540
gtctggcttg acaaaaaata tcatccagtt cgcattccac ctgaattcag atctaaattt      600
gttcagttcc ttcggcatga ggagtct                                          627

<210> SEQ ID NO 115
<211> LENGTH: 624
<212> TYPE: DNA
<213> ORGANISM: Vitis vinifera

<400> SEQUENCE: 115
atgttgcagg ctctcctctc ccccacgcac atggcggttc ccgcctcacg tgcccacaca       60 agggcctcc gtctctatcg tccaccactt cttctcccgg cacctcagcc tcctagcaat       120
tgtcgctccc cacgactccg atcagtcccc gccgtgagga gcgccagtgg actcgctttt      180
gatttcaaag gcggaaaagg aatgagtggg ttccttgatg ttgagctcaa agtccgggat      240
tatgaattgg atcaatatgg tgttgtaaac aatgctgttt atgcaagtta ttgtcaacat      300
ggtcggcatg agcttctgga aaagattggt gtcaatgctg atgctgttgc tcgcactggt      360
gatgcattag cactttcaga gctgacactc aaattccttg cacctctgag aagtggagac      420
aggtttgtgg tgaaggtgag ggtctctgat tcctcagctg cccgcttata ctttgaacac      480
ttcatcttca agctcccaaa tgaagagccc atcttggaag ctagggccac agcagtatgt      540
ctcgacaaaa actaccgtcc cgttcgaata ccaacagaga taagatctaa attggttcaa      600
ttcctacgac atgaggaatc ccat                                             624

<210> SEQ ID NO 116
```

<211> LENGTH: 624
<212> TYPE: DNA
<213> ORGANISM: Vitis vinifera

<400> SEQUENCE: 116

```
atgttgcagg ctctcctctc ccccacgcac atggcggttc ccgcctcacg tgccgacaca    60
aggggcctcc gtctctactg tccaccactt cttctcccgg cacctcagcc tcctagcaat   120
tgtcgctccc cacgtctccg atcagtcccc gccgtgagga gcgccagtgg acttgctttt   180
gatttcaaag gcggaaaagg aatgagtggg ttccttgatg ttgagctcaa agtccgggat   240
tatgaattgg atcaatatgg tgttgtaaac aatgctgttt atgcaagtta ttgtcaacat   300
ggtcggcatg agcttctgga aaagattggt ctcaatgctg atgctgttgc ttgcattggt   360
gacgctgtag cactttcaga gctgacactc aaattccttg cacctctgag aagtggagac   420
aggtttgtgg tgaaggtgag ggtctctgat gcctcagctg ctcgcttata ctttgaacac   480
ttcatcttca agctcccaaa tgaagagccc atcttggaag ctagggccac aggagtatgt   540
ctcgacaaaa actaccgtcc cgttcgaata ccaacagaga taagatctat attggttcaa   600
ttcctacgac atgaggaatc ccat                                          624
```

<210> SEQ ID NO 117
<211> LENGTH: 570
<212> TYPE: DNA
<213> ORGANISM: Arabidopsis thaliana

<400> SEQUENCE: 117

```
atgtttcttc aggttaccgg cacggcgact ccggctatgc ctgcggtagt gtttctcaat    60
tcatggagac gaccacttag tattcctctc cggagcgtaa aaaccttcaa gcctctagca   120
ttcttcgatc tcaaaggagg caaaggaatg agtgagttcc atgaggttga actcaaagtt   180
cgtgattatg aattggatca gtttggtgtt gtgaacaatg ctgtttacgc aaactactgt   240
caacacggtc gacatgagtt tctagagagt atcggtatca actgcgacga gtagcacgt   300
tctggggaag ccttagcaat ttcagagttg acaatgaagt tcctttcacc tttacgtagc   360
ggagacaaat tcgtggtgaa agcgaggata tcggggacat ctgctgcgcg tatttacttc   420
gatcatttca tctttaaact tccaaatcaa gagcctatat tggaggcaaa aggaatagct   480
gtgtggctcg acaacaagta ccgtcctgtt cgcatcccat cttctatacg ttctaaattt   540
gttcacttcc tacgccaaga cgacgccgtt                                    570
```

<210> SEQ ID NO 118
<211> LENGTH: 564
<212> TYPE: DNA
<213> ORGANISM: Arabidopsis thaliana

<400> SEQUENCE: 118

```
atgattcggg ttaccggcac ggcggctccg gctatgtctg tggtgtttcc gacttcatgg    60
agacaaccgg ttatgcttcc tctccggagc gcaaagacct tcaagcctca cacatttctt   120
gatcttaaag gaggcaaaga aatgagtgag ttccatgagg ttgagcttaa agttcgtgat   180
tatgaattgg atcagtttgg tgttgtgaac aatgctgttt acgcaaacta ctgccaacac   240
ggcatgcacg aatttctaga gagtattggt atcaactgtg atgaagttgc ccgttctggt   300
gaagccttag caatatcaga gttgacaatg aatttccttg cacctttacg tagcggagac   360
aagtttgtat tgaaagtgaa catatctaga acatctgctc gcgtatttta cttcgatcat   420
tccatcttga aacttccaaa tcaagaggtt atattggagg cgaaagcaac agttgtatgg   480
```

```
cttgacaaca agcaccgtcc tgttcgtatc ccatcttcga tacgctctaa atttgttcac     540
ttcctacgcc aaaacgacac agtt                                            564

<210> SEQ ID NO 119
<211> LENGTH: 570
<212> TYPE: DNA
<213> ORGANISM: Arabidopsis thaliana

<400> SEQUENCE: 119
atgcttaaag ctaccggcac agtggctccg gctatgcacg tggtgtttcc ctgttttcg      60 agtcgaccgc ttatcctacc tctccggagc acaaagacct tcaaacctct ctcatgtttc    120
aaacagcaag gaggcaaagg aatgaatgga gtccatgaga ttgaacttaa agttcgtgat    180
tatgaattag accaatttgg tgttgtgaac aacgctgttt atgcaaacta ctgccaacac    240
ggtcaacacg agtttatgga gactatcggt atcaactgtg atgaagtgtc ccgttctggt    300
gaagcattgg cagtttctga attgacaata aagtttcttg cacctttacg tagtggatgc    360
aagtttgtgg tgaaaacgag gatatcgggg acatctatga cgcgcattta ctttgaacag    420
ttcatcttta aacttccaaa tcaagagcct attttggagg caaaaggaat ggctgtgtgg    480
cttgacaaga ggtaccgtcc tgtttgtatc ccgtcttaca tacgctctaa tttcggtcac    540
ttccaacgtc aacacgttgt cgaatattga                                     570

<210> SEQ ID NO 120
<211> LENGTH: 456
<212> TYPE: DNA
<213> ORGANISM: Picea sitchensis

<400> SEQUENCE: 120
atgtacaaca tggatctttt cggagccaaa ggtatggcta gaccttttga gctcgagtta     60
aaagtgcgtg attatgaatt ggaccaatat ggagttgtca acaatgcaac ttatgcaagt    120
tattgccaac attgtcgtca tgaactctgt gaagcaattg ggtttagccc agatgtaata    180
gcgcgtactg ggaatgccct tgcattgtca gaattgtctt tgaagtacct tgcacctcta    240
agaagtggtg atagttttgt tgtcactgca aggatctctg gttcatctgc tgtacgcctg    300
ttttttgagc acttcatcta aagttacct aatagagagc ctgtcttgga agcaaaggcc    360
acagctgttt atcttgataa aatctatcga cctgttcgac ttccagctga ttttaaatct    420
aagatcacgc tatttcttcg taatgaagaa ttgaac                              456

<210> SEQ ID NO 121
<211> LENGTH: 645
<212> TYPE: DNA
<213> ORGANISM: Picea sitchensis

<400> SEQUENCE: 121
atgaccacag caatgggtgc aatatcaggt gggatttcag tgggagtaag cgccaggtat     60
cctcatgttc agtgcagcag cttcattcaa aatcccacca aaaaattgtc gagagccctt    120
gcatttcctt ctcttcgcac agcgtcttgt aatcccgttt ttagaagggc attgcctccc    180
attgccaaca tgtacaacat ggatcttttc ggagccaaag gtatggctag acctttgag    240 ctcgagttaa aagtgcgtga ttatgaattg gaccaatatg gagttgtcaa caatgcaact    300
tatgcaagtt attgcgaaca ttgtcttcat gaactctttg aagcaattgg gtttagccca    360
gatgcaatag cgcgtactgg gaatgccctt gcattgtcag aattgtcttt gaagtacctt    420
```

```
gcacctctaa gaagtggtga tagttttgtt gtcactgcaa ggatctccgg ttcatctgct      480
gtacgcctgt ttattgagca cttcatctat aagttaccta atagagagcc tgtcttggaa      540
gcaaaggcca cagctgttta tcttgataaa atctatcgac ctgttcgact ccagctgat       600 tttaaatcta agatcacgct atttcttcgt aatgaagaat tgaac                      645

<210> SEQ ID NO 122
<211> LENGTH: 630
<212> TYPE: DNA
<213> ORGANISM: Oryza sativa

<400> SEQUENCE: 122
atgcaccacc agatttggcg cctcctcccc agcgccctct cgccgatcca cgccggagct      60
ccccggccga ccgcccgcc ggcgcggcta ggccgcccctt caccgcaacg acggcgggcg     120
ctcgcgctca cgcacctcgc cacccggcgc acatgtcgcc tcctcgctgt ctccgcccag     180
tccgccagcc cccacgccgg cttgaggttg atcagttttt cgaggtggga gatgaaggta     240
cgagattatg aactcgacca atatggggtt gtcaacaatg ccatctatgc tagttactgc     300
caacatggtc gtcatgagct acttgaaagt gtaggcataa gtgcagatgc agtagcacgc     360
agcggtgagt cgctggccct ctctgaactg cacctcaagt actacgcgcc tttgagaagt     420
ggtgacaagt tcgtcgttaa ggtcaggctt gcgagcacaa aaggtataag gatgatattc     480
gagcacttca ttgaaaagct gcctaatcgt gagctcattt tggaagcgaa ggcaacagcg     540
gtttgtttga caaagacta ccgccccacc cgtatatctc cagagttcct gtccaagctg     600
cagttcttca cttctgaagg cagtagcagt                                      630

<210> SEQ ID NO 123
<211> LENGTH: 639
<212> TYPE: DNA
<213> ORGANISM: Oryza sativa

<400> SEQUENCE: 123
atgcaccacc agatttggcg cctcctcccc agcgccctct cgccgatcca cgccggagct      60
ccccggccga ccgcccgcc ggcgcggcta ggccgcccctt caccgcaacg acggcgggcg     120
ctcgcgctcg cgctcgcgca cctcgccacc cggcgcacat gccgcctcct cgctgtctcc     180
gcccagtccg ccagccccca cgccggcttg aggttggatc agttttttcga ggtgagatg     240 aaggtacgag attatgaact cgaccaatat ggggttgtca acaatgccat ctatgctagt     300
tactgccaac atggtcgtca tgagctactt gaatgtgtag gcataagtgc agatgcagta     360
gcacgcagcg gtgagtcgct ggccctctct gaactgcacc tcaagtacta cgcgcctttg     420
agaagtggtg acaagttcgt cgttaaggtc aggcttgcga gcacaaaagg tataaggatg     480
atattcgagc acttcattga aaagctgcct aatcgtgagc tcattttgga agcgaaggca     540
acagcggttt gtttgaacaa agactaccgc cccacccgta tatctccaga gttcctgtcc     600
aagctgcagt tcttcacttc tgaaggcagt agcagttaa                            639

<210> SEQ ID NO 124
<211> LENGTH: 654
<212> TYPE: DNA
<213> ORGANISM: Zea mays

<400> SEQUENCE: 124
atgcatcacc ggttcgcggg cctcgtgccc accgcccgcc ccgctctgcc gccgatccac      60
ggcggagtcg tcggccggag ctatccgccc gtccaccggt ccttggcgct tcgcctggcg     120
```

```
ccgtttgcct ccgcgtctgt ccgacgcgcg tgccgccccc tcgccgtctc cgcccaatcc    180
accagcctcc ggccggagaa gttttttgaa gtggagatga aggtgcgcga ctatgaaatt    240
gaccagtatg gtgttgtcaa caatgcaatc tatgctagct actgccaaca tggtcgtcac    300
gagctgcttg agagcgtagg catcagtgca gatgcagtgg cgcgcagtgg ggaatccctg    360
gctctctctg agttgaacct caagtacttt gcccctttga ggagtggcga taagtttgtt    420
gttaaggtga ggcttgcagg catcaaaggt gtacggatga tattcgacca catcattaca    480
aaactgccta atcatgagct aattctggag gcaaaggcaa cggctgtttg cctgaacaaa    540
gactactatc ctacccgtat tcctcgtgaa ctattgtcca agatgcagct cttcttaccc    600
gtggacagca gagggtcaaa tgaagacgtt aataatcgga ataacagctg caac          654
```

```
<210> SEQ ID NO 125
<211> LENGTH: 669
<212> TYPE: DNA
<213> ORGANISM: Sorghum bicolor

<400> SEQUENCE: 125
atgcatcacc agttcgcgcg cctcgtgccc accgcccgcc ccgcgctgcc gccgatccac     60
ggcggagccg tcggccggag ctctccgcac gtccaccggg ccgtggcgct tcgacgggcg    120
ccgctcgcct ccgcggctgg ccggcgcgcg tgccgccccc tcgccgtctc cgcccaatcc    180
accagccccc aggccggctt gaggctggag gagaagtttt ttgaagtgga gatgaaggtg    240
cgtgactatg aacttgacca gtatggtgtt gtcaacaatg ccgtctatgc tagctactgc    300
caacatggtc gtcacgagct acttgagagt gtaggcatca gtgcggatgc agtggcgcgc    360
agtggggagt cgctggccct ctctgagcta aacctaaagt actttggccc tttgaggagc    420
ggcgacaagt ttgttgttaa ggtgaggctt gtgggcatca aaggtgtacg gatgatattc    480
gagcacatca ttgagaaact tcctaatcac gagctaattc tggaggcaaa ggcaacagct    540
gtttgcctga acaaagacta ctatcctacc cgcattcctc gtgaactatt gtccaagatg    600
cagctcttct catccgagga cagcagaggg tcaaataaag acgttaataa tcggaataac    660
agctgcaac                                                            669
```

```

<210> SEQ ID NO 126
<211> LENGTH: 666
<212> TYPE: DNA
<213> ORGANISM: Phyllostachys edulis

<400> SEQUENCE: 126
atgctggcac tccggcgcgc cgcaccagtc cactccaccg cgatgcgcca ccagatttgg     60
cgcctcgtgc ccaacgccca gtcgccgctc ccgccgatcc acgccgatgc tcgccggagc    120
tgctcccgga ccgtcaaccc tacaccgctc cgcctgccgg cgctcgcctc cgccgccacc    180
cgaggcatat gccgccccct cgccgtctcc gctcagtcag ccagccccca cgccggcctg    240
agggtggata agtttttcga agtggcgatg aaggtgcgcg actatgaact cgaccagtat    300
ggagttgtca acaatgctgt ctatgctagc tactgccaac atggccgtca tgagctactt    360
gagagtgtag gcataagtgc agatgcagta gcgcgcagtg gtgagtcgct ggccctctct    420
gatctgcacc tcaagttctt cgcgcctttg agaagtggtg acgagtttgt cgttaaggtg    480
agacttgcaa gcatcaaagg tgtaaggatg atattcgagc actccattga gaagctgcct    540
aaccgcgagt tgattttgga agcaaaggca acagctgttt gtctcaacaa ggactaccgt    600
```

```
ccaacccgtg tatccccaga gttcctgtcc aggctgcagc tcttctcatc caaggacagc    660
aagggt                                                                666

<210> SEQ ID NO 127
<211> LENGTH: 648
<212> TYPE: DNA
<213> ORGANISM: Picea glauca

<400> SEQUENCE: 127
atggccacag caatgggtgc aatatcaggt gggatttcag tgggagtaaa cgccaggtat     60
cctcatgttc agtgcagcag tttcattcaa aatcccacca aaaaattgtc gagagccctt    120
gcatttcctt ctcttcgcac agcgtcttgt aatcccgtat ttagaagggc attgcctccc    180
attgccgaca tgtacaacat ggaactttc ggagccaaag gtatggctag acctttgag     240 ctcgagttaa aagtgcgtga ttatgaattg gaccaatatg gagttgtcaa caatgcaact    300
tatgcaagtt attgccaaca ttgtcgtcat gaactctgtg aagcaattgg gtttagccca    360
gatgcaatag cgcgtactgg gaatgccctt gcattgtcag aattgtcttt gaagtacctt    420
gcacctctaa gaagtggtga tagttttgtt gtcactgcaa ggatctccgg ttcatctgct    480
gtacgcctgt tttttgagca cttcatctat aagttaccta atagagagcc tgtcttggaa    540
gcaaaggcca cagctgttta tcttgataaa atctatcgac ctgttcgact ccagctgat    600 tttaaatcta agatcacgct atttcttcgt aatgaagaat tgaactag                648

<210> SEQ ID NO 128
<211> LENGTH: 618
<212> TYPE: DNA
<213> ORGANISM: Gossypium hirsutum

<400> SEQUENCE: 128
atgctccagg cttcggtttt cccggcgcac gccgccttgc cttcccctcg tccaaatgct     60
acttttctca atcttcaccg tccatcttca tcctttccaa tctctccgct gttgatgccg    120
ctgcgtgtcc ctacgctctc cacctcaagg agcttcactg tcggagcact ttttgatctc    180
aaaggcggcc aaggaatgac ttcgttccat gaggttgagc tcaaagtccg tgactacgaa    240
ctggatcagt atggagttgt taataatgct gtttatgcaa gttattgtca acacggtcgc    300
catgaactac ttgaaagtat tggtatcagc tgtgatgaag ttgcccgcac tggtgattca    360
ttagcactgt cagagttgtc gctcaaattt cttggacctt aaggagtgg agacaatttt    420 gttgttaagg tgagggtttc caactcctca ggggctcgcc tgtactttga gcatttcatc    480
tttaagatgc caaatgaagt gcctattctg gaggcaaagg ccacagctgt atggcttgac    540
aaaaattatc gtcctgctcg tatccctcca gaattcagat caaaatttgt tcaattcctt    600
cgttgtgagg aacctagt                                                  618

<210> SEQ ID NO 129
<211> LENGTH: 612
<212> TYPE: DNA
<213> ORGANISM: Glycine max

<400> SEQUENCE: 129
atgctctaca accacacttc ctcgatgtca ttgccttccc cattgtacct gaatactacg     60
tcgtttcgcc tcacgcgcca atctcctttt cctttccc gccggcgctt caatccaccg     120
gctttccgat cagtttcgcc gttgagttcc agccctctg catcactctt cgatctcaga     180
gggggcaaag gaatgagtgg attccatgac gttgaactga aggtgcgcga ctatgagttg    240
```

```
gatcagtacg gtgtggttaa caatgcagtt tatgctagtt attgccagca cggtcgtcat    300
gaactcttgc aaaacattgg tattaattgc gatgctgtgg ctcgcagtgg tgatgcattg    360
gcattgtctg aactatcgct caaattcctt gcacctctaa gaagtggaga caaatttgtt    420
gtaagagtta ggatttctgg ctcttcagct gctcgtttat actttgatca cttcatctat    480
aagctgccaa accaagagcc tattttggaa gccaaggcca tagcggtgcg gcttgacaaa    540
aactatcgtc ctatacgaat tccagcagag atgaagtcta aatttgtaaa gtttattcga    600
attgaggact ct                                                        612
```

<210> SEQ ID NO 130
<211> LENGTH: 669
<212> TYPE: DNA
<213> ORGANISM: Saccharum sp.
<220> FEATURE:
<221> NAME/KEY: modified_base
<222> LOCATION: (614)..(614)
<223> OTHER INFORMATION: a, c, t, g, unknown or other

<400> SEQUENCE: 130

```
atgcatcacc agttcgcgcg cctcgtgccc gccgcccgcc ccgcgctgcc gccgatccac     60
ggcggagccg ttgggcggag ctctccgccc gtccaccggg ccgtggcgct cgccgggcg    120 ccgctcgcct ccgcggctgg ccggcgcgcg taccgccccc tggccgtctc cgcccaatcc    180
accagccccc aagccggctt gaggctggag gagaagtttt ttgaagtgga gatgaaggtg    240
cgtgactatg aacttgacca gtatggtgtt gtcaacaatg cagtctatgc tagctactgc    300
caacatggtc gtcacgaggt gcttgagagt gtaggcatca gtgcggatgc agtggctcgc    360
agtggggagt cgctggccct ctctgagcta aacctaaagt actttgcccc tttgaggagt    420
ggcgacaagt tgttgttaa ggtaaggctt gtgggcatca aaggcatacg gatgatattc     480
gagcacatca ttgagaagct gcctaatcac gagctaattc tggaggcaaa ggcaacagct    540
gtttgcctga acaaagacta ctatcctacc cgcattcctc gtgaactact ggccaagatg    600
cagctcttct catnccgagg cagcagaggg acaaatgacg acattaataa tcggaataac    660
agctgcaac                                                            669
```

<210> SEQ ID NO 131
<211> LENGTH: 426
<212> TYPE: DNA
<213> ORGANISM: Artificial Sequence
<220> FEATURE:
<223> OTHER INFORMATION: Synthetic polynucleotide

<400> SEQUENCE: 131

```
atggcttcag aatttcacga agttgaattg aaggttagag attatgaact cgatcagttc     60
ggcgtcgtta ataacgcagt ttatgctaac tactgccagc acggcagaca cgagtttctc    120
gagtccattg gcattaactg tgacgaggtc gcaaggtcag gagaagcact tgcaatttcc    180
gagcttacta tgaagttctt gtctcctctt aggagtggtg ataagtttgt cgttaaagct    240
agaatatccg ggacttctgc tgctaggatt tatttcgatc actttatatt caaactccca    300
aaccaagaac caattcttga ggctaaaggt atagcagttt ggcttgataa taagtacaga    360
cctgtacgta tcccaagctc tattaggtca aagtttgtac actttcttcg tcaggatgat    420
gcagtg                                                               426
```

<210> SEQ ID NO 132

```
<211> LENGTH: 426
<212> TYPE: DNA
<213> ORGANISM: Artificial Sequence
<220> FEATURE:
<223> OTHER INFORMATION: Synthetic polynucleotide

<400> SEQUENCE: 132
atggcttcag aatttcacga agttgaattg aaggttagag attatgaact cgatcagttc      60
ggcgtcgtta ataacgcagt gtatgctaat tattgtcaac atggtatgca tgagtttctc     120
gaatccattg gcatcaactg tgatgaagtg gccagaagtg gtgaggcttt agcaatttca     180
gaactcacaa tgaatttcct tgcacctctt aggagtggtg ataaattcgt agtgaaggtt     240
aacataagta gaacaagtgc agccagaatc tactttgatc attcaatatt gaaacttccc     300
aatcaggagg tgattcttga ggctaaggcc accgttgttt ggttggataa caagcatagg     360
cctgtgcgta ttccatcttc aatcaggtca aagttcgtcc acttcttgag acagaacgac     420
actgtt                                                                426

<210> SEQ ID NO 133
<211> LENGTH: 429
<212> TYPE: DNA
<213> ORGANISM: Artificial Sequence
<220> FEATURE:
<223> OTHER INFORMATION: Synthetic polynucleotide

<400> SEQUENCE: 133
atggctaatg gtgtacatga aattgaattg aaggttagag attatgaact cgatcagttc      60
ggcgtcgtta ataacgcagt ttatgccaat tactgccagc atggccagca tgagttcatg     120
gaaacaatcg gaattaactg cgacgaagtt tcaaggtctg gtgaagcact tgcagtctca     180
gaactcacta taaagttcct tgcacctctt aggagtggtt gcaaatttgt cgtcaagact     240
aggatatccg gtacctctat gactcgtatc tatttcgaac aattcatctt caagttacct     300
aaccaagaac caattcttga ggctaagggt atggctgtat ggttggacaa gagatacagg     360
cctgtttgta ttccatctta catccgtagc aatttcggtc atttccaaag gcagcacgtg     420
gtcgaatat                                                             429

<210> SEQ ID NO 134
<211> LENGTH: 423
<212> TYPE: DNA
<213> ORGANISM: Artificial Sequence
<220> FEATURE:
<223> OTHER INFORMATION: Synthetic polynucleotide

<400> SEQUENCE: 134
atggcttctg gtcttgttga agtcgaattg aaggttagag attatgaact cgatcagttc      60
ggcgtcgtta ataacgcagt ttatgccagt tattgccaac atggaagaca tgagctcttg     120
gaaagaatag gcgtgtccgc agatgtcgtc gctaggacag gcgatgcatt ggctttgtca     180
gagcttagtc tcaaattctt ggctcctctt aggagtggtg atcgttttgt tgttaaggtt     240
cgtatatctg gaagctctgc cgcaaggctt tactttgaac atttcatctt ccgtttgcct     300
aatgaggaac ccattcttga ggctaaagct accgccgtct ggcttgacaa gaagtatcat     360
ccagtgagaa taccacctga gttcagatct aagttcgtcc agttcttgag gcatgaagag     420
tct                                                                   423

<210> SEQ ID NO 135
<211> LENGTH: 426
```

<212> TYPE: DNA
<213> ORGANISM: Artificial Sequence
<220> FEATURE:
<223> OTHER INFORMATION: Synthetic polynucleotide

<400> SEQUENCE: 135

```
atggctaata gcttcgttgg agtagaattg aaggttagag attatgaact cgatcagtac    60
ggcgtcgtta ataacgcagt ctacgcaagc tattgtcagc atggaaggca tgagttactt   120
gaaaggattg gagtgtcagc tgacgctgtt gcccgtacag gcgatgcact tgcattgagt   180
gagctttcct tgaagtttct cgcacctctt aggagtggtg acagatttgt cgtgaaggtt   240
agaatctccg gctcaagcgc cgctaggttg tacttcgacc actttatatt caaactccct   300
aacgaggaac caattcttga ggctaaggcc actgccgtat ggctcgacaa gaattacagg   360
cctgtcagga tcccttctga tatgaggtct aaacttgttc aattccttaa acacgaggaa   420
agtaac                                                              426
```

<210> SEQ ID NO 136
<211> LENGTH: 426
<212> TYPE: DNA
<213> ORGANISM: Artificial Sequence
<220> FEATURE:
<223> OTHER INFORMATION: Synthetic polynucleotide

<400> SEQUENCE: 136

```
atggcttcag ggttcttgga tgttgaattg aaggttagag attatgaact cgatcagtac    60
ggcgtcgtta ataacgcagt ctatgccagt tactgtcaac atggaaggca cgagctcctt   120
gagaagatag gagtgaatgc agatgctgtt gcacgtaccg gcgatgccct tgcactcagc   180
gagttaactc ttaagttctt ggctcctctt aggagtggtg ataggtttgt ggtgaaggtt   240
agagtgtccg actcatccgc tgccaggctc tacttcgagc actttatatt caagctccca   300
aatgaggagc ctattcttga ggctagagca acagcagtct gtctcgataa gaactaccgt   360
cctgttagga tacctactga aattagaagc aaactcgtcc agtttctcag gcacgaagaa   420
tcacat                                                              426
```

<210> SEQ ID NO 137
<211> LENGTH: 426
<212> TYPE: DNA
<213> ORGANISM: Artificial Sequence
<220> FEATURE:
<223> OTHER INFORMATION: Synthetic polynucleotide

<400> SEQUENCE: 137

```
atggcttcag ggttcttgga tgttgaattg aaggttagag attatgaact cgatcagtac    60
ggcgtcgtta ataacgcagt ctacgcatca tattgccagc atgggaggca tgaattgctc   120
gaaaagatag gtttgaatgc agatgccgtt gcctgtatcg gcgacgctgt tgcactttcc   180
gagcttactt tgaagttttt agctcctctt aggagtggtg acagattcgt tgttaaggtg   240
agagtgtccg acgcttccgc agccaggctc tacttcgagc actttatctt caagttgcct   300
aatgaagaac ctattcttga ggctagggcc actggcgttt gtctcgataa gaactataga   360
cctgttagaa tccctaccga aatcagatct atattggttc aattccttag gcacgaagaa   420
tcccat                                                              426
```

<210> SEQ ID NO 138
<211> LENGTH: 438
<212> TYPE: DNA

<213> ORGANISM: Artificial Sequence
<220> FEATURE:
<223> OTHER INFORMATION: Synthetic polynucleotide

<400> SEQUENCE: 138

```
atggctggtc ttagattgga tcagttcttc gaagttgaaa tgaaggtgag ggattacgaa      60
ttggatcagt acggcgtcgt taataacgca atctacgcta gctattgcca gcatggcagg     120
catgagcttc ttgaatcagt tggaatttcc gctgatgctg ttgctagaag tggtgagtca     180
ttggccttat cagagttgca cttaaagtac tatgcacctc ttaggagtgg tgataagttc     240
gttgtgaagg ttaggctcgc ctctaccaag ggtattagaa tgatatttga gcactttata     300
gagaagctcc ctaacagaga gcttatactt gaagccaagg ctactgctgt ttgcttgaac     360
aaggactaca gacctacacg tatttcacca gagttcttgt ccaagctcca attcttcacc     420
tctgagggtt ctagttca                                                   438
```

<210> SEQ ID NO 139
<211> LENGTH: 438
<212> TYPE: DNA
<213> ORGANISM: Artificial Sequence
<220> FEATURE:
<223> OTHER INFORMATION: Synthetic polynucleotide

<400> SEQUENCE: 139

```
atggctggtc ttagattgga tcagttcttc gaagttgaaa tgaaggtgag ggattacgaa      60
ttggatcagt acggcgtcgt taataacgca atctacgctu gctattgcca gcatggcagg     120
catgagcttc ttgaatcagt tggaatttcc gctgatgctg ttgctagaag tggtgagtca     180
ttggccttat cagagttgca cttaaagtac tatgcacctc ttaggagtgg tgataagttc     240
gttgtgaagg ttaggctcgc ctctaccaag ggtattagaa tgatatttga gcactttata     300
gagaagctcc ctaacagaga gcttatactt gaagccaagg ctactgctgt ttgcttgaac     360
aaggactaca gacctacacg tatttcacca gagttcttgt ccaagctcca attcttcacc     420
tctgagggtt ctagttca                                                   438
```

<210> SEQ ID NO 140
<211> LENGTH: 441
<212> TYPE: DNA
<213> ORGANISM: Artificial Sequence
<220> FEATURE:
<223> OTHER INFORMATION: Synthetic polynucleotide

<400> SEQUENCE: 140

```
atggctggtc ttagagtgga taagttcttc gaagttgcaa tgaaggtgag ggattacgaa      60
ttggatcagt acggcgtcgt taataacgca gtctacgcta gctattgcca gcatggcagg     120
catgagcttc ttgaatcagt tggaatttcc gctgatgctg ttgctagaag tggtgagtca     180
ttggccttat cagatttgca cttaaagttc tttgcacctc ttaggagtgg tgatgagttc     240
gttgtgaagg ttaggctcgc ctctatcaag ggtgttagaa tgatatttga gcactctata     300
gagaagctcc ctaacagaga gcttatactt gaagccaagg ctactgctgt ttgcttgaac     360
aaggactaca gacctacacg tgtttcacca gagttcttgt ccaggctcca gttgttcagc     420
tctaaggatt ctaaaggatg a                                               441
```

<210> SEQ ID NO 141
<211> LENGTH: 468
<212> TYPE: DNA
<213> ORGANISM: Artificial Sequence
<220> FEATURE:
<223> OTHER INFORMATION: Synthetic polynucleotide

<400> SEQUENCE: 141

```
atggcagaga agttctttga agtcgagatg aaagttagag attacgagat agatcagtat      60
ggagtcgtta ataatgcaat ctatgccagc tattgtcagc atggtagaca cgagttgctc     120
gaatccgtgg gcatatctgc cgatgctgtt gctaggtctg gagagtcact tgcattgtct     180
gaactcaacc tcaaatactt cgcacctctt cgttctggag acaagtttgt tgtcaaagtt     240
aggctcgctg gaattaaggg tgttcgtatg atatttgatc acattatcac caaacttcct     300
aatcatgagt tgatcttgga ggctaaagct acagctgttt gcctcaataa ggattattat     360
cctacaagga taccaaggga acttcttagt aagatgcagc tcttccttcc agtcgacagc     420
agaggtagta atgaagacgt gaacaatcgt aataattcat gcaattga                  468
```

<210> SEQ ID NO 142
<211> LENGTH: 480
<212> TYPE: DNA
<213> ORGANISM: Artificial Sequence
<220> FEATURE:
<223> OTHER INFORMATION: Synthetic polynucleotide

<400> SEQUENCE: 142

```
atggcaggtt tgagacttga ggagaagttc tttgaagtcg agatgaaagt tagagattac      60
gagttagatc agtatggagt cgttaataat gcagtctatg ccagctattg tcagcatggt     120
agacacgagt tgctcgaatc cgtgggcata tctgccgatg ctgttgctag gtctggagag     180
tcacttgcat tgtctgaact caacctcaaa tacttcggac ctcttcgttc tggagacaag     240
tttgttgtca agttaggct cgttggaatt aagggtgttc gtatgatatt tgagcacatt     300
atcgagaaac ttcctaatca tgagttgatc ttggaggcta aagctacagc tgtttgcctc     360
aataaggatt attatcctac aaggatacca agggaacttc ttagtaagat gcagctcttc     420
tcttcagagg acagcagagg tagtaataaa gacgtgaaca atcgtaataa ttcatgcaat     480
```

<210> SEQ ID NO 143
<211> LENGTH: 423
<212> TYPE: DNA
<213> ORGANISM: Artificial Sequence
<220> FEATURE:
<223> OTHER INFORMATION: Synthetic polynucleotide

<400> SEQUENCE: 143

```
atgaacgagt ccatgaagt tgaactcaaa gtcagggact atgaattgga tcagtatggt      60
gttgtaaaca atgctatcta tgcaagttat tgccaacatt gccgtcatga gctccttgaa     120
aggattggta taagtgctga tgaagtggca cgtaatggtg acgcacttgc acttacagag     180
ttgtcactta gtatcttgc acctcttagg agtggagata gatttgtcgt gaaagctaga     240
atatctgatt cttcagctgc tcgtttgttc tttgaacact tcatcttcaa acttcctgat     300
caagagccca tcttggaggc aagaggaata gcagtgtggc tcaacaagag ttaccgtcct     360
gtcagaatcc catctgagtt cagatcaaaa tttgttcagt tccttcgtca ggaggcatcc     420
aac                                                                  423
```

<210> SEQ ID NO 144
<211> LENGTH: 423
<212> TYPE: DNA
<213> ORGANISM: Artificial Sequence
<220> FEATURE:

<223> OTHER INFORMATION: Synthetic polynucleotide

<400> SEQUENCE: 144

```
atgaatgagt tccatgaagt cgaactcaaa gtcagggact atgagttgga tcaatatggt      60
gttgtaaaca atgctatcta tgctagttat tgccaacatt gtaggcatga gcttcttgaa     120
aagattggcg taaatgctga tgcagtggca cgtaatggtg aagcattagc acttacagag     180
cttacactca agtatcttgc acctctcagg agtggagaca gattcgttgt gaaagttaga     240
atatctgact cttcagctgc tcgtttgttc tttgaacact tcatcttcaa acttcctgat     300
caagagccta tcttggaggc aagaggaaca gcagtgtggc ttaacaagag ttaccgtcct     360
gtcagaatcc cttcagagtt cagatcaaaa ttcgttcagt tccttcgtca ggaggcatcc     420
aac                                                                  423
```

<210> SEQ ID NO 145
<211> LENGTH: 450
<212> TYPE: DNA
<213> ORGANISM: Artificial Sequence
<220> FEATURE:
<223> OTHER INFORMATION: Synthetic polynucleotide

<400> SEQUENCE: 145

```
atgagtgatc aggtctatca ccatgaagtc gaactcaaag tcaggyacta tgagttggat      60
caatatggtt ttgtaaacaa tgctatctat gctagttatt gccaacattg taggcatgag     120
cttcttgaaa agattggcgt aaatgctgat gcagtggcac gtaatggtga agcattagca     180
cttacagaga tgacactcaa gtatcttgca cctctcagga gtggagacag attcattgtg     240
aaagttagaa tatctgactc ttcagctgct cgtttgttct ttgaacactt catcttcaaa     300
cttcctgatc aagagcctat cttggaggca agaggaacag cagtgtggct taacaagagt     360
taccgtcctg tcagaatccc ttcagagttc agatcaaaat tcgttcagtt ccttcaccag     420
aagagttgcg gtgtacaaca tcatctctga                                     450
```

<210> SEQ ID NO 146
<211> LENGTH: 420
<212> TYPE: DNA
<213> ORGANISM: Artificial Sequence
<220> FEATURE:
<223> OTHER INFORMATION: Synthetic polynucleotide

<400> SEQUENCE: 146

```
atgaatgagt tccatgacgt tgaactcaca gtcagggact atgagttgga tcagtttggt      60
gttgtaaata atgctactta tgctagttat tgtcaacatt gtcgtcatgc tttccttgag     120
aagattggtg ttagtgttga tgaagtaacc cgtaatggtg atgcattagc tgtaacagag     180
ctctcactta agtttcttgc accacttagg agtggagata gattcgtggt gagggctaga     240
ttgtcccact ttacagtagc tagattgttc tttgagcatt tcattttcaa acttcctgat     300
caagagccta tattggaggc aagaggaata gcagtgtggc ttaatagaag ttatcgtcct     360
attcgtattc catcagagtt caattcaaaa tttgttaaat tccttcgtca ggaggcatga     420
```

<210> SEQ ID NO 147
<211> LENGTH: 450
<212> TYPE: DNA
<213> ORGANISM: Artificial Sequence
<220> FEATURE:
<223> OTHER INFORMATION: Synthetic polynucleotide

<400> SEQUENCE: 147

```
atggctagtg atcaggtcta tcaccatgaa gttgaactca aagtccggga ctatgaattg      60
gatcagtatg gtgttgtaaa caatgctatt tatgcaagtt attgtcaaca ttgtcgtcat     120
gcgtttctag aaaaaattgg tgttagtgtt gatgaagtaa cgcgaaatgg tgatgcatta     180
gccgtaacag agctctcact taagtttcta gcaccactaa ggagtggaga tagattcgtg     240
gtgagggcgc gattatccca ctttacagta gctcgattgt ttttcgagca tttcatcttc     300
aaacttccag atcaagagcc tatattggag gcaagaggaa tagcagtgtg gcttaataga     360
agttatcgtc ctattcgaat tccgtcagag ttcaattcaa aatttgttaa attccttcac     420
cagaagagtt gcggtgtaca acatcatctc                                      450
```

<210> SEQ ID NO 148
<211> LENGTH: 450
<212> TYPE: DNA
<213> ORGANISM: Artificial Sequence
<220> FEATURE:
<223> OTHER INFORMATION: Synthetic polynucleotide

<400> SEQUENCE: 148

```
atggctagtg atcaggtcta tcaccatgac gttgaactca cagtcaggga ctatgagttg      60
gatcagtttg gtgttgtaaa taatgctact tatgcgagtt attgtcaaca ttgtcgtcat     120
gcgtttctag aaaaaattgg tgttagtgtt gatgaagtaa cgcgaaatgg tgatgcatta     180
gccgtaacag agctctcact taagtttcta gcaccactaa ggagtggaga tagattcgtg     240
gtgagggcgc gattatccca ctttacagta gctcgattgt ttttcgagca tttcatcttc     300
aaacttccag atcaagagcc tatattggag gcaagaggaa tagcagtgtg gctcaataaa     360
agttaccgtc ctgtccgaat cccggcagag ttcagatcaa aatttgttca gttccttcgc     420
cagaagagtt gcggtgtaca acatcatctc                                      450
```

<210> SEQ ID NO 149
<211> LENGTH: 423
<212> TYPE: DNA
<213> ORGANISM: Artificial Sequence
<220> FEATURE:
<223> OTHER INFORMATION: Synthetic polynucleotide

<400> SEQUENCE: 149

```
atggctgagt tccatgacgt tgaactcaca gtcagggact atgagttgga tcagtttggt      60
gttgtaaata atgctactta tgcgagttat tgccaacatg gtcgtcatga gcttctagaa     120
aggattggta agtgctga tgaagtggca cgcagtggtg acgcactagc actaacagag      180
ctgtcactta gtatctagc acctctaagg agtggagata gatttgtcgt gaaggcacga      240
atatctgatt cttcagctgc tcgtttgttt ttcgaacact tcatcttcaa acttccagat     300
caagagccca tcttggaggc aagaggaata gcagtgtggc tcaataaaag ttaccgtcct     360
gtccgaatcc cggcagagtt cagatcaaaa tttgttcagt tccttcgcca ggaggcatcc     420
aac                                                                   423
```

<210> SEQ ID NO 150
<211> LENGTH: 423
<212> TYPE: DNA
<213> ORGANISM: Artificial Sequence
<220> FEATURE:
<223> OTHER INFORMATION: Synthetic polynucleotide

<400> SEQUENCE: 150

```
atggctgagt tccatgaagt tgaactcaaa gtccgggact atgaattgga tcagtatggt      60
gttgtaaaca atgctattta tgcaagttat tgccaacatg gtcgtcatga gcttctagaa     120
aggattggta taagtgctga tgaagtggca cgcagtggtg acgcactagc actaacagag     180
ctgtcactta agtatctagc acctctaagg agtggagata gatttgtcgt gaaggcacga     240
atatctgatt cttcagctgc tcgtttgttt ttcgaacact tcatcttcaa acttccagat     300
caagagccca tcttggaggc aagaggaata gcagtgtggc ttaatagaag ttatcgtcct     360
attcgaattc cgtcagagtt caattcaaaa tttgttaaat tccttcacca ggaggcatcc     420
aac                                                                   423

<210> SEQ ID NO 151
<211> LENGTH: 450
<212> TYPE: DNA
<213> ORGANISM: Artificial Sequence
<220> FEATURE:
<223> OTHER INFORMATION: Synthetic polynucleotide

<400> SEQUENCE: 151
atgggtgatc agctctatca ccatgacgtt gaactcacag tcagggacta tgagttggat      60
cagtttggtg ttgtaaataa tgctacttat gctagttatt gtcaacattg tcgtcatgct     120
ttccttgaga agattggtgt tagtgttgat gaagtaaccc gtaatggtga tgcattagct     180
gtaacagagc tctcacttaa gtttcttgca ccacttagga gtggagatag attcgtggtg     240
agggctagat tgtcccactt tacagtagct agattgttct ttgagcattt cattttcaaa     300
cttcctgatc aagagcctat attggaggca agaggaatag cagtgtggct taatagaagt     360
tatcgtccta ttcgtattcc atcagagttc aattcaaaat tgttaaatt ccttcaccag     420 aagagttgcg gtgtacaaca tcatctctga                                      450

<210> SEQ ID NO 152
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 152
atgagtgatc aggtctatca gcatgaggtt gaactccaag tcagggacta tgagttggat      60
cagtttggtg ttgtaaataa tgctacttat gctagttatt gtcaacattg tcgtcatgct     120
ttccttgaga agattggtgt tagtgttgat gaagtaaccc gtaatggtga tgcattagct     180
gtaacagagc tctcacttaa gtttcttgca ccacttagga gtggagatag attcgtggtg     240
agggctagat tgtcccactt tacagtagct agattgttct ttgagcattt cattttcaaa     300
cttcctgatc aagagcctat attggaggca agaggaatag cagtgtggct taatagaagt     360
tatcgtccta ttcgtattcc atcagagttc aattcaaaat tgttaaatt ccttcaccag     420 aagagttgcg gtgtacaaca tcatctc                                         447

<210> SEQ ID NO 153
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 153
atgagtgatc aggtctatca ccatgacgtt gaactcacag tcagggacta tgagttggat      60
```

```
cagtttggtg ttgtaaataa tgctacttat gctagttatt gtcaacattg tcgtcatgag    120
ttccttgaga agattggtgt tagtgttgat gaagtaaccc gtaatggtga tgcattagct    180
gtaacagagc tctcacttaa gtttcttgca ccacttagga gtggagatag attcgtggtg    240
agggctagat tgtcccactt tacagtagct agattgttct ttgagcattt cattttcaaa    300
cttcctgatc aagagcctat attggaggca agaggaatag cagtgtggct taatagaagt    360
tatcgtccta ttcgtattcc atcagagttc aattcaaaat ttgttaaatt ccttcaccag    420
aagagttgcg gtgtacaaca tcatctc                                        447
```

<210> SEQ ID NO 154
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 154

```
atgagtgatc aggtctatca ccatgacgtt gaactcacag tcaggactga tgagttggat     60
cagtttggtg ttgtaaataa tgctacttat gctagttatt gtcaacattg tcgtcatgct    120
ttccttgaga agattggtgt tagtgttgat gaagtatgcc gtactggtga tgcattagct    180
gtaacagagc tctcacttaa gtttcttgca ccacttagga gtggagatag attcgtggtg    240
agggctagat tgtcccactt tacagtagct agattgttct ttgagcattt cattttcaaa    300
cttcctgatc aagagcctat attggaggca agaggaatag cagtgtggct taatagaagt    360
tatcgtccta ttcgtattcc atcagagttc aattcaaaat ttgttaaatt ccttcaccag    420
aagagttgcg gtgtacaaca tcatctc                                        447
```

<210> SEQ ID NO 155
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 155

```
atgagtgatc aggtctatca ccatgacgtt gaactcacag tcaggactga tgagttggat     60
cagtttggtg ttgtaaataa tgctacttat gctagttatt gtcaacattg tcgtcatgct    120
ttccttgaga agattggtgt tagtgttgat gaagtaaccc gtaatggtga ggcattagct    180
acaacagagc tctcacttaa gtatcttgca ccacttagga gtggagatag attcgtggtg    240
agggctagat tgtcccactt tacagtagct agattgttct ttgagcattt cattttcaaa    300
cttcctgatc aagagcctat attggaggca agaggaatag cagtgtggct taatagaagt    360
tatcgtccta ttcgtattcc atcagagttc aattcaaaat ttgttaaatt ccttcaccag    420
aagagttgcg gtgtacaaca tcatctc                                        447
```

<210> SEQ ID NO 156
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 156

```
atgagtgatc aggtctatca ccatgacgtt gaactcacag tcaggactga tgagttggat     60
```

```
cagtttggtg ttgtaaataa tgctacttat gctagttatt gtcaacattg tcgtcatgct    120
ttccttgaga agattggtgt tagtgttgat gaagtaaccc gtaatggtga tgcattagct    180
gtaacagagc tctcacttaa gtttcttgca ccacttagga gtggagatag attcgtggtg    240
aaggttagaa tctcccgctc tacagcagct agattgttct ttgagcattt cattttcaaa    300
cttcctgatc aagagcctat attggaggca agaggaatag cagtgtggct taatagaagt    360
tatcgtccta ttcgtattcc atcagagttc aattcaaaat tgttaaaatt ccttcaccag    420
aagagttgcg gtgtacaaca tcatctc                                        447

<210> SEQ ID NO 157
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 157
atgagtgatc aggtctatca ccatgacgtt gaactcacag tcaggggacta tgagttggat      60 cagtttggtg ttgtaaataa tgctacttat gctagttatt gtcaacattg tcgtcatgct    120
ttccttgaga agattggtgt tagtgttgat gaagtaaccc gtaatggtga tgcattagct    180
gtaacagagc tctcacttaa gtttcttgca ccacttagga gtggagatag attcgtggtg    240
agggctagat tgtcccactt tacagtagct agattgttct ttgagcattt cattttcaaa    300
cttcctgatc aagagcctat attggaggca agaggaatag cagtgtggct taatagaagt    360
tatcgtccta ttcgtattcc atcagagttc agttcaaaat tgttcaatt ccttcaccag    420 aagagttgcg gtgtacaaca tcatctc                                        447

<210> SEQ ID NO 158
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 158
atgagtgatc aggtctatca ccatgacgtt gaactcacag tcagggacta tgagttggat      60
cagtttggtg ttgtaaataa tgctacttat gctagttatt gtcaacattg tcgtcatgct    120
ttccttgaga agattggtgt tagtgttgat gaagtaaccc gtaatggtga tgcattagct    180
gtaacagagc tctcacttaa gtttcttgca ccacttagga gtggagatag attcgtggtg    240
agggctagat tgtcccactt tacagtagct agattgttct ttgagcattt cattttcaaa    300
cttcctgatc aagagcctat attggaggca agaggaatag cagtgtggct taatagaagt    360
tatcgtccta ttcgtattcc atcagagttc aattcaaaat tgttaaaatt ccttcaccag    420
aagagttgcg gtacacaaca tcgtctc                                        447

<210> SEQ ID NO 159
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 159
atgggtgatc agctctatca acatgaagtt gaactccaag tcagggacta tgagttggat      60
cagtttggtg ttgtaaataa tgctacttat gctagttatt gtcaacattg tcgccatgct    120
```

```
ttccttgaga agattggtgt tagtgttgat gaagtaaccc gtaatggtga tgcattagct      180
gtaacagagc tctcacttaa gtttcttgca ccacttagga gtggagatag attcgtggtg      240
agggctagat tgtcccactt tacagtagct agattgttct ttgagcattt cattttcaaa      300
cttcctgatc aagagcctat attggaggca agaggaatag cagtgtggct taatagaagt      360
tatcgtccta ttcgtattcc atcagagttc agttcaaagt ttgttcagtt ccttcaccag      420
aagagttgcg gtacacaaca ccgtctc                                          447
```

<210> SEQ ID NO 160
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 160

```
atgagtgatc aggtctatca acatgaagtt gaactccaag tcagggacta tgaattggat       60
cagtttggtg ttgtaaacaa tgctacttat gcaagttatt gtcaacattg ccgtcatgag      120
tttcttgaga agattggtgt aagtgttgat gaagtatgta gaactggtga agcattagca      180
acaacagagc tttcacttaa gtatcttgca cctctcagga gtggagatag atttgtggtg      240
aaggtgagaa tatccaggtc tacagcagct cgtttgttct tcgagcattt catcttcaaa      300
cttccagatc aagagcctat attggaggca agaggaatag cagtgtggct taatagaagt      360
taccgtccta tcagaatacc atcagagttc agttcaaagt ttgttcagtt ccttcaccag      420
aagagttgcg gtacacaaca ccgtctc                                          447
```

<210> SEQ ID NO 161
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 161

```
atgggtgatc agctctatca ccatgatgtt gaactcacag tcagggacta tgaattggat       60
cagtttggtg ttgtaaacaa tgctacttat gcaagttatt gtcaacattg ccgtcatgag      120
tttcttgaga agattggtgt aagtgttgat gaagtatgta gaactggtga agcattagca      180
acaacagagc tttcacttaa gtatcttgca cctctcagga gtggagatag atttgtggtg      240
aaggtgagaa tatccaggtc tacagcagct cgtttgttct tcgagcattt catcttcaaa      300
cttccagatc aagagcctat attggaggca agaggaatag cagtgtggct taatagaagt      360
taccgtccta tcagaatacc atcagagttc agttcaaagt ttgttcagtt ccttcaccag      420
aagagttgcg gtacacaaca ccgtctc                                          447
```

<210> SEQ ID NO 162
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 162

```
atgggtgatc agctctatca acatgaagtt gaactccaag tcagggacta tgaattggat       60
cagtttggtg ttgtaaacaa tgctacttat gcaagttatt gtcaacattg ccgtcatgca      120
```

```
tttcttgaga agattggtgt aagtgttgat gaagtatgta gaactggtga agcattagca        180
acaacagagc tttcacttaa gtatcttgca cctctcagga gtggagatag atttgtggtg        240
aaggtgagaa tatccaggtc tacagcagct cgtttgttct tcgagcattt catcttcaaa        300
cttccagatc aagagcctat attggaggca agaggaatag cagtgtggct taatagaagt        360
taccgtccta tcagaatacc atcagagttc agttcaaagt ttgttcagtt ccttcaccag        420
aagagttgcg gtacacaaca ccgtctc                                            447

<210> SEQ ID NO 163
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 163
atgggtgatc agctctatca acatgaagtt gaactccaag tcagggacta tgaattggat         60
cagtttggtg ttgtaaacaa tgctacttat gcaagttatt gtcaacattg ccgtcatgag        120
tttcttgaga agattggtgt aagtgttgat gaagtaacta gaaatggtga agcattagca        180
acaacagagc tttcacttaa gtatcttgca cctctcagga gtggagatag atttgtggtg        240
aaggtgagaa tatccaggtc tacagcagct cgtttgttct tcgagcattt catcttcaaa        300
cttccagatc aagagcctat attggaggca agaggaatag cagtgtggct taatagaagt        360
taccgtccta tcagaatacc atcagagttc agttcaaagt ttgttcagtt ccttcaccag        420
aagagttgcg gtacacaaca ccgtctc                                            447

<210> SEQ ID NO 164
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 164
atgggtgatc agctctatca acatgaagtt gaactccaag tcagggacta tgaattggat         60
cagtttggtg ttgtaaacaa tgctacttat gcaagttatt gtcaacattg ccgtcatgag        120
tttcttgaga agattggtgt aagtgttgat gaagtatgta gaactggtga tgcattagca        180
gttacagagc tttcacttaa gtttcttgca cctctcagga gtggagatag atttgtggtg        240
aaggtgagaa tatccaggtc tacagcagct cgtttgttct tcgagcattt catcttcaaa        300
cttccagatc aagagcctat attggaggca agaggaatag cagtgtggct taatagaagt        360
taccgtccta tcagaatacc atcagagttc agttcaaagt ttgttcagtt ccttcaccag        420
aagagttgcg gtacacaaca ccgtctc                                            447

<210> SEQ ID NO 165
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 165
atgggtgatc agctctatca acatgaagtt gaactccaag tcagggacta tgaattggat         60
cagtttggtg ttgtaaacaa tgctacttat gcaagttatt gtcaacattg ccgtcatgag        120
tttcttgaga agattggtgt aagtgttgat gaagtatgta gaactggtga agcattagca        180
```

```
acaacagagc tttcacttaa gtatcttgca cctctcagga gtggagatag atttgtggtg    240
agggcgagat tatcccattt cacagtagct cgtttgttct tcgagcattt catcttcaaa    300
cttccagatc aagagcctat attggaggca agaggaatag cagtgtggct taatagaagt    360
taccgtccta tcagaatacc atcagagttc agttcaaagt tgttcagtt ccttcaccag     420 aagagttgcg gtacacaaca ccgtctc                                         447
```

<210> SEQ ID NO 166
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 166

```
atgggtgatc agctctatca acatgaagtt gaactccaag tcagggacta tgaattggat    60
cagtttggtg ttgtaaacaa tgctacttat gcaagttatt gtcaacattg ccgtcatgag   120
tttcttgaga agattggtgt aagtgttgat gaagtatgta gaactggtga agcattagca   180
acaacagagc tttcacttaa gtatcttgca cctctcagga gtggagatag atttgtggtg   240
aaggtgagaa tatccaggtc tacagcagct cgtttgttct tcgagcattt catcttcaaa   300
cttccagatc aagagcctat attggaggca agaggaatag cagtgtggct taatagaagt   360
taccgtccta tcagaatacc atcagagttc aattcaaagt tgttaagtt ccttcaccag    420 aagagttgcg gtacacaaca ccgtctc                                        447
```

<210> SEQ ID NO 167
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 167

```
atgggtgatc agctctatca acatgaagtt gaactccaag tcagggacta tgaattggat    60
cagtttggtg ttgtaaacaa tgctacttat gcaagttatt gtcaacattg ccgtcatgag   120
tttcttgaga agattggtgt aagtgttgat gaagtatgta gaactggtga agcattagca   180
acaacagagc tttcacttaa gtatcttgca cctctcagga gtggagatag atttgtggtg   240
aaggtgagaa tatccaggtc tacagcagct cgtttgttct tcgagcattt catcttcaaa   300
cttccagatc aagagcctat attggaggca agaggaatag cagtgtggct taatagaagt   360
taccgtccta tcagaatacc atcagagttc agttcaaagt tgttcagtt ccttcaccag    420 aagagttgcg gtgtacaaca ccatctc                                        447
```

<210> SEQ ID NO 168
<211> LENGTH: 447
<212> TYPE: DNA
<213> ORGANISM: Artificial Sequence
<220> FEATURE:
<223> OTHER INFORMATION: Synthetic polynucleotide

<400> SEQUENCE: 168

```
atgagtgatc aggtctatca ccatgacgtt gaactcacag tcagggacta tgaattggat    60
cagtttggtg ttgtaaacaa tgctacttat gcaagttatt gtcaacattg ccgtcatgag   120
tttcttgaga agattggtgt aagtgttgat gaagtatgta gaactggtga agcattagca   180
```

```
acaacagagc tttcacttaa gtatcttgca cctctcagga gtggagatag atttgtggtg      240
aaggtgagaa tatccaggtc tacagcagct cgtttgttct tcgagcattt catcttcaaa      300
cttccagatc aagagcctat attggaggca agaggaatag cagtgtggct aatagaagt       360 taccgtccta tcagaatacc atcagagttc aattcaaaat tgttaaaatt ccttcaccag      420
aagagttgcg gtgtacaaca tcatctc                                         447
```

<210> SEQ ID NO 169
<211> LENGTH: 561
<212> TYPE: DNA
<213> ORGANISM: Artificial Sequence
<220> FEATURE:
<223> OTHER INFORMATION: Synthetic polynucleotide

<400> SEQUENCE: 169

```
atggcttcaa tttgtacttc aaattttcac tttctatgca gaaaaaacaa ttctagccct       60
atttctcatc atctactgtt atctccctct tctttatcct tctcacgttg cggcggattg      120
cggttgtgtc gtgcggccgc agagttccat gaagttgaac tcaaagtccg ggactatgaa      180
ttggatcagt atggtgttgt aaacaatgct atttatgcaa gttattgcca acatggtcgt      240
catgagcttc tagaaaggat tggtataagt gctgatgaag tggcacgcag tggtgacgca      300
ctagcactaa cagagctgtc acttaagtat ctagcacctc taaggagtgg agatagattt      360
gtcgtgaagg cacgaatatc tgattcttca gctgctcgtt tgtttttcga cacttcatc      420 ttcaaacttc cagatcaaga gcccatcttg gaggcaagag gaatagcagt gtggctcaat      480
aaaagttacc gtcctgtccg aatcccggca gagttcagat caaaatttgt tcagttcctt      540
cgccaggagg catccaactg a                                                561
```

<210> SEQ ID NO 170
<211> LENGTH: 210
<212> TYPE: PRT
<213> ORGANISM: Ricinus communis

<400> SEQUENCE: 170

```
Met Ala Leu Gln Gln Ala Phe Ile Tyr Pro Met Gln Val Thr Thr Pro
 1               5                  10                  15

Leu Ser Arg Ala Asn Thr Thr Trp Ile Asn Leu His Arg Pro Ser Ala
            20                  25                  30

Ser Leu Leu Phe Arg Val Ser Arg Pro Pro Met Ser Pro Val Val Arg
        35                  40                  45

Ser Leu Pro Thr Val Lys Ser Cys Arg Gly Leu Ser Phe Leu Asp Ile
    50                  55                  60

Arg Gly Gly Lys Gly Met Asn Ser Phe Val Gly Val Glu Leu Lys Val
65                  70                  75                  80

Arg Asp Tyr Glu Leu Asp Gln Tyr Gly Val Val Asn Asn Ala Val Tyr
                85                  90                  95

Ala Ser Tyr Cys Gln His Gly Arg His Glu Leu Leu Glu Arg Ile Gly
            100                 105                 110

Val Ser Ala Asp Ala Val Ala Arg Thr Gly Asp Ala Leu Ala Leu Ser
        115                 120                 125

Glu Leu Ser Leu Lys Phe Leu Ala Pro Leu Arg Ser Gly Asp Arg Phe
    130                 135                 140

Val Val Lys Val Arg Ile Ser Gly Ser Ser Ala Ala Arg Leu Tyr Phe
145                 150                 155                 160

Asp His Phe Ile Phe Lys Leu Pro Asn Glu Glu Pro Ile Leu Glu Ala
```

```
                    165                 170                 175

Lys Ala Thr Ala Val Trp Leu Asp Lys Asn Tyr Arg Pro Val Arg Ile
            180                 185                 190

Pro Ser Asp Met Arg Ser Lys Leu Val Gln Phe Leu Lys His Glu Glu
        195                 200                 205

Ser Asn
    210

<210> SEQ ID NO 171
<211> LENGTH: 209
<212> TYPE: PRT
<213> ORGANISM: Populus trichocarpa

<400> SEQUENCE: 171

Met Ile Leu Gln Ala Leu Ala Ile Thr Pro Pro His Val Thr Phe
1               5                   10                  15

Pro Thr Thr Ser Arg Ala Cys Ala Lys Trp Met Ile His Leu Pro Arg
            20                  25                  30

Gln Ser Ser Ala Pro Phe Pro Thr Ser Arg Pro His Val Arg
        35                  40                  45

Ser Leu Pro Leu Ile Arg Asn Cys Thr Ser Leu Pro Phe Ile Asp Leu
    50                  55                  60

Lys Ala Gly Lys Gly Met Ser Gly Leu Val Glu Val Glu Leu Lys Val
65                  70                  75                  80

Arg Asp Tyr Glu Leu Asp Gln Phe Gly Val Val Asn Asn Ala Val Tyr
                85                  90                  95

Ala Ser Tyr Cys Gln His Gly Arg His Glu Leu Leu Glu Arg Ile Gly
            100                 105                 110

Val Ser Ala Asp Val Val Ala Arg Thr Gly Asp Ala Leu Ala Leu Ser
        115                 120                 125

Glu Leu Ser Leu Lys Phe Leu Ala Pro Leu Arg Ser Gly Asp Arg Phe
    130                 135                 140

Val Val Lys Val Arg Ile Ser Gly Ser Ser Ala Ala Arg Leu Tyr Phe
145                 150                 155                 160

Glu His Phe Ile Phe Arg Leu Pro Asn Glu Glu Pro Ile Leu Glu Ala
                165                 170                 175

Lys Ala Thr Ala Val Trp Leu Asp Lys Lys Tyr His Pro Val Arg Ile
            180                 185                 190

Pro Pro Glu Phe Arg Ser Lys Phe Val Gln Phe Leu Arg His Glu Glu
        195                 200                 205

Ser

<210> SEQ ID NO 172
<211> LENGTH: 208
<212> TYPE: PRT
<213> ORGANISM: Vitis vinifera

<400> SEQUENCE: 172

Met Leu Gln Ala Leu Leu Ser Pro Thr His Met Ala Val Pro Ala Ser
1               5                   10                  15

Arg Ala His Thr Arg Gly Leu Arg Leu Tyr Arg Pro Pro Leu Leu Leu
            20                  25                  30

Pro Ala Pro Gln Pro Pro Ser Asn Cys Arg Ser Arg Pro Arg Leu Arg Ser
        35                  40                  45

Val Pro Ala Val Arg Ser Ala Ser Gly Leu Ala Phe Asp Phe Lys Gly
    50                  55                  60
```

```
Gly Lys Gly Met Ser Gly Phe Leu Asp Val Glu Leu Lys Val Arg Asp
 65                  70                  75                  80

Tyr Glu Leu Asp Gln Tyr Gly Val Val Asn Asn Ala Val Tyr Ala Ser
                 85                  90                  95

Tyr Cys Gln His Gly Arg His Glu Leu Leu Lys Ile Gly Val Asn
                100                 105                 110

Ala Asp Ala Val Ala Arg Thr Gly Asp Ala Leu Ala Leu Ser Glu Leu
                115                 120                 125

Thr Leu Lys Phe Leu Ala Pro Leu Arg Ser Gly Asp Arg Phe Val Val
    130                 135                 140

Lys Val Arg Val Ser Asp Ser Ser Ala Ala Arg Leu Tyr Phe Glu His
145                 150                 155                 160

Phe Ile Phe Lys Leu Pro Asn Glu Glu Pro Ile Leu Glu Ala Arg Ala
                    165                 170                 175

Thr Ala Val Cys Leu Asp Lys Asn Tyr Arg Pro Val Arg Ile Pro Thr
                180                 185                 190

Glu Ile Arg Ser Lys Leu Val Gln Phe Leu Arg His Glu Glu Ser His
                195                 200                 205
```

```
<210> SEQ ID NO 173
<211> LENGTH: 208
<212> TYPE: PRT
<213> ORGANISM: Vitis vinifera

<400> SEQUENCE: 173
```

```
Met Leu Gln Ala Leu Leu Ser Pro Thr His Met Ala Val Pro Ala Ser
  1               5                  10                  15

Arg Ala Asp Thr Arg Gly Leu Arg Leu Tyr Cys Pro Pro Leu Leu Leu
                 20                  25                  30

Pro Ala Pro Gln Pro Pro Ser Asn Cys Arg Ser Pro Arg Leu Arg Ser
                 35                  40                  45

Val Pro Ala Val Arg Ser Ala Ser Gly Leu Ala Phe Asp Phe Lys Gly
     50                  55                  60

Gly Lys Gly Met Ser Gly Phe Leu Asp Val Glu Leu Lys Val Arg Asp
 65                  70                  75                  80

Tyr Glu Leu Asp Gln Tyr Gly Val Val Asn Asn Ala Val Tyr Ala Ser
                 85                  90                  95

Tyr Cys Gln His Gly Arg His Glu Leu Leu Lys Ile Gly Leu Asn
                100                 105                 110

Ala Asp Ala Val Ala Cys Ile Gly Asp Ala Val Ala Leu Ser Glu Leu
                115                 120                 125

Thr Leu Lys Phe Leu Ala Pro Leu Arg Ser Gly Asp Arg Phe Val Val
    130                 135                 140

Lys Val Arg Val Ser Asp Ala Ser Ala Ala Arg Leu Tyr Phe Glu His
145                 150                 155                 160

Phe Ile Phe Lys Leu Pro Asn Glu Glu Pro Ile Leu Glu Ala Arg Ala
                    165                 170                 175

Thr Gly Val Cys Leu Asp Lys Asn Tyr Arg Pro Val Arg Ile Pro Thr
                180                 185                 190

Glu Ile Arg Ser Ile Leu Val Gln Phe Leu Arg His Glu Glu Ser His
                195                 200                 205
```

```
<210> SEQ ID NO 174
<211> LENGTH: 190
<212> TYPE: PRT
```

<213> ORGANISM: Arabidopsis thaliana

<400> SEQUENCE: 174

Met Phe Leu Gln Val Thr Gly Thr Ala Thr Pro Ala Met Pro Ala Val
1               5                   10                  15

Val Phe Leu Asn Ser Trp Arg Arg Pro Leu Ser Ile Pro Leu Arg Ser
                20                  25                  30

Val Lys Thr Phe Lys Pro Leu Ala Phe Phe Asp Leu Lys Gly Gly Lys
            35                  40                  45

Gly Met Ser Glu Phe His Glu Val Glu Leu Lys Val Arg Asp Tyr Glu
        50                  55                  60

Leu Asp Gln Phe Gly Val Val Asn Asn Ala Val Tyr Ala Asn Tyr Cys
65                  70                  75                  80

Gln His Gly Arg His Glu Phe Leu Glu Ser Ile Gly Ile Asn Cys Asp
                85                  90                  95

Glu Val Ala Arg Ser Gly Glu Ala Leu Ala Ile Ser Glu Leu Thr Met
            100                 105                 110

Lys Phe Leu Ser Pro Leu Arg Ser Gly Asp Lys Phe Val Val Lys Ala
        115                 120                 125

Arg Ile Ser Gly Thr Ser Ala Ala Arg Ile Tyr Phe Asp His Phe Ile
    130                 135                 140

Phe Lys Leu Pro Asn Gln Glu Pro Ile Leu Glu Ala Lys Gly Ile Ala
145                 150                 155                 160

Val Trp Leu Asp Asn Lys Tyr Arg Pro Val Arg Ile Pro Ser Ser Ile
                165                 170                 175

Arg Ser Lys Phe Val His Phe Leu Arg Gln Asp Ala Val
            180                 185                 190

<210> SEQ ID NO 175
<211> LENGTH: 188
<212> TYPE: PRT
<213> ORGANISM: Arabidopsis thaliana

<400> SEQUENCE: 175

Met Ile Arg Val Thr Gly Thr Ala Ala Pro Ala Met Ser Val Val Phe
1               5                   10                  15

Pro Thr Ser Trp Arg Gln Pro Val Met Leu Pro Leu Arg Ser Ala Lys
                20                  25                  30

Thr Phe Lys Pro His Thr Phe Leu Asp Leu Lys Gly Lys Glu Met
            35                  40                  45

Ser Glu Phe His Glu Val Glu Leu Lys Val Arg Asp Tyr Glu Leu Asp
        50                  55                  60

Gln Phe Gly Val Val Asn Asn Ala Val Tyr Ala Asn Tyr Cys Gln His
65                  70                  75                  80

Gly Met His Glu Phe Leu Glu Ser Ile Gly Ile Asn Cys Asp Glu Val
                85                  90                  95

Ala Arg Ser Gly Glu Ala Leu Ala Ile Ser Glu Leu Thr Met Asn Phe
            100                 105                 110

Leu Ala Pro Leu Arg Ser Gly Asp Lys Phe Val Val Lys Val Asn Ile
        115                 120                 125

Ser Arg Thr Ser Ala Ala Arg Ile Tyr Phe Asp His Ser Ile Leu Lys
    130                 135                 140

Leu Pro Asn Gln Glu Val Ile Leu Glu Ala Lys Ala Thr Val Val Trp
145                 150                 155                 160

Leu Asp Asn Lys His Arg Pro Val Arg Ile Pro Ser Ser Ile Arg Ser

```
                    165                 170                 175

Lys Phe Val His Phe Leu Arg Gln Asn Asp Thr Val
            180                 185

<210> SEQ ID NO 176
<211> LENGTH: 189
<212> TYPE: PRT
<213> ORGANISM: Arabidopsis thaliana

<400> SEQUENCE: 176

Met Leu Lys Ala Thr Gly Thr Val Ala Pro Ala Met His Val Phe
1               5                   10                  15

Pro Cys Phe Ser Ser Arg Pro Leu Ile Leu Pro Leu Arg Ser Thr Lys
                20                  25                  30

Thr Phe Lys Pro Leu Ser Cys Phe Lys Gln Gln Gly Gly Lys Gly Met
            35                  40                  45

Asn Gly Val His Glu Ile Glu Leu Lys Val Arg Asp Tyr Glu Leu Asp
50                  55                  60

Gln Phe Gly Val Val Asn Ala Val Tyr Ala Asn Tyr Cys Gln His
65                  70                  75                  80

Gly Gln His Glu Phe Met Glu Thr Ile Gly Ile Asn Cys Asp Glu Val
                85                  90                  95

Ser Arg Ser Gly Glu Ala Leu Ala Val Ser Glu Leu Thr Ile Lys Phe
            100                 105                 110

Leu Ala Pro Leu Arg Ser Gly Cys Lys Phe Val Val Lys Thr Arg Ile
        115                 120                 125

Ser Gly Thr Ser Met Thr Arg Ile Tyr Phe Glu Gln Phe Ile Phe Lys
    130                 135                 140

Leu Pro Asn Gln Glu Pro Ile Leu Glu Ala Lys Gly Met Ala Val Trp
145                 150                 155                 160

Leu Asp Lys Arg Tyr Arg Pro Val Cys Ile Pro Ser Tyr Ile Arg Ser
                165                 170                 175

Asn Phe Gly His Phe Gln Arg Gln His Val Val Glu Tyr
            180                 185

<210> SEQ ID NO 177
<211> LENGTH: 152
<212> TYPE: PRT
<213> ORGANISM: Picea sitchensis

<400> SEQUENCE: 177

Met Tyr Asn Met Asp Leu Phe Gly Ala Lys Gly Met Ala Arg Pro Phe
1               5                   10                  15

Glu Leu Glu Leu Lys Val Arg Asp Tyr Glu Leu Asp Gln Tyr Gly Val
                20                  25                  30

Val Asn Asn Ala Thr Tyr Ala Ser Tyr Cys Gln His Cys Arg His Glu
            35                  40                  45

Leu Cys Glu Ala Ile Gly Phe Ser Pro Asp Val Ile Ala Arg Thr Gly
        50                  55                  60

Asn Ala Leu Ala Leu Ser Glu Leu Ser Leu Lys Tyr Leu Ala Pro Leu
65                  70                  75                  80

Arg Ser Gly Asp Ser Phe Val Val Thr Ala Arg Ile Ser Gly Ser Ser
                85                  90                  95

Ala Val Arg Leu Phe Phe Glu His Phe Ile Tyr Lys Leu Pro Asn Arg
            100                 105                 110

Glu Pro Val Leu Glu Ala Lys Ala Thr Ala Val Tyr Leu Asp Lys Ile
```

```
                115                 120                 125
Tyr Arg Pro Val Arg Leu Pro Ala Asp Phe Lys Ser Lys Ile Thr Leu
        130                 135                 140

Phe Leu Arg Asn Glu Glu Leu Asn
145                 150

<210> SEQ ID NO 178
<211> LENGTH: 215
<212> TYPE: PRT
<213> ORGANISM: Picea sitchensis

<400> SEQUENCE: 178

Met Thr Thr Ala Met Gly Ala Ile Ser Gly Ile Ser Val Gly Val
1               5                   10                  15

Ser Ala Arg Tyr Pro His Val Gln Cys Ser Ser Phe Ile Gln Asn Pro
            20                  25                  30

Thr Lys Lys Leu Ser Arg Ala Leu Ala Phe Pro Ser Leu Arg Thr Ala
        35                  40                  45

Ser Cys Asn Pro Val Phe Arg Arg Ala Leu Pro Pro Ile Ala Asn Met
50                  55                  60

Tyr Asn Met Asp Leu Phe Gly Ala Lys Gly Met Ala Arg Pro Phe Glu
65                  70                  75                  80

Leu Glu Leu Lys Val Arg Asp Tyr Glu Leu Asp Gln Tyr Gly Val Val
                85                  90                  95

Asn Asn Ala Thr Tyr Ala Ser Tyr Cys Glu His Cys Leu His Glu Leu
            100                 105                 110

Phe Glu Ala Ile Gly Phe Ser Pro Asp Ala Ile Ala Arg Thr Gly Asn
        115                 120                 125

Ala Leu Ala Leu Ser Glu Leu Ser Leu Lys Tyr Leu Ala Pro Leu Arg
    130                 135                 140

Ser Gly Asp Ser Phe Val Val Thr Ala Arg Ile Ser Gly Ser Ser Ala
145                 150                 155                 160

Val Arg Leu Phe Ile Glu His Phe Ile Tyr Lys Leu Pro Asn Arg Glu
                165                 170                 175

Pro Val Leu Glu Ala Lys Ala Thr Ala Val Tyr Leu Asp Lys Ile Tyr
            180                 185                 190

Arg Pro Val Arg Leu Pro Ala Asp Phe Lys Ser Lys Ile Thr Leu Phe
        195                 200                 205

Leu Arg Asn Glu Glu Leu Asn
    210                 215

<210> SEQ ID NO 179
<211> LENGTH: 210
<212> TYPE: PRT
<213> ORGANISM: Oryza sativa

<400> SEQUENCE: 179

Met His His Gln Ile Trp Arg Leu Leu Pro Ser Ala Leu Ser Pro Ile
1               5                   10                  15

His Ala Gly Ala Pro Arg Pro Ser Arg Pro Ala Arg Leu Gly Arg
            20                  25                  30

Pro Ser Pro Gln Arg Arg Ala Leu Ala Leu Thr His Leu Ala Thr
        35                  40                  45

Arg Arg Thr Cys Arg Leu Leu Ala Val Ser Ala Gln Ser Ala Ser Pro
50                  55                  60

His Ala Gly Leu Arg Leu Asp Gln Phe Phe Glu Val Glu Met Lys Val
```

```
                    65                  70                  75                  80
Arg Asp Tyr Glu Leu Asp Gln Tyr Gly Val Val Asn Asn Ala Ile Tyr
                85                  90                  95

Ala Ser Tyr Cys Gln His Gly Arg His Glu Leu Leu Glu Ser Val Gly
            100                 105                 110

Ile Ser Ala Asp Ala Val Ala Arg Ser Gly Glu Ser Leu Ala Leu Ser
        115                 120                 125

Glu Leu His Leu Lys Tyr Tyr Ala Pro Leu Arg Ser Gly Asp Lys Phe
    130                 135                 140

Val Val Lys Val Arg Leu Ala Ser Thr Lys Gly Ile Arg Met Ile Phe
145                 150                 155                 160

Glu His Phe Ile Glu Lys Leu Pro Asn Arg Glu Leu Ile Leu Glu Ala
                165                 170                 175

Lys Ala Thr Ala Val Cys Leu Asn Lys Asp Tyr Arg Pro Thr Arg Ile
            180                 185                 190

Ser Pro Glu Phe Leu Ser Lys Leu Gln Phe Phe Thr Ser Glu Gly Ser
        195                 200                 205

Ser Ser
    210

<210> SEQ ID NO 180
<211> LENGTH: 212
<212> TYPE: PRT
<213> ORGANISM: Oryza sativa

<400> SEQUENCE: 180

Met His His Gln Ile Trp Arg Leu Leu Pro Ser Ala Leu Ser Pro Ile
1               5                   10                  15

His Ala Gly Ala Pro Arg Pro Ser Arg Pro Ala Arg Leu Gly Arg
            20                  25                  30

Pro Ser Pro Gln Arg Arg Arg Ala Leu Ala Leu Ala Leu Ala His Leu
        35                  40                  45

Ala Thr Arg Arg Thr Cys Arg Leu Leu Ala Val Ser Ala Gln Ser Ala
    50                  55                  60

Ser Pro His Ala Gly Leu Arg Leu Asp Gln Phe Phe Glu Val Glu Met
65                  70                  75                  80

Lys Val Arg Asp Tyr Glu Leu Asp Gln Tyr Gly Val Val Asn Asn Ala
                85                  90                  95

Ile Tyr Ala Ser Tyr Cys Gln His Gly Arg His Glu Leu Leu Glu Cys
            100                 105                 110

Val Gly Ile Ser Ala Asp Ala Val Ala Arg Ser Gly Glu Ser Leu Ala
        115                 120                 125

Leu Ser Glu Leu His Leu Lys Tyr Tyr Ala Pro Leu Arg Ser Gly Asp
    130                 135                 140

Lys Phe Val Val Lys Val Arg Leu Ala Ser Thr Lys Gly Ile Arg Met
145                 150                 155                 160

Ile Phe Glu His Phe Ile Glu Lys Leu Pro Asn Arg Glu Leu Ile Leu
                165                 170                 175

Glu Ala Lys Ala Thr Ala Val Cys Leu Asn Lys Asp Tyr Arg Pro Thr
            180                 185                 190

Arg Ile Ser Pro Glu Phe Leu Ser Lys Leu Gln Phe Phe Thr Ser Glu
        195                 200                 205

Gly Ser Ser Ser
    210
```

<210> SEQ ID NO 181
<211> LENGTH: 218
<212> TYPE: PRT
<213> ORGANISM: Zea mays

<400> SEQUENCE: 181

Met His His Arg Phe Ala Gly Leu Val Pro Thr Ala Arg Pro Ala Leu
1               5                   10                  15

Pro Pro Ile His Gly Gly Val Val Gly Arg Ser Tyr Pro Pro Val His
            20                  25                  30

Arg Ser Leu Ala Leu Arg Leu Ala Pro Phe Ala Ser Ala Ser Val Arg
        35                  40                  45

Arg Ala Cys Arg Pro Leu Ala Val Ser Ala Gln Ser Thr Ser Leu Arg
    50                  55                  60

Pro Glu Lys Phe Phe Glu Val Glu Met Lys Val Arg Asp Tyr Glu Ile
65                  70                  75                  80

Asp Gln Tyr Gly Val Val Asn Asn Ala Ile Tyr Ala Ser Tyr Cys Gln
                85                  90                  95

His Gly Arg His Glu Leu Leu Glu Ser Val Gly Ile Ser Ala Asp Ala
            100                 105                 110

Val Ala Arg Ser Gly Glu Ser Leu Ala Leu Ser Glu Leu Asn Leu Lys
        115                 120                 125

Tyr Phe Ala Pro Leu Arg Ser Gly Asp Lys Phe Val Val Lys Val Arg
    130                 135                 140

Leu Ala Gly Ile Lys Gly Val Arg Met Ile Phe Asp His Ile Ile Thr
145                 150                 155                 160

Lys Leu Pro Asn His Glu Leu Ile Leu Glu Ala Lys Ala Thr Ala Val
                165                 170                 175

Cys Leu Asn Lys Asp Tyr Tyr Pro Thr Arg Ile Pro Arg Glu Leu Leu
            180                 185                 190

Ser Lys Met Gln Leu Phe Leu Pro Val Asp Ser Arg Gly Ser Asn Glu
        195                 200                 205

Asp Val Asn Asn Arg Asn Asn Ser Cys Asn
    210                 215

<210> SEQ ID NO 182
<211> LENGTH: 223
<212> TYPE: PRT
<213> ORGANISM: Sorghum bicolor

<400> SEQUENCE: 182

Met His His Gln Phe Ala Arg Leu Val Pro Thr Ala Arg Pro Ala Leu
1               5                   10                  15

Pro Pro Ile His Gly Gly Ala Val Gly Arg Ser Ser Pro His Val His
            20                  25                  30

Arg Ala Val Ala Leu Arg Arg Ala Pro Leu Ala Ser Ala Ala Gly Arg
        35                  40                  45

Arg Ala Cys Arg Pro Leu Ala Val Ser Ala Gln Ser Thr Ser Pro Gln
    50                  55                  60

Ala Gly Leu Arg Leu Glu Glu Lys Phe Phe Glu Val Glu Met Lys Val
65                  70                  75                  80

Arg Asp Tyr Glu Leu Asp Gln Tyr Gly Val Val Asn Asn Ala Val Tyr
                85                  90                  95

Ala Ser Tyr Cys Gln His Gly Arg His Glu Leu Leu Glu Ser Val Gly
            100                 105                 110

```
Ile Ser Ala Asp Ala Val Ala Arg Ser Gly Glu Ser Leu Ala Leu Ser
            115                 120                 125

Glu Leu Asn Leu Lys Tyr Phe Gly Pro Leu Arg Ser Gly Asp Lys Phe
    130                 135                 140

Val Val Lys Val Arg Leu Val Gly Ile Lys Gly Val Arg Met Ile Phe
145                 150                 155                 160

Glu His Ile Ile Glu Lys Leu Pro Asn His Glu Leu Ile Leu Glu Ala
                165                 170                 175

Lys Ala Thr Ala Val Cys Leu Asn Lys Asp Tyr Tyr Pro Thr Arg Ile
            180                 185                 190

Pro Arg Glu Leu Leu Ser Lys Met Gln Leu Phe Ser Ser Glu Asp Ser
        195                 200                 205

Arg Gly Ser Asn Lys Asp Val Asn Asn Arg Asn Asn Ser Cys Asn
    210                 215                 220

<210> SEQ ID NO 183
<211> LENGTH: 222
<212> TYPE: PRT
<213> ORGANISM: Phyllostachys edulis

<400> SEQUENCE: 183

Met Leu Ala Leu Arg Ala Ala Pro Val His Ser Thr Ala Met Arg
1               5                   10                  15

His Gln Ile Trp Arg Leu Val Pro Asn Ala Gln Ser Pro Leu Pro Pro
            20                  25                  30

Ile His Ala Asp Ala Arg Arg Ser Cys Ser Arg Thr Val Asn Pro Thr
        35                  40                  45

Pro Leu Arg Leu Pro Ala Leu Ala Ser Ala Ala Thr Arg Gly Ile Cys
    50                  55                  60

Arg Pro Leu Ala Val Ser Ala Gln Ser Ala Ser Pro His Ala Gly Leu
65                  70                  75                  80

Arg Val Asp Lys Phe Phe Glu Val Ala Met Lys Val Arg Asp Tyr Glu
                85                  90                  95

Leu Asp Gln Tyr Gly Val Val Asn Asn Ala Val Tyr Ala Ser Tyr Cys
            100                 105                 110

Gln His Gly Arg His Glu Leu Leu Glu Ser Val Gly Ile Ser Ala Asp
        115                 120                 125

Ala Val Ala Arg Ser Gly Glu Ser Leu Ala Leu Ser Asp Leu His Leu
    130                 135                 140

Lys Phe Phe Ala Pro Leu Arg Ser Gly Asp Glu Phe Val Val Lys Val
145                 150                 155                 160

Arg Leu Ala Ser Ile Lys Gly Val Arg Met Ile Phe Glu His Ser Ile
                165                 170                 175

Glu Lys Leu Pro Asn Arg Glu Leu Ile Leu Glu Ala Lys Ala Thr Ala
            180                 185                 190

Val Cys Leu Asn Lys Asp Tyr Arg Pro Thr Arg Val Ser Pro Glu Phe
        195                 200                 205

Leu Ser Arg Leu Gln Leu Phe Ser Ser Lys Asp Ser Lys Gly
    210                 215                 220

<210> SEQ ID NO 184
<211> LENGTH: 215
<212> TYPE: PRT
<213> ORGANISM: Picea glauca

<400> SEQUENCE: 184
```

```
Met Ala Thr Ala Met Gly Ala Ile Ser Gly Ile Ser Val Gly Val
1               5                   10                  15

Asn Ala Arg Tyr Pro His Val Gln Cys Ser Ser Phe Ile Gln Asn Pro
            20                  25                  30

Thr Lys Lys Leu Ser Arg Ala Leu Ala Phe Pro Ser Leu Arg Thr Ala
        35                  40                  45

Ser Cys Asn Pro Val Phe Arg Arg Ala Leu Pro Pro Ile Ala Asp Met
50                  55                  60

Tyr Asn Met Glu Leu Phe Gly Ala Lys Gly Met Ala Arg Pro Phe Glu
65                  70                  75                  80

Leu Glu Leu Lys Val Arg Asp Tyr Glu Leu Asp Gln Tyr Gly Val Val
                85                  90                  95

Asn Asn Ala Thr Tyr Ala Ser Tyr Cys Gln His Cys Arg His Glu Leu
            100                 105                 110

Cys Glu Ala Ile Gly Phe Ser Pro Asp Ala Ile Ala Arg Thr Gly Asn
        115                 120                 125

Ala Leu Ala Leu Ser Glu Leu Ser Leu Lys Tyr Leu Ala Pro Leu Arg
130                 135                 140

Ser Gly Asp Ser Phe Val Val Thr Ala Arg Ile Ser Gly Ser Ser Ala
145                 150                 155                 160

Val Arg Leu Phe Phe Glu His Phe Ile Tyr Lys Leu Pro Asn Arg Glu
                165                 170                 175

Pro Val Leu Glu Ala Lys Ala Thr Ala Val Tyr Leu Asp Lys Ile Tyr
            180                 185                 190

Arg Pro Val Arg Leu Pro Ala Asp Phe Lys Ser Lys Ile Thr Leu Phe
        195                 200                 205

Leu Arg Asn Glu Glu Leu Asn
    210                 215

<210> SEQ ID NO 185
<211> LENGTH: 206
<212> TYPE: PRT
<213> ORGANISM: Gossypium hirsutum

<400> SEQUENCE: 185

Met Leu Gln Ala Ser Val Phe Pro Ala His Ala Ala Leu Pro Ser Pro
1               5                   10                  15

Arg Pro Asn Ala Thr Phe Leu Asn Leu His Arg Pro Ser Ser Ser Phe
            20                  25                  30

Pro Ile Ser Pro Leu Leu Met Pro Leu Arg Val Pro Thr Leu Ser Thr
        35                  40                  45

Ser Arg Ser Phe Thr Val Gly Ala Leu Phe Asp Leu Lys Gly Gly Gln
50                  55                  60

Gly Met Thr Ser Phe His Glu Val Glu Leu Lys Val Arg Asp Tyr Glu
65                  70                  75                  80

Leu Asp Gln Tyr Gly Val Val Asn Asn Ala Val Tyr Ala Ser Tyr Cys
                85                  90                  95

Gln His Gly Arg His Glu Leu Leu Glu Ser Ile Gly Ile Ser Cys Asp
            100                 105                 110

Glu Val Ala Arg Thr Gly Asp Ser Leu Ala Leu Ser Glu Leu Ser Leu
        115                 120                 125

Lys Phe Leu Gly Pro Leu Arg Ser Gly Asp Asn Phe Val Val Lys Val
130                 135                 140

Arg Val Ser Asn Ser Ser Gly Ala Arg Leu Tyr Phe Glu His Phe Ile
145                 150                 155                 160
```

```
Phe Lys Met Pro Asn Glu Val Pro Ile Leu Glu Ala Lys Ala Thr Ala
                165                 170                 175

Val Trp Leu Asp Lys Asn Tyr Arg Pro Ala Arg Ile Pro Pro Glu Phe
            180                 185                 190

Arg Ser Lys Phe Val Gln Phe Leu Arg Cys Glu Glu Pro Ser
        195                 200                 205

<210> SEQ ID NO 186
<211> LENGTH: 204
<212> TYPE: PRT
<213> ORGANISM: Glycine max

<400> SEQUENCE: 186

Met Leu Tyr Asn His Thr Ser Ser Met Ser Leu Pro Ser Pro Leu Tyr
1               5                   10                  15

Leu Asn Thr Thr Ser Phe Arg Leu Thr Arg Gln Ser Pro Phe Pro Phe
            20                  25                  30

Pro Arg Arg Arg Phe Asn Pro Pro Ala Phe Arg Ser Val Ser Pro Leu
        35                  40                  45

Ser Ser Ser Pro Ser Ala Ser Leu Phe Asp Leu Arg Gly Gly Lys Gly
    50                  55                  60

Met Ser Gly Phe His Asp Val Glu Leu Lys Val Arg Asp Tyr Glu Leu
65                  70                  75                  80

Asp Gln Tyr Gly Val Val Asn Asn Ala Val Tyr Ala Ser Tyr Cys Gln
                85                  90                  95

His Gly Arg His Glu Leu Leu Gln Asn Ile Gly Ile Asn Cys Asp Ala
            100                 105                 110

Val Ala Arg Ser Gly Asp Ala Leu Ala Leu Ser Glu Leu Ser Leu Lys
        115                 120                 125

Phe Leu Ala Pro Leu Arg Ser Gly Asp Lys Phe Val Val Arg Val Arg
    130                 135                 140

Ile Ser Gly Ser Ser Ala Ala Arg Leu Tyr Phe Asp His Phe Ile Tyr
145                 150                 155                 160

Lys Leu Pro Asn Gln Glu Pro Ile Leu Glu Ala Lys Ala Ile Ala Val
                165                 170                 175

Arg Leu Asp Lys Asn Tyr Arg Pro Ile Arg Ile Pro Ala Glu Met Lys
            180                 185                 190

Ser Lys Phe Val Lys Phe Ile Arg Ile Glu Asp Ser
        195                 200

<210> SEQ ID NO 187
<211> LENGTH: 223
<212> TYPE: PRT
<213> ORGANISM: Saccharum sp.
<220> FEATURE:
<221> NAME/KEY: MOD_RES
<222> LOCATION: (205)..(205)
<223> OTHER INFORMATION: Any amino acid

<400> SEQUENCE: 187

Met His His Gln Phe Ala Arg Leu Val Pro Ala Ala Arg Pro Ala Leu
1               5                   10                  15

Pro Pro Ile His Gly Gly Ala Val Gly Arg Ser Ser Pro Val His
            20                  25                  30

Arg Ala Val Ala Leu Arg Arg Ala Pro Leu Ala Ser Ala Ala Gly Arg
        35                  40                  45

Arg Ala Tyr Arg Pro Leu Ala Val Ser Ala Gln Ser Thr Ser Pro Gln
```

Ala Gly Leu Arg Leu Glu Glu Lys Phe Phe Glu Val Glu Met Lys Val
65                  70                  75                  80

Arg Asp Tyr Glu Leu Asp Gln Tyr Gly Val Val Asn Asn Ala Val Tyr
            85                  90                  95

Ala Ser Tyr Cys Gln His Gly Arg His Glu Val Leu Glu Ser Val Gly
        100                 105                 110

Ile Ser Ala Asp Ala Val Ala Arg Ser Gly Glu Ser Leu Ala Leu Ser
    115                 120                 125

Glu Leu Asn Leu Lys Tyr Phe Ala Pro Leu Arg Ser Gly Asp Lys Phe
130                 135                 140

Val Val Lys Val Arg Leu Val Gly Ile Lys Gly Ile Arg Met Ile Phe
145                 150                 155                 160

Glu His Ile Ile Glu Lys Leu Pro Asn His Glu Leu Ile Leu Glu Ala
                165                 170                 175

Lys Ala Thr Ala Val Cys Leu Asn Lys Asp Tyr Tyr Pro Thr Arg Ile
            180                 185                 190

Pro Arg Glu Leu Leu Ala Lys Met Gln Leu Phe Ser Xaa Arg Gly Ser
        195                 200                 205

Arg Gly Thr Asn Asp Asp Ile Asn Asn Arg Asn Asn Ser Cys Asn
    210                 215                 220

<210> SEQ ID NO 188
<211> LENGTH: 142
<212> TYPE: PRT
<213> ORGANISM: Artificial Sequence
<220> FEATURE:
<223> OTHER INFORMATION: Synthetic polypeptide

<400> SEQUENCE: 188

Met Ala Ser Glu Phe His Glu Val Glu Leu Lys Val Arg Asp Tyr Glu
1               5                   10                  15

Leu Asp Gln Phe Gly Val Val Asn Asn Ala Val Tyr Ala Asn Tyr Cys
            20                  25                  30

Gln His Gly Arg His Glu Phe Leu Glu Ser Ile Gly Ile Asn Cys Asp
        35                  40                  45

Glu Val Ala Arg Ser Gly Glu Ala Leu Ala Ile Ser Glu Leu Thr Met
    50                  55                  60

Lys Phe Leu Ser Pro Leu Arg Ser Gly Asp Lys Phe Val Val Lys Ala
65                  70                  75                  80

Arg Ile Ser Gly Thr Ser Ala Ala Arg Ile Tyr Phe Asp His Phe Ile
                85                  90                  95

Phe Lys Leu Pro Asn Gln Glu Pro Ile Leu Glu Ala Lys Gly Ile Ala
            100                 105                 110

Val Trp Leu Asp Asn Lys Tyr Arg Pro Val Arg Ile Pro Ser Ser Ile
        115                 120                 125

Arg Ser Lys Phe Val His Phe Leu Arg Gln Asp Asp Ala Val
    130                 135                 140

<210> SEQ ID NO 189
<211> LENGTH: 142
<212> TYPE: PRT
<213> ORGANISM: Artificial Sequence
<220> FEATURE:
<223> OTHER INFORMATION: Synthetic polypeptide

<400> SEQUENCE: 189

Met Ala Ser Glu Phe His Glu Val Glu Leu Lys Val Arg Asp Tyr Glu
1               5                   10                  15

Leu Asp Gln Phe Gly Val Val Asn Asn Ala Val Tyr Ala Asn Tyr Cys
            20                  25                  30

Gln His Gly Met His Glu Phe Leu Glu Ser Ile Gly Ile Asn Cys Asp
        35                  40                  45

Glu Val Ala Arg Ser Gly Glu Ala Leu Ala Ile Ser Glu Leu Thr Met
    50                  55                  60

Asn Phe Leu Ala Pro Leu Arg Ser Gly Asp Lys Phe Val Lys Val
65                  70                  75                  80

Asn Ile Ser Arg Thr Ser Ala Ala Arg Ile Tyr Phe Asp His Ser Ile
                85                  90                  95

Leu Lys Leu Pro Asn Gln Glu Val Ile Leu Glu Ala Lys Ala Thr Val
            100                 105                 110

Val Trp Leu Asp Asn Lys His Arg Pro Val Arg Ile Pro Ser Ser Ile
            115                 120                 125

Arg Ser Lys Phe Val His Phe Leu Arg Gln Asn Asp Thr Val
            130                 135                 140

<210> SEQ ID NO 190
<211> LENGTH: 143
<212> TYPE: PRT
<213> ORGANISM: Artificial Sequence
<220> FEATURE:
<223> OTHER INFORMATION: Synthetic polypeptide

<400> SEQUENCE: 190

Met Ala Asn Gly Val His Glu Ile Glu Leu Lys Val Arg Asp Tyr Glu
1               5                   10                  15

Leu Asp Gln Phe Gly Val Val Asn Asn Ala Val Tyr Ala Asn Tyr Cys
            20                  25                  30

Gln His Gly Gln His Glu Phe Met Gly Thr Ile Gly Ile Asn Cys Asp
        35                  40                  45

Glu Val Ser Arg Ser Gly Glu Ala Leu Ala Val Ser Glu Leu Thr Ile
    50                  55                  60

Lys Phe Leu Ala Pro Leu Arg Ser Gly Cys Lys Phe Val Val Lys Thr
65                  70                  75                  80

Arg Ile Ser Gly Thr Ser Met Thr Arg Ile Tyr Phe Glu Gln Phe Ile
                85                  90                  95

Phe Lys Leu Pro Asn Gln Glu Pro Ile Leu Glu Ala Lys Gly Met Ala
            100                 105                 110

Val Trp Leu Asp Lys Arg Tyr Arg Pro Val Cys Ile Pro Ser Tyr Ile
            115                 120                 125

Arg Ser Asn Phe Gly His Phe Gln Arg Gln His Val Val Glu Tyr
            130                 135                 140

<210> SEQ ID NO 191
<211> LENGTH: 141
<212> TYPE: PRT
<213> ORGANISM: Artificial Sequence
<220> FEATURE:
<223> OTHER INFORMATION: Synthetic polypeptide

<400> SEQUENCE: 191

Met Ala Ser Gly Leu Val Glu Val Glu Leu Lys Val Arg Asp Tyr Glu
1               5                   10                  15

Leu Asp Gln Phe Gly Val Val Asn Asn Ala Val Tyr Ala Ser Tyr Cys
            20                  25                  30

Gln His Gly Arg His Glu Leu Leu Glu Arg Ile Gly Val Ser Ala Asp
        35                  40                  45

Val Val Ala Arg Thr Gly Asp Ala Leu Ala Leu Ser Glu Leu Ser Leu
 50                  55                  60

Lys Phe Leu Ala Pro Leu Arg Ser Gly Asp Arg Phe Val Val Lys Val
 65                  70                  75                  80

Arg Ile Ser Gly Ser Ser Ala Ala Arg Leu Tyr Phe Glu His Phe Ile
                 85                  90                  95

Phe Arg Leu Pro Asn Glu Glu Pro Ile Leu Glu Ala Lys Ala Thr Ala
            100                 105                 110

Val Trp Leu Asp Lys Lys Tyr His Pro Val Arg Ile Pro Pro Glu Phe
            115                 120                 125

Arg Ser Lys Phe Val Gln Phe Leu Arg His Glu Glu Ser
            130                 135                 140

<210> SEQ ID NO 192
<211> LENGTH: 142
<212> TYPE: PRT
<213> ORGANISM: Artificial Sequence
<220> FEATURE:
<223> OTHER INFORMATION: Synthetic polypeptide

<400> SEQUENCE: 192

Met Ala Asn Ser Phe Val Gly Val Glu Leu Lys Val Arg Asp Tyr Glu
 1               5                  10                  15

Leu Asp Gln Tyr Gly Val Val Asn Asn Ala Val Tyr Ala Ser Tyr Cys
                20                  25                  30

Gln His Gly Arg His Glu Leu Leu Glu Arg Ile Gly Val Ser Ala Asp
        35                  40                  45

Ala Val Ala Arg Thr Gly Asp Ala Leu Ala Leu Ser Glu Leu Ser Leu
 50                  55                  60

Lys Phe Leu Ala Pro Leu Arg Ser Gly Asp Arg Phe Val Val Lys Val
 65                  70                  75                  80

Arg Ile Ser Gly Ser Ser Ala Ala Arg Leu Tyr Phe Asp His Phe Ile
                 85                  90                  95

Phe Lys Leu Pro Asn Glu Glu Pro Ile Leu Glu Ala Lys Ala Thr Ala
            100                 105                 110

Val Trp Leu Asp Lys Asn Tyr Arg Pro Val Arg Ile Pro Ser Asp Met
            115                 120                 125

Arg Ser Lys Leu Val Gln Phe Leu Lys His Glu Glu Ser Asn
            130                 135                 140

<210> SEQ ID NO 193
<211> LENGTH: 142
<212> TYPE: PRT
<213> ORGANISM: Artificial Sequence
<220> FEATURE:
<223> OTHER INFORMATION: Synthetic polypeptide

<400> SEQUENCE: 193

Met Ala Ser Gly Phe Leu Asp Val Glu Leu Lys Val Arg Asp Tyr Glu
 1               5                  10                  15

Leu Asp Gln Tyr Gly Val Val Asn Asn Ala Val Tyr Ala Ser Tyr Cys
                20                  25                  30

Gln His Gly Arg His Glu Leu Leu Glu Lys Ile Gly Val Asn Ala Asp
        35                  40                  45

Ala Val Ala Arg Thr Gly Asp Ala Leu Ala Leu Ser Glu Leu Thr Leu

```
                50                  55                  60
Lys Phe Leu Ala Pro Leu Arg Ser Gly Asp Arg Phe Val Val Lys Val
 65                  70                  75                  80

Arg Val Ser Asp Ser Ser Ala Ala Arg Leu Tyr Phe Glu His Phe Ile
                 85                  90                  95

Phe Lys Leu Pro Asn Glu Glu Pro Ile Leu Glu Ala Arg Ala Thr Ala
                100                 105                 110

Val Cys Leu Asp Lys Asn Tyr Arg Pro Val Arg Ile Pro Thr Glu Ile
                115                 120                 125

Arg Ser Lys Leu Val Gln Phe Leu Arg His Glu Glu Ser His
            130                 135                 140

<210> SEQ ID NO 194
<211> LENGTH: 142
<212> TYPE: PRT
<213> ORGANISM: Artificial Sequence
<220> FEATURE:
<223> OTHER INFORMATION: Synthetic polypeptide

<400> SEQUENCE: 194

Met Ala Ser Gly Phe Leu Asp Val Glu Leu Lys Val Arg Asp Tyr Glu
  1               5                  10                  15

Leu Asp Gln Tyr Gly Val Val Asn Asn Ala Val Tyr Ala Ser Tyr Cys
                 20                  25                  30

Gln His Gly Arg His Glu Leu Leu Glu Lys Ile Gly Leu Asn Ala Asp
                 35                  40                  45

Ala Val Ala Cys Ile Gly Asp Ala Val Ala Leu Ser Glu Leu Thr Leu
             50                  55                  60

Lys Phe Leu Ala Pro Leu Arg Ser Gly Asp Arg Phe Val Val Lys Val
 65                  70                  75                  80

Arg Val Ser Asp Ala Ser Ala Ala Arg Leu Tyr Phe Glu His Phe Ile
                 85                  90                  95

Phe Lys Leu Pro Asn Glu Glu Pro Ile Leu Glu Ala Arg Ala Thr Gly
                100                 105                 110

Val Cys Leu Asp Lys Asn Tyr Arg Pro Val Arg Ile Pro Thr Glu Ile
                115                 120                 125

Arg Ser Ile Leu Val Gln Phe Leu Arg His Glu Glu Ser His
            130                 135                 140

<210> SEQ ID NO 195
<211> LENGTH: 146
<212> TYPE: PRT
<213> ORGANISM: Artificial Sequence
<220> FEATURE:
<223> OTHER INFORMATION: Synthetic polypeptide

<400> SEQUENCE: 195

Met Ala Gly Leu Arg Leu Asp Gln Phe Phe Glu Val Glu Met Lys Val
  1               5                  10                  15

Arg Asp Tyr Glu Leu Asp Gln Tyr Gly Val Val Asn Asn Ala Ile Tyr
                 20                  25                  30

Ala Ser Tyr Cys Gln His Gly Arg His Glu Leu Leu Glu Ser Val Gly
                 35                  40                  45

Ile Ser Ala Asp Ala Val Ala Arg Ser Gly Glu Ser Leu Ala Leu Ser
             50                  55                  60

Glu Leu His Leu Lys Tyr Tyr Ala Pro Leu Arg Ser Gly Asp Lys Phe
 65                  70                  75                  80
```

Val Val Lys Val Arg Leu Ala Ser Thr Lys Gly Ile Arg Met Ile Phe
                85                  90                  95

Glu His Phe Ile Glu Lys Leu Pro Asn Arg Glu Leu Ile Leu Glu Ala
            100                 105                 110

Lys Ala Thr Ala Val Cys Leu Asn Lys Asp Tyr Arg Pro Thr Arg Ile
        115                 120                 125

Ser Pro Glu Phe Leu Ser Lys Leu Gln Phe Phe Thr Ser Glu Gly Ser
    130                 135                 140

Ser Ser
145

<210> SEQ ID NO 196
<211> LENGTH: 146
<212> TYPE: PRT
<213> ORGANISM: Artificial Sequence
<220> FEATURE:
<223> OTHER INFORMATION: Synthetic polypeptide

<400> SEQUENCE: 196

Met Ala Gly Leu Arg Leu Asp Gln Phe Phe Glu Val Glu Met Lys Val
1               5                   10                  15

Arg Asp Tyr Glu Leu Asp Gln Tyr Gly Val Val Asn Asn Ala Ile Tyr
            20                  25                  30

Ala Cys Tyr Cys Gln His Gly Arg His Glu Leu Leu Glu Ser Val Gly
        35                  40                  45

Ile Ser Ala Asp Ala Val Ala Arg Ser Gly Glu Ser Leu Ala Leu Ser
    50                  55                  60

Glu Leu His Leu Lys Tyr Tyr Ala Pro Leu Arg Ser Gly Asp Lys Phe
65                  70                  75                  80

Val Val Lys Val Arg Leu Ala Ser Thr Lys Gly Ile Arg Met Ile Phe
                85                  90                  95

Glu His Phe Ile Glu Lys Leu Pro Asn Arg Glu Leu Ile Leu Glu Ala
            100                 105                 110

Lys Ala Thr Ala Val Cys Leu Asn Lys Asp Tyr Arg Pro Thr Arg Ile
        115                 120                 125

Ser Pro Glu Phe Leu Ser Lys Leu Gln Phe Phe Thr Ser Glu Gly Ser
    130                 135                 140

Ser Ser
145

<210> SEQ ID NO 197
<211> LENGTH: 146
<212> TYPE: PRT
<213> ORGANISM: Artificial Sequence
<220> FEATURE:
<223> OTHER INFORMATION: Synthetic polypeptide

<400> SEQUENCE: 197

Met Ala Gly Leu Arg Val Asp Lys Phe Phe Glu Val Ala Met Lys Val
1               5                   10                  15

Arg Asp Tyr Glu Leu Asp Gln Tyr Gly Val Val Asn Asn Ala Val Tyr
            20                  25                  30

Ala Ser Tyr Cys Gln His Gly Arg His Glu Leu Leu Glu Ser Val Gly
        35                  40                  45

Ile Ser Ala Asp Ala Val Ala Arg Ser Gly Glu Ser Leu Ala Leu Ser
    50                  55                  60

Asp Leu His Leu Lys Phe Phe Ala Pro Leu Arg Ser Gly Asp Glu Phe
65                  70                  75                  80

```
Val Val Lys Val Arg Leu Ala Ser Ile Lys Gly Val Arg Met Ile Phe
            85                  90                  95

Glu His Ser Ile Glu Lys Leu Pro Asn Arg Glu Leu Ile Leu Glu Ala
            100                 105                 110

Lys Ala Thr Ala Val Cys Leu Asn Lys Asp Tyr Arg Pro Thr Arg Val
            115                 120                 125

Ser Pro Glu Phe Leu Ser Arg Leu Gln Leu Phe Ser Ser Lys Asp Ser
            130                 135                 140

Lys Gly
145

<210> SEQ ID NO 198
<211> LENGTH: 155
<212> TYPE: PRT
<213> ORGANISM: Artificial Sequence
<220> FEATURE:
<223> OTHER INFORMATION: Synthetic polypeptide

<400> SEQUENCE: 198

Met Ala Glu Lys Phe Phe Glu Val Glu Met Lys Val Arg Asp Tyr Glu
1               5                   10                  15

Ile Asp Gln Tyr Gly Val Val Asn Asn Ala Ile Tyr Ala Ser Tyr Cys
            20                  25                  30

Gln His Gly Arg His Glu Leu Leu Glu Ser Val Gly Ile Ser Ala Asp
            35                  40                  45

Ala Val Ala Arg Ser Gly Glu Ser Leu Ala Leu Ser Glu Leu Asn Leu
            50                  55                  60

Lys Tyr Phe Ala Pro Leu Arg Ser Gly Asp Lys Phe Val Val Lys Val
65                  70                  75                  80

Arg Leu Ala Gly Ile Lys Gly Val Arg Met Ile Phe Asp His Ile Ile
            85                  90                  95

Thr Lys Leu Pro Asn His Glu Leu Ile Leu Glu Ala Lys Ala Thr Ala
            100                 105                 110

Val Cys Leu Asn Lys Asp Tyr Tyr Pro Thr Arg Ile Pro Arg Glu Leu
            115                 120                 125

Leu Ser Lys Met Gln Leu Phe Leu Pro Val Asp Ser Arg Gly Ser Asn
            130                 135                 140

Glu Asp Val Asn Arg Asn Asn Ser Cys Asn
145                 150                 155

<210> SEQ ID NO 199
<211> LENGTH: 160
<212> TYPE: PRT
<213> ORGANISM: Artificial Sequence
<220> FEATURE:
<223> OTHER INFORMATION: Synthetic polypeptide

<400> SEQUENCE: 199

Met Ala Gly Leu Arg Leu Glu Glu Lys Phe Phe Glu Val Glu Met Lys
1               5                   10                  15

Val Arg Asp Tyr Glu Leu Asp Gln Tyr Gly Val Val Asn Asn Ala Val
            20                  25                  30

Tyr Ala Ser Tyr Cys Gln His Gly Arg His Glu Leu Leu Glu Ser Val
            35                  40                  45

Gly Ile Ser Ala Asp Ala Val Ala Arg Ser Gly Glu Ser Leu Ala Leu
            50                  55                  60

Ser Glu Leu Asn Leu Lys Tyr Phe Gly Pro Leu Arg Ser Gly Asp Lys
```

```
                65                  70                  75                  80
Phe Val Val Lys Val Arg Leu Val Gly Ile Lys Gly Val Arg Met Ile
                    85                  90                  95
Phe Glu His Ile Ile Glu Lys Leu Pro Asn His Glu Leu Ile Leu Glu
                   100                 105                 110
Ala Lys Ala Thr Ala Val Cys Leu Asn Lys Asp Tyr Tyr Pro Thr Arg
                   115                 120                 125
Ile Pro Arg Glu Leu Leu Ser Lys Met Gln Leu Phe Ser Ser Glu Asp
                   130                 135                 140
Ser Arg Gly Ser Asn Lys Asp Val Asn Arg Asn Asn Ser Cys Asn
145                 150                 155                 160
```

<210> SEQ ID NO 200
<211> LENGTH: 141
<212> TYPE: PRT
<213> ORGANISM: Artificial Sequence
<220> FEATURE:
<223> OTHER INFORMATION: Synthetic polypeptide

<400> SEQUENCE: 200

```
Met Asn Glu Phe His Glu Val Glu Leu Lys Val Arg Asp Tyr Glu Leu
1               5                   10                  15
Asp Gln Tyr Gly Val Val Asn Asn Ala Ile Tyr Ala Ser Tyr Cys Gln
                    20                  25                  30
His Cys Arg His Glu Leu Leu Glu Arg Ile Gly Ile Ser Ala Asp Glu
                    35                  40                  45
Val Ala Arg Asn Gly Asp Ala Leu Ala Leu Thr Glu Leu Ser Leu Lys
                    50                  55                  60
Tyr Leu Ala Pro Leu Arg Ser Gly Asp Arg Phe Val Val Lys Ala Arg
65                  70                  75                  80
Ile Ser Asp Ser Ser Ala Ala Arg Leu Phe Phe Glu His Phe Ile Phe
                    85                  90                  95
Lys Leu Pro Asp Gln Glu Pro Ile Leu Glu Ala Arg Gly Ile Ala Val
                   100                 105                 110
Trp Leu Asn Lys Ser Tyr Arg Pro Val Arg Ile Pro Ser Glu Phe Arg
                   115                 120                 125
Ser Lys Phe Val Gln Phe Leu Arg Gln Glu Ala Ser Asn
                   130                 135                 140
```

<210> SEQ ID NO 201
<211> LENGTH: 141
<212> TYPE: PRT
<213> ORGANISM: Artificial Sequence
<220> FEATURE:
<223> OTHER INFORMATION: Synthetic polypeptide

<400> SEQUENCE: 201

```
Met Asn Glu Phe His Glu Val Glu Leu Lys Val Arg Asp Tyr Glu Leu
1               5                   10                  15
Asp Gln Tyr Gly Val Val Asn Asn Ala Ile Tyr Ala Ser Tyr Cys Gln
                    20                  25                  30
His Cys Arg His Glu Leu Leu Glu Lys Ile Gly Val Asn Ala Asp Ala
                    35                  40                  45
Val Ala Arg Asn Gly Glu Ala Leu Ala Leu Thr Glu Leu Thr Leu Lys
                    50                  55                  60
Tyr Leu Ala Pro Leu Arg Ser Gly Asp Arg Phe Val Val Lys Val Arg
65                  70                  75                  80
```

```
Ile Ser Asp Ser Ser Ala Ala Arg Leu Phe Phe Glu His Phe Ile Phe
            85                  90                  95

Lys Leu Pro Asp Gln Glu Pro Ile Leu Glu Ala Arg Gly Thr Ala Val
        100                 105                 110

Trp Leu Asn Lys Ser Tyr Arg Pro Val Arg Ile Pro Ser Glu Phe Arg
            115                 120                 125

Ser Lys Phe Val Gln Phe Leu Arg Gln Glu Ala Ser Asn
        130                 135                 140
```

<210> SEQ ID NO 202
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 202

```
Met Ser Asp Gln Val Tyr His His Glu Val Glu Leu Lys Val Arg Asp
1               5                   10                  15

Tyr Glu Leu Asp Gln Tyr Gly Val Val Asn Asn Ala Ile Tyr Ala Ser
            20                  25                  30

Tyr Cys Gln His Cys Arg His Glu Leu Leu Glu Lys Ile Gly Val Asn
        35                  40                  45

Ala Asp Ala Val Ala Arg Asn Gly Glu Ala Leu Ala Leu Thr Glu Met
    50                  55                  60

Thr Leu Lys Tyr Leu Ala Pro Leu Arg Ser Gly Asp Arg Phe Ile Val
65                  70                  75                  80

Lys Val Arg Ile Ser Asp Ser Ser Ala Ala Arg Leu Phe Phe Glu His
                85                  90                  95

Phe Ile Phe Lys Leu Pro Asp Gln Glu Pro Ile Leu Glu Ala Arg Gly
            100                 105                 110

Thr Ala Val Trp Leu Asn Lys Ser Tyr Arg Pro Val Arg Ile Pro Ser
        115                 120                 125

Glu Phe Arg Ser Lys Phe Val Gln Phe Leu His Gln Lys Ser Cys Gly
    130                 135                 140

Val Gln His His Leu
145
```

<210> SEQ ID NO 203
<211> LENGTH: 139
<212> TYPE: PRT
<213> ORGANISM: Artificial Sequence
<220> FEATURE:
<223> OTHER INFORMATION: Synthetic polypeptide

<400> SEQUENCE: 203

```
Met Asn Glu Phe His Asp Val Glu Leu Thr Val Arg Asp Tyr Glu Leu
1               5                   10                  15

Asp Gln Phe Gly Val Val Asn Asn Ala Thr Tyr Ala Ser Tyr Cys Gln
            20                  25                  30

His Cys Arg His Ala Phe Leu Glu Lys Ile Gly Val Ser Val Asp Glu
        35                  40                  45

Val Thr Arg Asn Gly Asp Ala Leu Ala Val Thr Glu Leu Ser Leu Lys
    50                  55                  60

Phe Leu Ala Pro Leu Arg Ser Gly Asp Arg Phe Val Val Arg Ala Arg
65                  70                  75                  80

Leu Ser His Phe Thr Val Ala Arg Leu Phe Phe Glu His Phe Ile Phe
                85                  90                  95
```

```
Lys Leu Pro Asp Gln Glu Pro Ile Leu Glu Ala Arg Gly Ile Ala Val
            100                 105                 110
Trp Leu Asn Arg Ser Tyr Arg Pro Ile Arg Ile Pro Ser Glu Phe Asn
            115                 120                 125
Ser Lys Phe Val Lys Phe Leu Arg Gln Glu Ala
    130                 135

<210> SEQ ID NO 204
<211> LENGTH: 150
<212> TYPE: PRT
<213> ORGANISM: Artificial Sequence
<220> FEATURE:
<223> OTHER INFORMATION: Synthetic polypeptide

<400> SEQUENCE: 204

Met Ala Ser Asp Gln Val Tyr His His Glu Val Glu Leu Lys Val Arg
1               5                   10                  15
Asp Tyr Glu Leu Asp Gln Tyr Gly Val Val Asn Asn Ala Ile Tyr Ala
            20                  25                  30
Ser Tyr Cys Gln His Cys Arg His Ala Phe Leu Glu Lys Ile Gly Val
        35                  40                  45
Ser Val Asp Glu Val Thr Arg Asn Gly Asp Ala Leu Ala Val Thr Glu
    50                  55                  60
Leu Ser Leu Lys Phe Leu Ala Pro Leu Arg Ser Gly Asp Arg Phe Val
65                  70                  75                  80
Val Arg Ala Arg Leu Ser His Phe Thr Val Ala Arg Leu Phe Phe Glu
                85                  90                  95
His Phe Ile Phe Lys Leu Pro Asp Gln Glu Pro Ile Leu Glu Ala Arg
            100                 105                 110
Gly Ile Ala Val Trp Leu Asn Arg Ser Tyr Arg Pro Ile Arg Ile Pro
            115                 120                 125
Ser Glu Phe Asn Ser Lys Phe Val Lys Phe Leu His Gln Lys Ser Cys
    130                 135                 140
Gly Val Gln His His Leu
145                 150

<210> SEQ ID NO 205
<211> LENGTH: 150
<212> TYPE: PRT
<213> ORGANISM: Artificial Sequence
<220> FEATURE:
<223> OTHER INFORMATION: Synthetic polypeptide

<400> SEQUENCE: 205

Met Ala Ser Asp Gln Val Tyr His His Asp Val Glu Leu Thr Val Arg
1               5                   10                  15
Asp Tyr Glu Leu Asp Gln Phe Gly Val Val Asn Asn Ala Thr Tyr Ala
            20                  25                  30
Ser Tyr Cys Gln His Cys Arg His Ala Phe Leu Glu Lys Ile Gly Val
        35                  40                  45
Ser Val Asp Glu Val Thr Arg Asn Gly Asp Ala Leu Ala Val Thr Glu
    50                  55                  60
Leu Ser Leu Lys Phe Leu Ala Pro Leu Arg Ser Gly Asp Arg Phe Val
65                  70                  75                  80
Val Arg Ala Arg Leu Ser His Phe Thr Val Ala Arg Leu Phe Phe Glu
                85                  90                  95
His Phe Ile Phe Lys Leu Pro Asp Gln Glu Pro Ile Leu Glu Ala Arg
```

```
                100             105             110
Gly Ile Ala Val Trp Leu Asn Lys Ser Tyr Arg Pro Val Arg Ile Pro
            115                 120                 125

Ala Glu Phe Arg Ser Lys Phe Val Gln Phe Leu Arg Gln Lys Ser Cys
        130                 135                 140

Gly Val Gln His His Leu
145             150

<210> SEQ ID NO 206
<211> LENGTH: 141
<212> TYPE: PRT
<213> ORGANISM: Artificial Sequence
<220> FEATURE:
<223> OTHER INFORMATION: Synthetic polypeptide

<400> SEQUENCE: 206

Met Ala Glu Phe His Asp Val Glu Leu Thr Val Arg Asp Tyr Glu Leu
1               5                   10                  15

Asp Gln Phe Gly Val Val Asn Asn Ala Thr Tyr Ala Ser Tyr Cys Gln
            20                  25                  30

His Gly Arg His Glu Leu Leu Glu Arg Ile Gly Ile Ser Ala Asp Glu
        35                  40                  45

Val Ala Arg Ser Gly Asp Ala Leu Ala Leu Thr Glu Leu Ser Leu Lys
    50                  55                  60

Tyr Leu Ala Pro Leu Arg Ser Gly Asp Arg Phe Val Val Lys Ala Arg
65                  70                  75                  80

Ile Ser Asp Ser Ser Ala Ala Arg Leu Phe Phe Glu His Phe Ile Phe
                85                  90                  95

Lys Leu Pro Asp Gln Glu Pro Ile Leu Glu Ala Arg Gly Ile Ala Val
            100                 105                 110

Trp Leu Asn Lys Ser Tyr Arg Pro Val Arg Ile Pro Ala Glu Phe Arg
        115                 120                 125

Ser Lys Phe Val Gln Phe Leu Arg Gln Glu Ala Ser Asn
    130                 135                 140

<210> SEQ ID NO 207
<211> LENGTH: 141
<212> TYPE: PRT
<213> ORGANISM: Artificial Sequence
<220> FEATURE:
<223> OTHER INFORMATION: Synthetic polypeptide

<400> SEQUENCE: 207

Met Ala Glu Phe His Glu Val Glu Leu Lys Val Arg Asp Tyr Glu Leu
1               5                   10                  15

Asp Gln Tyr Gly Val Val Asn Asn Ala Ile Tyr Ala Ser Tyr Cys Gln
            20                  25                  30

His Gly Arg His Glu Leu Leu Glu Arg Ile Gly Ile Ser Ala Asp Glu
        35                  40                  45

Val Ala Arg Ser Gly Asp Ala Leu Ala Leu Thr Glu Leu Ser Leu Lys
    50                  55                  60

Tyr Leu Ala Pro Leu Arg Ser Gly Asp Arg Phe Val Val Lys Ala Arg
65                  70                  75                  80

Ile Ser Asp Ser Ser Ala Ala Arg Leu Phe Phe Glu His Phe Ile Phe
                85                  90                  95

Lys Leu Pro Asp Gln Glu Pro Ile Leu Glu Ala Arg Gly Ile Ala Val
            100                 105                 110
```

```
Trp Leu Asn Arg Ser Tyr Arg Pro Ile Arg Ile Pro Ser Glu Phe Asn
            115                 120                 125

Ser Lys Phe Val Lys Phe Leu His Gln Glu Ala Ser Asn
    130                 135                 140

<210> SEQ ID NO 208
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 208

Met Gly Asp Gln Leu Tyr His His Asp Val Glu Leu Thr Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Ala Phe Leu Glu Lys Ile Gly Val Ser
        35                  40                  45

Val Asp Glu Val Thr Arg Asn Gly Asp Ala Leu Ala Val Thr Glu Leu
    50                  55                  60

Ser Leu Lys Phe Leu Ala Pro Leu Arg Ser Gly Asp Arg Phe Val Val
65                  70                  75                  80

Arg Ala Arg Leu Ser His Phe Thr Val Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Arg Ser Tyr Arg Pro Ile Arg Ile Pro Ser
        115                 120                 125

Glu Phe Asn Ser Lys Phe Val Lys Phe Leu His Gln Lys Ser Cys Gly
    130                 135                 140

Val Gln His His Leu
145

<210> SEQ ID NO 209
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 209

Met Ser Asp Gln Val Tyr Gln His Glu Val Glu Leu Gln Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Ala Phe Leu Glu Lys Ile Gly Val Ser
        35                  40                  45

Val Asp Glu Val Thr Arg Asn Gly Asp Ala Leu Ala Val Thr Glu Leu
    50                  55                  60

Ser Leu Lys Phe Leu Ala Pro Leu Arg Ser Gly Asp Arg Phe Val Val
65                  70                  75                  80

Arg Ala Arg Leu Ser His Phe Thr Val Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Arg Ser Tyr Arg Pro Ile Arg Ile Pro Ser
        115                 120                 125
```

Glu Phe Asn Ser Lys Phe Val Lys Phe Leu His Gln Lys Ser Cys Gly
            130                 135                 140

Val Gln His His Leu
145

<210> SEQ ID NO 210
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 210

Met Ser Asp Gln Val Tyr His His Asp Val Glu Leu Thr Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Glu Phe Leu Glu Lys Ile Gly Val Ser
        35                  40                  45

Val Asp Glu Val Thr Arg Asn Gly Asp Ala Leu Ala Val Thr Glu Leu
    50                  55                  60

Ser Leu Lys Phe Leu Ala Pro Leu Arg Ser Gly Asp Arg Phe Val Val
65                  70                  75                  80

Arg Ala Arg Leu Ser His Phe Thr Val Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Arg Ser Tyr Arg Pro Ile Arg Ile Pro Ser
        115                 120                 125

Glu Phe Asn Ser Lys Phe Val Lys Phe Leu His Gln Lys Ser Cys Gly
    130                 135                 140

Val Gln His His Leu
145

<210> SEQ ID NO 211
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 211

Met Ser Asp Gln Val Tyr His His Asp Val Glu Leu Thr Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Ala Phe Leu Glu Lys Ile Gly Val Ser
        35                  40                  45

Val Asp Glu Val Cys Arg Thr Gly Asp Ala Leu Ala Val Thr Glu Leu
    50                  55                  60

Ser Leu Lys Phe Leu Ala Pro Leu Arg Ser Gly Asp Arg Phe Val Val
65                  70                  75                  80

Arg Ala Arg Leu Ser His Phe Thr Val Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Arg Ser Tyr Arg Pro Ile Arg Ile Pro Ser

```
            115                 120                 125
Glu Phe Asn Ser Lys Phe Val Lys Phe Leu His Gln Lys Ser Cys Gly
    130                 135                 140

Val Gln His His Leu
145

<210> SEQ ID NO 212
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 212

Met Ser Asp Gln Val Tyr His His Asp Val Glu Leu Thr Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Ala Phe Leu Glu Lys Ile Gly Val Ser
        35                  40                  45

Val Asp Glu Val Thr Arg Asn Gly Glu Ala Leu Ala Thr Thr Glu Leu
    50                  55                  60

Ser Leu Lys Tyr Leu Ala Pro Leu Arg Ser Gly Asp Arg Phe Val Val
65                  70                  75                  80

Arg Ala Arg Leu Ser His Phe Thr Val Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Arg Ser Tyr Arg Pro Ile Arg Ile Pro Ser
        115                 120                 125

Glu Phe Asn Ser Lys Phe Val Lys Phe Leu His Gln Lys Ser Cys Gly
    130                 135                 140

Val Gln His His Leu
145

<210> SEQ ID NO 213
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 213

Met Ser Asp Gln Val Tyr His His Asp Val Glu Leu Thr Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Ala Phe Leu Glu Lys Ile Gly Val Ser
        35                  40                  45

Val Asp Glu Val Thr Arg Asn Gly Asp Ala Leu Ala Val Thr Glu Leu
    50                  55                  60

Ser Leu Lys Phe Leu Ala Pro Leu Arg Ser Gly Asp Arg Phe Val Val
65                  70                  75                  80

Lys Val Arg Ile Ser Arg Ser Thr Ala Ala Arg Leu Phe Phe Glu His
                85                  90                  95

Phe Ile Phe Lys Leu Pro Asp Gln Glu Pro Ile Leu Glu Ala Arg Gly
            100                 105                 110
```

```
Ile Ala Val Trp Leu Asn Arg Ser Tyr Arg Pro Ile Arg Ile Pro Ser
            115                 120                 125

Glu Phe Asn Ser Lys Phe Val Lys Phe Leu His Gln Lys Ser Cys Gly
        130                 135                 140

Val Gln His His Leu
145

<210> SEQ ID NO 214
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 214

Met Ser Asp Gln Val Tyr His His Asp Val Glu Leu Thr Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Ala Phe Leu Glu Lys Ile Gly Val Ser
        35                  40                  45

Val Asp Glu Val Thr Arg Asn Gly Asp Ala Leu Ala Val Thr Glu Leu
    50                  55                  60

Ser Leu Lys Phe Leu Ala Pro Leu Arg Ser Gly Asp Arg Phe Val Val
65                  70                  75                  80

Arg Ala Arg Leu Ser His Phe Thr Val Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Arg Ser Tyr Arg Pro Ile Arg Ile Pro Ser
        115                 120                 125

Glu Phe Ser Ser Lys Phe Val Gln Phe Leu His Gln Lys Ser Cys Gly
    130                 135                 140

Val Gln His His Leu
145

<210> SEQ ID NO 215
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 215

Met Ser Asp Gln Val Tyr His His Asp Val Glu Leu Thr Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Ala Phe Leu Glu Lys Ile Gly Val Ser
        35                  40                  45

Val Asp Glu Val Thr Arg Asn Gly Asp Ala Leu Ala Val Thr Glu Leu
    50                  55                  60

Ser Leu Lys Phe Leu Ala Pro Leu Arg Ser Gly Asp Arg Phe Val Val
65                  70                  75                  80

Arg Ala Arg Leu Ser His Phe Thr Val Ala Arg Leu Phe Phe Glu His
                85                  90                  95

Phe Ile Phe Lys Leu Pro Asp Gln Glu Pro Ile Leu Glu Ala Arg Gly
            100                 105                 110
```

```
Ile Ala Val Trp Leu Asn Arg Ser Tyr Arg Pro Ile Arg Ile Pro Ser
            115                 120                 125

Glu Phe Asn Ser Lys Phe Val Lys Phe Leu His Gln Lys Ser Cys Gly
        130                 135                 140

Thr Gln His Arg Leu
145

<210> SEQ ID NO 216
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 216

Met Gly Asp Gln Leu Tyr Gln His Glu Val Glu Leu Gln Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Ala Phe Leu Glu Lys Ile Gly Val Ser
        35                  40                  45

Val Asp Glu Val Thr Arg Asn Gly Asp Ala Leu Ala Val Thr Glu Leu
    50                  55                  60

Ser Leu Lys Phe Leu Ala Pro Leu Arg Ser Gly Asp Arg Phe Val Val
65                  70                  75                  80

Arg Ala Arg Leu Ser His Phe Thr Val Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Arg Ser Tyr Arg Pro Ile Arg Ile Pro Ser
        115                 120                 125

Glu Phe Ser Ser Lys Phe Val Gln Phe Leu His Gln Lys Ser Cys Gly
    130                 135                 140

Thr Gln His Arg Leu
145

<210> SEQ ID NO 217
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 217

Met Ser Asp Gln Val Tyr Gln His Glu Val Glu Leu Gln Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Glu Phe Leu Glu Lys Ile Gly Val Ser
        35                  40                  45

Val Asp Glu Val Cys Arg Thr Gly Glu Ala Leu Ala Thr Thr Glu Leu
    50                  55                  60

Ser Leu Lys Tyr Leu Ala Pro Leu Arg Ser Gly Asp Arg Phe Val Val
65                  70                  75                  80

Lys Val Arg Ile Ser Arg Ser Thr Ala Ala Arg Leu Phe Phe Glu His
                85                  90                  95

Phe Ile Phe Lys Leu Pro Asp Gln Glu Pro Ile Leu Glu Ala Arg Gly
```

Ile Ala Val Trp Leu Asn Arg Ser Tyr Arg Pro Ile Arg Ile Pro Ser
            115                 120                 125

Glu Phe Ser Ser Lys Phe Val Gln Phe Leu His Gln Lys Ser Cys Gly
    130                 135                 140

Thr Gln His Arg Leu
145

<210> SEQ ID NO 218
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 218

Met Gly Asp Gln Leu Tyr His His Asp Val Glu Leu Thr Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Glu Phe Leu Glu Lys Ile Gly Val Ser
        35                  40                  45

Val Asp Glu Val Cys Arg Thr Gly Glu Ala Leu Ala Thr Thr Glu Leu
    50                  55                  60

Ser Leu Lys Tyr Leu Ala Pro Leu Arg Ser Gly Asp Arg Phe Val Val
65                  70                  75                  80

Lys Val Arg Ile Ser Arg Ser Thr Ala Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Arg Ser Tyr Arg Pro Ile Arg Ile Pro Ser
            115                 120                 125

Glu Phe Ser Ser Lys Phe Val Gln Phe Leu His Gln Lys Ser Cys Gly
    130                 135                 140

Thr Gln His Arg Leu
145

<210> SEQ ID NO 219
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 219

Met Gly Asp Gln Leu Tyr Gln His Glu Val Glu Leu Gln Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Ala Phe Leu Glu Lys Ile Gly Val Ser
        35                  40                  45

Val Asp Glu Val Cys Arg Thr Gly Glu Ala Leu Ala Thr Thr Glu Leu
    50                  55                  60

Ser Leu Lys Tyr Leu Ala Pro Leu Arg Ser Gly Asp Arg Phe Val Val
65                  70                  75                  80

Lys Val Arg Ile Ser Arg Ser Thr Ala Ala Arg Leu Phe Phe Glu His
                85                  90                  95

Phe Ile Phe Lys Leu Pro Asp Gln Glu Pro Ile Leu Glu Ala Arg Gly
                100                 105                 110

Ile Ala Val Trp Leu Asn Arg Ser Tyr Arg Pro Ile Arg Ile Pro Ser
            115                 120                 125

Glu Phe Ser Ser Lys Phe Val Gln Phe Leu His Gln Lys Ser Cys Gly
        130                 135                 140

Thr Gln His Arg Leu
145

<210> SEQ ID NO 220
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 220

Met Gly Asp Gln Leu Tyr Gln His Glu Val Glu Leu Gln Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Glu Phe Leu Glu Lys Ile Gly Val Ser
        35                  40                  45

Val Asp Glu Val Thr Arg Asn Gly Ala Leu Ala Thr Thr Glu Leu
50                  55                  60

Ser Leu Lys Tyr Leu Ala Pro Leu Arg Ser Gly Asp Arg Phe Val Val
65                  70                  75                  80

Lys Val Arg Ile Ser Arg Ser Thr Ala Ala Arg Leu Phe Phe Glu His
                85                  90                  95

Phe Ile Phe Lys Leu Pro Asp Gln Glu Pro Ile Leu Glu Ala Arg Gly
                100                 105                 110

Ile Ala Val Trp Leu Asn Arg Ser Tyr Arg Pro Ile Arg Ile Pro Ser
            115                 120                 125

Glu Phe Ser Ser Lys Phe Val Gln Phe Leu His Gln Lys Ser Cys Gly
        130                 135                 140

Thr Gln His Arg Leu
145

<210> SEQ ID NO 221
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 221

Met Gly Asp Gln Leu Tyr Gln His Glu Val Glu Leu Gln Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Glu Phe Leu Glu Lys Ile Gly Val Ser
        35                  40                  45

Val Asp Glu Val Cys Arg Thr Gly Asp Ala Leu Ala Val Thr Glu Leu
50                  55                  60

Ser Leu Lys Phe Leu Ala Pro Leu Arg Ser Gly Asp Arg Phe Val Val
65                  70                  75                  80

Lys Val Arg Ile Ser Arg Ser Thr Ala Ala Arg Leu Phe Phe Glu His
                85                  90                  95

Phe Ile Phe Lys Leu Pro Asp Gln Glu Pro Ile Leu Glu Ala Arg Gly
                100                 105                 110

Ile Ala Val Trp Leu Asn Arg Ser Tyr Arg Pro Ile Arg Ile Pro Ser
            115                 120                 125

Glu Phe Ser Ser Lys Phe Val Gln Phe Leu His Gln Lys Ser Cys Gly
        130                 135                 140

Thr Gln His Arg Leu
145

<210> SEQ ID NO 222
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 222

Met Gly Asp Gln Leu Tyr Gln His Glu Val Glu Leu Gln Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Glu Phe Leu Glu Lys Ile Gly Val Ser
        35                  40                  45

Val Asp Glu Val Cys Arg Thr Gly Glu Ala Leu Ala Thr Thr Glu Leu
    50                  55                  60

Ser Leu Lys Tyr Leu Ala Pro Leu Arg Ser Gly Asp Arg Phe Val Val
65                  70                  75                  80

Arg Ala Arg Leu Ser His Phe Thr Val Ala Arg Leu Phe Phe Glu His
                85                  90                  95

Phe Ile Phe Lys Leu Pro Asp Gln Glu Pro Ile Leu Glu Ala Arg Gly
                100                 105                 110

Ile Ala Val Trp Leu Asn Arg Ser Tyr Arg Pro Ile Arg Ile Pro Ser
            115                 120                 125

Glu Phe Ser Ser Lys Phe Val Gln Phe Leu His Gln Lys Ser Cys Gly
        130                 135                 140

Thr Gln His Arg Leu
145

<210> SEQ ID NO 223
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 223

Met Gly Asp Gln Leu Tyr Gln His Glu Val Glu Leu Gln Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Glu Phe Leu Glu Lys Ile Gly Val Ser
        35                  40                  45

Val Asp Glu Val Cys Arg Thr Gly Glu Ala Leu Ala Thr Thr Glu Leu
    50                  55                  60

Ser Leu Lys Tyr Leu Ala Pro Leu Arg Ser Gly Asp Arg Phe Val Val
65                  70                  75                  80

Lys Val Arg Ile Ser Arg Ser Thr Ala Ala Arg Leu Phe Phe Glu His 85                  90                  95

Phe Ile Phe Lys Leu Pro Asp Gln Glu Pro Ile Leu Glu Ala Arg Gly
            100                 105                 110

Ile Ala Val Trp Leu Asn Arg Ser Tyr Arg Pro Ile Arg Ile Pro Ser
            115                 120                 125

Glu Phe Asn Ser Lys Phe Val Lys Phe Leu His Gln Lys Ser Cys Gly
        130                 135                 140

Thr Gln His Arg Leu
145

<210> SEQ ID NO 224
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 224

Met Gly Asp Gln Leu Tyr Gln His Glu Val Glu Leu Gln Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Glu Phe Leu Glu Lys Ile Gly Val Ser
        35                  40                  45

Val Asp Glu Val Cys Arg Thr Gly Glu Ala Leu Ala Thr Thr Glu Leu
    50                  55                  60

Ser Leu Lys Tyr Leu Ala Pro Leu Arg Ser Gly Asp Arg Phe Val Val
65                  70                  75                  80

Lys Val Arg Ile Ser Arg Ser Thr Ala Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Arg Ser Tyr Arg Pro Ile Arg Ile Pro Ser
            115                 120                 125

Glu Phe Ser Ser Lys Phe Val Gln Phe Leu His Gln Lys Ser Cys Gly
        130                 135                 140

Val Gln His His Leu
145

<210> SEQ ID NO 225
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 225

Met Ser Asp Gln Val Tyr His His Asp Val Glu Leu Thr Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Glu Phe Leu Glu Lys Ile Gly Val Ser
        35                  40                  45

Val Asp Glu Val Cys Arg Thr Gly Glu Ala Leu Ala Thr Thr Glu Leu
    50                  55                  60

Ser Leu Lys Tyr Leu Ala Pro Leu Arg Ser Gly Asp Arg Phe Val Val
65                  70                  75                  80

```
Lys Val Arg Ile Ser Arg Ser Thr Ala Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Arg Ser Tyr Arg Pro Ile Arg Ile Pro Ser
        115                 120                 125

Glu Phe Asn Ser Lys Phe Val Lys Phe Leu His Gln Lys Ser Cys Gly
    130                 135                 140

Val Gln His His Leu
145

<210> SEQ ID NO 226
<211> LENGTH: 186
<212> TYPE: PRT
<213> ORGANISM: Artificial Sequence
<220> FEATURE:
<223> OTHER INFORMATION: Synthetic polypeptide

<400> SEQUENCE: 226

Met Ala Ser Ile Cys Thr Ser Asn Phe His Phe Leu Cys Arg Lys Asn
1               5                   10                  15

Asn Ser Ser Pro Ile Ser His His Leu Leu Leu Ser Pro Ser Ser Leu
            20                  25                  30

Ser Phe Ser Arg Cys Gly Gly Leu Arg Leu Cys Arg Ala Ala Ala Glu
        35                  40                  45

Phe His Glu Val Glu Leu Lys Val Arg Asp Tyr Glu Leu Asp Gln Tyr
    50                  55                  60

Gly Val Val Asn Asn Ala Ile Tyr Ala Ser Tyr Cys Gln His Gly Arg
65                  70                  75                  80

His Glu Leu Leu Glu Arg Ile Gly Ile Ser Ala Asp Glu Val Ala Arg
                85                  90                  95

Ser Gly Asp Ala Leu Ala Leu Thr Glu Leu Ser Leu Lys Tyr Leu Ala
            100                 105                 110

Pro Leu Arg Ser Gly Asp Arg Phe Val Val Lys Ala Arg Ile Ser Asp
        115                 120                 125

Ser Ser Ala Ala Arg Leu Phe Phe Glu His Phe Ile Phe Lys Leu Pro
    130                 135                 140

Asp Gln Glu Pro Ile Leu Glu Ala Arg Gly Ile Ala Val Trp Leu Asn
145                 150                 155                 160

Lys Ser Tyr Arg Pro Val Arg Ile Pro Ala Glu Phe Arg Ser Lys Phe
                165                 170                 175

Val Gln Phe Leu Arg Gln Glu Ala Ser Asn
            180                 185

<210> SEQ ID NO 227
<211> LENGTH: 926
<212> TYPE: DNA
<213> ORGANISM: Artificial Sequence
<220> FEATURE:
<223> OTHER INFORMATION: Synthetic polynucleotide

<400> SEQUENCE: 227
ggccggccaa agcacatact tatcgattta aatttcatcg aagagattaa tatcgaataa      60
tcatatacat actttaaata cataacaaat tttaaataca tatatctggt atataattaa     120
ttttttaaag tcatgaagta tgtatcaaat acacatatgg aaaaaattaa ctattcataa     180
tttaaaaaat agaaaagata catctagtga aattaggtgc atgtatcaaa tacattagga     240
```

```
aaagggcata tatcttgatc tagataatta acgattttga tttatgtata atttccaaat      300
gaaggtttat atctacttca gaaataacaa tatactttta tcagaacatt caacaaagca      360
acaaccaact agagtgaaaa atacacattg ttctctagac atacaaaatt gagaaaagaa      420
tctcaaaatt tagagaaaca aatctgaatt tctagaagaa aaaataatt atgcactttg       480 ctattgctcg aaaaataaat gaaagaaatt agactttttt aaaagatgtt agactagata      540
tactcaaaag ctattaaagg agtaatattc ttcttacatt aagtatttta gttacagtcc      600
tgtaattaaa gacacatttt agattgtatc taaacttaaa tgtatctaga atacatatat      660
ttgaatgcat catatacatg tatccgacac accaattctc ataaaaaacg taatatccta      720
aactaattta tccttcaagt caacttaagc ccaatataca ttttcatctc taaaggccca      780
agtggcacaa aatgtcaggc ccaattacga agaaaagggc ttgtaaaacc ctaataaagt      840
ggcactggca gagcttacac tctcattcca tcaacaaaga aaccctaaaa gccgcagcgc      900
cactgatttc tctcctccag gcgaag                                          926
```

<210> SEQ ID NO 228
<211> LENGTH: 416
<212> TYPE: DNA
<213> ORGANISM: Artificial Sequence
<220> FEATURE:
<223> OTHER INFORMATION: Synthetic polynucleotide

<400> SEQUENCE: 228

```
gtttaaactg attttaatgt ttagcaaatg tcttatcagt tttctctttt tgtcgaacgg       60
taatttagag ttttttttgc tatatggatt ttcgttttg atgtatgtga caaccctcgg      120
gattgttgat ttatttcaaa actaagagtt tttgtcttat tgttctcgtc tattttggat      180
atcaatctta gttttatatc ttttctagtt ctctacgtgt taaatgttca acacactagc      240
aatttggcct gccagcgtat ggattatgga actatcaagt gtgtgggatc gataaatatg      300
cttctcagga atttgagatt ttacagtctt tatgctcatt gggttgagta taatatagta      360
aaaaaatagt aaatttaagc aataatgtta ggtgctatgt gtctgtcgag actatt         416
```

<210> SEQ ID NO 229
<211> LENGTH: 132
<212> TYPE: DNA
<213> ORGANISM: Artificial Sequence
<220> FEATURE:
<223> OTHER INFORMATION: Synthetic polynucleotide

<400> SEQUENCE: 229

```
atggcttcaa tttgtacttc aaattttcac tttctttgca ggaagaacaa ttctagccct       60
atttctcatc atctactttt atctccctct tctttatcct tctcacgttg cggcggattg      120
cgtttgtgtc gt                                                         132
```

<210> SEQ ID NO 230
<211> LENGTH: 44
<212> TYPE: PRT
<213> ORGANISM: Artificial Sequence
<220> FEATURE:
<223> OTHER INFORMATION: Synthetic polypeptide

<400> SEQUENCE: 230

```
Met Ala Ser Ile Cys Thr Ser Asn Phe His Phe Leu Cys Arg Lys Asn
1               5                   10                  15

Asn Ser Ser Pro Ile Ser His His Leu Leu Leu Ser Pro Ser Ser Leu
            20                  25                  30
```

Ser Phe Ser Arg Cys Gly Gly Leu Arg Leu Cys Arg
        35                  40

<210> SEQ ID NO 231
<211> LENGTH: 150
<212> TYPE: DNA
<213> ORGANISM: Artificial Sequence
<220> FEATURE:
<223> OTHER INFORMATION: Synthetic polynucleotide

<400> SEQUENCE: 231
atggcttcaa tttgtacttc aaattttcac tttctttgca ggaagaacaa ttctagccct      60
atttctcatc atctactttt atctccctct tctttatcct tctcacgttg cggcggattg     120
cgtttgtgtc gttgcgctgc agtgaagacc                                      150

<210> SEQ ID NO 232
<211> LENGTH: 50
<212> TYPE: PRT
<213> ORGANISM: Artificial Sequence
<220> FEATURE:
<223> OTHER INFORMATION: Synthetic polypeptide

<400> SEQUENCE: 232

Met Ala Ser Ile Cys Thr Ser Asn Phe His Phe Leu Cys Arg Lys Asn
1               5                   10                  15

Asn Ser Ser Pro Ile Ser His His Leu Leu Leu Ser Pro Ser Ser Leu
            20                  25                  30

Ser Phe Ser Arg Cys Gly Gly Leu Arg Leu Cys Arg Cys Ala Ala Val
        35                  40                  45

Lys Thr
    50

<210> SEQ ID NO 233
<211> LENGTH: 314
<212> TYPE: DNA
<213> ORGANISM: Artificial Sequence
<220> FEATURE:
<223> OTHER INFORMATION: Synthetic polynucleotide

<400> SEQUENCE: 233
cgtgatcaag gtaaatttct gtgttcctta ttctctcaaa atcttcgatt ttgttttcgt      60
tcgatcccaa tttcgtatat gttctttggt ttagattctg ttaatcttag atcgaagacg     120
attttctggg tttgatcgtt agatatcatc ttaattctcg attagggttt catagatatc     180
atccgatttg ttcaaataat ttgagttttg tcgaataatt actcttcgat ttgtgatttc     240
tatcttgatc tggtgttagt ttctagtttg tgcgatcgaa tttgtcgatt aatctgagtt     300
tttctgatta acag                                                       314

<210> SEQ ID NO 234
<211> LENGTH: 8
<212> TYPE: PRT
<213> ORGANISM: Artificial Sequence
<220> FEATURE:
<223> OTHER INFORMATION: Synthetic peptide

<400> SEQUENCE: 234

Ala Ala His His His His His His
1               5

<210> SEQ ID NO 235

```
<211> LENGTH: 12
<212> TYPE: PRT
<213> ORGANISM: Artificial Sequence
<220> FEATURE:
<223> OTHER INFORMATION: Synthetic peptide

<400> SEQUENCE: 235

Ala Ala Ala Tyr Pro Tyr Asp Val Pro Asp Tyr Ala
1               5                   10

<210> SEQ ID NO 236
<211> LENGTH: 20
<212> TYPE: PRT
<213> ORGANISM: Artificial Sequence
<220> FEATURE:
<223> OTHER INFORMATION: Synthetic peptide

<400> SEQUENCE: 236

Ala Ala Ala Tyr Pro Tyr Asp Val Pro Asp Tyr Ala Ala Ala His His
1               5                   10                  15

His His His His
            20

<210> SEQ ID NO 237
<211> LENGTH: 11
<212> TYPE: PRT
<213> ORGANISM: Artificial Sequence
<220> FEATURE:
<223> OTHER INFORMATION: Synthetic peptide

<400> SEQUENCE: 237

Ala Ala Ser Trp Lys Asp Ala Ser Gly Trp Ser
1               5                   10

<210> SEQ ID NO 238
<211> LENGTH: 10
<212> TYPE: PRT
<213> ORGANISM: Artificial Sequence
<220> FEATURE:
<223> OTHER INFORMATION: Synthetic peptide

<400> SEQUENCE: 238

Ala Ala Asp Tyr Lys Asp Asp Asp Asp Lys
1               5                   10

<210> SEQ ID NO 239
<211> LENGTH: 12
<212> TYPE: PRT
<213> ORGANISM: Artificial Sequence
<220> FEATURE:
<223> OTHER INFORMATION: Synthetic peptide

<400> SEQUENCE: 239

Ala Ala Glu Gln Lys Leu Ile Ser Glu Glu Asp Leu
1               5                   10

<210> SEQ ID NO 240
<211> LENGTH: 713
<212> TYPE: DNA
<213> ORGANISM: Artificial Sequence
<220> FEATURE:
<223> OTHER INFORMATION: Synthetic polynucleotide

<400> SEQUENCE: 240
cccatatgtc ctacacaatg tgaatttgaa ttagtttggt catacggtat atcatatgat      60
tataaataaa aaaaattagc aaaagaatat aatttattaa atatttttaca ccataccaaa    120
```

```
cacaaccgca ttatatataa tcttaattat cattatcacc agcatcaaca ttataatgat      180 tccccctatgc gttggaacgt cattatagtt attctaaaca agaaagaaat tgttcttga      240 catcagacat ctagtattat aactctagtg gagcttacct tttcttttcc ttctttttt      300 tcttcttaaa aaaattatca cttttttaaat cttgtatatt agttaagctt atctaaacaa    360
agttttaaat tcatttctta aacgtccatt acaatgtaat ataacttagt cgtctcaatt     420
aaaccattaa tgtgaaatat aaatcaaaaa agccaaagg gcggtgggac ggcgccaatc      480
atttgtccta gtccactcaa ataaggccca tggtcggcaa aaccaaacac aaaatgtgtt    540 attttttaatt ttttcctctt ttattgttaa agttgcaaaa tgtgttattt ttggtaagac   600
cctatggata tataaagaca ggttatgtga aacttggaaa accatcaagt tttaagcaaa    660
accctcttaa gaacttaaat tgagcttctt ttggggcatt tttctagtga gaa            713
```

<210> SEQ ID NO 241
<211> LENGTH: 1232
<212> TYPE: DNA
<213> ORGANISM: Artificial Sequence
<220> FEATURE:
<223> OTHER INFORMATION: Synthetic polynucleotide

<400> SEQUENCE: 241

```
ggtccgattg agactttca acaaagggta atatccggaa acctcctcgg attccattgc       60
ccagctatct gtcactttat tgtgaagata gtggaaaagg aaggtggctc ctacaaatgc     120
catcattgcg ataaaggaaa ggccatcgtt gaagatgcct ctgccgacag tggtcccaaa     180
gatggacccc cacccacgag gagcatcgtg gaaaaagaag acgttccaac cacgtcttca    240
aagcaagtgg attgatgtga tatctccact gacgtaaggg atgacgcaca atcccactat    300
ccttcgcaat tcccaaagca catacttatc gatttaaatt tcatcgaaga gattaatatc    360
gaataatcat atacatactt taaatacata acaaattttta aatacatata tctggtatat   420 aattaattttt ttaaagtcat gaagtatgta tcaaatacac atatggaaaa aattaactat   480
tcataattta aaaaatagaa agatacatc tagtgaaatt aggtgcatgt atcaaataca     540
ttaggaaaag ggcatatatc ttgatctaga taattaacga ttttgattta tgtataattt    600
ccaaatgaag gttatatatct acttcagaaa taacaatata cttttatcag aacattcaac   660
aaagcaacaa ccaactagag tgaaaaatac acattgttct ctagacatac aaaattgaga    720
aaagaatctc aaaatttaga gaaacaaatc tgaatttcta gaagaaaaaa ataattatgc    780
actttgctat tgctcgaaaa ataaatgaaa gaaattagac tttttttaaaa gatgttagac   840 tagatatact caaaagctat taaggagta atattcttct tacattaagt attttagtta     900
cagtcctgta attaaagaca cattttagat tgtatctaaa cttaaatgta tctagaatac    960
atatatttga atgcatcata tacatgtatc cgacacacca attctcataa aaaacgtaat   1020
atcctaaact aatttatcct tcaagtcaac ttaagcccaa tatacatttt catctctaaa   1080
ggcccaagtg gcacaaaatg tcaggcccaa ttacgaagaa aagggcttgt aaaacccctaa  1140 taaagtggca ctggcagagc ttacactctc attccatcaa caaagaaacc ctaaaagccg   1200
cagcgccact gatttctctc ctccaggcga ag                                 1232
```

<210> SEQ ID NO 242
<211> LENGTH: 155
<212> TYPE: PRT
<213> ORGANISM: Artificial Sequence
<220> FEATURE:

```
<223> OTHER INFORMATION: Synthetic polypeptide
<220> FEATURE:
<221> NAME/KEY: MOD_RES
<222> LOCATION: (1)..(15)
<223> OTHER INFORMATION: This region may be 1 to 2 residues in length
      selected from "Leu," "Met" or "Met Ala" or is any amino acid
      and encompasses 1 to 15 residues in length, wherein
      some residues may be absent
<220> FEATURE:
<221> NAME/KEY: MOD_RES
<222> LOCATION: (16)..(16)
<223> OTHER INFORMATION: Ser, Asn, Arg, Ala, Thr or Gly
<220> FEATURE:
<221> NAME/KEY: MOD_RES
<222> LOCATION: (17)..(17)
<223> OTHER INFORMATION: Asp, Glu, Gly, Arg, Ser, Leu or absent
<220> FEATURE:
<221> NAME/KEY: MOD_RES
<222> LOCATION: (18)..(18)
<223> OTHER INFORMATION: Phe, His, Gln, Pro, Leu or Val
<220> FEATURE:
<221> NAME/KEY: MOD_RES
<222> LOCATION: (19)..(19)
<223> OTHER INFORMATION: His, Tyr, Phe, Leu or Val
<220> FEATURE:
<221> NAME/KEY: MOD_RES
<222> LOCATION: (20)..(20)
<223> OTHER INFORMATION: Asp, Glu or Gly
<220> FEATURE:
<221> NAME/KEY: MOD_RES
<222> LOCATION: (24)..(24)
<223> OTHER INFORMATION: Lys, Thr or Gln
<220> FEATURE:
<221> NAME/KEY: MOD_RES
<222> LOCATION: (33)..(33)
<223> OTHER INFORMATION: Phe or Tyr
<220> FEATURE:
<221> NAME/KEY: MOD_RES
<222> LOCATION: (40)..(40)
<223> OTHER INFORMATION: Thr, Ile or Val
<220> FEATURE:
<221> NAME/KEY: MOD_RES
<222> LOCATION: (48)..(48)
<223> OTHER INFORMATION: Cys or Gly
<220> FEATURE:
<221> NAME/KEY: MOD_RES
<222> LOCATION: (51)..(51)
<223> OTHER INFORMATION: Glu or Ala
<220> FEATURE:
<221> NAME/KEY: MOD_RES
<222> LOCATION: (52)..(52)
<223> OTHER INFORMATION: Leu, Phe or Val
<220> FEATURE:
<221> NAME/KEY: MOD_RES
<222> LOCATION: (55)..(55)
<223> OTHER INFORMATION: Lys, Arg, Ala, Ser, Asn, Thr or Cys
<220> FEATURE:
<221> NAME/KEY: MOD_RES
<222> LOCATION: (58)..(58)
<223> OTHER INFORMATION: Val, Ile, Phe or Leu
<220> FEATURE:
<221> NAME/KEY: MOD_RES
<222> LOCATION: (59)..(59)
<223> OTHER INFORMATION: Ser or Asn
<220> FEATURE:
<221> NAME/KEY: MOD_RES
<222> LOCATION: (60)..(60)
<223> OTHER INFORMATION: Ala, Val, Cys or Pro
<220> FEATURE:
<221> NAME/KEY: MOD_RES
<222> LOCATION: (62)..(62)
<223> OTHER INFORMATION: Glu, Ala or Val
<220> FEATURE:
<221> NAME/KEY: MOD_RES
<222> LOCATION: (64)..(64)
<223> OTHER INFORMATION: Ala, Thr, Cys or Ser
<220> FEATURE:
<221> NAME/KEY: MOD_RES
<222> LOCATION: (66)..(66)
```

```
<223> OTHER INFORMATION: Ser, Asn, Thr or Ile
<220> FEATURE:
<221> NAME/KEY: MOD_RES
<222> LOCATION: (68)..(68)
<223> OTHER INFORMATION: Asp, Glu or Asn
<220> FEATURE:
<221> NAME/KEY: MOD_RES
<222> LOCATION: (72)..(72)
<223> OTHER INFORMATION: Leu, Val, Ile or Thr
<220> FEATURE:
<221> NAME/KEY: MOD_RES
<222> LOCATION: (73)..(73)
<223> OTHER INFORMATION: Thr or Ser
<220> FEATURE:
<221> NAME/KEY: MOD_RES
<222> LOCATION: (75)..(75)
<223> OTHER INFORMATION: Leu or Met
<220> FEATURE:
<221> NAME/KEY: MOD_RES
<222> LOCATION: (76)..(76)
<223> OTHER INFORMATION: Ser, Thr, His or Asn
<220> FEATURE:
<221> NAME/KEY: MOD_RES
<222> LOCATION: (79)..(79)
<223> OTHER INFORMATION: Phe or Tyr
<220> FEATURE:
<221> NAME/KEY: MOD_RES
<222> LOCATION: (90)..(90)
<223> OTHER INFORMATION: Val or Ile
<220> FEATURE:
<221> NAME/KEY: MOD_RES
<222> LOCATION: (92)..(92)
<223> OTHER INFORMATION: Thr, Lys or Arg
<220> FEATURE:
<221> NAME/KEY: MOD_RES
<222> LOCATION: (93)..(93)
<223> OTHER INFORMATION: Val, Ala or Thr
<220> FEATURE:
<221> NAME/KEY: MOD_RES
<222> LOCATION: (95)..(95)
<223> OTHER INFORMATION: Leu, Ile or Val
<220> FEATURE:
<221> NAME/KEY: MOD_RES
<222> LOCATION: (97)..(97)
<223> OTHER INFORMATION: His, Arg, Asp, Gly, Ser or Asn
<220> FEATURE:
<221> NAME/KEY: MOD_RES
<222> LOCATION: (98)..(98)
<223> OTHER INFORMATION: Ser, Thr, Ile, Phe or Ala
<220> FEATURE:
<221> NAME/KEY: MOD_RES
<222> LOCATION: (99)..(99)
<223> OTHER INFORMATION: Ser, Thr or Lys
<220> FEATURE:
<221> NAME/KEY: MOD_RES
<222> LOCATION: (100)..(100)
<223> OTHER INFORMATION: Ala, Gly, Val or Met
<220> FEATURE:
<221> NAME/KEY: MOD_RES
<222> LOCATION: (104)..(104)
<223> OTHER INFORMATION: Phe, Tyr or Ile
<220> FEATURE:
<221> NAME/KEY: MOD_RES
<222> LOCATION: (114)..(114)
<223> OTHER INFORMATION: Asp or Asn
<220> FEATURE:
<221> NAME/KEY: MOD_RES
<222> LOCATION: (115)..(115)
<223> OTHER INFORMATION: Arg, Gln, Glu or His
<220> FEATURE:
<221> NAME/KEY: MOD_RES
<222> LOCATION: (122)..(122)
<223> OTHER INFORMATION: Arg or Lys
<220> FEATURE:
<221> NAME/KEY: MOD_RES
<222> LOCATION: (123)..(123)
<223> OTHER INFORMATION: Gly or Ala
<220> FEATURE:
<221> NAME/KEY: MOD_RES
```

```
<222> LOCATION: (124)..(124)
<223> OTHER INFORMATION: Ile, Thr, Met or Val
<220> FEATURE:
<221> NAME/KEY: MOD_RES
<222> LOCATION: (127)..(127)
<223> OTHER INFORMATION: Tyr, Trp, Cys or Arg
<220> FEATURE:
<221> NAME/KEY: MOD_RES
<222> LOCATION: (129)..(129)
<223> OTHER INFORMATION: Asn or Asp
<220> FEATURE:
<221> NAME/KEY: MOD_RES
<222> LOCATION: (130)..(130)
<223> OTHER INFORMATION: Arg, Lys or Asn
<220> FEATURE:
<221> NAME/KEY: MOD_RES
<222> LOCATION: (131)..(131)
<223> OTHER INFORMATION: Ile, Ser, Asn, Lys, Asp or Arg
<220> FEATURE:
<221> NAME/KEY: MOD_RES
<222> LOCATION: (135)..(135)
<223> OTHER INFORMATION: Ile, Val, Thr or Ala
<220> FEATURE:
<221> NAME/KEY: MOD_RES
<222> LOCATION: (139)..(139)
<223> OTHER INFORMATION: Ser, Thr, Ala, Pro or Arg
<220> FEATURE:
<221> NAME/KEY: MOD_RES
<222> LOCATION: (141)..(141)
<223> OTHER INFORMATION: Phe, Ile, Met or Leu
<220> FEATURE:
<221> NAME/KEY: MOD_RES
<222> LOCATION: (142)..(142)
<223> OTHER INFORMATION: Lys, Arg, Asn, Ser or Leu
<220> FEATURE:
<221> NAME/KEY: MOD_RES
<222> LOCATION: (145)..(145)
<223> OTHER INFORMATION: Phe, Leu, Ile or Met
<220> FEATURE:
<221> NAME/KEY: MOD_RES
<222> LOCATION: (147)..(147)
<223> OTHER INFORMATION: Leu, Gln, Lys, His or Phe
<220> FEATURE:
<221> NAME/KEY: MOD_RES
<222> LOCATION: (150)..(150)
<223> OTHER INFORMATION: His, Arg or Lys
<220> FEATURE:
<221> NAME/KEY: MOD_RES
<222> LOCATION: (151)..(151)
<223> OTHER INFORMATION: Gln, Asn, His, Cys or Ile
<220> FEATURE:
<221> NAME/KEY: MOD_RES
<222> LOCATION: (153)..(153)
<223> OTHER INFORMATION: Ala, Glu or Asp
<220> FEATURE:
<221> NAME/KEY: MOD_RES
<222> LOCATION: (154)..(155)
<223> OTHER INFORMATION: This region may encompass 1 to 2 residues
      selected from "Ser," "Ser His," "Ser Asn," "Leu Asn" or "Pro Ser"
      wherein the residue at position 155 may be absent or
      this region is absent in its entirety
<220> FEATURE:
<223> OTHER INFORMATION: see specification as filed for detailed
      description of substitutions and preferred embodiments

<400> SEQUENCE: 242

Xaa Xaa Xaa Xaa Xaa Xaa Xaa Xaa Xaa Xaa Xaa Xaa Xaa Xaa Xaa
1               5                   10                  15

Xaa Xaa Xaa Xaa Val Glu Leu Xaa Val Arg Asp Tyr Glu Leu Asp Gln
            20                  25                  30

Xaa Gly Val Val Asn Asn Ala Xaa Tyr Ala Ser Tyr Cys Gln His Xaa
        35                  40                  45

Arg His Xaa Xaa Leu Glu Xaa Ile Gly Xaa Xaa Xaa Asp Xaa Val Xaa
    50                  55                  60
```

```
Arg Xaa Gly Xaa Ala Leu Ala Xaa Xaa Glu Xaa Xaa Leu Lys Xaa Leu
 65                  70                  75                  80

Ala Pro Leu Arg Ser Gly Asp Arg Phe Xaa Val Xaa Xaa Arg Xaa Ser
                 85                  90                  95

Xaa Xaa Xaa Xaa Ala Arg Leu Xaa Phe Glu His Phe Ile Phe Lys Leu
            100                 105                 110

Pro Xaa Xaa Glu Pro Ile Leu Glu Ala Xaa Xaa Ala Val Xaa Leu
        115                 120                 125

Xaa Xaa Xaa Tyr Arg Pro Xaa Arg Ile Pro Xaa Glu Xaa Xaa Ser Lys
    130                 135                 140

Xaa Val Xaa Phe Leu Xaa Xaa Glu Xaa Xaa Xaa
145                 150                 155
```

<210> SEQ ID NO 243
<211> LENGTH: 163
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(15)
<223> OTHER INFORMATION: This region may be 1 to 2 residues in length
      selected from "Leu," "Met" or "Met Ala" or is any amino acid
      and encompasses 1 to 15 residues in length, wherein
      some residues may be absent
<220> FEATURE:
<221> NAME/KEY: MOD_RES
<222> LOCATION: (16)..(16)
<223> OTHER INFORMATION: Ser, Asn, Arg, Ala, Thr or Gly
<220> FEATURE:
<221> NAME/KEY: MOD_RES
<222> LOCATION: (17)..(17)
<223> OTHER INFORMATION: Asp, Glu, Gly, Arg, Ser, Leu or absent
<220> FEATURE:
<221> NAME/KEY: MOD_RES
<222> LOCATION: (18)..(18)
<223> OTHER INFORMATION: Gln, Leu, Glu or Val
<220> FEATURE:
<221> NAME/KEY: MOD_RES
<222> LOCATION: (19)..(19)
<223> OTHER INFORMATION: Val, Leu, Asp or Glu
<220> FEATURE:
<221> NAME/KEY: MOD_RES
<222> LOCATION: (20)..(20)
<223> OTHER INFORMATION: Tyr, Lys or Gln
<220> FEATURE:
<221> NAME/KEY: MOD_RES
<222> LOCATION: (21)..(21)
<223> OTHER INFORMATION: Phe, His, Gln, Pro, Leu or Val
<220> FEATURE:
<221> NAME/KEY: MOD_RES
<222> LOCATION: (22)..(22)
<223> OTHER INFORMATION: His, Tyr, Phe, Leu or Val
<220> FEATURE:
<221> NAME/KEY: MOD_RES
<222> LOCATION: (23)..(23)
<223> OTHER INFORMATION: Asp, Glu or Gly
<220> FEATURE:
<221> NAME/KEY: MOD_RES
<222> LOCATION: (27)..(27)
<223> OTHER INFORMATION: Lys, Thr or Gln
<220> FEATURE:
<221> NAME/KEY: MOD_RES
<222> LOCATION: (36)..(36)
<223> OTHER INFORMATION: Phe or Tyr
<220> FEATURE:
<221> NAME/KEY: MOD_RES
<222> LOCATION: (43)..(43)
<223> OTHER INFORMATION: Thr, Ile or Val
<220> FEATURE:
<221> NAME/KEY: MOD_RES
<222> LOCATION: (51)..(51)

```
<223> OTHER INFORMATION: Cys or Gly
<220> FEATURE:
<221> NAME/KEY: MOD_RES
<222> LOCATION: (54)..(54)
<223> OTHER INFORMATION: Glu or Ala
<220> FEATURE:
<221> NAME/KEY: MOD_RES
<222> LOCATION: (55)..(55)
<223> OTHER INFORMATION: Leu, Phe or Val
<220> FEATURE:
<221> NAME/KEY: MOD_RES
<222> LOCATION: (58)..(58)
<223> OTHER INFORMATION: Lys, Arg, Ala, Ser, Asn, Thr or Cys
<220> FEATURE:
<221> NAME/KEY: MOD_RES
<222> LOCATION: (61)..(61)
<223> OTHER INFORMATION: Val, Ile, Phe or Leu
<220> FEATURE:
<221> NAME/KEY: MOD_RES
<222> LOCATION: (62)..(62)
<223> OTHER INFORMATION: Ser or Asn
<220> FEATURE:
<221> NAME/KEY: MOD_RES
<222> LOCATION: (63)..(63)
<223> OTHER INFORMATION: Ala, Val, Cys or Pro
<220> FEATURE:
<221> NAME/KEY: MOD_RES
<222> LOCATION: (65)..(65)
<223> OTHER INFORMATION: Glu, Ala or Val
<220> FEATURE:
<221> NAME/KEY: MOD_RES
<222> LOCATION: (67)..(67)
<223> OTHER INFORMATION: Ala, Thr, Cys or Ser
<220> FEATURE:
<221> NAME/KEY: MOD_RES
<222> LOCATION: (69)..(69)
<223> OTHER INFORMATION: Ser, Asn, Thr or Ile
<220> FEATURE:
<221> NAME/KEY: MOD_RES
<222> LOCATION: (71)..(71)
<223> OTHER INFORMATION: Asp, Glu or Asn
<220> FEATURE:
<221> NAME/KEY: MOD_RES
<222> LOCATION: (75)..(75)
<223> OTHER INFORMATION: Leu, Val, Ile or Thr
<220> FEATURE:
<221> NAME/KEY: MOD_RES
<222> LOCATION: (76)..(76)
<223> OTHER INFORMATION: Thr or Ser
<220> FEATURE:
<221> NAME/KEY: MOD_RES
<222> LOCATION: (78)..(78)
<223> OTHER INFORMATION: Leu or Met
<220> FEATURE:
<221> NAME/KEY: MOD_RES
<222> LOCATION: (79)..(79)
<223> OTHER INFORMATION: Ser, Thr, His or Asn
<220> FEATURE:
<221> NAME/KEY: MOD_RES
<222> LOCATION: (82)..(82)
<223> OTHER INFORMATION: Phe or Tyr
<220> FEATURE:
<221> NAME/KEY: MOD_RES
<222> LOCATION: (93)..(93)
<223> OTHER INFORMATION: Val or Ile
<220> FEATURE:
<221> NAME/KEY: MOD_RES
<222> LOCATION: (95)..(95)
<223> OTHER INFORMATION: Thr, Lys or Arg
<220> FEATURE:
<221> NAME/KEY: MOD_RES
<222> LOCATION: (96)..(96)
<223> OTHER INFORMATION: Val, Ala or Thr
<220> FEATURE:
<221> NAME/KEY: MOD_RES
<222> LOCATION: (98)..(98)
<223> OTHER INFORMATION: Leu, Ile or Val
<220> FEATURE:
<221> NAME/KEY: MOD_RES
```

```
<222> LOCATION: (100)..(100)
<223> OTHER INFORMATION: His, Arg, Asp, Gly, Ser or Asn
<220> FEATURE:
<221> NAME/KEY: MOD_RES
<222> LOCATION: (101)..(101)
<223> OTHER INFORMATION: Ser, Thr, Ile, Phe or Ala
<220> FEATURE:
<221> NAME/KEY: MOD_RES
<222> LOCATION: (102)..(102)
<223> OTHER INFORMATION: Ser, Thr or Lys
<220> FEATURE:
<221> NAME/KEY: MOD_RES
<222> LOCATION: (103)..(103)
<223> OTHER INFORMATION: Ala, Gly, Val or Met
<220> FEATURE:
<221> NAME/KEY: MOD_RES
<222> LOCATION: (107)..(107)
<223> OTHER INFORMATION: Phe, Tyr or Ile
<220> FEATURE:
<221> NAME/KEY: MOD_RES
<222> LOCATION: (117)..(117)
<223> OTHER INFORMATION: Asp or Asn
<220> FEATURE:
<221> NAME/KEY: MOD_RES
<222> LOCATION: (118)..(118)
<223> OTHER INFORMATION: Arg, Gln, Glu or His
<220> FEATURE:
<221> NAME/KEY: MOD_RES
<222> LOCATION: (125)..(125)
<223> OTHER INFORMATION: Arg or Lys
<220> FEATURE:
<221> NAME/KEY: MOD_RES
<222> LOCATION: (126)..(126)
<223> OTHER INFORMATION: Gly or Ala
<220> FEATURE:
<221> NAME/KEY: MOD_RES
<222> LOCATION: (127)..(127)
<223> OTHER INFORMATION: Ile, Thr, Met or Val
<220> FEATURE:
<221> NAME/KEY: MOD_RES
<222> LOCATION: (130)..(130)
<223> OTHER INFORMATION: Tyr, Trp, Cys or Arg
<220> FEATURE:
<221> NAME/KEY: MOD_RES
<222> LOCATION: (132)..(132)
<223> OTHER INFORMATION: Asn or Asp
<220> FEATURE:
<221> NAME/KEY: MOD_RES
<222> LOCATION: (133)..(133)
<223> OTHER INFORMATION: Arg, Lys or Asn
<220> FEATURE:
<221> NAME/KEY: MOD_RES
<222> LOCATION: (134)..(134)
<223> OTHER INFORMATION: Ile, Ser, Asn, Lys, Asp or Arg
<220> FEATURE:
<221> NAME/KEY: MOD_RES
<222> LOCATION: (138)..(138)
<223> OTHER INFORMATION: Ile, Val, Thr or Ala
<220> FEATURE:
<221> NAME/KEY: MOD_RES
<222> LOCATION: (142)..(142)
<223> OTHER INFORMATION: Ser, Thr, Ala, Pro or Arg
<220> FEATURE:
<221> NAME/KEY: MOD_RES
<222> LOCATION: (144)..(144)
<223> OTHER INFORMATION: Phe, Ile, Met or Leu
<220> FEATURE:
<221> NAME/KEY: MOD_RES
<222> LOCATION: (145)..(145)
<223> OTHER INFORMATION: Lys, Arg, Asn, Ser or Leu
<220> FEATURE:
<221> NAME/KEY: MOD_RES
<222> LOCATION: (148)..(148)
<223> OTHER INFORMATION: Phe, Leu, Ile or Met
<220> FEATURE:
<221> NAME/KEY: MOD_RES
<222> LOCATION: (150)..(150)
<223> OTHER INFORMATION: Leu, Gln, Lys, His or Phe
<220> FEATURE:
```

<220> FEATURE:
<221> NAME/KEY: MOD_RES
<222> LOCATION: (153)..(153)
<223> OTHER INFORMATION: His, Arg or Lys
<220> FEATURE:
<221> NAME/KEY: MOD_RES
<222> LOCATION: (154)..(154)
<223> OTHER INFORMATION: Gln, Asn, His, Cys or Ile
<220> FEATURE:
<221> NAME/KEY: MOD_RES
<222> LOCATION: (159)..(159)
<223> OTHER INFORMATION: Val, Thr or Ile
<220> FEATURE:
<221> NAME/KEY: MOD_RES
<222> LOCATION: (162)..(162)
<223> OTHER INFORMATION: His, Arg or Lys
<220> FEATURE:
<223> OTHER INFORMATION: see specification as filed for detailed description of substitutions and preferred embodiments

<400> SEQUENCE: 243

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Val Glu Leu Xaa Val Arg Asp Tyr Glu
            20                  25                  30

Leu Asp Gln Xaa Gly Val Val Asn Asn Ala Xaa Tyr Ala Ser Tyr Cys
        35                  40                  45

Gln His Xaa Arg His Xaa Xaa Leu Glu Xaa Ile Gly Xaa Xaa Xaa Asp
    50                  55                  60

Xaa Val Xaa Arg Xaa Gly Ala Leu Ala Xaa Xaa Glu Xaa Xaa Xaa Leu
65                  70                  75                  80

Lys Xaa Leu Ala Pro Leu Arg Ser Gly Asp Arg Phe Xaa Val Xaa Xaa
            85                  90                  95

Arg Xaa Ser Xaa Xaa Xaa Xaa Ala Arg Leu Xaa Phe Glu His Phe Ile
            100                 105                 110

Phe Lys Leu Pro Xaa Xaa Glu Pro Ile Leu Glu Ala Xaa Xaa Xaa Ala
            115                 120                 125

Val Xaa Leu Xaa Xaa Xaa Tyr Arg Pro Xaa Arg Ile Pro Xaa Glu Xaa
        130                 135                 140

Xaa Ser Lys Xaa Val Xaa Phe Leu Xaa Xaa Lys Ser Cys Gly Xaa Gln
145                 150                 155                 160

His Xaa Leu
```

<210> SEQ ID NO 244
<211> LENGTH: 173
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(15)
<223> OTHER INFORMATION: This region may be 1 to 2 residues in length selected from "Leu," "Met" or "Met Ala" or is any amino acid and encompasses 1 to 15 residues in length, wherein some residues may be absent
<220> FEATURE:
<221> NAME/KEY: MOD_RES
<222> LOCATION: (16)..(16)
<223> OTHER INFORMATION: Ser, Asn, Arg, Ala, Thr or Gly
<220> FEATURE:
<221> NAME/KEY: MOD_RES
<222> LOCATION: (17)..(17)
<223> OTHER INFORMATION: Asp, Glu, Gly, Arg, Ser, Leu or absent
<220> FEATURE:
<221> NAME/KEY: MOD_RES
<222> LOCATION: (18)..(18)
<223> OTHER INFORMATION: Gln, Leu, Glu or Val -continued

```
<220> FEATURE:
<221> NAME/KEY: MOD_RES
<222> LOCATION: (19)..(19)
<223> OTHER INFORMATION: Val, Leu, Asp or Glu
<220> FEATURE:
<221> NAME/KEY: MOD_RES
<222> LOCATION: (20)..(20)
<223> OTHER INFORMATION: Tyr, Lys or Gln
<220> FEATURE:
<221> NAME/KEY: MOD_RES
<222> LOCATION: (21)..(21)
<223> OTHER INFORMATION: Phe, His, Gln, Pro, Leu or Val
<220> FEATURE:
<221> NAME/KEY: MOD_RES
<222> LOCATION: (22)..(22)
<223> OTHER INFORMATION: His, Tyr, Phe, Leu or Val
<220> FEATURE:
<221> NAME/KEY: MOD_RES
<222> LOCATION: (23)..(23)
<223> OTHER INFORMATION: Asp, Glu or Gly
<220> FEATURE:
<221> NAME/KEY: MOD_RES
<222> LOCATION: (27)..(27)
<223> OTHER INFORMATION: Lys, Thr or Gln
<220> FEATURE:
<221> NAME/KEY: MOD_RES
<222> LOCATION: (36)..(36)
<223> OTHER INFORMATION: Phe or Tyr
<220> FEATURE:
<221> NAME/KEY: MOD_RES
<222> LOCATION: (43)..(43)
<223> OTHER INFORMATION: Thr, Ile or Val
<220> FEATURE:
<221> NAME/KEY: MOD_RES
<222> LOCATION: (51)..(51)
<223> OTHER INFORMATION: Cys or Gly
<220> FEATURE:
<221> NAME/KEY: MOD_RES
<222> LOCATION: (54)..(54)
<223> OTHER INFORMATION: Glu or Ala
<220> FEATURE:
<221> NAME/KEY: MOD_RES
<222> LOCATION: (55)..(55)
<223> OTHER INFORMATION: Leu, Phe or Val
<220> FEATURE:
<221> NAME/KEY: MOD_RES
<222> LOCATION: (58)..(58)
<223> OTHER INFORMATION: Lys, Arg, Ala, Ser, Asn, Thr or Cys
<220> FEATURE:
<221> NAME/KEY: MOD_RES
<222> LOCATION: (61)..(61)
<223> OTHER INFORMATION: Val, Ile, Phe or Leu
<220> FEATURE:
<221> NAME/KEY: MOD_RES
<222> LOCATION: (62)..(62)
<223> OTHER INFORMATION: Ser or Asn
<220> FEATURE:
<221> NAME/KEY: MOD_RES
<222> LOCATION: (63)..(63)
<223> OTHER INFORMATION: Ala, Val, Cys or Pro
<220> FEATURE:
<221> NAME/KEY: MOD_RES
<222> LOCATION: (65)..(65)
<223> OTHER INFORMATION: Glu, Ala or Val
<220> FEATURE:
<221> NAME/KEY: MOD_RES
<222> LOCATION: (67)..(67)
<223> OTHER INFORMATION: Ala, Thr, Cys or Ser
<220> FEATURE:
<221> NAME/KEY: MOD_RES
<222> LOCATION: (69)..(69)
<223> OTHER INFORMATION: Ser, Asn, Thr or Ile
<220> FEATURE:
<221> NAME/KEY: MOD_RES
<222> LOCATION: (71)..(71)
<223> OTHER INFORMATION: Asp, Glu or Asn
<220> FEATURE:
<221> NAME/KEY: MOD_RES
<222> LOCATION: (75)..(75)
```

```
<223> OTHER INFORMATION: Leu, Val, Ile or Thr
<220> FEATURE:
<221> NAME/KEY: MOD_RES
<222> LOCATION: (76)..(76)
<223> OTHER INFORMATION: Thr or Ser
<220> FEATURE:
<221> NAME/KEY: MOD_RES
<222> LOCATION: (78)..(78)
<223> OTHER INFORMATION: Leu or Met
<220> FEATURE:
<221> NAME/KEY: MOD_RES
<222> LOCATION: (79)..(79)
<223> OTHER INFORMATION: Ser, Thr, His or Asn
<220> FEATURE:
<221> NAME/KEY: MOD_RES
<222> LOCATION: (82)..(82)
<223> OTHER INFORMATION: Phe or Tyr
<220> FEATURE:
<221> NAME/KEY: MOD_RES
<222> LOCATION: (93)..(93)
<223> OTHER INFORMATION: Val or Ile
<220> FEATURE:
<221> NAME/KEY: MOD_RES
<222> LOCATION: (95)..(95)
<223> OTHER INFORMATION: Thr, Lys or Arg
<220> FEATURE:
<221> NAME/KEY: MOD_RES
<222> LOCATION: (96)..(96)
<223> OTHER INFORMATION: Val, Ala or Thr
<220> FEATURE:
<221> NAME/KEY: MOD_RES
<222> LOCATION: (98)..(98)
<223> OTHER INFORMATION: Leu, Ile or Val
<220> FEATURE:
<221> NAME/KEY: MOD_RES
<222> LOCATION: (100)..(100)
<223> OTHER INFORMATION: His, Arg, Asp, Gly, Ser or Asn
<220> FEATURE:
<221> NAME/KEY: MOD_RES
<222> LOCATION: (101)..(101)
<223> OTHER INFORMATION: Ser, Thr, Ile, Phe or Ala
<220> FEATURE:
<221> NAME/KEY: MOD_RES
<222> LOCATION: (102)..(102)
<223> OTHER INFORMATION: Ser, Thr or Lys
<220> FEATURE:
<221> NAME/KEY: MOD_RES
<222> LOCATION: (103)..(103)
<223> OTHER INFORMATION: Ala, Gly, Val or Met
<220> FEATURE:
<221> NAME/KEY: MOD_RES
<222> LOCATION: (107)..(107)
<223> OTHER INFORMATION: Phe, Tyr or Ile
<220> FEATURE:
<221> NAME/KEY: MOD_RES
<222> LOCATION: (117)..(117)
<223> OTHER INFORMATION: Asp or Asn
<220> FEATURE:
<221> NAME/KEY: MOD_RES
<222> LOCATION: (118)..(118)
<223> OTHER INFORMATION: Arg, Gln, Glu or His
<220> FEATURE:
<221> NAME/KEY: MOD_RES
<222> LOCATION: (125)..(125)
<223> OTHER INFORMATION: Arg or Lys
<220> FEATURE:
<221> NAME/KEY: MOD_RES
<222> LOCATION: (126)..(126)
<223> OTHER INFORMATION: Gly or Ala
<220> FEATURE:
<221> NAME/KEY: MOD_RES
<222> LOCATION: (127)..(127)
<223> OTHER INFORMATION: Ile, Thr, Met or Val
<220> FEATURE:
<221> NAME/KEY: MOD_RES
<222> LOCATION: (130)..(130)
<223> OTHER INFORMATION: Tyr, Trp, Cys or Arg
<220> FEATURE:
<221> NAME/KEY: MOD_RES
```

```
<222> LOCATION: (132)..(132)
<223> OTHER INFORMATION: Asn or Asp
<220> FEATURE:
<221> NAME/KEY: MOD_RES
<222> LOCATION: (133)..(133)
<223> OTHER INFORMATION: Arg, Lys or Asn
<220> FEATURE:
<221> NAME/KEY: MOD_RES
<222> LOCATION: (134)..(134)
<223> OTHER INFORMATION: Ile, Ser, Asn, Lys, Asp or Arg
<220> FEATURE:
<221> NAME/KEY: MOD_RES
<222> LOCATION: (138)..(138)
<223> OTHER INFORMATION: Ile, Val, Thr or Ala
<220> FEATURE:
<221> NAME/KEY: MOD_RES
<222> LOCATION: (142)..(142)
<223> OTHER INFORMATION: Ser, Thr, Ala, Pro or Arg
<220> FEATURE:
<221> NAME/KEY: MOD_RES
<222> LOCATION: (144)..(144)
<223> OTHER INFORMATION: Phe, Ile, Met or Leu
<220> FEATURE:
<221> NAME/KEY: MOD_RES
<222> LOCATION: (145)..(145)
<223> OTHER INFORMATION: Lys, Arg, Asn, Ser or Leu
<220> FEATURE:
<221> NAME/KEY: MOD_RES
<222> LOCATION: (148)..(148)
<223> OTHER INFORMATION: Phe, Leu, Ile or Met
<220> FEATURE:
<221> NAME/KEY: MOD_RES
<222> LOCATION: (150)..(150)
<223> OTHER INFORMATION: Leu, Gln, Lys, His or Phe
<220> FEATURE:
<221> NAME/KEY: MOD_RES
<222> LOCATION: (152)..(152)
<223> OTHER INFORMATION: Thr, Ser or Leu
<220> FEATURE:
<221> NAME/KEY: MOD_RES
<222> LOCATION: (154)..(154)
<223> OTHER INFORMATION: Glu, Lys, Arg or Val
<220> FEATURE:
<221> NAME/KEY: MOD_RES
<222> LOCATION: (155)..(155)
<223> OTHER INFORMATION: Gly or Asp
<220> FEATURE:
<221> NAME/KEY: MOD_RES
<222> LOCATION: (157)..(157)
<223> OTHER INFORMATION: Ser, Arg or Lys
<220> FEATURE:
<221> NAME/KEY: MOD_RES
<222> LOCATION: (158)..(173)
<223> OTHER INFORMATION: This region may be 1 to 16 residues in length
      selected from "Ser," "Gly" or "Gly Xaa Xaa Xaa Xaa Xaa Xaa Xaa
      Xaa Xaa Xaa Xaa Xaa Xaa Xaa Xaa" wherein "Xaa" is any
      amino acid and the "Xaa's" may ecompass 1 to 15 residues
<220> FEATURE:
<221> NAME/KEY: MOD_RES
<222> LOCATION: (158)..(173)
<223> OTHER INFORMATION: contd. from above; in length, wherein some
      residues may be absent
<220> FEATURE:
<223> OTHER INFORMATION: see specification as filed for detailed
      description of substitutions and preferred embodiments

<400> SEQUENCE: 244

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Val Glu Met Xaa Val Arg Asp Tyr Glu
            20                  25                  30

Leu Asp Gln Xaa Gly Val Val Asn Asn Ala Xaa Tyr Ala Ser Tyr Cys
        35                  40                  45

Gln His Xaa Arg His Xaa Xaa Leu Glu Xaa Val Gly Xaa Xaa Xaa Asp
    50                  55                  60
```

```
Xaa Val Xaa Arg Xaa Gly Ser Leu Ala Xaa Xaa Glu Xaa Xaa Leu
 65                  70                  75                  80

Lys Xaa Phe Ala Pro Leu Arg Ser Gly Asp Arg Phe Xaa Val Xaa Xaa
                 85                  90                  95

Arg Xaa Ala Xaa Xaa Xaa Ala Arg Leu Xaa Phe Glu His Phe Ile
            100                 105                 110

Phe Lys Leu Pro Xaa Xaa Glu Pro Ile Leu Glu Ala Xaa Xaa Xaa Ala
            115                 120                 125

Val Xaa Leu Xaa Xaa Xaa Tyr Arg Pro Xaa Arg Ile Pro Xaa Glu Xaa
        130                 135                 140

Xaa Ser Lys Xaa Gln Xaa Phe Xaa Ser Xaa Xaa Ser Xaa Xaa Xaa Xaa
145                 150                 155                 160

Xaa Xaa Xaa Xaa Xaa Xaa Xaa Xaa Xaa Xaa Xaa Xaa Xaa
                165                 170
```

<210> SEQ ID NO 245
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 245
atacatccat gg                                                           12

<210> SEQ ID NO 246
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 246
atacataagc tt                                                           12

<210> SEQ ID NO 247
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 247
gctgcacatc accatcatca ccac                                              24

<210> SEQ ID NO 248
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 248
gctgcagcct atccatacga tgtgcctgac tatgct                                 36

<210> SEQ ID NO 249
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 249
gctgcagcct atccatacga tgtgcctgac tatgctgctg cacatcacca tcatcaccac    60

<210> SEQ ID NO 250
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 250
gcagcctctt ggaaagatgc gagcggctgg tct    33

<210> SEQ ID NO 251
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 251
gcagccgact acaaagacga tgacgacaaa    30

<210> SEQ ID NO 252
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 252
gcagccgaac agaaactgat ctctgaagaa gatctg    36

<210> SEQ ID NO 253
<211> LENGTH: 141
<212> TYPE: PRT
<213> ORGANISM: Picea glauca

<400> SEQUENCE: 253

Met Ala Arg Pro Phe Glu Leu Glu Leu Lys Val Arg Asp Tyr Glu Leu
1               5                   10                  15

Asp Gln Tyr Gly Val Val Asn Asn Ala Thr Tyr Ala Ser Tyr Cys Gln
            20                  25                  30

His Cys Arg His Glu Leu Cys Glu Ala Ile Gly Phe Ser Pro Asp Ala
        35                  40                  45

Ile Ala Arg Thr Gly Asn Ala Leu Ala Leu Ser Glu Leu Ser Leu Lys
    50                  55                  60

Tyr Leu Ala Pro Leu Arg Ser Gly Asp Ser Phe Val Val Thr Ala Arg
65                  70                  75                  80

Ile Ser Gly Ser Ser Ala Val Arg Leu Phe Phe Glu His Phe Ile Tyr
                85                  90                  95

Lys Leu Pro Asn Arg Glu Pro Val Leu Glu Ala Lys Ala Thr Ala Val
            100                 105                 110

Tyr Leu Asp Lys Ile Tyr Arg Pro Val Arg Leu Pro Ala Asp Phe Lys
        115                 120                 125

Ser Lys Ile Thr Leu Phe Leu Arg Asn Glu Glu Leu Asn
    130                 135                 140

<210> SEQ ID NO 254
<211> LENGTH: 141
<212> TYPE: PRT
<213> ORGANISM: Picea sitchensis

<400> SEQUENCE: 254

Met Ala Arg Pro Phe Glu Leu Glu Leu Lys Val Arg Asp Tyr Glu Leu
1               5                   10                  15

Asp Gln Tyr Gly Val Val Asn Asn Ala Thr Tyr Ala Ser Tyr Cys Gln
            20                  25                  30

His Cys Arg His Glu Leu Cys Glu Ala Ile Gly Phe Ser Pro Asp Val
        35                  40                  45

Ile Ala Arg Thr Gly Asn Ala Leu Ala Leu Ser Glu Leu Ser Leu Lys
    50                  55                  60

Tyr Leu Ala Pro Leu Arg Ser Gly Asp Ser Phe Val Val Thr Ala Arg
65                  70                  75                  80

Ile Ser Gly Ser Ser Ala Val Arg Leu Phe Phe Glu His Phe Ile Tyr
                85                  90                  95

Lys Leu Pro Asn Arg Glu Pro Val Leu Glu Ala Lys Ala Thr Ala Val
            100                 105                 110

Tyr Leu Asp Lys Ile Tyr Arg Pro Val Arg Leu Pro Ala Asp Phe Lys
        115                 120                 125

Ser Lys Ile Thr Leu Phe Leu Arg Asn Glu Glu Leu Asn
    130                 135                 140

<210> SEQ ID NO 255
<211> LENGTH: 141
<212> TYPE: PRT
<213> ORGANISM: Picea sitchensis

<400> SEQUENCE: 255

Met Ala Arg Pro Phe Glu Leu Glu Leu Lys Val Arg Asp Tyr Glu Leu
1               5                   10                  15

Asp Gln Tyr Gly Val Val Asn Asn Ala Thr Tyr Ala Ser Tyr Cys Glu
            20                  25                  30

His Cys Leu His Glu Leu Phe Glu Ala Ile Gly Phe Ser Pro Asp Ala
        35                  40                  45

Ile Ala Arg Thr Gly Asn Ala Leu Ala Leu Ser Glu Leu Ser Leu Lys
    50                  55                  60

Tyr Leu Ala Pro Leu Arg Ser Gly Asp Ser Phe Val Val Thr Ala Arg
65                  70                  75                  80

Ile Ser Gly Ser Ser Ala Val Arg Leu Phe Ile Glu His Phe Ile Tyr
                85                  90                  95

Lys Leu Pro Asn Arg Glu Pro Val Leu Glu Ala Lys Ala Thr Ala Val
            100                 105                 110

Tyr Leu Asp Lys Ile Tyr Arg Pro Val Arg Leu Pro Ala Asp Phe Lys
        115                 120                 125

Ser Lys Ile Thr Leu Phe Leu Arg Asn Glu Glu Leu Asn
    130                 135                 140

<210> SEQ ID NO 256
<211> LENGTH: 141
<212> TYPE: PRT
<213> ORGANISM: Ricinus communis

<400> SEQUENCE: 256

Met Asn Ser Phe Val Gly Val Glu Leu Lys Val Arg Asp Tyr Glu Leu
1               5                   10                  15

Asp Gln Tyr Gly Val Val Asn Asn Ala Val Tyr Ala Ser Tyr Cys Gln
            20                  25                  30

His Gly Arg His Glu Leu Leu Glu Arg Ile Gly Val Ser Ala Asp Ala
                35                  40                  45

Val Ala Arg Thr Gly Asp Ala Leu Ala Leu Ser Glu Leu Ser Leu Lys
 50                  55                  60

Phe Leu Ala Pro Leu Arg Ser Gly Asp Arg Phe Val Lys Val Arg
 65                  70                  75                  80

Ile Ser Gly Ser Ser Ala Ala Arg Leu Tyr Phe Asp His Phe Ile Phe
                 85                  90                  95

Lys Leu Pro Asn Glu Glu Pro Ile Leu Glu Ala Lys Ala Thr Ala Val
                100                 105                 110

Trp Leu Asp Lys Asn Tyr Arg Pro Val Arg Ile Pro Ser Asp Met Arg
                115                 120                 125

Ser Lys Leu Val Gln Phe Leu Lys His Glu Glu Ser Asn
    130                 135                 140

<210> SEQ ID NO 257
<211> LENGTH: 140
<212> TYPE: PRT
<213> ORGANISM: Populus trichocarpa

<400> SEQUENCE: 257

Met Ser Gly Leu Val Glu Val Glu Leu Lys Val Arg Asp Tyr Glu Leu
 1               5                  10                  15

Asp Gln Phe Gly Val Val Asn Asn Ala Val Tyr Ala Ser Tyr Cys Gln
                20                  25                  30

His Gly Arg His Glu Leu Leu Glu Arg Ile Gly Val Ser Ala Asp Val
                35                  40                  45

Val Ala Arg Thr Gly Asp Ala Leu Ala Leu Ser Glu Leu Ser Leu Lys
 50                  55                  60

Phe Leu Ala Pro Leu Arg Ser Gly Asp Arg Phe Val Lys Val Arg
 65                  70                  75                  80

Ile Ser Gly Ser Ser Ala Ala Arg Leu Tyr Phe Glu His Phe Ile Phe
                 85                  90                  95

Arg Leu Pro Asn Glu Glu Pro Ile Leu Glu Ala Lys Ala Thr Ala Val
                100                 105                 110

Trp Leu Asp Lys Lys Tyr His Pro Val Arg Ile Pro Pro Glu Phe Arg
                115                 120                 125

Ser Lys Phe Val Gln Phe Leu Arg His Glu Glu Ser
    130                 135                 140

<210> SEQ ID NO 258
<211> LENGTH: 141
<212> TYPE: PRT
<213> ORGANISM: Vitis vinifera

<400> SEQUENCE: 258

Met Ser Gly Phe Leu Asp Val Glu Leu Lys Val Arg Asp Tyr Glu Leu
 1               5                  10                  15

Asp Gln Tyr Gly Val Val Asn Asn Ala Val Tyr Ala Ser Tyr Cys Gln
                20                  25                  30

His Gly Arg His Glu Leu Leu Glu Lys Ile Gly Val Asn Ala Asp Ala
                35                  40                  45

Val Ala Arg Thr Gly Asp Ala Leu Ala Leu Ser Glu Leu Thr Leu Lys
 50                  55                  60

Phe Leu Ala Pro Leu Arg Ser Gly Asp Arg Phe Val Lys Val Arg
 65                  70                  75                  80

Val Ser Asp Ser Ser Ala Ala Arg Leu Tyr Phe Glu His Phe Ile Phe
            85                  90                  95

Lys Leu Pro Asn Glu Glu Pro Ile Leu Glu Ala Arg Ala Thr Ala Val
            100                 105                 110

Cys Leu Asp Lys Asn Tyr Arg Pro Val Arg Ile Pro Thr Glu Ile Arg
            115                 120                 125

Ser Lys Leu Val Gln Phe Leu Arg His Glu Glu Ser His
130                 135                 140

<210> SEQ ID NO 259
<211> LENGTH: 141
<212> TYPE: PRT
<213> ORGANISM: Vitis vinifera

<400> SEQUENCE: 259

Met Ser Gly Phe Leu Asp Val Glu Leu Lys Val Arg Asp Tyr Glu Leu
1               5                   10                  15

Asp Gln Tyr Gly Val Val Asn Asn Ala Val Tyr Ala Ser Tyr Cys Gln
            20                  25                  30

His Gly Arg His Glu Leu Leu Glu Lys Ile Gly Leu Asn Ala Asp Ala
        35                  40                  45

Val Ala Cys Ile Gly Asp Ala Val Ala Leu Ser Glu Leu Thr Leu Lys
    50                  55                  60

Phe Leu Ala Pro Leu Arg Ser Gly Asp Arg Phe Val Val Lys Val Arg
65                  70                  75                  80

Val Ser Asp Ala Ser Ala Ala Arg Leu Tyr Phe Glu His Phe Ile Phe
            85                  90                  95

Lys Leu Pro Asn Glu Glu Pro Ile Leu Glu Ala Arg Ala Thr Gly Val
            100                 105                 110

Cys Leu Asp Lys Asn Tyr Arg Pro Val Arg Ile Pro Thr Glu Ile Arg
            115                 120                 125

Ser Ile Leu Val Gln Phe Leu Arg His Glu Glu Ser His
130                 135                 140

<210> SEQ ID NO 260
<211> LENGTH: 141
<212> TYPE: PRT
<213> ORGANISM: Gossypium hirsutum

<400> SEQUENCE: 260

Met Thr Ser Phe His Glu Val Glu Leu Lys Val Arg Asp Tyr Glu Leu
1               5                   10                  15

Asp Gln Tyr Gly Val Val Asn Asn Ala Val Tyr Ala Ser Tyr Cys Gln
            20                  25                  30

His Gly Arg His Glu Leu Leu Glu Ser Ile Gly Ile Ser Cys Asp Glu
        35                  40                  45

Val Ala Arg Thr Gly Asp Ser Leu Ala Leu Ser Glu Leu Ser Leu Lys
    50                  55                  60

Phe Leu Gly Pro Leu Arg Ser Gly Asp Asn Phe Val Val Lys Val Arg
65                  70                  75                  80

Val Ser Asn Ser Ser Gly Ala Arg Leu Tyr Phe Glu His Phe Ile Phe
            85                  90                  95

Lys Met Pro Asn Glu Val Pro Ile Leu Glu Ala Lys Ala Thr Ala Val
            100                 105                 110

Trp Leu Asp Lys Asn Tyr Arg Pro Ala Arg Ile Pro Pro Glu Phe Arg
            115                 120                 125

Ser Lys Phe Val Gln Phe Leu Arg Cys Glu Glu Pro Ser
    130                 135                 140

<210> SEQ ID NO 261
<211> LENGTH: 140
<212> TYPE: PRT
<213> ORGANISM: Glycine max

<400> SEQUENCE: 261

Met Ser Gly Phe His Asp Val Glu Leu Lys Val Arg Asp Tyr Glu Leu
1               5                   10                  15

Asp Gln Tyr Gly Val Val Asn Asn Ala Val Tyr Ala Ser Tyr Cys Gln
            20                  25                  30

His Gly Arg His Glu Leu Leu Gln Asn Ile Gly Ile Asn Cys Asp Ala
        35                  40                  45

Val Ala Arg Ser Gly Asp Ala Leu Ala Leu Ser Glu Leu Ser Leu Lys
    50                  55                  60

Phe Leu Ala Pro Leu Arg Ser Gly Asp Lys Phe Val Arg Val Arg
65                  70                  75                  80

Ile Ser Gly Ser Ser Ala Ala Arg Leu Tyr Phe Asp His Phe Ile Tyr
                85                  90                  95

Lys Leu Pro Asn Gln Glu Pro Ile Leu Glu Ala Lys Ala Ile Ala Val
            100                 105                 110

Arg Leu Asp Lys Asn Tyr Arg Pro Ile Arg Pro Ala Glu Met Lys
        115                 120                 125

Ser Lys Phe Val Lys Phe Ile Arg Ile Glu Asp Ser
    130                 135                 140

<210> SEQ ID NO 262
<211> LENGTH: 141
<212> TYPE: PRT
<213> ORGANISM: Lycopersicon esculentum

<400> SEQUENCE: 262

Met Ala Glu Phe His Glu Val Glu Leu Lys Val Arg Asp Tyr Glu Leu
1               5                   10                  15

Asp Gln Tyr Gly Val Val Asn Asn Ala Ile Tyr Ala Ser Tyr Cys Gln
            20                  25                  30

His Gly Arg His Glu Leu Leu Glu Arg Ile Gly Ile Ser Ala Asp Glu
        35                  40                  45

Val Ala Arg Ser Gly Asp Ala Leu Ala Leu Thr Glu Leu Ser Leu Lys
    50                  55                  60

Tyr Leu Ala Pro Leu Arg Ser Gly Asp Arg Phe Val Val Lys Ala Arg
65                  70                  75                  80

Ile Ser Asp Ser Ser Ala Ala Arg Leu Phe Phe Glu His Phe Ile Phe
                85                  90                  95

Lys Leu Pro Asp Gln Glu Pro Ile Leu Glu Ala Arg Gly Ile Ala Val
            100                 105                 110

Trp Leu Asn Lys Ser Tyr Arg Pro Val Arg Ile Pro Ala Glu Phe Arg
        115                 120                 125

Ser Lys Phe Val Gln Phe Leu Arg Gln Glu Ala Ser Asn
    130                 135                 140

<210> SEQ ID NO 263
<211> LENGTH: 139
<212> TYPE: PRT
<213> ORGANISM: Petunia integrifolia

<400> SEQUENCE: 263

Met Asn Glu Phe Tyr Glu Val Glu Leu Lys Val Arg Asp Tyr Glu Leu
1               5                   10                  15

Asp Gln Tyr Gly Val Val Asn Asn Ala Ile Tyr Ala Ser Tyr Cys Gln
            20                  25                  30

His Cys Arg His Glu Leu Leu Glu Lys Ile Gly Val Asn Ala Asp Ala
        35                  40                  45

Val Ala Arg Asn Gly Glu Ala Leu Ala Leu Thr Glu Met Thr Leu Lys
50                  55                  60

Tyr Leu Ala Pro Leu Arg Ser Gly Asp Arg Phe Ile Val Lys Val Arg
65                  70                  75                  80

Ile Ser Asp Ser Ser Ala Ala Arg Leu Phe Phe Glu His Phe Ile Phe
                85                  90                  95

Lys Leu Pro Asp Gln Glu Pro Ile Leu Glu Ala Arg Gly Thr Ala Val
            100                 105                 110

Trp Leu Asn Lys Ser Tyr Arg Pro Val Arg Ile Pro Ser Glu Phe Arg
        115                 120                 125

Ser Lys Phe Val Gln Phe Leu Arg Gln Glu Ala
    130                 135

<210> SEQ ID NO 264
<211> LENGTH: 149
<212> TYPE: PRT
<213> ORGANISM: Lycopersicon hirsutum

<400> SEQUENCE: 264

Met Ser Asp Gln Val Tyr His His Asp Val Glu Leu Thr Val Arg Asp
1               5                   10                  15

Tyr Glu Leu Asp Gln Phe Gly Val Val Asn Asn Ala Thr Tyr Ala Ser
            20                  25                  30

Tyr Cys Gln His Cys Arg His Ala Phe Leu Glu Lys Ile Gly Val Ser
        35                  40                  45

Val Asp Glu Val Thr Arg Asn Gly Asp Ala Leu Ala Val Thr Glu Leu
50                  55                  60

Ser Leu Lys Phe Leu Ala Pro Leu Arg Ser Gly Asp Arg Phe Val Val
65                  70                  75                  80

Arg Ala Arg Leu Ser His Phe Thr Val Ala Arg Leu Phe Phe Glu His
                85                  90                  95

Phe Ile Phe Lys Leu Pro Asp Gln Glu Pro Ile Leu Glu Ala Arg Gly
            100                 105                 110

Ile Ala Val Trp Leu Asn Arg Ser Tyr Arg Pro Ile Arg Ile Pro Ser
        115                 120                 125

Glu Phe Asn Ser Lys Phe Val Lys Phe Leu His Gln Lys Ser Cys Gly
    130                 135                 140

Val Gln His His Leu
145

<210> SEQ ID NO 265
<211> LENGTH: 149
<212> TYPE: PRT
<213> ORGANISM: Solanum tuberosum

<400> SEQUENCE: 265

Met Gly Asp Gln Leu Tyr Gln His Glu Val Glu Leu Gln Val Arg Asp
1               5                   10                  15

Tyr Glu Leu Asp Gln Phe Gly Val Val Asn Asn Ala Thr Tyr Ala Ser

```
                    20                  25                  30
Tyr Cys Gln His Cys Arg His Glu Phe Leu Glu Lys Ile Gly Val Ser
                35                  40                  45
Val Asp Glu Val Cys Arg Thr Gly Glu Ala Leu Ala Thr Thr Glu Leu
 50                  55                  60
Ser Leu Lys Tyr Leu Ala Pro Leu Arg Ser Gly Asp Arg Phe Val Val
 65                  70                  75                  80
Lys Val Arg Ile Ser Arg Ser Thr Ala Ala Arg Leu Phe Phe Glu His
                85                  90                  95
Phe Ile Phe Lys Leu Pro Asp Gln Glu Pro Ile Leu Glu Ala Arg Gly
                100                 105                 110
Ile Ala Val Trp Leu Asn Arg Ser Tyr Arg Pro Ile Arg Ile Pro Ser
                115                 120                 125
Glu Phe Ser Ser Lys Phe Val Gln Phe Leu His Gln Lys Ser Cys Gly
                130                 135                 140
Thr Gln His Arg Leu
145

<210> SEQ ID NO 266
<211> LENGTH: 141
<212> TYPE: PRT
<213> ORGANISM: Arabidopsis thaliana

<400> SEQUENCE: 266

Met Ser Glu Phe His Glu Val Glu Leu Lys Val Arg Asp Tyr Glu Leu
 1               5                  10                  15
Asp Gln Phe Gly Val Val Asn Asn Ala Val Tyr Ala Asn Tyr Cys Gln
                20                  25                  30
His Gly Arg His Glu Phe Leu Glu Ser Ile Gly Ile Asn Cys Asp Glu
                35                  40                  45
Val Ala Arg Ser Gly Glu Ala Leu Ala Ile Ser Glu Leu Thr Met Lys
 50                  55                  60
Phe Leu Ser Pro Leu Arg Ser Gly Asp Lys Phe Val Val Lys Ala Arg
 65                  70                  75                  80
Ile Ser Gly Thr Ser Ala Ala Arg Ile Tyr Phe Asp His Phe Ile Phe
                85                  90                  95
Lys Leu Pro Asn Gln Glu Pro Ile Leu Glu Ala Lys Gly Ile Ala Val
                100                 105                 110
Trp Leu Asp Asn Lys Tyr Arg Pro Val Arg Ile Pro Ser Ser Ile Arg
                115                 120                 125
Ser Lys Phe Val His Phe Leu Arg Gln Asp Asp Ala Val
                130                 135                 140

<210> SEQ ID NO 267
<211> LENGTH: 141
<212> TYPE: PRT
<213> ORGANISM: Arabidopsis thaliana

<400> SEQUENCE: 267

Met Ser Glu Phe His Glu Val Glu Leu Lys Val Arg Asp Tyr Glu Leu
 1               5                  10                  15
Asp Gln Phe Gly Val Val Asn Asn Ala Val Tyr Ala Asn Tyr Cys Gln
                20                  25                  30
His Gly Met His Glu Phe Leu Glu Ser Ile Gly Ile Asn Cys Asp Glu
                35                  40                  45
Val Ala Arg Ser Gly Glu Ala Leu Ala Ile Ser Glu Leu Thr Met Asn
```

```
                    50                  55                  60
Phe Leu Ala Pro Leu Arg Ser Gly Asp Lys Phe Val Lys Val Asn
 65                  70                  75                  80

Ile Ser Arg Thr Ser Ala Ala Arg Ile Tyr Phe Asp His Ser Ile Leu
                     85                  90                  95

Lys Leu Pro Asn Gln Glu Val Ile Leu Glu Ala Lys Ala Thr Val Val
                    100                 105                 110

Trp Leu Asp Asn Lys His Arg Pro Val Arg Ile Pro Ser Ser Ile Arg
                    115                 120                 125

Ser Lys Phe Val His Phe Leu Arg Gln Asn Asp Thr Val
                    130                 135                 140

<210> SEQ ID NO 268
<211> LENGTH: 142
<212> TYPE: PRT
<213> ORGANISM: Arabidopsis thaliana

<400> SEQUENCE: 268

Met Asn Gly Val His Glu Ile Glu Leu Lys Val Arg Asp Tyr Glu Leu
 1               5                  10                  15

Asp Gln Phe Gly Val Val Asn Asn Ala Val Tyr Ala Asn Tyr Cys Gln
                20                  25                  30

His Gly Gln His Glu Phe Met Glu Thr Ile Gly Ile Asn Cys Asp Glu
            35                  40                  45

Val Ser Arg Ser Gly Glu Ala Leu Ala Val Ser Glu Leu Thr Ile Lys
     50                  55                  60

Phe Leu Ala Pro Leu Arg Ser Gly Cys Lys Phe Val Val Lys Thr Arg
 65                  70                  75                  80

Ile Ser Gly Thr Ser Met Thr Arg Ile Tyr Phe Glu Gln Phe Ile Phe
                 85                  90                  95

Lys Leu Pro Asn Gln Glu Pro Ile Leu Glu Ala Lys Gly Met Ala Val
                    100                 105                 110

Trp Leu Asp Lys Arg Tyr Arg Pro Val Cys Ile Pro Ser Tyr Ile Arg
                    115                 120                 125

Ser Asn Phe Gly His Phe Gln Arg Gln His Val Val Glu Tyr
                    130                 135                 140

<210> SEQ ID NO 269
<211> LENGTH: 143
<212> TYPE: PRT
<213> ORGANISM: Oryza sativa

<400> SEQUENCE: 269

Leu Arg Leu Asp Gln Phe Phe Glu Val Glu Met Lys Val Arg Asp Tyr
 1               5                  10                  15

Glu Leu Asp Gln Tyr Gly Val Val Asn Asn Ala Ile Tyr Ala Ser Tyr
                20                  25                  30

Cys Gln His Gly Arg His Glu Leu Leu Glu Ser Val Gly Ile Ser Ala
            35                  40                  45

Asp Ala Val Ala Arg Ser Gly Glu Ser Leu Ala Leu Ser Glu Leu His
     50                  55                  60

Leu Lys Tyr Tyr Ala Pro Leu Arg Ser Gly Asp Lys Phe Val Val Lys
 65                  70                  75                  80

Val Arg Leu Ala Ser Thr Lys Gly Ile Arg Met Ile Phe Glu His Phe
                 85                  90                  95

Ile Glu Lys Leu Pro Asn Arg Glu Leu Ile Leu Glu Ala Lys Ala Thr
```

```
                100                 105                 110
Ala Val Cys Leu Asn Lys Asp Tyr Arg Pro Thr Arg Ile Ser Pro Glu
            115                 120                 125

Phe Leu Ser Lys Leu Gln Phe Phe Thr Ser Glu Gly Ser Ser Ser
        130                 135                 140

<210> SEQ ID NO 270
<211> LENGTH: 143
<212> TYPE: PRT
<213> ORGANISM: Oryza sativa

<400> SEQUENCE: 270

Leu Arg Leu Asp Gln Phe Phe Glu Val Glu Met Lys Val Arg Asp Tyr
1               5                   10                  15

Glu Leu Asp Gln Tyr Gly Val Val Asn Asn Ala Ile Tyr Ala Ser Tyr
            20                  25                  30

Cys Gln His Gly Arg His Glu Leu Leu Glu Cys Val Gly Ile Ser Ala
        35                  40                  45

Asp Ala Val Ala Arg Ser Gly Glu Ser Leu Ala Leu Ser Glu Leu His
    50                  55                  60

Leu Lys Tyr Tyr Ala Pro Leu Arg Ser Gly Asp Lys Phe Val Val Lys
65                  70                  75                  80

Val Arg Leu Ala Ser Thr Lys Gly Ile Arg Met Ile Phe Glu His Phe
                85                  90                  95

Ile Glu Lys Leu Pro Asn Arg Glu Leu Ile Leu Glu Ala Lys Ala Thr
            100                 105                 110

Ala Val Cys Leu Asn Lys Asp Tyr Arg Pro Thr Arg Ile Ser Pro Glu
        115                 120                 125

Phe Leu Ser Lys Leu Gln Phe Phe Thr Ser Glu Gly Ser Ser Ser
    130                 135                 140

<210> SEQ ID NO 271
<211> LENGTH: 143
<212> TYPE: PRT
<213> ORGANISM: Phyllostachys edulis

<400> SEQUENCE: 271

Leu Arg Val Asp Lys Phe Phe Glu Val Ala Met Lys Val Arg Asp Tyr
1               5                   10                  15

Glu Leu Asp Gln Tyr Gly Val Val Asn Asn Ala Val Tyr Ala Ser Tyr
            20                  25                  30

Cys Gln His Gly Arg His Glu Leu Leu Glu Ser Val Gly Ile Ser Ala
        35                  40                  45

Asp Ala Val Ala Arg Ser Gly Glu Ser Leu Ala Leu Ser Asp Leu His
    50                  55                  60

Leu Lys Phe Phe Ala Pro Leu Arg Ser Gly Asp Glu Phe Val Val Lys
65                  70                  75                  80

Val Arg Leu Ala Ser Ile Lys Gly Val Arg Met Ile Phe Glu His Ser
                85                  90                  95

Ile Glu Lys Leu Pro Asn Arg Glu Leu Ile Leu Glu Ala Lys Ala Thr
            100                 105                 110

Ala Val Cys Leu Asn Lys Asp Tyr Arg Pro Thr Arg Val Ser Pro Glu
        115                 120                 125

Phe Leu Ser Arg Leu Gln Leu Phe Ser Ser Lys Asp Ser Lys Gly
    130                 135                 140
```

```
<210> SEQ ID NO 272
<211> LENGTH: 157
<212> TYPE: PRT
<213> ORGANISM: Sorghum bicolor

<400> SEQUENCE: 272

Leu Arg Leu Glu Glu Lys Phe Phe Glu Val Glu Met Lys Val Arg Asp
1               5                   10                  15

Tyr Glu Leu Asp Gln Tyr Gly Val Val Asn Asn Ala Val Tyr Ala Ser
            20                  25                  30

Tyr Cys Gln His Gly Arg His Glu Leu Leu Glu Ser Val Gly Ile Ser
        35                  40                  45

Ala Asp Ala Val Ala Arg Ser Gly Glu Ser Leu Ala Leu Ser Glu Leu
    50                  55                  60

Asn Leu Lys Tyr Phe Gly Pro Leu Arg Ser Gly Asp Lys Phe Val Val
65                  70                  75                  80

Lys Val Arg Leu Val Gly Ile Lys Gly Val Arg Met Ile Phe Glu His
                85                  90                  95

Ile Ile Glu Lys Leu Pro Asn His Glu Leu Ile Leu Glu Ala Lys Ala
                100                 105                 110

Thr Ala Val Cys Leu Asn Lys Asp Tyr Tyr Pro Thr Arg Ile Pro Arg
            115                 120                 125

Glu Leu Leu Ser Lys Met Gln Leu Phe Ser Ser Glu Asp Ser Arg Gly
        130                 135                 140

Ser Asn Lys Asp Val Asn Asn Arg Asn Asn Ser Cys Asn
145                 150                 155

<210> SEQ ID NO 273
<211> LENGTH: 157
<212> TYPE: PRT
<213> ORGANISM: Saccharum sp.

<400> SEQUENCE: 273

Leu Arg Leu Glu Glu Lys Phe Phe Glu Val Glu Met Lys Val Arg Asp
1               5                   10                  15

Tyr Glu Leu Asp Gln Tyr Gly Val Val Asn Asn Ala Val Tyr Ala Ser
            20                  25                  30

Tyr Cys Gln His Gly Arg His Glu Val Leu Glu Ser Val Gly Ile Ser
        35                  40                  45

Ala Asp Ala Val Ala Arg Ser Gly Glu Ser Leu Ala Leu Ser Glu Leu
    50                  55                  60

Asn Leu Lys Tyr Phe Ala Pro Leu Arg Ser Gly Asp Lys Phe Val Val
65                  70                  75                  80

Lys Val Arg Leu Val Gly Ile Lys Gly Ile Arg Met Ile Phe Glu His
                85                  90                  95

Ile Ile Glu Lys Leu Pro Asn His Glu Leu Ile Leu Glu Ala Lys Ala
                100                 105                 110

Thr Ala Val Cys Leu Asn Lys Asp Tyr Tyr Pro Thr Arg Ile Pro Arg
            115                 120                 125

Glu Leu Leu Ala Lys Met Gln Leu Phe Ser Ser Arg Gly Ser Arg Gly
        130                 135                 140

Thr Asn Asp Asp Ile Asn Asn Arg Asn Asn Ser Cys Asn
145                 150                 155

<210> SEQ ID NO 274
<211> LENGTH: 153
<212> TYPE: PRT
```

<213> ORGANISM: Zea mays

<400> SEQUENCE: 274

```
Glu Lys Phe Phe Glu Val Glu Met Lys Val Arg Asp Tyr Glu Ile Asp
1               5                   10                  15

Gln Tyr Gly Val Val Asn Asn Ala Ile Tyr Ala Ser Tyr Cys Gln His
            20                  25                  30

Gly Arg His Glu Leu Leu Glu Ser Val Gly Ile Ser Ala Asp Ala Val
        35                  40                  45

Ala Arg Ser Gly Glu Ser Leu Ala Leu Ser Glu Leu Asn Leu Lys Tyr
    50                  55                  60

Phe Ala Pro Leu Arg Ser Gly Asp Lys Phe Val Lys Val Arg Leu
65                  70                  75                  80

Ala Gly Ile Lys Gly Val Arg Met Ile Phe Asp His Ile Ile Thr Lys
                85                  90                  95

Leu Pro Asn His Glu Leu Ile Leu Glu Ala Lys Ala Thr Ala Val Cys
            100                 105                 110

Leu Asn Lys Asp Tyr Tyr Pro Thr Arg Ile Pro Arg Glu Leu Leu Ser
        115                 120                 125

Lys Met Gln Leu Phe Leu Pro Val Asp Ser Arg Gly Ser Asn Glu Asp
    130                 135                 140

Val Asn Arg Asn Asn Ser Cys Asn
145                 150
```

<210> SEQ ID NO 275
<211> LENGTH: 450
<212> TYPE: DNA
<213> ORGANISM: Lycopersicon hirsutum
<220> FEATURE:
<221> NAME/KEY: CDS
<222> LOCATION: (1)..(447)

<400> SEQUENCE: 275

```
atg agt gat cag gtc tat cac cat gac gtt gaa ctc aca gtc agg gac       48
Met Ser Asp Gln Val Tyr His His Asp Val Glu Leu Thr Val Arg Asp
1               5                   10                  15 tat gag ttg gat cag ttt ggt gtt gta aat aat gct act tat gcg agt       96
Tyr Glu Leu Asp Gln Phe Gly Val Val Asn Asn Ala Thr Tyr Ala Ser
            20                  25                  30 tat tgt caa cat tgt cgt cat gcg ttt cta gaa aaa att ggt gtt agt      144
Tyr Cys Gln His Cys Arg His Ala Phe Leu Glu Lys Ile Gly Val Ser
        35                  40                  45 gtt gat gaa gta acg cga aat ggt gat gca tta gct gta aca gag ctc      192
Val Asp Glu Val Thr Arg Asn Gly Asp Ala Leu Ala Val Thr Glu Leu
    50                  55                  60 tca ctt aag ttt cta gca cca cta agg agt gga gat aga ttc gtg gtg      240
Ser Leu Lys Phe Leu Ala Pro Leu Arg Ser Gly Asp Arg Phe Val Val
65                  70                  75                  80 agg gcg cga tta tcc cac ttt aca gta gct cga ttg ttt ttc gag cat      288
Arg Ala Arg Leu Ser His Phe Thr Val Ala Arg Leu Phe Phe Glu His
                85                  90                  95 ttc atc ttc aag ctt cca gat caa gag cct ata ttg gag gca aga gga      336
Phe Ile Phe Lys Leu Pro Asp Gln Glu Pro Ile Leu Glu Ala Arg Gly
            100                 105                 110 ata gca gtg tgg ctt aat aga agt tat cgt cct att cga att ccg tca      384
Ile Ala Val Trp Leu Asn Arg Ser Tyr Arg Pro Ile Arg Ile Pro Ser
        115                 120                 125 gag ttc aat tca aaa ttt gtt aaa ttc ctt cac cag aag agt tgc ggt      432
Glu Phe Asn Ser Lys Phe Val Lys Phe Leu His Gln Lys Ser Cys Gly
```

```
                      130                 135                 140
gta caa cat cat ctc tga                                                    450
Val Gln His His Leu
145

<210> SEQ ID NO 276
<211> LENGTH: 149
<212> TYPE: PRT
<213> ORGANISM: Lycopersicon hirsutum

<400> SEQUENCE: 276

Met Ser Asp Gln Val Tyr His His Asp Val Glu Leu Thr Val Arg Asp
1               5                   10                  15

Tyr Glu Leu Asp Gln Phe Gly Val Val Asn Asn Ala Thr Tyr Ala Ser
                20                  25                  30

Tyr Cys Gln His Cys Arg His Ala Phe Leu Glu Lys Ile Gly Val Ser
            35                  40                  45

Val Asp Glu Val Thr Arg Asn Gly Asp Ala Leu Ala Val Thr Glu Leu
        50                  55                  60

Ser Leu Lys Phe Leu Ala Pro Leu Arg Ser Gly Asp Arg Phe Val Val
65                  70                  75                  80

Arg Ala Arg Leu Ser His Phe Thr Val Ala Arg Leu Phe Glu His
                85                  90                  95

Phe Ile Phe Lys Leu Pro Asp Gln Glu Pro Ile Leu Glu Ala Arg Gly
                100                 105                 110

Ile Ala Val Trp Leu Asn Arg Ser Tyr Arg Pro Ile Arg Ile Pro Ser
            115                 120                 125

Glu Phe Asn Ser Lys Phe Val Lys Phe Leu His Gln Lys Ser Cys Gly
        130                 135                 140

Val Gln His His Leu
145

<210> SEQ ID NO 277
<211> LENGTH: 426
<212> TYPE: DNA
<213> ORGANISM: Lycopersicon esculentum
<220> FEATURE:
<221> NAME/KEY: CDS
<222> LOCATION: (1)..(423)

<400> SEQUENCE: 277 atg gct gag ttc cat gaa gtt gaa ctc aaa gtc cgg gac tat gaa ttg      48
Met Ala Glu Phe His Glu Val Glu Leu Lys Val Arg Asp Tyr Glu Leu
1               5                   10                  15 gat cag tat ggt gtt gta aac aat gct att tat gca agt tat tgc caa      96
Asp Gln Tyr Gly Val Val Asn Asn Ala Ile Tyr Ala Ser Tyr Cys Gln
                20                  25                  30 cat ggt cgt cat gag ctt cta gaa agg att ggt ata agt gct gat gaa     144
His Gly Arg His Glu Leu Leu Glu Arg Ile Gly Ile Ser Ala Asp Glu
            35                  40                  45 gtg gca cgc agt ggt gac gca cta gca cta aca gag ctg tca ctt aag     192
Val Ala Arg Ser Gly Asp Ala Leu Ala Leu Thr Glu Leu Ser Leu Lys
        50                  55                  60 tat cta gca cct cta agg agt gga gat aga ttc gtc gtg aag gca cga     240
Tyr Leu Ala Pro Leu Arg Ser Gly Asp Arg Phe Val Val Lys Ala Arg
65                  70                  75                  80 ata tct gat tct tca gct gct cgt ttg ttt ttc gaa cac ttc atc ttc     288
Ile Ser Asp Ser Ser Ala Ala Arg Leu Phe Phe Glu His Phe Ile Phe
                85                  90                  95
```

```
aag ctt cca gat caa gag ccc atc ttg gag gca aga gga ata gca gtg      336
Lys Leu Pro Asp Gln Glu Pro Ile Leu Glu Ala Arg Gly Ile Ala Val
            100                 105                 110 tgg ctc aat aaa agt tac cgt cct gtc cga atc ccg gca gag ttc aga      384
Trp Leu Asn Lys Ser Tyr Arg Pro Val Arg Ile Pro Ala Glu Phe Arg
            115                 120                 125 tca aaa ttt gtt cag ttc ctt cgc cag gag gca tcc aac tga              426
Ser Lys Phe Val Gln Phe Leu Arg Gln Glu Ala Ser Asn
            130                 135             140

<210> SEQ ID NO 278
<211> LENGTH: 141
<212> TYPE: PRT
<213> ORGANISM: Lycopersicon esculentum

<400> SEQUENCE: 278

Met Ala Glu Phe His Glu Val Glu Leu Lys Val Arg Asp Tyr Glu Leu
1               5                   10                  15

Asp Gln Tyr Gly Val Val Asn Asn Ala Ile Tyr Ala Ser Tyr Cys Gln
            20                  25                  30

His Gly Arg His Glu Leu Leu Glu Arg Ile Gly Ile Ser Ala Asp Glu
        35                  40                  45

Val Ala Arg Ser Gly Asp Ala Leu Ala Leu Thr Glu Leu Ser Leu Lys
    50                  55                  60

Tyr Leu Ala Pro Leu Arg Ser Gly Asp Arg Phe Val Val Lys Ala Arg
65                  70                  75                  80

Ile Ser Asp Ser Ser Ala Ala Arg Leu Phe Phe Glu His Phe Ile Phe
                85                  90                  95

Lys Leu Pro Asp Gln Glu Pro Ile Leu Glu Ala Arg Gly Ile Ala Val
            100                 105                 110

Trp Leu Asn Lys Ser Tyr Arg Pro Val Arg Ile Pro Ala Glu Phe Arg
            115                 120                 125

Ser Lys Phe Val Gln Phe Leu Arg Gln Glu Ala Ser Asn
            130                 135             140

<210> SEQ ID NO 279
<211> LENGTH: 6
<212> TYPE: PRT
<213> ORGANISM: Artificial Sequence
<220> FEATURE:
<223> OTHER INFORMATION: Synthetic 6xHis tag

<400> SEQUENCE: 279

His His His His His His
1               5
```